US012065469B2

(12) United States Patent
Poma et al.

(10) Patent No.: US 12,065,469 B2
(45) **Date of Patent: *Aug. 20, 2024**

(54) DE-IMMUNIZED SHIGA TOXIN A SUBUNIT EFFECTOR POLYPEPTIDES FOR APPLICATIONS IN MAMMALS

(71) Applicant: Molecular Templates, Inc., Austin, TX (US)

(72) Inventors: Eric Poma, New York, NY (US); Erin Willert, Round Rock, TX (US); Garrett Lee Robinson, Austin, TX (US); Sangeetha Rajagopalan, Round Rock, TX (US); Brigitte Brieschke, Austin, TX (US)

(73) Assignee: Molecular Templates, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/345,576

(22) Filed: Jun. 11, 2021

(65) Prior Publication Data

US 2022/0275030 A1 Sep. 1, 2022

Related U.S. Application Data

(63) Continuation of application No. 15/114,487, filed as application No. PCT/US2015/012970 on Jan. 26, 2015, now abandoned.

(60) Provisional application No. 62/049,325, filed on Sep. 11, 2014, provisional application No. 61/932,000, filed on Jan. 27, 2014.

(51) Int. Cl.

| | |
|---|---|
| ***C07K 16/00*** | (2006.01) |
| ***A61K 39/00*** | (2006.01) |
| ***C07K 14/245*** | (2006.01) |
| ***C07K 14/25*** | (2006.01) |
| ***C07K 16/08*** | (2006.01) |
| ***C07K 16/10*** | (2006.01) |
| ***C07K 16/28*** | (2006.01) |
| ***C07K 16/32*** | (2006.01) |
| ***C12N 9/10*** | (2006.01) |
| ***C12N 9/24*** | (2006.01) |
| ***C12N 15/62*** | (2006.01) |

(52) U.S. Cl.

CPC ............ *C07K 14/25* (2013.01); *C07K 14/245* (2013.01); *C07K 16/00* (2013.01); *C07K 16/085* (2013.01); *C07K 16/088* (2013.01); *C07K 16/1063* (2013.01); *C07K 16/286* (2013.01); *C07K 16/2863* (2013.01); *C07K 16/2866* (2013.01); *C07K 16/2887* (2013.01); *C07K 16/32* (2013.01); *C12N 9/1077* (2013.01); *C12N 9/2497* (2013.01); *C12N 15/62* (2013.01); *C12Y 204/02036* (2013.01); *C12Y 302/02022* (2013.01); *A61K 2039/6037* (2013.01); *C07K 2319/04* (2013.01); *C07K 2319/33* (2013.01); *C07K 2319/40* (2013.01); *C07K 2319/55* (2013.01)

(58) Field of Classification Search

None

See application file for complete search history.

(56) References Cited

U.S. PATENT DOCUMENTS

| | | | |
|---|---|---|---|
| 5,080,898 | A | 1/1992 | Murphy |
| 5,135,736 | A | 8/1992 | Anderson et al. |
| 5,552,144 | A | 9/1996 | Samuel et al. |
| 5,635,384 | A | 6/1997 | Walsh et al. |
| 5,668,255 | A | 9/1997 | Murphy |
| 5,858,682 | A | 1/1999 | Gruenwald et al. |
| 6,022,950 | A | 2/2000 | Murphy |
| 6,080,400 | A | 6/2000 | Williams et al. |
| 6,492,498 | B1 | 12/2002 | Vallera et al. |
| 6,652,857 | B2 | 11/2003 | Williams et al. |
| 6,770,456 | B1 | 8/2004 | Coulie et al. |
| 7,144,991 | B2 | 12/2006 | Goshom et al. |
| 7,267,973 | B2 | 9/2007 | Backer et al. |

(Continued)

FOREIGN PATENT DOCUMENTS

| | | | |
|---|---|---|---|
| AU | 750367 | B2 | 7/2002 |
| AU | 2004202331 | A1 | 6/2004 |

(Continued)

OTHER PUBLICATIONS https://www.genome.gov/genetics-glossary/antisense; retrieved on Jul. 17, 2021, 2 pages.

(Continued)

*Primary Examiner* — S. Devi

(74) *Attorney, Agent, or Firm* — COOLEY LLP

(57) ABSTRACT

The present invention relates to Shiga toxin effector polypeptides with reduced antigenic and/or immunogenic potential. Immunogenicity can be a limitation for the repeated administration to mammals of proteins and polypeptides derived from Shiga toxins. The Shiga toxin effector polypeptides of the present invention have uses as components of therapeutics, diagnostics, and immunization materials. The cytotoxic proteins of the present invention have uses for selective killing of specific cell types and as therapeutics for the treatment of a variety of diseases, including cancers, immune disorders, and microbial infections. The proteins of the present invention also have uses for detecting specific cell types, collecting diagnostic information, and monitoring the treatment of a variety of diseases, such as, e.g., cancers, immune disorders, and microbial infections.

14 Claims, 5 Drawing Sheets

Specification includes a Sequence Listing.

(56) References Cited

U.S. PATENT DOCUMENTS

| | | | |
|---|---|---|---|
| 7,527,787 | B2 | 5/2009 | Chang et al. |
| 7,700,557 | B2 | 4/2010 | Backer et al. |
| 7,713,915 | B1 | 5/2010 | Gariepy et al. |
| 7,799,900 | B2 | 9/2010 | Adams |
| 7,834,258 | B2 | 11/2010 | Choe et al. |
| 7,887,801 | B2 | 2/2011 | Wels et al. |
| 8,048,985 | B2 | 11/2011 | Harrison et al. |
| 8,147,832 | B2 | 4/2012 | Carr et al. |
| 8,337,844 | B2 | 12/2012 | Carr et al. |
| 8,470,314 | B2 | 6/2013 | Davis et al. |
| 8,530,637 | B2 | 9/2013 | Wels et al. |
| 8,865,866 | B2 | 10/2014 | Harrison et al. |
| 8,895,006 | B2 | 11/2014 | Tumer et al. |
| 8,969,529 | B2 | 3/2015 | O'Brien et al. |
| 9,175,059 | B2 | 11/2015 | Pieczykolan et al. |
| 9,364,557 | B2 | 6/2016 | Neville, Jr. et al. |
| 10,421,958 | B2 | 9/2019 | Poma et al. |
| 10,815,469 | B2 | 10/2020 | Poma et al. |
| 11,136,395 | B2 | 10/2021 | Poma et al. |
| 11,225,509 | B2 | 1/2022 | Poma et al. |
| 11,312,751 | B2 | 4/2022 | Poma et al. |
| 11,365,223 | B2 * | 6/2022 | Poma ........................ A61P 7/00 |
| 11,389,542 | B1 * | 7/2022 | Poma ..................... A61K 38/04 |
| 11,406,692 | B2 * | 8/2022 | Poma ................. A61K 47/6851 |
| 11,713,347 | B2 * | 8/2023 | Chattopadhyay .... C12N 9/2497 424/134.1 |
| 11,857,628 | B2 | 1/2024 | Poma et al. |
| 2002/0012658 | A1 | 1/2002 | Williams et al. |
| 2002/0168370 | A1 | 11/2002 | McDonald, Jr. et al. |
| 2003/0166196 | A1 | 9/2003 | Better et al. |
| 2004/0141982 | A1 | 7/2004 | Lust et al. |
| 2004/0166565 | A1 | 8/2004 | Backer et al. |
| 2005/0054835 | A1 | 3/2005 | Better et al. |
| 2005/0069545 | A1 | 3/2005 | Carr et al. |
| 2006/0008475 | A1 | 1/2006 | Johannes et al. |
| 2008/0286310 | A1 | 11/2008 | Zhu et al. |
| 2009/0023649 | A1 | 1/2009 | Backer et al. |
| 2009/0092578 | A1 | 4/2009 | Su et al. |
| 2009/0156417 | A1 | 6/2009 | Gariepy et al. |
| 2009/0156502 | A1 | 6/2009 | Harrison et al. |
| 2009/0214533 | A1 | 8/2009 | Clynes |
| 2010/0093563 | A1 | 4/2010 | Williamson et al. |
| 2010/0285004 | A1 | 11/2010 | Tesar et al. |
| 2011/0189209 | A1 | 8/2011 | Neville, Jr. et al. |
| 2012/0039908 | A1 | 2/2012 | Combs et al. |
| 2012/0149650 | A1 | 6/2012 | Harrison et al. |
| 2012/0213781 | A1 | 8/2012 | Hilbert |
| 2012/0251542 | A1 | 10/2012 | Tumer et al. |
| 2012/0258104 | A1 | 10/2012 | Echeverri |
| 2013/0071325 | A1 | 3/2013 | Sahin et al. |
| 2013/0189271 | A1 | 7/2013 | De Goeij et al. |
| 2013/0196928 | A1 | 8/2013 | Gariepy et al. |
| 2013/0202598 | A1 | 8/2013 | Benhar et al. |
| 2014/0030273 | A1 | 1/2014 | Verploegen et al. |
| 2015/0044210 | A1 | 2/2015 | Mechaly et al. |
| 2015/0259428 | A1 | 9/2015 | Poma et al. |
| 2016/0017047 | A1 | 1/2016 | Poma et al. |
| 2016/0017784 | A1 | 1/2016 | Kumar |
| 2016/0068577 | A1 | 1/2016 | Poma et al. |
| 2016/0130362 | A1 | 5/2016 | de Weers |
| 2016/0177284 | A1 | 6/2016 | Poma et al. |
| 2016/0340394 | A1 | 11/2016 | Poma et al. |
| 2016/0347798 | A1 | 12/2016 | Poma et al. |
| 2016/0376328 | A1 | 12/2016 | Poma et al. |
| 2017/0002046 | A1 | 1/2017 | Shishido et al. |
| 2017/0143814 | A1 | 5/2017 | Poma et al. |
| 2017/0275382 | A1 | 9/2017 | Poma et al. |
| 2018/0057544 | A1 | 3/2018 | Poma et al. |
| 2018/0243432 | A1 | 8/2018 | Poma et al. |
| 2018/0258143 | A1 | 9/2018 | Poma et al. |
| 2018/0258144 | A1 | 9/2018 | Poma et al. |
| 2018/0291359 | A1 | 10/2018 | Poma et al. |
| 2019/0083644 | A1 | 3/2019 | Yoo et al. |
| 2019/0100597 | A1 | 4/2019 | Keyt et al. |
| 2019/0153044 | A1 | 5/2019 | Poma et al. |
| 2019/0153471 | A1 | 5/2019 | Paul et al. |
| 2019/0249145 | A1 | 8/2019 | Jang et al. |
| 2019/0382755 | A1 | 12/2019 | Poma et al. |
| 2020/0002387 | A1 | 1/2020 | Poma et al. |
| 2020/0024312 | A1 | 1/2020 | Poma et al. |
| 2020/0231650 | A1 * | 7/2020 | Chattopadhyay .... C12N 9/2497 |
| 2021/0008208 | A1 | 1/2021 | Poma et al. |
| 2021/0017512 | A1 | 1/2021 | Poma et al. |
| 2021/0040160 | A1 | 2/2021 | Poma et al. |
| 2021/0079098 | A1 | 3/2021 | Poma et al. |
| 2021/0253648 | A1 | 8/2021 | Poma et al. |
| 2021/0253649 | A1 | 8/2021 | Poma et al. |
| 2021/0268085 | A1 | 9/2021 | Poma et al. |
| 2022/0152213 | A1 | 5/2022 | Poma et al. |
| 2022/0267384 | A1 | 8/2022 | Poma et al. |
| 2022/0281926 | A1 * | 9/2022 | Poma ........................ A61P 7/00 |
| 2022/0306700 | A1 | 9/2022 | Poma et al. |
| 2022/0306701 | A1 | 9/2022 | Poma et al. |
| 2022/0354938 | A1 | 11/2022 | Poma et al. |
| 2022/0401568 | A1 | 12/2022 | Poma et al. |

FOREIGN PATENT DOCUMENTS

| | | | |
|---|---|---|---|
| CN | 1272882 | A | 11/2000 |
| CN | 101384614 | A | 3/2009 |
| CN | 101622352 | A | 1/2010 |
| CN | 101629158 | A | 1/2010 |
| CN | 102257000 | A | 11/2011 |
| CN | 103501818 | A | 1/2014 |
| CN | 103648525 | A | 3/2014 |
| CN | 105713087 | A | 6/2016 |
| EP | 1 654 287 | A2 | 8/2010 |
| EP | 2 778 173 | A1 | 9/2014 |
| EP | 3 265 575 | A2 | 1/2018 |
| EP | 3 448 874 | A1 | 3/2019 |
| GB | 2 456 904 | B | 10/2009 |
| GB | 2 519 786 | A | 5/2015 |
| JP | 1993-502880 | A | 5/1993 |
| JP | 2001-500730 | A | 1/2001 |
| JP | 2002-521019 | A | 7/2002 |
| JP | 2002-544173 | A | 12/2002 |
| JP | 2003-531588 | A | 10/2003 |
| JP | 2004-536778 | A | 12/2004 |
| JP | 2006-502699 | A | 1/2006 |
| JP | 2006-513691 | A | 4/2006 |
| JP | 2007-536905 | A | 12/2007 |
| JP | 2008-533977 | A | 8/2008 |
| JP | 2009-502936 | A | 1/2009 |
| JP | 2009-530468 | A | 8/2009 |
| JP | 2011-050388 | A | 3/2011 |
| JP | 2011-507389 | A | 3/2011 |
| JP | 2012-044997 | A | 3/2012 |
| JP | 2012-070737 | A | 4/2012 |
| JP | 2012-515551 | A | 7/2012 |
| JP | 2014-515921 | A | 7/2014 |
| KR | 2011-0033233 | A | 3/2011 |
| KR | 2011-0119725 | A | 11/2011 |
| TW | 201235469 | A | 9/2012 |
| WO | WO 91/009871 | A1 | 7/1991 |
| WO | WO 94/26910 | A1 | 11/1994 |
| WO | WO 96/30043 | A1 | 10/1996 |
| WO | WO 96/040200 | A1 | 12/1996 |
| WO | WO 98/11229 | A3 | 3/1998 |
| WO | WO 99/40185 | A1 | 8/1999 |
| WO | WO 00/04926 | A2 | 2/2000 |
| WO | WO 00/55207 | A1 | 9/2000 |
| WO | WO 00/67795 | A1 | 11/2000 |
| WO | WO 01/70945 | A1 | 9/2001 |
| WO | WO 01/77342 | A1 | 10/2001 |
| WO | WO 02/40506 | A2 | 5/2002 |
| WO | WO 03/066854 | A1 | 8/2003 |
| WO | WO 03/072746 | A2 | 9/2003 |
| WO | WO 03/074567 | A2 | 9/2003 |
| WO | WO 2004/056312 | A2 | 7/2004 |
| WO | WO 2004/058158 | A2 | 7/2004 |
| WO | WO 2005/000902 | A1 | 1/2005 |
| WO | WO 2005/016969 | A2 | 2/2005 |
| WO | WO 2005/017148 | A1 | 2/2005 |
| WO | WO 2005/052006 | A2 | 6/2005 |

(56) References Cited

FOREIGN PATENT DOCUMENTS

| | | | |
|---|---|---|---|
| WO | WO 2005/052129 | A2 | 6/2005 |
| WO | WO 2005/092917 | A1 | 10/2005 |
| WO | WO 2006/047517 | A2 | 5/2006 |
| WO | WO 2006/099875 | A1 | 9/2006 |
| WO | WO 2007/005874 | A2 | 1/2007 |
| WO | WO 2007/014238 | A2 | 2/2007 |
| WO | WO 2007/033497 | A1 | 3/2007 |
| WO | WO 2007/071061 | A1 | 6/2007 |
| WO | WO 2007/098201 | A2 | 8/2007 |
| WO | WO 2007/107779 | A1 | 9/2007 |
| WO | WO 2008/080218 | A1 | 7/2008 |
| WO | WO 2008/097817 | A2 | 8/2008 |
| WO | WO 2009/014835 | A2 | 1/2009 |
| WO | WO 2009/017823 | A2 | 2/2009 |
| WO | WO 2009/032954 | A1 | 3/2009 |
| WO | WO 2009/064815 | A1 | 5/2009 |
| WO | WO 2009/088403 | A2 | 7/2009 |
| WO | WO 2009/110944 | A1 | 9/2009 |
| WO | WO 2010/011697 | A1 | 1/2010 |
| WO | WO 2010/085539 | A1 | 7/2010 |
| WO | WO 2011/009624 | A1 | 1/2011 |
| WO | WO 2012/022985 | A1 | 2/2012 |
| WO | WO 2012/093158 | A1 | 7/2012 |
| WO | WO 2012/101235 | A1 | 8/2012 |
| WO | WO 2012/104344 | A1 | 8/2012 |
| WO | WO 2012/154530 | A1 | 11/2012 |
| WO | WO 2012/162418 | A1 | 11/2012 |
| WO | WO 2013/080147 | A2 | 6/2013 |
| WO | WO 2014/086952 | A1 | 6/2014 |
| WO | WO 2014/164680 | A1 | 10/2014 |
| WO | WO 2014/164693 | A2 | 10/2014 |
| WO | WO 2015/063187 | A1 | 5/2015 |
| WO | WO 2015/113005 | A1 | 7/2015 |
| WO | WO 2015/113007 | A1 | 7/2015 |
| WO | WO 2015/120058 | A2 | 8/2015 |
| WO | WO 2015/138435 | A1 | 9/2015 |
| WO | WO 2015/138452 | A1 | 9/2015 |
| WO | WO 2015/191764 | A1 | 12/2015 |
| WO | WO 2015/191883 | A1 | 12/2015 |
| WO | WO 2015/193411 | A1 | 12/2015 |
| WO | WO 2016/126950 | A1 | 8/2016 |
| WO | WO 2016/196344 | A1 | 12/2016 |
| WO | WO 2017/019623 | A2 | 2/2017 |
| WO | WO 2018/080812 | A1 | 5/2018 |
| WO | WO 2018/106895 | A1 | 6/2018 |
| WO | WO 2018/140427 | A1 | 8/2018 |
| WO | WO 2018/159615 | A1 | 9/2018 |
| WO | WO 2018/162749 | A1 | 9/2018 |
| WO | WO 2019/059400 | A1 | 3/2019 |
| WO | WO 2020/081493 | A1 | 4/2020 |
| WO | WO 2020/154475 | A1 | 7/2020 |

OTHER PUBLICATIONS

Muzard, J. et al., “Grafting of protein L-binding activity onto recombinant antibody fragments,” Analytical Biochemistry, 388(2):331-338 (2009).

Nilson, B. H. K. et al., “Protein L from Peptostreptococcus magnus binds to the kappa light chain variable domain,” Journal of Biological Chemistry, 267(4):2234-2239 (1992).

Nilson, B. H. K. et al., “Purification of antibodies using protein L-binding framework structures in the light chain variable domain,” Journal of Immunological Methods, 164(1):33-40 (1993).

Amino Acids; https://www.promega.com/-/media/files/resources/technical-references/amino-acid-abbreviations-and-molecular-weights.pdf; retrieved on Feb. 26, 2018, 1 page.

UniProtKB/Swiss-Prot P09385 (STXA_BP933), Shiga-like toxin 2 subunit A, retrieved from https://www.ncbi.nlm.nih.gov/protein/P09385.2 on Jan. 10, 2018, 7 pages.

Aatsinki, J. T. et al., “An alternative use of basic pGEX vectors for producing both N- and C-terminal fusion proteins for production and affinity purification of antibodies,” Protein Expression and Purification, 40(2):287-291 (2005).

Ackerman, R. et al., “SLT-VEGF Reduces Lung Metastases, Decreases Tumor Recurrence, and Improves Survival in an Orthotropic Melanoma Model,” Toxins (Basel), 2(9):224-257 (2010).

Adotevi, O. et al., “B Subunit of Shiga Toxin-Based Vaccines Synergize with α-Galactosylceramide to Break Tolerance against Self Antigen and Elicit Antiviral Immunity,” The Journal of Immunology, 179(5):3371-3379 (2007).

Al-Jaufy, A. Y. et al., “Cytotoxicity of a Shiga toxin A Subunit-CD4 Fusion Protein to Human Immunodeficiency Virus-Infected Cells,” Infection and Immunity, 62(3):956-960 (1994).

Al-Jaufy, A. Y. et al., “Purification and Characterization of a Shiga-Toxin A Subunit-CD4 Fusion Protein Cytotoxic to Human Immunodeficiency Virus-Infected Cells,” Infection and Immunity, 63(8):3073-3078 (1995).

Antignani, A. & Fitzgerald, D., “Immunotoxins: The Role of the Toxin,” Toxins, 5(8):1486-1502 (2013).

Apostolpoulos, V. et al., “MUC1 peptide epitopes associated with five different H-2 class I molecules,” European Journal of Immunology, 27(10):2579-2587 (1997).

Backer, M. V. et al., “Shiga-like toxin-VEGF fusion proteins are selectively cytotoxic to endothelial cells overexpressing VEGFR-2,” Journal of Controlled Release, 74(1-3):349-355 (2001).

Backer, M. V. & Backer, J. M., “Targeting Endothelial Cells Overexpressing VEGFR-2: Selective Toxicity of Shiga-like Toxin-VEGF Fusion Proteins,” Bioconjugate Chemistry, 12(6):1066-1073 (2001).

Baker, M. P. et al., “Immunogenicity of Protein Therapeutics: the Key Causes, Consequences and Challenges,” Self/Nonself, 1(4):314-322 (2010).

Ballard, J. D. et al., “Anthrax Toxin-Mediated Delivery In Vivo and In Vitro of a Cytotoxic T-Lymphocyte Epitope from Ovalbumin,” Infection and Immunity, 66(2):615-619 (1998).

Ballard, J. D. et al., “Anthrax Toxin as a Molecular Tool for Stimulation of Cytotoxic T Lymphocytes: Disulfide-Linked Epitopes, Multiple Injections, and Role of CD4+ Cells,” Infection and Immunity, 66(10):4696-4699 (1998).

Barnd, D. L. et al., “Specific, Major Histocompatibility Complex-Unrestricted Recognition of Tumor-Associated Mucins by Human Cytotoxic T cells,” Proceedings of the National Academy of Sciences U.S.A., 86(18):7159-7163 (1989).

Barratt-Boyes, S. M. et al., “Immunization of Chimpanzees with Tumor Antigen MUC1 Mucin Tandem Repeat Peptide Elicits Both Helper and Cytotoxic T-cell Responses,” Clinical Cancer Research, 5(7):1918-1924 (1999).

Beers, S. A. et al., “Type II (tositumomab) anti-CD20 monoclonal antibody out performs type I (rituximab-like) reagents in B-cell depletion regardless of complement activation,” Blood, 112:4170-4177 (2008).

Beers, S. A. et al., “CD20 as a Target for Therapeutic type I and II Monoclonal Antibodies,” Seminars in Hematology, 47(2):107-114 (2010).

Beers, S. A. et al., “Antigenic modulation limits the efficacy of anti-CD20 antibodies: implications for antibody selection,” Blood, 1115(25):5191-5201 (2010).

Bera, T. K. et al., “A Bivalent Disulfide-stabilized Fv with Improved Antigen Binding to erbB2,” Journal of Molecular Biology, 281(3):475-483 (1998).

Bera, T. K. et al., “Pharmacokinetics and Antitumor Activity of a Bivalent Disulfide-stabilized Fv Immunotoxin with Improved Antigen Binding to erbB2,” Cancer Research, 59(16):4018-4022 (1999).

Beum, P. V. et al., “The Shaving Reaction: Rituximab/CD20 Complexes Are Removed from Mantle Cell Lymphoma and Chronic Lymphocytic Leukemia Cells by THP-1 Monocytes,” The Journal of Immunology, 176(4):2600-2609 (2006).

Beum, P. V. et al., “Loss of CD20 and Bound CD20 Antibody from Opsonized B Cells Occurs More Rapidly Because of Trogocytosis Mediated by Fc Receptor-Expressing Effector Cells than Direct Internalization by the B Cells,” The Journal of Immunology, 187(6):3438-3447 (2011).

Bevan et al. “Real-time 96-well antibody internalization assays using IncuCyte FabFlour Red Antibody Labeling Reagent, Application Note, Sartorious”, Essen BioScience (2017).

(56) References Cited

OTHER PUBLICATIONS

Bibby, M. C., "Orthotopic models of cancer for preclinical drug evaluation: advantages and disadvantages," European Journal of Cancer, 40(6):852-857 (2004).
Boes, A. et al., "Affinity Purification of a Framework 1 Engineered Mouse/Human Chimeric IgA2 Antibody From Tobacco," Biotechnology Bioengineering, 108(12):2804-2814 (2011).
Böldicke, T., "Blocking translocation of cell surface molecules from the ER to the cell surface by intracellular antibodies targeted to the ER," J. Cell. Mol., 11(1):54-70 (2007).
Bolognesi, A. et al., "A comparison of anti-lymphocyte immunotoxins containing different ribosome-inactivating proteins and antibodies," Clinical & Experimental Immunology, 89(3):341-346 (1992).
Bonifaz, L. et al., "Efficient targeting of protein antigen to the dendritic cell receptor DEC-205 in the steady state leads to antigen presentation on major histocompatibility complex class I products and peripheral CD8+ T cell tolerance," Journal of Experimental Medicine, 196(12):1627-1638 (2002).
Boross, P. et al., "Both activating and inhibitory Fc gamma receptors mediate rituximab-induced trogocytosis of CD20 in mice," Immunology Letters, 143(1):44-52 (2012).
Boross, P. et al., "Mechanisms of action of CD20 antibodies," American Journal of Cancer Research, 2(6):676-690 (2012).
Braslawsky, G. R. et al., "Adriamycin(hydrazone)-antibody conjugates require internalization and intracellular acid hydrolysis for antitumor activity," Cancer Immunology, Immunotherapy, 33:367-374 (1991).
Bray, M. R. et al., "Probing the surface of eukaryotic cells using combinatorial toxin libraries," Current Biology, 11(9):697-701 (2001).
Brieschke, B. et al., "Targeted Engineered Toxin Bodies provide a novel mechanism of action against HER2 positive cancers," Cancer Research, 78 (13 Suppl), (Jul. 2018), Abstract 5769.
Brieschke, B. et al., "Targeted Engineered Toxin Bodies provide a novel mechanism of action against HER2 positive cancers," Proceedings: American Association for Cancer Research (AACR) Annual Meeting 2018, (Apr. 18, 2018).
Brieschke, B. et al., "Identification and Functional Profiling of PD-L1 Targeted Engineered Toxin Bodies for Antigen Seeding Technology (AST) and Redirection of T cell Response to Tumors," 33rd Annual Meeting of the Society for Immunotherapy of Cancer (SITC), Washington, D.C., Poster # 11078, (Nov. 7-11, 2018).
Brieschke, B. et al., "Identification and functional profiling of PD-L1 targeted engineered toxin bodies for antigen seeding technology and redirection of T cell response to tumors," Journal of Immuno Therapy of Cancer, 6(Suppl 1): 114, (Nov. 6, 2018), Abstract P9.
Brieschke, B. et al., "Identification and functional profiling of PD-L1 targeted engineered toxin bodies for antigen seeding technology and redirection of T cell response to tumors," Journal for Immunotherapy of Cancer, 6(S1):p. 5 (2018).
Brieschke, B. et al., "Antigen Seeding Technology by engineered Toxin bodies Provides a Targeted Immuno-Oncology Approach for Treatment of Cancers," Proceedings: American Association for Cancer Research (AACR) Annual Meeting 2018, Poster 2777, Abstract #4912 (Apr. 14-18, 2018).
Brigotti, M. et al., "Damage to Nuclear DNA Induced by Shiga Toxin 1 and Ricin in Human Endothelial Cells," The FASEB Journal, 16(3):365-372 (2002).
Brigotti, M. et al., "Change in Conformation with Reduction of a-Helix Content Causes Loss of Neutrophil Binding Activity in Fully Cytotoxic Shiga toxin 1," The Journal of Biological Chemistry, 286(40):34514-34521 (2011).
Bujny, M. V. et al., "The retromer component sorting nexin-1 is required for efficient retrograde transport of Shiga toxin from early endosome to the trans Golgi network," Journal of Cell Science, 120(Pt 12):2010-2021 (2007).
Burgess, B. J. et al., "Proteolytic cleavage at arginine residues within the hydrophilic disulphide loop of the *Escherichia coli* Shiga-like toxin I A subunit is not essential for cytotoxicity," Molecular Microbiology, 10(1):171-179 (1993).
Cao, C. et al., "Construction of mutant genes for a non-toxic verotoxin 2 variant (VT2vp1) of *Escherichia coli* and characterization of purified mutant toxins," Microbiology and Immunology, 38(6):441-447 (1994).
Cao, Y. et al., "Design optimization and characterization of Her2/neu-targeted immunotoxins: comparative in vitro and in vivo efficacy studies," Oncogene, 33(4):1-11 (2013).
Cao, Y. et al., "Construction and characterization of novel, recombinant immunotoxins targeting the Her2/neu oncogene product: in vitro and in vivo studies," Cancer Research, 69(23): 8987-8995 (2009).
Carbonetti, N. H. et al., "Intracellular Delivery of a Cytolytic T-Lymphocyte Epitope Peptide by Pertussis Toxin to Major Histocompatibility Complex Class I without Involvement of the Cytosolic Class I Antigen Processing Pathway," Infection and Immunity, 67(2):602-607 (1999).
Carbonetti, N. H. et al., "Stimulation of HIV gp120-specific cytolytic T lymphocyte responses in vitro and in vivo using a detoxified pertussis toxin vector," AIDS Research and Human Retroviruses, 17(9):819-827 (2001).
Carbonetti, N. H., "Pertussis toxin and adenylate cyclase toxin: key virulence factors of Bordetella pertussis and cell biology tools," Future Microbiology, 5:455-469 (2010).
Casalini, P. et al., "Use of combination of Monoclonal Antibodies Directed Against three distinct epitopes of a Tumor-Associated Antigen: Analysis of Cell-Binding and Internalization," International Journal of Cancer, 48:2 284-290 (1991).
Casset, F. et al., "A peptide mimetic of an anti-CD4 monoclonal antibody by rational design," Biochemical and Biophysical Research Communications, 307(1):198-205 (2003).
Chatterjee, S. et al., "Noninvasive Imaging of Immune Checkpoint Ligand PD-L1 in Tumors and Metastases for Guiding Immunotherapy," Molecular Imaging, 16:1-5 (2017).
Cheung, M. C. et al., "An evolved ribo-inactivating protein targets and kills human melanoma cells in vitro and in vivo," Molecular Cancer, 9(28):1-14 (2010).
Cheung, M. C. et al., "A Ribosome-inactivating Protein Toxin as a Template for Cancer Drug Discovery", thesis, University of Toronto, (2012), retrieved from http://hdl.handle.net/1807/33952, 202 pages.
Cizeau, J. P. A. et al., "DeBouganin: A de-immunized toxin payload and its applications in oncology," 8th Fabisch—Symposium, 3rd Targeted Tumor Therapies, Berlin 2012, Mar. 21, 2012.
Cizeau, J. et al., "Fusogenics: A Recombinant Immunotoxin-Based Screening Platform to Select Internalizing Tumor-Specific Antibody Fragments," Journal of Biomolecular Screening 16(1):90-100 (2011).
Cleton-Jansen, A. et al., "A Single Amino Acid Substitution Changes the Substrate Specificity of Quinoprotein Glucose Dehydrogenase in Gluconobacter oxydans," Molecular and General Genetics, 229(2):206-212 (1991).
Cragg, M. S. et al., "Apparent modulation of CD20 by rituximab: an alternative explanation," Blood, 103(10):3889-3990 (2004).
Cuesta, A. M. et al., "Mutivalent antibodies: when design surpasses evolution," Trends in Biotechnology, 28(7):355-362 (2010).
Dadaglio, G, et al., "Induction of a Polarized Th1 Response by Insertion of Multiple Copies of a Viral T-Cell Epitope into Adenylate Cyclase of Bordetella pertussis," Infection and Immunity, 68(7):3867-3872 (2000).
Dadaglio, G, et al., "Recombinant adenylate cyclase toxin of Bordetella pertussis induces cytotoxic T lymphocyte responses against HLA*0201-restricted melanoma epitopes," International Immunology, 15(12):1423-1430 (2003).
De Pascalis, R. et al., "Grafting of "abbreviated" complementarity-determining regions containing specificity-determining residues essential for ligand contact to engineer a less immunogenic humanized monoclonal antibody," The Journal of Immunology, 169(6):3076-3084 (2002).
Dekker et al., "Engineered Toxin Bodies delivering immunogenic MHC class I peptides to tumor cells summon polyfunctional and relevant CTL responses against cancers," Presented at: Immunology 2019™, Annual Meeting of the American Association of Immunologists, May 10, 2019, The American Association of Immunologists, Inc., San Diego, Abstract 1791.

(56) References Cited

OTHER PUBLICATIONS

Dekker, J. D. et al., Abstract 1791, "Engineered toxin bodies delivering immunogenic MHC class I peptides to tumor cells summon polyfunctional and relevant CTL responses against cancers," Molecular Templates, AAI 2019, Poster, 2 pages.
Deresiewicz, R. L. et al., "Mutations Affecting the Activity of the Shiga-like Toxin I A-Chain," Biochemistry, 31(12):3272-3280 (1992).
Deresiewicz, R. L. et al., "The role of tyrosine-114 in the enzymatic activity of the Shiga-like toxin I A-chain," Mol. Gen. Genet., 241:467-473 (1993).
Déret, S. et al., "SUBIM: a program for analysing the Kabat database and determining the variability subgroup of a new immunoglobulin sequence," CABIOS, 11(4):435-439 (1995).
Dermer, G. B., "Another Anniversary for the War on Cancer," Bio/Technology 12:320 (1994).
Di, R. et al., "Identification of amino acids critical for the cytotoxicity of Shiga toxin 1 and 2 in *Saccharomyces cerevisiae*," Toxicon, 57(4):525-539 (2011).
Doling, A. M. et al., "Cytotoxic T-Lymphocyte Epitopes Fused to Anthrax toxin Induce protective Antiviral Immunity," Infection and Immunity, 67(7):3290-3296 (1999).
Donnelly, J. J. et al., "Targeted delivery of peptide epitopes to class I major histocompatibility molecules by a modified Pseudomonas exotoxin," Proceedings of the National Academy of Sciences U.S. A., 90:3530-3534 (1993).
Edelman, G. M. & Gally, J. A., "Degeneracy and complexity in biological systems," PNAS, 98(24):13763-13768 (2001).
Engedal, N. et al., "Shiga toxin and its use in targeted cancer therapy and imaging," Microbiology Biotechnology, 4(1):32-46 (2011).
Eriksson, K. et al., "Coupling of antigen to cholera toxin for dendritic cell vaccination promotes the induction of MHC class I-restricted cytotoxic T cells and the rejection of a cognate antigen-expressing model tumor," European Journal of Immunology, 34(5):1272-1281 (2004).
Ewers, H. & Helenius, A., "Lipid-Mediated Endocytosis," Cold Spring Harbor Perspectives in Biology, 3(8):1-14 (2011).
Fanale, M. A. et al., "Phase I/Ib study of the novel CD20-targeted immunotoxin MT-3724 in relapsed/refractory non-Hodgkin's B-cell lymphoma," Proceedings of the 107th Annual Meeting of the American Association for Cancer Research (AACR), Abstract # CT049, (Apr. 16-20, 2016), 2 pages.
Fanale, M. A. et al., "Phase I/Ib study of the novel CD20-targeted immunotoxin MT-3724 in relapsed/refractory non-Hodgkin's B-cell lymphoma," Cancer Research, 76(14 Suppl), (Jul. 2016), Abstract nr CT049.
Fayolle, C. et al., "Delivery of Multiple Epitopes by Recombinant Detoxified Adenylate Cyclase of Bordetella pertussis Induces Protective Antiviral Immunity," Journal of Virology, 75(16):7330-7338 (2001).
Fayolle, C, et al., "Therapy of Murine Tumors with Recombinant Bordetella pertussis Adenylate Cyclase Carrying a Cytotoxic T Cell Epitope," The Journal of Immunology, 162(7):4157-4162 (1999).
Filpula, D., "Releasable PEGylation of Mesothelin Targeted Immunotoxin SSIP Achieves Single Dosage Complete Regression of a Human Carcinoma in Mice," Bioconjugate Chemistry, 18(3):773-784 (2007).
Freshney, R.I., "Culture of Animal Cells: A Manual of Basic Technique," Alan R. Liss, Inc., 1983, New York, pp. 3-4.
Gannon, V. P. et al., "Molecular cloning and nucleotide sequence of another variant of the *Escherichia coli* Shiga-like toxin II family," Journal of General Microbiology, 136(6):1125-1135 (1990).
Garred, O. et al., "Role of processing and intracellular transport for optimal toxicity of Shiga toxin and toxin mutants," Experimental Cell Research, 218(1):39-49 (1995).
Garred, O. et al., "Furin-induced cleavage and activation of Shiga toxin," Journal of Biological Chemistry, 270(18):10817-10821 (1995).
Gavrilov, B. K. et al., "Effects of Glycosylation on Antigenicity and Immunogenicity of Classical Swine Fever Virus Envelope Proteins," Virology, 420(2):135-145 (2011).
Gendler, S. et al., "A Highly Immunogenic Region of a Human Polymorphic Epithelial Mucin Expressed by Carcinomas Is Made Up of Tandem Repeats," Journal of Biological Chemistry, 263(26):12820-12823 (1988).
Ghetie, M. A. et al., "Homodimers but not monomers of Rituxan (chimeric anti-CD20) induce apoptosis in human B-lymphoma cells and synergize with a chemotherapeutic agent and an immunotoxin," Blood, 97(5):1392-1398 (2001).
Giansanti, F. et al., "Strategies to Improve the Clinical Utility of Saporin-Based Targeted Toxins," Toxins, 10(82):1-32 (2018).
Gielis, S. et al., "Detection of Enriched T Cell Epitope Specificity in Full T Cell Receptor Sequence Repertoires," Frontiers in Immunology, vol. 10, Article 2820, pp. 1-13 (2019).
Gilliland, D. G. et al., "Antibody-directed cytotoxic agents: use of monoclonal antibody to direct the action of toxin A chains to colorectal carcinoma cells," Proceedings of the National Academy of Sciences of the United States of America, 77(8):4539-43 (1980).
Glennie, M. J. et al., "Mechanisms of killing by anti-CD20 monoclonal antibodies," Molecular Immunology, 44(16):3823-3837 (2007).
Gong, J. et al., "Selection and characterization of MUC1-specific CD8+ T cells from MUC1 transgenic mice immunized with dendritic-carcinoma fusion cells," Immunology, 101(3):316-324 (2000).
Gordon, V. M. et al., "An enzymatic Mutant of Shiga-like Toxin II Variant is a vaccine Candidate for Edema Disease of Swine," Infection and Immunity, 60(2):485-490 (1992).
Goulet, A. C. et al., "Conjugation of Blocked Ricin to an Anti-CD19 Monoclonal Antibody Increases Antibody-Induced cell Calcium Mobilization and CD 19 Internalization," Blood 90(6): 2364-2375 (1995).
Grant, K. et al., "Abstract 1380: Engineered toxin bodies with specific activity against EGFR and HER2 expressing cells," Proceedings of the 102nd Annual Meeting of the American Association for Cancer Research (AACR); Apr. 2-6, 2011; The Journal of Cancer Research, 71 (8 Suppl): Abstract #1380, (Apr. 2011).
Grotzke, J. E. et al., "The ongoing saga of the mechanism(s) of MHC class I-restricted cross-presentation," Current Opinion in Immunology, 46:89-96 (2017).
Guermonprez, P. et al., "Les Toxines Bacteriennes Recombinantes: De Nouveaux Vecteurs Pour La Vaccination?" M/S Medicine Sciences, Societe Des Periodiques Flammarion, 16(5):653-662 (2000).
Guermonprez, P. et al., "The Adenylate Cyclase Toxin of *Bordetella pertussis* Binds to Target Cells via the aMB2 Integrin (CD11b/CD18)," Journal of Experimental Medicine, 193(9):1035-1044 (2001).
Güssow, D. & Seeman, G., "Humanization of Monoclonal Antibodies," Methods in Enzymology, 203:99-121 (1991).
Haddad, J. E. et al., "Minimum Domain of the Shiga Toxin A subunit Required for Enzymatic Activity," Journal of Bacteriology, 175(16):4970-4978 (1993).
Haicheur, N. et al., "The B Subunit of Shiga Toxin Fused to a Tumor Antigen Elicits CTL and Targets Dendritic Cells to Allow MHC Class I-Restricted Presentation of Peptides Derived from Exogenous Antigens," The Journal of Immunology, 165(6):3301-3308 (2000).
Haisma, H. J. et al., "Construction and Characterization of a Fusion Protein Single-Chain Anti-CD20 Antibody and Human beta-glucuronidase for Antibody-Directed Enzyme Prodrug Therapy," Blood, 92(1):184-190 (1998).
Hamlin, P. A. et al., "Safety and Efficacy of Anti-CD20 Immunotoxin MT-3724 in Relapsed/refractory B-cell Non-Hodgkin Lymphoma (NHL) in a Phase 1 study," American Society of Clinical Oncology Annual Meeting—Abstract 7580 (2018).
Harris, B., "Exploiting antibody-based technologies to manage environmental pollution," Trends in Biotechnology, Diagram figure taken from 17(7):290-296 (1999).
Harwerth, I. M. et al., Monoclonal Antibodies against the Extracellular Domain of the erbB-2 Receptor Function as Partial Ligand Agonists, Journal of Biol. Chem, 267(21):15160-15167 (1992).
Head, S. C. et al., "Preparation of VT1 and VT2 hybrid toxins from their purified dissociated subunits. Evidence for B subunit modulation of a subunit function," Journal of Biological Chemistry, 266(6):3617-3621 (1991).

(56) References Cited

OTHER PUBLICATIONS

Hegde, N. R. et al., "The use of databases, data mining and immunoinformatics in vaccinology: where are we?" Expert Opinion on Drug Discovery, 13(2):117-130 (2018).
Hexham, J. M. et al., "Influence of relative binding affinity on efficacy in a panel of anti-CD3 scFv immunotoxins," Molecular Immunology, 38(5):397-408 (2001).
Higgins, J. P. et al., "Engineered toxin bodies with specific cell kill activity against mesenchymal cells," Cancer Research, 71(8 Suppl) (Apr. 2011), Abstract #1751.
Hiraga, J. et al., "Down-regulation of CD20 expression in B-cell lymphoma cells after treatment with rituximab-containing combination chemotherapies: its prevalence and clinical significance," Blood, 113(20):4885-4893 (2009).
Holubova, J. et al., "Delivery of Large Heterologous Polypeptides across the Cytoplasmic Membrane of Antigen-Presenting Cells by the Bordetella RTX Hemolysin Moiety Lacking the Adenylyl Cyclase Domain," Infection and Immunity, 80(3):1181-1192 (2012).
Hooijberg et al., "Characterization of a series of isotype switch variants of new CD20 monoclonal antibody," Hybridoma, 15(1):23-31 (1996).
Hotz, B. et al., "Specific Targeting of Tumor Endothelial Cells by a Shiga-like Toxin-Vascular Endothelial Growth Factor Fusion Protein as a Novel Treatment Strategy for Pancreatic Cancer," Neoplasia, 12(10):797-806 (2010).
Hovde, C. J. et al., "Evidence that glutamic acid 167 is an active-site residue of Shiga-like toxin-I," Proceedings of the National Academy of Sciences of the United States of America, 85(8):2568-2572 (1988).
Huang, S. et al., "The CD20-specific engineered toxin antibody MT-3724 exhibits lethal effects against mantle cell lymphoma," Blood Cancer Journal, 8(3):33 (2018).
Huang, S. et al. "Abstract 3651: Preclinical examination of the effects of MT-3724, an engineered toxin body targeting CD20, in mantle cell lymphoma," AACR Annual Meeting Abstract (2017).
Huang, S. et al. "AACR 2017 | Poster 3651/24—Preclinical examination of the effects of a CD20-specific engineered toxin body, MT-3724, in Mantle Cell Lymphoma," AACR Annual Meeting, Poster 3651/24 (2017).
Iberg, A. et al., "Design and Characterization of Bispecific Engineered Toxin Bodies for Targeted Cancer Therapy," Proceedings: American Association for Cancer Research (AACR) Annual Meeting 2019, Poster #2984 (2019).
Ishikawa, S. et al., "Protection against Shiga Toxin I Challenge by Immunization of Mice with Purified Mutant Shiga Toxin 1," Infection and Immunity, 71(6):3235-3239 (2003).
Jackson, R. L. et al., "Mutational analysis of the Shiga Toxin and Shiga-like toxin II enzymatic subunits," Journal of Bacteriology, 172(6):3346-3350 (1990).
Jackson, M. E. et al., "The KDEL retrieval system is exploited by Pseudomonas exotoxin A, but not by Shiga-like toxin-1, during retrograde transport from the Golgi complex to the endoplasmic reticulum," Journal of Cell Science, 112(4):467-475 (1999).
Jain, R. K., "Barriers to Drug Delivery in Solid Tumors," Scientific American, 271(1):58-65 (1994).
Jilani, I. et al., "Anti-Idiotype versus anti-mouse Ig for detecting ritumixab," Blood, 103(10):3990 (2004).
Jilani, I. et al., "Transient down-modulation of CD20 by ritumixab in patients with chronic lymphocytic leukemia," Blood , 102(10):3514-3520 (2003).
Johannes, L. et al., "Retrograde Transport of KDEL-bearing B-fragment of Shiga Toxin," Journal of Biological Chemistry, 272(31):19554-19561 (1997).
Johannes, L. et al., "Shiga toxins—from cell biology to biomedical applications," Nature Reviews Microbiology, 8(2):105-116 (2010).
Johannes, L. & Decaudin, D., "Protein toxins: intracellular trafficking for targeted therapy," Gene Therapy, 12(18):1360-1368 (2005).
Johnson, N. et al., "Construction of an epitope vector utilizing the diphtheria toxin B-subunit," FEMS Microbiology Letters, 146(1):91-96 (1997).
Jones, D. T., "Critically Assessing the State-of-the-art in Protein Structure Prediction," The Pharmacogenomics Journal, 1(2):126-134 (2001).
Jubala, C. M. et al., "CD20 Expression in Normal Canine B cells and in Canine non-Hodgkin Lymphoma," Veterinary Pathology, 42(4):468-476 (2005).
Kar, P. et al., "Current methods for the prediction of T-cell epitopes," Peptide Science, 110:e24046 (2018), 17 pages; https://doi.org/10.1002/pep2.24046.
Karanikas, V. et al., "Antibody and T Cell Responses of Patients with Adenocarcinoma Immunized with Mannan-MUC1 Fusion Protein," Journal of Clinical Investigation, 100(11): 2783-2792 (1997).
Karimova, G. et al., "Charge-dependent translocation of *Bordetella pertussis* adenylate cyclase toxin into eukaryotic cells: Implication for the in vivo delivery of CD8+ T cell epitopes into antigen-presenting cells," Proc. Natl. Acad. Sci. USA, 95:12532-12537 (1998).
Kelland, L. R., "'Of mice and men': values and liabilities of the athymic nude mouse model in anticancer drug development," European Journal of Cancer, 40(6):827-836 (2004).
Kim, G. B. et al., "A fold-back single chain diabody format enhances the bioactivity of an anti-monkey CD3 recombinant diphtheria toxin-based immunotoxin," Protein Engineering, 20(9): 425-432 (2007).
Kotera, Y. et al., "Humoral Immunity against a Tandem Repeat Epitope of Human Mucin MUC-1 in Sera from Breast, Pancreatic, and Colon Cancer Patients," Cancer Research 54(11):2856-2860 (1994).
Kochenderfer, J. N. et al., "Construction and Pre-clinical Evaluation of an Anti-CD19 Chimeric Antigen Receptor," J Immunother., 32(7):689-702 (2009).
Kowanetz, M. et al., "Differential regulation of PD-L1 expression by immune and tumor cells in NSCLC and the response to treatment with atezolizumab (anti-PD-L1)," PNAS, 115(43):e10119-e10126 (2018).
Kurmanova, A. et al., "Structural requirements for furin-induced cleavage and activation of Shiga toxin," Biochemical and Biophysical Research Communications, 357(1):144-149 (2007).
Kyu, E., "Characterization of the A subunit mutants of Stx1 and Stx2 in *Saccharomyces cerevisiae*," Thesis, Rutgers, The State University of New Jersey, New Brunswick, retrieved from http://dx.doi.org/doi:10.7282/T34F1QWJ (2009), 57 pages.
Lakhrif, Z. et al., "A method to confer protein L binding ability to any antibody fragment," MAbs, 8(2):379-388 (2016).
Lambert, J. et al., "Purified Immunotoxins that are reactive with Human Lymphoid Cells: Monoclonal antibodies conjugated to the ribosome-inactivating proteins gelonin and the pokeweed antiviral proteins," Journal of Biological Chemistry, 260(22):12035-12041 (1985).
Lapointe, P. et al., "A Role for the Protease-sensitive Loop Region of Shiga-like Toxin 1 in the Retrotranslocation of its A Domain from the Endoplasmic Reticulum Lumen," Journal of Biological Chemistry, 280(24):23310-23318 (2005).
Laske, D. W. et al., "Intraventricular Immunotoxin Therapy for Leptomeningeal Neoplasia," Neurosurgery, 41(5):1039-1051 (1997).
Law, C. L. et al., "Efficient Elimination of B-Lineage Lymphomas by Anti-CD20-Auristatin Conjugates," Clinical Cancer Research, 10(23):7842-7851 (2004).
Lazar, E. et al., "Transforming Growth Factor alpha: Mutation of Aspartic Acid 47 and Leucine 48 Results in Different Biological Activities," Molecular and Cellular Biology, 8(3):247-1252 (1988).
Lea, N. et al., "Proteolytic cleavage of the A subunit is essential for maximal cytotoxicity of *Escherichia coli* O157:h7 Shiga-like toxin-1," Microbiology, 145(5):999-1004 (1999).
Lee, J. E. et al., "Phylogenetic analysis of Shiga toxin 1 and Shiga toxin 2 genes associated with disease outbreaks," BMC Microbiology, 7(1):109 (2007), 12 pages; doi.org/10.1186/1471-2180-7-109.
Lee, H. T. et al., "Molecular mechanism of PD-1/PD-L1 blockade via anti-PD-L1 antibodies atezolizumab and durvalumab," Scientific Reports, 7(1):5532 (2017), 12 pages; doi:10.1038/s41598-017-06002-8.

(56) References Cited

OTHER PUBLICATIONS

Lee, R. S. et al., "Major histocompatibility complex class I presentation of exogenous soluble tumor antigen fused to the B-fragment of Shiga toxin," European Journal of Immunology, 28: 2726-2737 (1998).
Lehmann, C. H. K. et al., "Direct Delivery of Antigens to Dendritic Cells via Antibodies Specific for Endocytic Receptors as a Promising Strategy for Future Therapies," Vaccines, 4(2):1-32 (2016).
Lev, A. et al., "Tumor-specific Ab-mediated targeting of MHC-peptide complexes induces regression of human tumor xenografts in vivo," PNAS, 101(24):9051-9056 (2004).
Li, H. et al., "The CD20 Calcium Channel is Localized to Microvilli and Constitutively Associated with Membrane Rafts: Antibody binding increases the affinity of the association through an epitope-dependent cross-linking-independent mechanism," Journal of Biological Chemistry, 279(19):19893-19901 (2004).
Li, B. et al., "Development of Novel Tetravalent Anti-CD20 Antibodies with Potent Antitumor Activity," Cancer Research, 68(7):2400-2408 (2008).
Li, M. et al., "Clinical targeting recombinant immunotoxins for cancer therapy," Onco Targets and Therapy, 10:3645-3665 (2017).
Li, Y. et al., "Correction to: Discovery and preclinical characterization of the antagonist anti-PD-L1 monoclonal antibody LY3300054," Journal for Immuno Therapy of Cancer, vol. 6, No. 1, Jun. 2018, p. 1.
Lim, S. H. et al., "Fc gamma receptor IIb on target B cells promotes rituximab internalization and reduces clinical efficacy," Blood, 118(9):2530-2540 (2011).
Ling, H. et al., "Structure of the Shiga-like Toxin I B-Pentameter complexed with an Analogue of Its Receptor Gb3," Biochemistry, 37(7):1777-1788 (1998).
Luqman, M. et al., "The antileukemia activity of a human antiCD40 antagonist antibody, HCD122, on human chronic lymphocytic leukemia cells," Blood, 112(3):711-720 (2008).
Lyu, M.-A. et al., "Cell-targeting fusion constructs containing recombinant gelonin," Methods in Enzymology, 502:167-214 (2012).
Maak, M. et al., "Tumor-Specific Targeting of Pancreatic Cancer with Shiga Toxin B-Subunit," Molecular Cancer Therapeutics, 10(10):1918-1928 (2011).
Mallard, F. et al., "Direct Pathway from Early/Recycling Endosomes to the Golgi Apparatus Revealed through the Study of Shiga Toxin B-fragment Transport," The Journal of Cell Biology, 143(4):973-990 (1998).
Mascarell, L. et al., "Induction of Neutralizing Antibodies and Th1-Polarized and CD4-Independent CD8+ T-Cell Responses following Delivery of Human Immunodeficiency Virus Type 1 Tat Protein by Recombinant Adenylate Cyclase of Bordetella pertussis," Journal of Virology, 79(15):9872-9884 (2005).
Mazor, Y. et al., "chFRP5-ZZ-PE38, a large IgG-toxin immunoconjugate outperforms the corresponding smaller FRP5(Fv)-ETA immunotoxin in eradicating ErbB2-expressing tumor xenografts," Cancer Letters, 257(1):124-135 (2007).
Mazor, R. et al., "Identification and elimination of an immunodominant T-cell epitope in recombinant immunotoxins based on Pseudomonas exotoxin A," Proceedings of the National Academy of Sciences U.S.A., 109(51):E3597-E3603 (2012).
McCluskey, A. J. et al., "The Catalytic Subunit of Shiga-like Toxin 1 Interacts with Ribosomal Stalk Proteins and is Inhibited by Their Conserved C-Terminal Domain," Journal of Molecular Biology, 378(2):375-386 (2008).
McCluskey et al., "Shiga-like Toxin 1: Molecular Mechanism of Toxicity and Discovery of Inhibitors", Thesis University of Toronto (2010); retrieved from the Internet: http://hdl.handle.net/1807/32046.
McCluskey et al., "Charged and hydrophobic Surfaces on the A chain of Shiga-like Toxin 1 recognize the C-terminal Domain of Ribosomal Stalk Proteins," PLoS One 7(2):e31191 (2012).
McKenzie, J, et al., "Passage through the Golgi is necessary for Shiga toxin B subunit to reach the endoplasmic reticulum," The FEBS Journal, 276(6):1581-1595, 2008.
Meeting Abstracts, "33rd Annual Meeting & Pre-Conference Programs of the Society for Immunotherapy of Cancer (SITC 2018)," Washington, D.C., USA, Nov. 7-11, 2018, Journal for Immuno Therapy of Cancer, vol. 6, Supplement No. 1, Nov. 2018, pp. 1-205.
Meeting Abstracts, "34th Annual Meeting & Pre-Conference Programs of the Society for Immunotherapy of Cancer (SITC 2019): Part 2: National Harbor, MD, USA, Nov. 10, 2019," Journal for Immuno Therapy of Cancer, vol. 7, Supplement No. 1, Nov. 2019, pp. 1-237, Abstract P804.
Michel, R. B. et al., "Intracellular Accumulation of the Anti-CD20 Antibody 1F5 in B-Lymphoma Cells," Clinical Cancer Research, 8(8):2701-2713 (2002).
Miller, R. B. et al., "Design, Construction, and In-Vitro analyses of Multivalent Antibodies," Journal of Immunology, 170(9):4854-4861 (2003).
Moise, L. et al., "T cell epitope engineering: an avian H7N9 influenza vaccine strategy for pandemic preparedness and response," Human Vaccines & Immunotherapeutics, 14(9):2203-2207 (2018).
Molecular Templates, Molecular Templates Provides Corporate Update and Outlines 2020 Milestones, Jan. 8, 2020, 2 pages.
Molecular Templates, Inc., R&D Day, Conference Call Transcript, Nov. 15, 2019, Fair Disclosure Wire, pp. 1-17; retrieved on Jan. 15, 2021 from https://dialog.proquest.com/professional/docview/2320577373.
Molecular Templates Corporate Presentation, Nov. 2019, 26 pages.
Newland, J. W. et al., "Cloning of Genes for Production of *Escherichia coli* Shiga-Like Toxin Type II," Infection and Immunity, 55(11):2675-2680 (1987).
Ninkovic, T. et al., "Identification of O-glycosylated decapeptides within the MUC1 repeat domain as potential MHC class I (A2) binding epitopes," Molecular Immunology 47(1):131-140 (2009).
Noakes, K. L. et al., "Exploiting retrograde transport of Shiga-like Toxin 1 for the delivery of exogenous antigens into the MHC class I presentation pathway," FEBS Letters, 453(1-2):95-99 (1999).
Ogishi, M. & Yotsuyanagi, H., "Quantitative Prediction of the Landscape of T Cell Epitope Immunogenicity in Sequence Space," Frontiers in Immunology, vol. 10, Article 827, pp. 1-20 (2019).
Ohmura, M. et al., "Characterization of non-toxic mutant toxins of Vero toxin I that were constructed by replacing amino acids in the A subunit," Microbial Pathogenesis, 15(3):169-176 (1993).
Olafsen, T. et al., "Recombinant Anti-CD20 Antibody fragments for Small-Animal PET Imaging of B-Cell Lymphomas," Journal of Nuclear Medicine, 50(9):1500-1508 (2009).
Olafsen, T. et al., "ImmunoPET imaging of B-cell lymphoma using anti-CD20 scFv dimers (diabodies)," Protein Engineering, Design & Selection, 23(4):243-249 (2010).
Oloomi, M. et al., "In vivo characterization of Fusion Protein Comprising of A1 Subunit of Shiga Toxin and Human GM-CSF: Assessment of Its immunogenicity and Toxicity," Iranian Biomedical Journal, 14(4):136-141 (2010).
Onda, M. et al., "An immunotoxin with greatly reduced immunogenicity by identification and removal of B cell epitopes," Proceedings of the National Academy of Sciences U.S.A., 105(32):11311-11316 (2008).
Osicka, R. et al., "Delivery of CD8+ T-cell epitopes into major histocompatibility complex class I antigen presentation," Infection and Immunity, 68(1):247-256 (2000).
Pai-Scherf, L. H. et al., "Hepatotoxicity in Cancer Patients Receiving erb-38, a Recombinant Immunotoxin that Targets the erbB2 Receptor," Clinical Cancer Research, 5(9):2311-2315 (1999).
Pastan, I. et al., "Immunotoxin Treatment of Cancer," Annual Review of Medicine, 58:221-237 (2007).
Paul, W. E. (Ed.) "Fundamental Immunology" 3rd Edition, Raven Press, 292-295 (1993).
Peng, K. W. et al., "Oncolytic measles viruses displaying a single-chain antibody against CD38, a myeloma cell marker," Blood, 101(7):2557-2562 (2003).
Perampalam, S. et al., "Designing combinatorial protein libraries based on a protein toxin template," Molecular & Cellular Proteomics, American Society for Biochemistry and Molecular Biology, Inc., US, vol. 2, No. 9, Jan. 11, 2003, p. 868.
Perampalam, S. et al., "Designing combinatorial protein libraries based on a protein toxin template," HUPO 2nd Annual & IUBMB

(56) References Cited

OTHER PUBLICATIONS

IXI World Congress, Oct. 8-11, Montreal, Poster Session 28 Proteomics & Biotechnology, 80.16 (Oct. 2003).
Perampalam, S. et al., "Cell-targeted Ribosome-Inactivating Proteins derived from Protein Combinatorial Libraries," Thesis-University of Toronto (2008), 172 pages.
Peterson, J. K. et al., "Integrating pharmacology and in vivo cancer models in preclinical and clinical drug development," European Journal of Cancer, 40(6):837-844 (2004).
Pirie, C. M. et al., "Convergent Potency of Internalized Gelonin Immunotoxins across Varied Cell Lines, Antigens, and Targeting Moieties," Journal of Biological Chemistry, 286(6):4165-4172 (2011).
Pisarev, V. M. et al., "T cells recognize PD(N/T)R motif common in a variable number of tandem repeat and degenerate repeat sequences of MUC1," International Immunopharmacology, 5(2):315-330 (2005).
Polito, L. et al., "The Conjugate Rituximab/saporin-S6 completely inhibits clonogenic growth of CD20-expressing cells and produces a synergistic toxic effect with Fludarabine," Leukemia 18(7):1215-1222 (2004).
Polito, L. et al., "Saporin-S6: A Useful Tool in Cancer Therapy," Toxins, 5:1698-1722 (2013).
Polson, A. G. et al., "Antibody-Drug Conjugates for the Treatment of Non-Hodgkin's Lymphoma: Target and Linker-Drug Selection," Cancer Research, 69(6):2358-2364 (2009).
Press, O. W. et al., "Endocytosis and Degradation of Monoclonal Antibodies Targeting Human B-Cell Malignancies," Cancer Research, 49(17):4906-4912 (1989).
Press, O. et al., "Retention of B-Cell Specific Monoclonal Antibodies by Human Lymphoma Cells," Blood, 83(5):1390-1397 (1994).
Preville, X, et al., "Eradication of Established Tumors by Vaccination With Recombinant Bordetella pertussis Adenylate Cyclase Carrying the Human Papillomavirus 16 E7 Oncoprotein," Cancer Research, 65(2):641-649 (2005).
Protein ID ABM97743, European Molecular Biology Laboratory (EMBL), Oloomi, M, et al., "synthetic construct partial A1-GMCSF chimeric protein", Sep. 10, 2007.
Promega Technical Reference, Amino Acids, 2018.
Rajagopalan, S. et al., "CD-20 Specific Engineered Toxin Body Demonstrates Direct Cell Kill of Multiple B-Cell Non-Hodgkin's Lymphoma Types," Blood, 122(21):5152 (2013).
Rajagopalan, S. et al., "CD20-specific Engineered Toxin Body demonstrates direct cell kill of multiple B-cell Non-Hodgkin's lymphoma types," The Journal of Cancer Research, 74(19 Suppl): Abstract # 647, (Oct. 1, 2014); Proceedings: AACR Annual Meeting 2014 (Apr. 5-9, 2014).
Rajagopalan, S, et al., "CD38-specific engineered toxin body: Therapeutic potential for multiple myeloma", The Journal of Cancer Research, 74(19 Suppl): Abstract #671, (Oct. 1, 2014) from American Association for Cancer Research (AACR) Annual Meeting 2014, (Apr. 5-9, 2014).
Rajagopalan, S. et al., "CD38-specific engineered toxin body: Therapeutic potential for multiple myeloma," The Journal of Cancer Research, 74(19 Suppl): Abstract nr 671 (Oct. 1, 2014).
Rajagopalan, S. et al., "HER2-targeted engineered toxin body demonstrates selective binding and cell kill of HER2-overexpressing breast cancer," The Journal of Cancer Research, 73(8 Suppl): Abstract #868 (Apr. 15, 2013).
Rajagopalan, S. et al., "HER2-targeted engineered toxin body demonstrates selective binding and cell kill of HER2-overexpressing breast cancer," Proceedings: American Association for Cancer Research (AACR) Annual Meeting 2013, Abstract # 868 (Apr. 6-10, 2013).
Rajagopalan, S. et al., "Next-generation engineered toxin bodies: CD38, PD-L1 and HER2 targeted ETBs," American Association for Cancer Research (AACR) Annual Meeting, 2016, Abstract #595 (Apr. 16-20, 2016).
Rajagopalan, S. et al., "Next-generation engineered toxin bodies: CD38, PD-L1 and HER2 targeted ETBs," The Journal of Cancer Research, 76(14 Suppl) (Jul. 15, 2016), Abstract nr 595.
Rajagopalan, S. et al., "A novel targeted engineered toxin body for treatment of HER2 positive breast cancer," Thirty-Seventh Annual CTRC-AACR San Antonio Breast Cancer Symposium, nr P4-15-17 (Dec. 9-13, 2014).
Ramakrishnan, S. & Houston, L., "Comparison of the Selective Cytotoxic Effects of Immunotoxins Containing Ricin A Chain or Pokeweed Antiviral Protein and Anti-Thy 1.1 Monoclonal Antibodies," Cancer Research, 44(1):201-208 (1984).
Ramos, H. J. et al., Abstract 3900, "The safety and efficacy profile of a PD-L1 directed, Engineered Toxin Body, as a novel targeted direct-cell kill approach for the treatment of PD-L1 expressing cancers," Molecular Templates, AACR Annual Meeting 2019; Mar. 29-Apr. 3, 2019; Atlanta, GA, AACR 2019, 2 pages.
Robinson, G. L. et al., "In vivo efficacy of a CD38-specific engineered toxin body," Clinical Cancer Research, 21(17 Suppl) (Sep. 21, 2015), Abstract A15.
Robinson, G. L. et al., "In vivo efficacy of a CD38-specific engineered toxin body," Proceedings: American Association for Cancer Research (AACR) Special Conference on Hematologic Malignancies: Translating Discoveries to Novel Therapies, Poster A15 (Sep. 21, 2015).
Robinson, G. L. et al., "MT-3724, an engineered toxin body targeting CD20 for non-Hodgkin's lymphoma," Proceedings: American Association for Cancer Research (AACR) 107th Annual Meeting 2016, Abstract #1483 (Apr. 6-10, 2016).
Robinson, G. L. et al., "MT-4019: a de-immunized engineered toxin body targeting CD38 for multiple myeloma," Proceedings: American Association for Cancer Research (AACR) Annual Meeting 2017, Poster, Abstract 2659 (Apr. 1-5, 2017).
Robinson, G. L. et al., "MT-3724, an engineered toxin body targeting CD20 for non-Hodgkin's lymphoma," Proceedings of the 107th Annual Meeting of the American Association for Cancer Research, Cancer Research, Jul. 15, 2016, 76(14 Suppl), Abstract 1483.
Romaniuk, S. I. et al., "Recombinant Diphtheria toxin derivatives: Perspectives of application," Russian Journal of Bioorganic Chemistry, 38(6):565-577 (2012).
Rosenthal, A. et al., "A phase 2 study of lenalidomide, rituximab, cyclophosphamide, and dexamethasone (LR-CD) for untreated low-grade non-Hodgkin lymphoma requiring therapy," Am J Hematol., 92(5):467-472 (2017).
Rossi, E. A. et al., "Novel Designs of Multivalent Anti-CD20 Humanized Antibodies as Improved Lymphoma Therapeutics," Cancer Research, 68(20):8384-8392 (2008).
Roudkenar, M. H. et al., "Selective cytotoxicity of recombinant STXA1-GM-CSF protein in hematopoietic cancer cells," Cell Biology and Toxicology, 22(3):213-219 (2006).
Rudikoff, S. et al., "Single amino acid substitution altering antigen-binding specificity," Proceedings of the National Academy of Sciences of the USA, 79(6):1979-1983 (1982).
Saijo, N. "What are the reasons for negative phase III trials of molecular-target-based drugs?" Cancer Science 95(10):772-776 (2004).
Sandvig, K. et al., "Protein toxins: mode of action and cell entry," Biochemical Society Transactions, 20(4):724-727 (1993).
Sandvig, K. et al., "Entry of Shiga Toxin into Cells," Zentralblatt für Bakteriologie, 278(2-3):296-305 (1993).
Saron, M. F. et al., "Anti-viral protection conferred by recombinant adenylate cyclase toxins from Bordetella pertussis carrying a CD8+ T cell epitope from lymphocytic choriomeningitis virus," Proceedings of the National Academy of Sciences U.S.A., 94(7):3314-3319 (1997).
Schindler, J. et al., "A Phase I Study of a Combination of anti-CD19 and anti-CD22 Immunotoxins (Combotox) in Adult Patients with Refractory B-Lineage Acute Lymphoblastic Leukemia," British Journal of Haematology, 154(4):1-11 (2011).
Schlecht, G. et al., "Antigen Targeting to CD11b Allows Efficient Presentation of CD4+ and CD8+ T Cell Epitopes and In Vivo Th1-Polarized T Cell Priming," The Journal of Immunology, 173(10):6089-6097 (2004).
Schuh, J. C., "Trials, Tribulations, and Trends in Tumor Modeling in Mice," Toxicologic Pathology, 32(Suppl. 1):53-66 (2004).

(56) References Cited

OTHER PUBLICATIONS

Schultz, J. C. et al., "A Tetravalent Single-chain Antibody-Streptavidin Fusion Protein for Pretargeted Lymphoma Therapy," Cancer Research, 60(23):6663-6669 (2000).
Schumacher, F.-R. et al., "Building proteomic tool boxes to monitor MHC class I and class II peptides," Proteomics, 17(1-2) (2017), 16 pages; doi:10.1002/pmic.201600061.
Sebo, P. et al., "Cell-Invasive Activity of Epitope-Tagged Adenylate Cyclase of Bordetella pertussis allows In Vitro Presentation of a Foreign Epitope to CD8+ Cytotoxic T Cells," Infection and Immunity, 63(10):3851-3857 (1995).
Sebo, P. et al., "In vivo induction of CTL responses by recombinant adenylate cyclase of Bordetella pertussis carrying multiple copies of a viral CD8+ T-cell epitope," FEMS Immunology & Medical Microbiology, 26(2):167-173 (1999).
Shan, D. et al., "Characterization of scFV-Ig Constructs Generated from the Anti-CD20 mAb 1F5 Using Linker Peptides of Varying Lengths," Journal of Immunology, 162(11):6589-6595 (1999).
Shaw, C. A. et al., "Stimulation of CD8+ T Cells following Diphtheria Toxin-Mediated Antigen Delivery into Dendritic Cells," Infection and Immunity, 74(2):1001-1008 (2006).
Shen, G. L. et al., "Evaluation of four CD22 antibodies as ricin A chain-containing immunotoxins for the in vivo therapy of human B-cell leukemias and lymphomas," International Journal of Cancer, 42(5):792-797 (1988).
Shete, V., "Generation and characterization of random site-directed mutants of Shiga-like toxin 1A by *Escherichia coli* O157:H7 in *Saccharomyces Cerevisiae*," Thesis, Rutgers, The State University of New Jersey, New Brunswick (2009), retrieved from http://dx.doi.org/doi:10.7282/T300029Z.
Shiba, Y. et al., "AGAP2 regulates retrograde transport between early endosomes and the TGN," Journal of Cell Science, 123(Pt 14):2381-2390 (2010).
Sieber, T. et al., "Selective internalization of monoclonal antibodies by B-cell chronic lymphocytic leukemia cells," 121(3):458-461 (2003).
Simsova, M. et al., "The adenylate cyclase toxin from Bordetella pertussis—a novel promising vehicle for antigen delivery to dendritic cells," International Journal of Medical Microbiology, 239:571-576 (2004).
Singh, N. K. et al., "Emerging Concepts in TCR Specificity: Rationalizing and (Maybe) Predicting Outcomes," J Immunol, 199:2203-2213 (2017).
Sivam, G. et al., "Immunotoxin to a Human Melanoma-associated Antigen: Comparison of Gelonin with Ricin and Other A Chain Conjugates," Cancer Research, 47(12):3169-3173 (1987).
Skinner, L. M. & Jackson, M. P., "Investigation of ribosome binding by the Shiga Toxin A1 subunit, using competition and site-directed mutagenesis," Journal of Bacteriology, 179(4): 1368-1374 (1997).
Skinner, L. M. & Jackson, M. P., "Inhibition of prokaryotic translation by the Shiga toxin enzymatic subunit," Microbial Pathogenesis, 24(2):117-122 (1998).
Smith, D. C. et al., "Exogenous Peptides Delivered by Ricin Require Processing by Signal Peptidase for Transporter Associated with Antigen Processing-Independent MHC Class I-Restricted Presentation," The Journal of Immunology, 169(1):99-107 (2002).
Stenmark, H. et al., "Peptides fused to the amino-terminal end of Diphtheria toxin are translocated to the cytosol," The Journal of Cell Biology, 113(5):1025-1032 (1991).
Stepanov, A. et al., "Design of Targeted B Cell Killing Agents," PLoS One, 6(6):e20991 (2011); doi:10.1371/journal.pone.0020991, 10 pages.
Strop, P. et al., "Location Matters: Site of Conjugation Modulates Stability and Pharmacokinetics of Antibody Drug Conjugates," Chemistry & Biology, 20:161-167 (2013).
Su, H. et al., "Clinical grade production and characterization of a fusion protein comprised of the chemokine CCL2-ligand genetically fused to a mutated and truncated form of the Shiga A1 subunit," Protein Expression and Purification, 66(2):149-157 (2009).
Suh, J. K. et al., "Shiga Toxin Attacks Bacterial Ribosomes as Effectively as Eucaryotic Ribosomes," Biochemistry, 37(26):9394-9398 (1998).
Suhan, M. L. et al., "Disruption of an Internal Membrane-Spanning Region in Shiga Toxin I Reduces Cytotoxicity," Infection and Immunity, 66(11):5252-5259 (1998).
Tacken, P. J. et al., "Effective induction of naive and recall T-cell responses by targeting antigen to human dendritic cells via a humanized anti-DC-SIGN antibody," Blood, 106(4): 1278-85 (2005).
Tesh, V. L. et al., "Comparison of the Relative Toxicities of Shiga-Like Toxins Type I and Type II for Mice," Infection and Immunity, 61(8):3392-3402 (1993).
Thompson, J. et al., "Improved binding of a bivalent single-chain immunotoxin results in increased efficacy for in vivo T-cell depletion," Protein Engineering, 14(12):1035-1041 (2001).
Thorpe, P. E. et al., "Cytotoxicity Acquired by Conjugation of an Anti-Thy1.1 Monoclonal Antibody and the Ribosome-Inactivating Protein, Gelonin," European Journal of Biochemistry, 116(3):447-454 (1981).
Torgersen, M. L. et al., "The A-subunit of surface-bound Shiga toxin stimulates clathrin-dependent uptake of the toxin," The FEBS Journal, 272(16):4103-4013 (2005).
Tosatto, C. E. et al., "Large-Scale Prediction of Protein Structure and Function from Sequence," Current Pharmaceutical Design, 12(17):2067-2086 (2006).
Vallera, D. A. et al., "Bioengineering a unique deimmunized bispecific targeted toxin that simultaneously recognizes human CD22 and CD19 Receptors in a mouse model of B-Cell metastases," Molecular Cancer Therapeutics, 9(6):1872-1883 (2010).
Varner, C. T. et al., "Recent Advances in Engineering Polyvalent Biological Interactions," Biomacromolecules, 16(1):43-55 (2014).
Vernet, E. et al., "Affinity-based entrapment of the HER2 receptor in the endoplasmic reticulum using an affibody molecule," Journal of Immunological Methods, 338:1-6 (2008).
Vervoordeldonk, S. F. et al., "Preclinical studies with radiolabeled monoclonal antibodies for treatment of patients with B-cell malignancies," Cancer, 73(3):1006-1011 (1994).
Vingert, B. et al., "The Shiga toxin B-subunit targets antigen in vivo to dendritic cells and elicits anti-tumor immunity," European Journal of Immunology, 36(5):1124-1135 (2006).
Von Minckwitz, G. et al., "Phase I clinical study of the recombinant antibody toxin scFv(FRP5)-ETA specific for the ErbB2/HER2 receptor in patients with advanced solid malignomas," Breast Cancer Research, 7(5):R617-R626 (2005).
Voskoglou-Nomikos, T. et al., "Clinical Predictive Value of the In Vitro Cell Line, Human Xenograft, and Mouse Allograft Preclinical Cancer Models," Clinical Cancer Research, 9(11): 4227-4239 (2003).
Wales, R. et al., "Addition of an endoplasmic reticulum retrieval sequence to ricin A chain significantly increases its cytotoxicity to mammalian cells," Journal of Biological Chemistry, 268(32):23986-23990 (1993).
Wang, E. et al., "T-cell-directed cancer vaccines: the melanoma model," Expert Opinion on Biological Therapy, 1(2):277-290 (2001).
Wargalla, U. D. & Reisfeld, R. A., "Rate of internalization of an immunotoxin correlates with cytotoxic activity against human tumor cells," PNAS USA, 86(13):5146-5150 (1989).
Weinstein, D. et al., "In vivo formation of hybrid toxins comprising Shiga toxin and the Shiga-like toxins and role of the B subunit in localization and cytotoxic activity," Infection and Immunity, 57(12):3743-3750 (1989).
Weldon, J. E. & Pastan, I., "A guide to taming a toxin: recombinant immunotoxins constructed from *Pseudomonas* exotoxin A for the treatment of cancer," FEBS Journal, 278(23):4683-4700 (2011).
Wels, W. et al., "Selective Inhibition of Tumor Cell Growth by a Recombinant Single-Chain Antibody-Toxin Specific for the erbB-2 Receptor," Cancer Research, 52:6310-6317 (1992).
Willert, E. K. et al., "Engineered toxin bodies: A next-generation immunotoxin scaffold with novel immuno-oncology functionality," Proceedings: American Association for Cancer Research (AACR) Annual Meeting 2015, Abstract #2477 (Apr. 18-22, 2015).
Willert, E. K. et al., "A novel targeted engineered toxin body for treatment of HER2 positive breast cancer," The Journal of Cancer Research, 75(9 Suppl) Abstract nr P4-15-17 (May 1, 2015).

(56) References Cited

OTHER PUBLICATIONS

Willert, E. K. et al., "Engineered toxin bodies: A next-generation immunotoxin scaffold with novel immuno-oncology functionality," The Journal of Cancer Research, 75(15 Suppl): Abstract nr 2477 (Aug. 1, 2015).
Willert, E. K. et al., "TAK-169, an exceptionally potent CD38 targeted engineered toxin body, as a novel direct cell kill approach for the treatment of multiple myeloma," Proceedings: American Association for Cancer Research (AACR) Annual Meeting 2019, Poster #2384 (Apr. 1, 2019).
Windschiegl, B. et al., "Lipid Reorganization Induced by Shiga Toxin Clustering on Planar Membranes," PLoS One, 4(7):e6238 (2009).
Wirth, R. et al., "Engineered Toxin Body demonstrating CD20-specific binding and cell kill in B-Cell Non-Hodgkin lymphoma cells," Proceedings: American Association for Cancer Research (AACR) 104th Annual Meeting 2013, Abstract #5477 (Apr. 6-10, 2013).
Wirth, R. et al., "Engineered Toxin Body demonstrating CD20-specific binding and cell kill in B-Cell Non-Hodgkin lymphoma cells," [Abstract]. In: Proceedings of the 104th Annual Meeting of the American Association for Cancer Research, Cancer Research, Apr. 15, 2013, 73(8 Suppl) Abstract #5477.
Wu, A. M. et al., "Multimerization of a chimeric anti-CD20 single chain Fv-Fc fusion protein is mediated through variable domain exchange," Protein Engineering, 14(12):1025-1033 (2001).
Wu, H. et al., "Humanization of a murine monoclonal antibody by simultaneous optimization of framework and CDR residues," J. Mol. Biol., 294:151-162 (1999).
Yamasaki, S. et al., "Importance of arginine at position 170 of the A subunit of Vero toxin 1 produced by enterohemorrahagic *Escherichia coli* for toxin activity," Microbial Pathogenesis, 11(1):1-9 (1991).
Yu, L. et al., "Interaction between bevacizumab and murine VEGF-A: a reassessment," Investigative Ophthalmology & Visual Science, 49(2):522-527 (2008).
Zacny, V. et al., "Novel toxin library for the discovery of oncology therapeutics," Cancer Research, 70(8 Suppl), Abstract #5506 (Apr. 2010).
Zahid, M. et al., "Design and reshaping of an scFv directed against human platelet glycoprotein VI with diagnostic potential," Analytical Biochemistry, 417(2):274-282 (2011).
Zapata, G. et al., "Engineering linear F(ab')2 fragments for efficient production in *Escherichia coli* and enhanced antiproliferative activity," Protein Engineering, 8(10):1057-1062 (1995).
U.S. Appl. No. 16/540,789, filed Aug. 14, 2019.
U.S. Appl. No. 17/030,657, filed Sep. 24, 2020.
U.S. Appl. No. 15/899,428, filed Feb. 20, 2018.
U.S. Appl. No. 17/228,579, filed Apr. 12, 2021.
U.S. Appl. No. 16/467,737, filed Jun. 7, 2019.
U.S. Appl. No. 17/314,563, filed May 7, 2021.
U.S. Appl. No. 16/220,468, filed Dec. 14, 2018.
U.S. Appl. No. 17/231,526, filed Apr. 15, 2021.
U.S. Appl. No. 17/233,911, filed Apr. 19, 2021.
U.S. Appl. No. 15/125,126, filed Sep. 9, 2016.
U.S. Appl. No. 15/114,487, filed Jul. 27, 2016.
U.S. Appl. No. 15/125,142, filed Sep. 9, 2016.
U.S. Appl. No. 16/013,600, filed Jun. 20, 2018.
U.S. Appl. No. 17/027,120, filed Sep. 21, 2020.
U.S. Appl. No. 17/314,563, Poma et al.
Passeri, D. & Spiegel, J., "Immunoconjugates: Magic Bullets for Cancer Therapy?" 1993; retrieved Mar. 9, 2022 from https://ntrs.nasa.gov/api/citations/19930016378/downloads/19930016378.pdf, 2 pages.
Passeri, D. & Spiegel, J., "Immunoconjugates: Magic Bullets for Cancer Therapy?" 1993; retrieved Mar. 23, 2022 from https://ntrs.nasa.gov/api/citations/19930016378/downloads/19930016378.pdf, 6 pages.
U.S. Appl. No. 17/697,564, filed Mar. 17, 2021, Poma et al.
U.S. Appl. No. 17/705,619, filed Mar. 28, 2022, Poma et al.
Batisse, C. et al., "A new delivery system for auristatin in STxB-drug conjugate therapy," Eur J Med Chem May 5, 2015; 95:483-91. doi: 10.1016/j.ejmech.2015.03.047. Epub Mar. 28, 2015.
Kostova, V. et al., "Targeted Shiga toxin-drug conjugates prepared via Cu-free click chemistry," Bioorg Med Chem. Nov. 15, 2015;23(22):7150-7. doi: 10.1016/j.bmc.2015.10.010. Epub Oct. 8, 2015.
Ge, Y. et al., "Prokaryotic Expression, Renaturalization and Antigenic Identification of Shiga Toxin I A Subunit," J Med Bol Biol, 5(4):319-322 (2008). English ABSTRACT.
Kim, S. et al., "Shiga toxin A subunit mutant of *Escherichia coli* 0157:H7 releases outer membrane vesicles containing the B-pentameric complex," FEMS Immunology & Medical Microbiology, vol. 58, Issue 3, Apr. 2010, pp. 412-420, https://doi.org/10.1111/j.1574-695X.2010.00654.x.

* cited by examiner

Figure 1. Schematic Drawing of the General Architecture of Exemplary Polypeptides and Cytotoxic Proteins
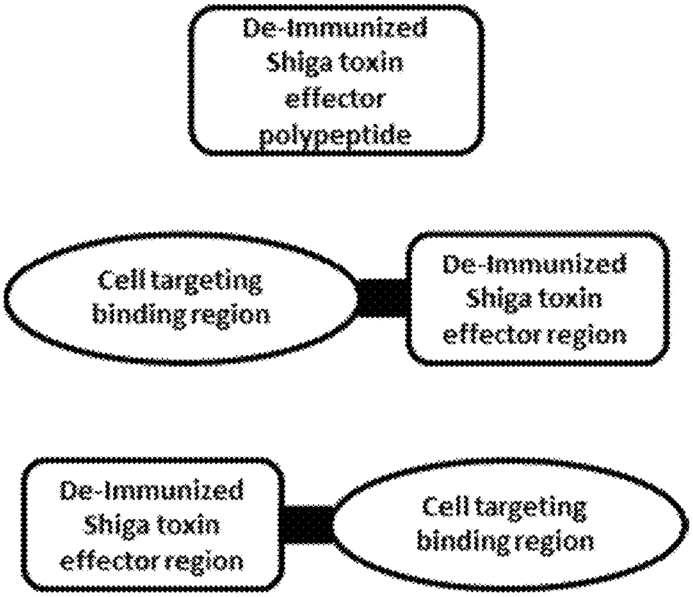

Figure 2. Western Blot Analysis of De-Immunized Shiga Toxin Effector Polypeptide: a protein comprising the D58A epitope disruption was not recognized by the antibody pAb2
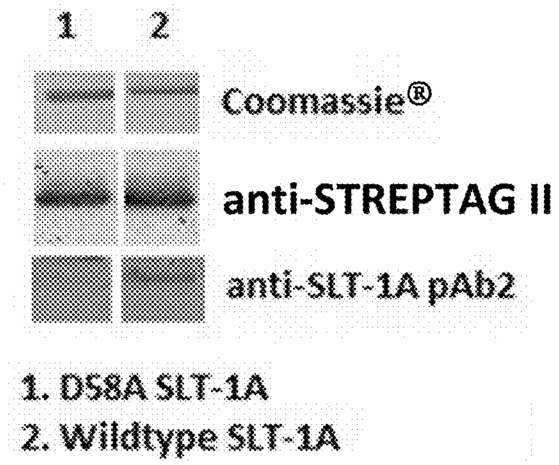
Figure 3. Western Blot Analysis of De-Immunized Shiga Toxin Effector Polypeptides
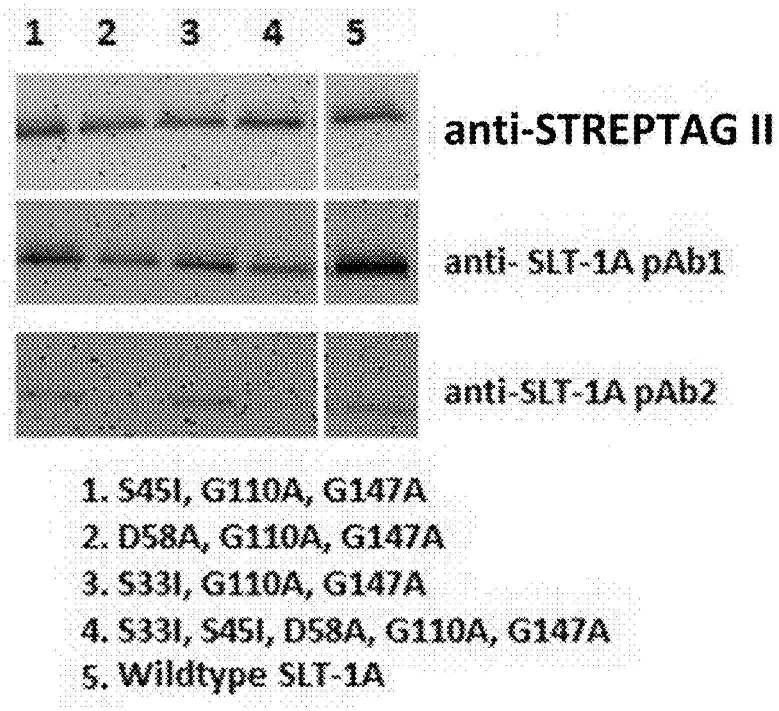

Figure 4. Western Blot Analysis of De-Immunized Shiga Toxin Effector Polypeptides
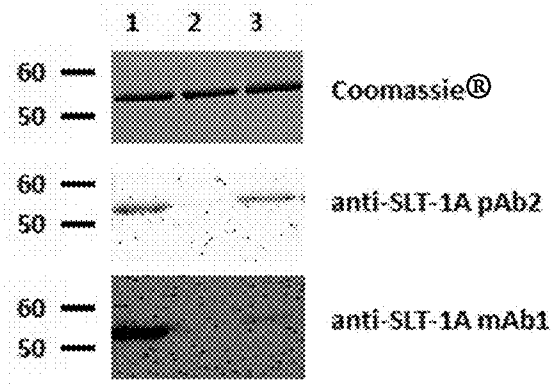
1. Wildtype
2. D58A, G110A, G147A
3. S45I, G110A, G147A

Figure 5. Western Blot Analysis of De-Immunized Shiga Toxin Effector Polypeptides
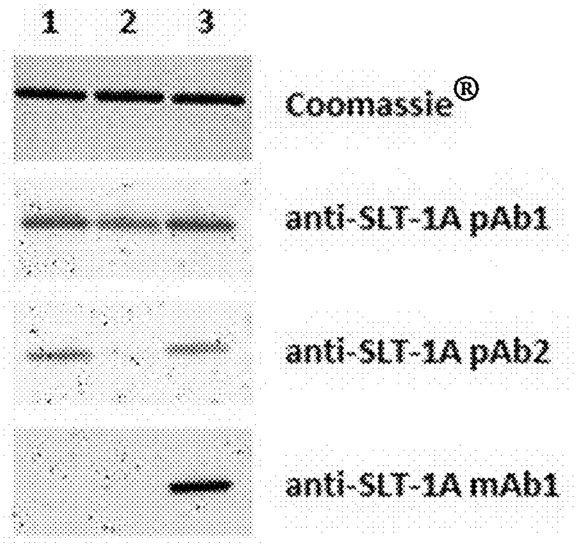
1. D183A, D184A, R188A
2. D58A, G110A, G147A, R188A
3. Wildtype SLT-1A

Figure 6. ELISA Analysis of De-Immunized Shiga Toxin Effector Polypeptides
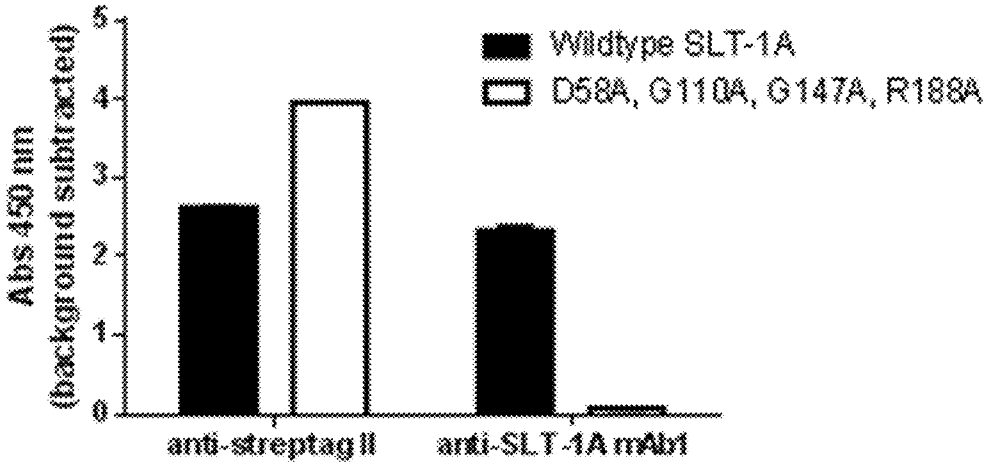
**Figure 7. Relative, *In Vivo*, Anti-Cytotoxic Protein, Antibody Responses:** Comparing a cytotoxic protein of the invention comprising an exemplary de-immunized Shiga toxin effector polypeptide to a cytotoxic protein comprising a wild-type Shiga toxin effector region
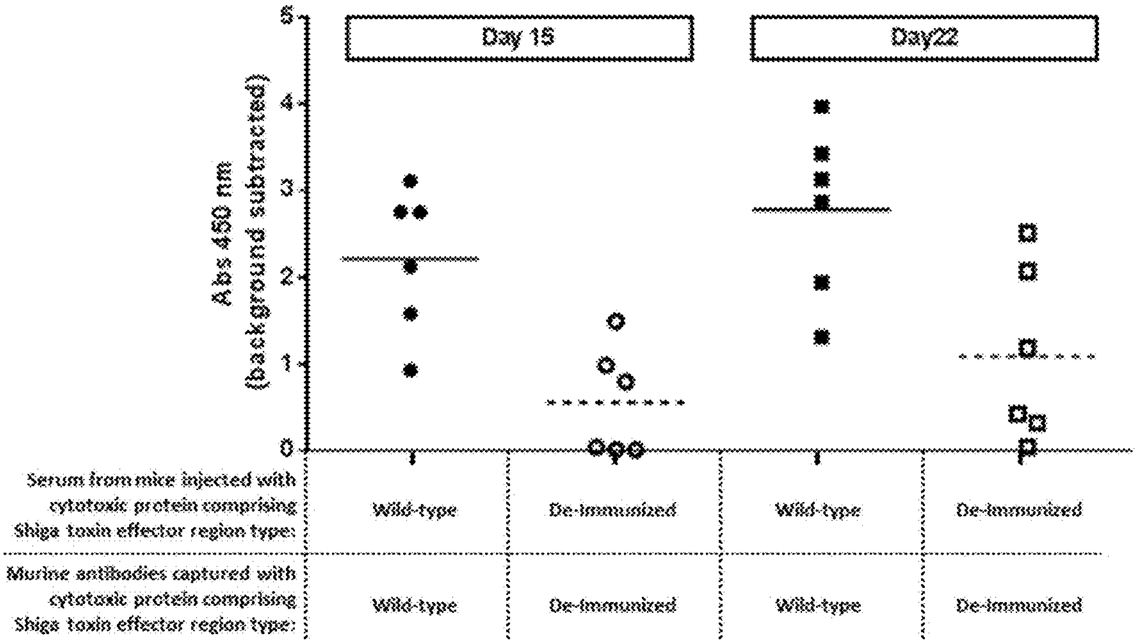

SEQUENCE LISTING

```
<160> NUMBER OF SEQ ID NOS: 136

<210> SEQ ID NO 1
<211> LENGTH: 293
<212> TYPE: PRT
<213> ORGANISM: Escherichia coli
<220> FEATURE:
<223> OTHER INFORMATION: Shiga-like toxin 1 Subunit A (SLT-1A)

<400> SEQUENCE: 1

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80
```

```
Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290


<210> SEQ ID NO 2
<211> LENGTH: 293
<212> TYPE: PRT
<213> ORGANISM: Shigella dysenteriae
<220> FEATURE:
<223> OTHER INFORMATION: Shiga toxin Subunit A (StxA)

<400> SEQUENCE: 2

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140
```

```
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290


<210> SEQ ID NO 3
<211> LENGTH: 297
<212> TYPE: PRT
<213> ORGANISM: Escherichia coli
<220> FEATURE:
<223> OTHER INFORMATION: Shiga-like toxin 2 Subunit A (SLT-2A)

<400> SEQUENCE: 3

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205
```

```
Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
        275                 280                 285

Pro Gln Asp Leu Thr Glu Pro Asn Gln
    290                 295


<210> SEQ ID NO 4
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (K1M)

<400> SEQUENCE: 4

Met Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 5
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: De-immunized SLT-1A (S8I)

<400> SEQUENCE: 5

```
Lys Glu Phe Thr Leu Asp Phe Ile Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 6
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: De-immunized SLT-1A (T9I)

<400> SEQUENCE: 6

```
Lys Glu Phe Thr Leu Asp Phe Ser Ile Ala Lys Thr Tyr Val Asp Ser
1               5                   10                  15

Leu Asn Val Ile Arg Ser Ala Ile Gly Thr Pro Leu Gln Thr Ile Ser
            20                  25                  30
```

```
Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 7
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (K11A)

<400> SEQUENCE: 7

Lys Glu Phe Thr Leu Asp Phe Ser Thr Ala Ala Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125
```

```
Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 8
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (S33I)

<400> SEQUENCE: 8

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ile Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220
```

```
Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 9
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (S45I)

<400> SEQUENCE: 9

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 10
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D53A)
```

<400> SEQUENCE: 10

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Ala Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 11
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (R55A)

<400> SEQUENCE: 11

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Ala Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
```

```
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 12
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D58A)

<400> SEQUENCE: 12

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Ala Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
```

```
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 13
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D58F)

<400> SEQUENCE: 13

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Phe Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 14
<211> LENGTH: 251
<212> TYPE: PRT
```

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (P59A)

<400> SEQUENCE: 14

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Ala Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 15
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (E60I)

<400> SEQUENCE: 15

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45
```

-continued

Leu Phe Ala Val Asp Val Arg Gly Ile Asp Pro Ile Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 16
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (E60R)

<400> SEQUENCE: 16

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Arg Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

```
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 17
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (E61A)

<400> SEQUENCE: 17

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Ala Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240
```

```
Asn Cys His His His Ala Ser Arg Val Ala Arg
                245                 250


<210> SEQ ID NO 18
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (G62A)

<400> SEQUENCE: 18

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Ala Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 19
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D94A)

<400> SEQUENCE: 19

Lys Glu Phe Thr Leu Asp Phe Ser Thr Ala Lys Thr Tyr Val Asp Ser
1               5                   10                  15
```

```
Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Ala Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 20
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (S96I)

<400> SEQUENCE: 20

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ile
                85                  90                  95

His Val Thr Phe Pro Gly Thr Thr Ala Val Thr Leu Ser Gly Asp Ser
            100                 105                 110
```

-continued

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 21
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (G110A)

<400> SEQUENCE: 21

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

```
Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 22
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (G147A)

<400> SEQUENCE: 22

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 23
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: De-immunized SLT-1A (R179A)

<400> SEQUENCE: 23

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Ala Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 24
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D183A)

<400> SEQUENCE: 24

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
```

65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Gly Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Gly Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Ala Asp Leu Ser Gly Arg Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 25
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: De-immunized SLT-1A (D184A)

<400> SEQUENCE: 25

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ser Gly Asp Asn
35 40 45

Leu Phe Ala Val Asp Val Arg Gly Ile Asp Pro Glu Glu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Gly Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Gly Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg

```
                165                 170                 175

Gly Phe Arg Thr Thr Leu Asp Ala Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 26
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D184F)

<400> SEQUENCE: 26

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Phe Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

-continued

<210> SEQ ID NO 27
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (S186A)

<400> SEQUENCE: 27

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ala Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 28
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (G187A)

<400> SEQUENCE: 28

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30
```

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Ala Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 29
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (R188A)

<400> SEQUENCE: 29

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

-continued

```
Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 30
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (S189A)

<400> SEQUENCE: 30

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ala Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220
```

```
Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 31
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (R205A)

<400> SEQUENCE: 31

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Ala Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 32
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (K1M, K11A)

<400> SEQUENCE: 32
```

```
Met Glu Phe Thr Leu Asp Phe Ser Thr Ala Ala Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 33
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (S45I, R188A)

<400> SEQUENCE: 33

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95
```

```
His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 34
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (E60I, G110A)

<400> SEQUENCE: 34

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Ile Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190
```

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 35
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (E60I, G147A)

<400> SEQUENCE: 35

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ser Gly Asp Asn
35 40 45

Leu Phe Ala Val Asp Val Arg Gly Ile Asp Pro Ile Glu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Gly Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Ala Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Asp Asp Leu Ser Gly Arg Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 36
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: De-immunized SLT-1A (D94A, S96I)

<400> SEQUENCE: 36

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Ala Phe Ile
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 37
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: De-immunized SLT-1A (S33I, G110A, G147A)

<400> SEQUENCE: 37

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ile Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
```

```
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 38
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (S45I, G110A, G147A)

<400> SEQUENCE: 38

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
```

```
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 39
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D58A, G110A, G147A)

<400> SEQUENCE: 39

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Ala Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
```

245 250

<210> SEQ ID NO 40
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (E60I, G110A, G147A)

<400> SEQUENCE: 40

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ser Gly Asp Asn
35 40 45

Leu Phe Ala Val Asp Val Arg Gly Ile Asp Pro Ile Glu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Ala Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Ala Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Asp Asp Leu Ser Gly Arg Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 41
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (D183A, D184A, R188A)

<400> SEQUENCE: 41

Lys Glu Phe Thr Leu Asp Phe Ser Thr Ala Lys Thr Tyr Val Asp Ser
1 5 10 15

```
Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Ala Ala Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 42
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D58A, G110A, G147A, S186A)

<400> SEQUENCE: 42

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Ala Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110
```

```
Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ala Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 43
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (D58A, G110A, G147A, G187A)

<400> SEQUENCE: 43

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Ala Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Ala Arg Ser Tyr Val Met
            180                 185                 190

Thr Ala Glu Asp Val Asp Leu Thr Leu Asn Trp Gly Arg Leu Ser Ser
        195                 200                 205
```

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 44
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (D58A, G110A, G147A, R188A)

<400> SEQUENCE: 44

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ser Gly Asp Asn
35 40 45

Leu Phe Ala Val Asp Val Arg Gly Ile Ala Pro Glu Glu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Ala Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Ala Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Asp Asp Leu Ser Gly Ala Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 45
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<223> OTHER INFORMATION: De-immunized SLT-1A (D58A, G110A, G147A, S189A)

<400> SEQUENCE: 45

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Ala Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ala Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 46
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (S45I D58A E60I G110A G147A)

<400> SEQUENCE: 46

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Val Arg Gly Ile Ala Pro Ile Glu Gly Arg Phe
    50                  55                  60

Asn Asn Leu Arg Leu Ile Val Glu Arg Asn Asn Leu Tyr Val Thr Gly
```

65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Ala Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Ala Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Asp Asp Leu Ser Gly Arg Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 47
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (D58A, G110A, G147A, S186A, R188A)

<400> SEQUENCE: 47

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ser Gly Asp Asn
35 40 45

Leu Phe Ala Val Asp Val Arg Gly Ile Ala Pro Glu Glu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Ala Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Ala Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Asp Asp Leu Ala Gly Ala Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 48
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (D58A, G110A, G147A, G187A, R188A)

<400> SEQUENCE: 48

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ser Gly Asp Asn
35 40 45

Leu Phe Ala Val Asp Val Arg Gly Ile Ala Pro Glu Glu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Ala Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Ala Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Asp Asp Leu Ser Ala Ala Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 49
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (S33I, S45I, D58A, G110A, G147A)

<400> SEQUENCE: 49

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ile Gly Gly Thr Ser Leu Leu Met Ile Asp Ser Gly Ile Gly Asp Asn
        35                  40                  45

Leu Phe Ala Val Asp Val Arg Gly Ile Ala Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 50
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: De-immunized SLT-1A (S45I G110A G147A, D183A, D184A, R188A)

<400> SEQUENCE: 50

```
Lys Glu Phe Thr Leu Asp Phe Ser Thr Ala Lys Thr Tyr Val Asp Ser
1               5                   10                  15
```

```
Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Ala Ala Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 51
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (S45I D58A E60I G110A
      G147A, D183A, D184A, R188A)

<400> SEQUENCE: 51

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Val Arg Gly Ile Ala Pro Ile Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
```

```
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Ala Ala Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250


<210> SEQ ID NO 52
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: De-immunized SLT-1A (S45I D58A E60I G62A G110A
      G147A, D183A, D184A, R188A)

<400> SEQUENCE: 52

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Val Arg Gly Ile Ala Pro Ile Glu Ala Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Ala Ala Leu Ser Gly Ala Ser Tyr Val Met
            180                 185                 190
```

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg
245 250

<210> SEQ ID NO 53
<211> LENGTH: 512
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Cytotoxic Protein: alpha-CD20 fused with de-immunized SLT-1A variant #1

<400> SEQUENCE: 53

Met Gln Val Gln Leu Gln Gln Pro Gly Ala Glu Leu Val Lys Pro Gly
1 5 10 15

Ala Ser Val Lys Met Ser Cys Lys Thr Ser Gly Tyr Thr Phe Thr Ser
20 25 30

Tyr Asn Val His Trp Val Lys Gln Thr Pro Gly Gln Gly Leu Glu Trp
35 40 45

Ile Gly Ala Ile Tyr Pro Gly Asn Gly Asp Thr Ser Phe Asn Gln Lys
50 55 60

Phe Lys Gly Lys Ala Thr Leu Thr Ala Asp Lys Ser Ser Ser Thr Val
65 70 75 80

Tyr Met Gln Leu Ser Ser Leu Thr Ser Glu Asp Ser Ala Val Tyr Tyr
85 90 95

Cys Ala Arg Ser Asn Tyr Tyr Gly Ser Ser Tyr Val Trp Phe Phe Asp
100 105 110

Val Trp Gly Ala Gly Thr Thr Val Thr Val Ser Ser Gly Ser Thr Ser
115 120 125

Gly Ser Gly Lys Pro Gly Ser Gly Glu Gly Ser Gln Ile Val Leu Ser
130 135 140

Gln Ser Pro Thr Ile Leu Ser Ala Ser Pro Gly Glu Lys Val Thr Met
145 150 155 160

Thr Cys Arg Ala Ser Ser Ser Val Ser Tyr Met Asp Trp Tyr Gln Gln
165 170 175

Lys Pro Gly Ser Ser Pro Lys Pro Trp Ile Tyr Ala Thr Ser Asn Leu
180 185 190

Ala Ser Gly Val Pro Ala Arg Phe Ser Gly Ser Gly Ser Gly Thr Ser
195 200 205

Tyr Ser Leu Thr Ile Ser Arg Val Glu Ala Glu Asp Ala Ala Thr Tyr
210 215 220

Tyr Cys Gln Gln Trp Ile Ser Asn Pro Pro Thr Phe Gly Ala Gly Thr
225 230 235 240

Lys Leu Glu Leu Lys Glu Phe Pro Lys Pro Ser Thr Pro Pro Gly Ser
245 250 255

Ser Gly Gly Ala Pro Lys Glu Phe Thr Leu Asp Phe Ser Thr Ala Lys
260 265 270

Thr Tyr Val Asp Ser Leu Asn Val Ile Arg Ser Ala Ile Gly Thr Pro
275 280 285

Leu Gln Thr Ile Ser Ile Gly Gly Thr Ser Leu Leu Met Ile Asp Ser
290 295 300

Gly Ile Gly Asp Asn Leu Phe Ala Val Asp Val Arg Gly Ile Ala Pro
305 310 315 320

Glu Glu Gly Arg Phe Asn Asn Leu Arg Leu Ile Val Glu Arg Asn Asn
325 330 335

Leu Tyr Val Thr Gly Phe Val Asn Arg Thr Asn Asn Val Phe Tyr Arg
340 345 350

Phe Ala Asp Phe Ser His Val Thr Phe Pro Gly Thr Thr Ala Val Thr
355 360 365

Leu Ser Ala Asp Ser Ser Tyr Thr Thr Leu Gln Arg Val Ala Gly Ile
370 375 380

Ser Arg Thr Gly Met Gln Ile Asn Arg His Ser Leu Thr Thr Ser Tyr
385 390 395 400

Leu Asp Leu Met Ser His Ser Ala Thr Ser Leu Thr Gln Ser Val Ala
405 410 415

Arg Ala Met Leu Arg Phe Val Thr Val Thr Ala Glu Ala Leu Arg Phe
420 425 430

Arg Gln Ile Gln Arg Gly Phe Arg Thr Thr Leu Asp Asp Leu Ser Gly
435 440 445

Arg Ser Tyr Val Met Thr Ala Glu Asp Val Asp Leu Thr Leu Asn Trp
450 455 460

Gly Arg Leu Ser Ser Val Leu Pro Asp Tyr His Gly Gln Asp Ser Val
465 470 475 480

Arg Val Gly Arg Ile Ser Phe Gly Ser Ile Asn Ala Ile Leu Gly Ser
485 490 495

Val Ala Leu Ile Leu Asn Cys His His His Ala Ser Ala Val Ala Arg
500 505 510

<210> SEQ ID NO 54
<211> LENGTH: 511
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Cytotoxic Protein: alpha-CD20 fused with de-immunized SLT-1A variant #2

<400> SEQUENCE: 54

Met Gln Val Gln Leu Val Gln Ser Gly Ala Glu Leu Val Lys Pro Gly
1 5 10 15

Ala Ser Val Lys Met Ser Cys Lys Ala Ser Gly Tyr Thr Phe Thr Ser
20 25 30

Tyr Asn Met His Trp Val Lys Gln Thr Pro Gly Gln Gly Leu Glu Trp
35 40 45

Ile Gly Ala Ile Tyr Pro Gly Asn Gly Asp Thr Ser Tyr Asn Gln Lys
50 55 60

Phe Lys Gly Lys Ala Thr Leu Thr Ala Asp Lys Ser Ser Ser Thr Ala
65 70 75 80

Tyr Met Gln Leu Ser Ser Leu Thr Ser Glu Asp Ser Ala Val Tyr Tyr
85 90 95

Cys Ala Arg Ala Gln Leu Arg Pro Asn Tyr Trp Tyr Phe Asp Val Trp
100 105 110

Gly Ala Gly Thr Thr Val Thr Val Ser Ser Gly Gly Gly Gly Ser Gly

```
        115                 120                 125

Gly Gly Gly Ser Gly Gly Gly Gly Ser Gly Gly Gly Gly Ser Gly Gly
    130                 135                 140

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
                165                 170                 175

Ser Tyr Met His Trp Tyr Gln Gln Lys Pro Gly Ser Ser Pro Lys Pro
            180                 185                 190

Trp Ile Tyr Ala Thr Ser Asn Leu Ala Ser Gly Val Pro Ala Arg Phe
        195                 200                 205

Ser Gly Ser Gly Ser Gly Thr Ser Tyr Ser Leu Thr Ile Ser Arg Val
    210                 215                 220

Glu Ala Glu Asp Ala Ala Thr Tyr Tyr Cys Gln Gln Trp Ile Ser Asn
225                 230                 235                 240

Pro Pro Thr Phe Gly Ala Gly Thr Lys Leu Glu Leu Lys Gly Gly Gly
                245                 250                 255

Gly Ser Gly Gly Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
        275                 280                 285

Gln Thr Ile Ser Ile Gly Gly Thr Ser Leu Leu Met Ile Asp Ser Gly
    290                 295                 300

Ile Gly Asp Asn Leu Phe Ala Val Asp Val Arg Gly Ile Ala Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
            340                 345                 350

Ala Asp Phe Ser His Val Thr Phe Pro Gly Thr Thr Ala Val Thr Leu
        355                 360                 365

Ser Ala Asp Ser Ser Tyr Thr Thr Leu Gln Arg Val Ala Gly Ile Ser
    370                 375                 380

Arg Thr Gly Met Gln Ile Asn Arg His Ser Leu Thr Thr Ser Tyr Leu
385                 390                 395                 400

Asp Leu Met Ser His Ser Ala Thr Ser Leu Thr Gln Ser Val Ala Arg
                405                 410                 415

Ala Met Leu Arg Phe Val Thr Val Thr Ala Glu Ala Leu Arg Phe Arg
            420                 425                 430

Gln Ile Gln Arg Gly Phe Arg Thr Thr Leu Asp Asp Leu Ser Gly Arg
        435                 440                 445

Ser Tyr Val Met Thr Ala Glu Asp Val Asp Leu Thr Leu Asn Trp Gly
    450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Cys His His His Ala Ser Ala Val Ala Arg
            500                 505                 510
```

<210> SEQ ID NO 55
<211> LENGTH: 513
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Cytotoxic Protein: alpha-CD20 fused with
de-immunized SLT-1A variant #3

<400> SEQUENCE: 55

```
Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Arg Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ser Thr Tyr Tyr Gly Gly Asp Trp Tyr Phe Asn Val Trp
            100                 105                 110

Gly Ala Gly Thr Thr Val Thr Val Ser Ala Gly Ser Thr Ser Gly Ser
        115                 120                 125

Gly Lys Pro Gly Ser Gly Glu Gly Ser Thr Lys Gly Gln Ile Val Leu
    130                 135                 140

Ser Gln Ser Pro Ala Ile Leu Ser Ala Ser Pro Gly Glu Lys Val Thr
145                 150                 155                 160

Met Thr Cys Arg Ala Ser Ser Ser Val Ser Tyr Ile His Trp Phe Gln
                165                 170                 175

Gln Lys Pro Gly Ser Ser Pro Lys Pro Trp Ile Tyr Ala Thr Ser Asn
            180                 185                 190

Leu Ala Ser Gly Val Pro Val Arg Phe Ser Gly Ser Gly Ser Gly Thr
        195                 200                 205

Ser Tyr Ser Leu Thr Ile Ser Arg Val Glu Ala Glu Asp Ala Ala Thr
    210                 215                 220

Tyr Tyr Cys Gln Gln Trp Thr Ser Asn Pro Pro Thr Phe Gly Gly Gly
225                 230                 235                 240

Thr Lys Leu Glu Ile Lys Glu Phe Pro Lys Pro Ser Thr Pro Pro Gly
                245                 250                 255

Ser Ser Gly Gly Ala Pro Lys Glu Phe Thr Leu Asp Phe Ser Thr Ala
            260                 265                 270

Lys Thr Tyr Val Asp Ser Leu Asn Val Ile Arg Ser Ala Ile Gly Thr
        275                 280                 285

Pro Leu Gln Thr Ile Ser Ile Gly Gly Thr Ser Leu Leu Met Ile Asp
    290                 295                 300

Ser Gly Ile Gly Asp Asn Leu Phe Ala Val Asp Val Arg Gly Ile Ala
305                 310                 315                 320

Pro Glu Glu Gly Arg Phe Asn Asn Leu Arg Leu Ile Val Glu Arg Asn
                325                 330                 335

Asn Leu Tyr Val Thr Gly Phe Val Asn Arg Thr Asn Asn Val Phe Tyr
            340                 345                 350

Arg Phe Ala Asp Phe Ser His Val Thr Phe Pro Gly Thr Thr Ala Val
        355                 360                 365

Thr Leu Ser Ala Asp Ser Ser Tyr Thr Thr Leu Gln Arg Val Ala Gly
```

```
370                 375                 380

Ile Ser Arg Thr Gly Met Gln Ile Asn Arg His Ser Leu Thr Thr Ser
385                 390                 395                 400

Tyr Leu Asp Leu Met Ser His Ser Ala Thr Ser Leu Thr Gln Ser Val
                405                 410                 415

Ala Arg Ala Met Leu Arg Phe Val Thr Val Thr Ala Glu Ala Leu Arg
            420                 425                 430

Phe Arg Gln Ile Gln Arg Gly Phe Arg Thr Thr Leu Asp Asp Leu Ser
        435                 440                 445

Gly Arg Ser Tyr Val Met Thr Ala Glu Asp Val Asp Leu Thr Leu Asn
    450                 455                 460

Trp Gly Arg Leu Ser Ser Val Leu Pro Asp Tyr His Gly Gln Asp Ser
465                 470                 475                 480

Val Arg Val Gly Arg Ile Ser Phe Gly Ser Ile Asn Ala Ile Leu Gly
                485                 490                 495

Ser Val Ala Leu Ile Leu Asn Cys His His His Ala Ser Ala Val Ala
            500                 505                 510

Arg


<210> SEQ ID NO 56
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: alpha-CD20 fused with
      de-immunized SLT-1A variant #4

<400> SEQUENCE: 56

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
        115                 120                 125

Gly Ser Gly Lys Pro Gly Ser Gly Glu Gly Ser Gln Ile Val Leu Ser
    130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
```

```
        195                 200                 205

Tyr Ser Leu Thr Ile Ser Arg Val Glu Ala Glu Asp Ala Ala Thr Tyr
    210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255

Ser Gly Gly Ala Pro Gly Ile Leu Gly Phe Val Phe Thr Leu Lys Glu
            260                 265                 270

Phe Thr Leu Asp Phe Ser Thr Ala Lys Thr Tyr Val Asp Ser Leu Asn
        275                 280                 285

Val Ile Arg Ser Ala Ile Gly Thr Pro Leu Gln Thr Ile Ser Ile Gly
    290                 295                 300

Gly Thr Ser Leu Leu Met Ile Asp Ser Gly Ile Gly Asp Asn Leu Phe
305                 310                 315                 320

Ala Val Asp Val Arg Gly Ile Ala Pro Glu Glu Gly Arg Phe Asn Asn
                325                 330                 335

Leu Arg Leu Ile Val Glu Arg Asn Asn Leu Tyr Val Thr Gly Phe Val
            340                 345                 350

Asn Arg Thr Asn Asn Val Phe Tyr Arg Phe Ala Asp Phe Ser His Val
        355                 360                 365

Thr Phe Pro Gly Thr Thr Ala Val Thr Leu Ser Ala Asp Ser Ser Tyr
    370                 375                 380

Thr Thr Leu Gln Arg Val Ala Gly Ile Ser Arg Thr Gly Met Gln Ile
385                 390                 395                 400

Asn Arg His Ser Leu Thr Thr Ser Tyr Leu Asp Leu Met Ser His Ser
                405                 410                 415

Ala Thr Ser Leu Thr Gln Ser Val Ala Arg Ala Met Leu Arg Phe Val
            420                 425                 430

Thr Val Thr Ala Glu Ala Leu Arg Phe Arg Gln Ile Gln Arg Gly Phe
        435                 440                 445

Arg Thr Thr Leu Asp Asp Leu Ser Gly Arg Ser Tyr Val Met Thr Ala
    450                 455                 460

Glu Asp Val Asp Leu Thr Leu Asn Trp Gly Arg Leu Ser Ser Val Leu
465                 470                 475                 480

Pro Asp Tyr His Gly Gln Asp Ser Val Arg Val Gly Arg Ile Ser Phe
                485                 490                 495

Gly Ser Ile Asn Ala Ile Leu Gly Ser Val Ala Leu Ile Leu Asn Cys
            500                 505                 510

His His His Ala Ser Ala Val Ala Arg
        515                 520


<210> SEQ ID NO 57
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: anti-HER2-VHH fused with
      de-immunized SLT-1A variant #1

<400> SEQUENCE: 57

Met Glu Val Gln Leu Val Glu Ser Gly Gly Gly Leu Val Gln Ala Gly
1               5                   10                  15
```

Gly Ser Leu Arg Leu Ser Cys Ala Ala Ser Gly Ile Thr Phe Ser Ile
20 25 30

Asn Thr Met Gly Trp Tyr Arg Gln Ala Pro Gly Lys Gln Arg Glu Leu
35 40 45

Val Ala Leu Ile Ser Ser Ile Gly Asp Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Lys Arg Phe Arg Thr Ala Ala Gln Gly Thr Asp Tyr Trp Gly Gln Gly
100 105 110

Thr Gln Val Thr Val Ser Ser Ala His His Ser Glu Asp Pro Ser Ser
115 120 125

Lys Ala Pro Lys Ala Pro Lys Glu Phe Thr Leu Asp Phe Ser Thr Ala
130 135 140

Lys Thr Tyr Val Asp Ser Leu Asn Val Ile Arg Ser Ala Ile Gly Thr
145 150 155 160

Pro Leu Gln Thr Ile Ser Ile Gly Gly Thr Ser Leu Leu Met Ile Asp
165 170 175

Ser Gly Ile Gly Asp Asn Leu Phe Ala Val Asp Val Arg Gly Ile Ala
180 185 190

Pro Glu Glu Gly Arg Phe Asn Asn Leu Arg Leu Ile Val Glu Arg Asn
195 200 205

Asn Leu Tyr Val Thr Gly Phe Val Asn Arg Thr Asn Asn Val Phe Tyr
210 215 220

Arg Phe Ala Asp Phe Ser His Val Thr Phe Pro Gly Thr Thr Ala Val
225 230 235 240

Thr Leu Ser Ala Asp Ser Ser Tyr Thr Thr Leu Gln Arg Val Ala Gly
245 250 255

Ile Ser Arg Thr Gly Met Gln Ile Asn Arg His Ser Leu Thr Thr Ser
260 265 270

Tyr Leu Asp Leu Met Ser His Ser Ala Thr Ser Leu Thr Gln Ser Val
275 280 285

Ala Arg Ala Met Leu Arg Phe Val Thr Val Thr Ala Glu Ala Leu Arg
290 295 300

Phe Arg Gln Ile Gln Arg Gly Phe Arg Thr Thr Leu Asp Asp Leu Ser
305 310 315 320

Gly Arg Ser Tyr Val Met Thr Ala Glu Asp Val Asp Leu Thr Leu Asn
325 330 335

Trp Gly Arg Leu Ser Ser Val Leu Pro Asp Tyr His Gly Gln Asp Ser
340 345 350

Val Arg Val Gly Arg Ile Ser Phe Gly Ser Ile Asn Ala Ile Leu Gly
355 360 365

Ser Val Ala Leu Ile Leu Asn Cys His His His Ala Ser Ala Val Ala
370 375 380

Arg
385

<210> SEQ ID NO 58
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Cytotoxic Protein: anti-HER2-VHH fused with de-immunized SLT-1A variant #2

<400> SEQUENCE: 58

```
Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ile Gly Gly Thr Ser Leu Leu Met Ile Asp Ser Gly Ile Gly Asp
        35                  40                  45

Asn Leu Phe Ala Val Asp Val Arg Gly Ile Ala Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Ala Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Arg Glu Phe Pro Lys
                245                 250                 255

Pro Ser Thr Pro Pro Gly Ser Ser Gly Gly Ala Pro Met Glu Val Gln
            260                 265                 270

Leu Val Glu Ser Gly Gly Gly Leu Val Gln Ala Gly Gly Ser Leu Arg
        275                 280                 285

Leu Ser Cys Ala Ala Ser Gly Ile Thr Phe Ser Ile Asn Thr Met Gly
    290                 295                 300

Trp Tyr Arg Gln Ala Pro Gly Lys Gln Arg Glu Leu Val Ala Leu Ile
305                 310                 315                 320

Ser Ser Ile Gly Asp Thr Tyr Tyr Ala Asp Ser Val Lys Gly Arg Phe
                325                 330                 335

Thr Ile Ser Arg Asp Asn Ala Lys Asn Thr Val Tyr Leu Gln Met Asn
            340                 345                 350

Ser Leu Lys Pro Glu Asp Thr Ala Val Tyr Tyr Cys Lys Arg Phe Arg
        355                 360                 365

Thr Ala Ala Gln Gly Thr Asp Tyr Trp Gly Gln Gly Thr Gln Val Thr
    370                 375                 380
```

Val Ser Ser
385

<210> SEQ ID NO 59
<211> LENGTH: 390
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Cytotoxic Protein: anti-HER2-VHH fused with de-immunized SLT-1A variant #3 (alpha-HER2-VHH::SLT-1A::KDEL)

<400> SEQUENCE: 59

Met Glu Val Gln Leu Val Glu Ser Gly Gly Gly Leu Val Gln Ala Gly
1 5 10 15

Gly Ser Leu Arg Leu Ser Cys Ala Ala Ser Gly Ile Thr Phe Ser Ile
20 25 30

Asn Thr Met Gly Trp Tyr Arg Gln Ala Pro Gly Lys Gln Arg Glu Leu
35 40 45

Val Ala Leu Ile Ser Ser Ile Gly Asp Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Lys Arg Phe Arg Thr Ala Ala Gln Gly Thr Asp Tyr Trp Gly Gln Gly
100 105 110

Thr Gln Val Thr Val Ser Ser Glu Phe Pro Lys Pro Ser Thr Pro Pro
115 120 125

Gly Ser Ser Gly Gly Ala Pro Lys Glu Phe Thr Leu Asp Phe Ser Thr
130 135 140

Ala Lys Thr Tyr Val Asp Ser Leu Asn Val Ile Arg Ser Ala Ile Gly
145 150 155 160

Thr Pro Leu Gln Thr Ile Ser Ile Gly Gly Thr Ser Leu Leu Met Ile
165 170 175

Asp Ser Gly Ile Gly Asp Asn Leu Phe Ala Val Asp Val Arg Gly Ile
180 185 190

Ala Pro Glu Glu Gly Arg Phe Asn Asn Leu Arg Leu Ile Val Glu Arg
195 200 205

Asn Asn Leu Tyr Val Thr Gly Phe Val Asn Arg Thr Asn Asn Val Phe
210 215 220

Tyr Arg Phe Ala Asp Phe Ser His Val Thr Phe Pro Gly Thr Thr Ala
225 230 235 240

Val Thr Leu Ser Ala Asp Ser Ser Tyr Thr Thr Leu Gln Arg Val Ala
245 250 255

Gly Ile Ser Arg Thr Gly Met Gln Ile Asn Arg His Ser Leu Thr Thr
260 265 270

Ser Tyr Leu Asp Leu Met Ser His Ser Ala Thr Ser Leu Thr Gln Ser
275 280 285

Val Ala Arg Ala Met Leu Arg Phe Val Thr Val Thr Ala Glu Ala Leu
290 295 300

Arg Phe Arg Gln Ile Gln Arg Gly Phe Arg Thr Thr Leu Asp Asp Leu
305 310 315 320

Ser Gly Arg Ser Tyr Val Met Thr Ala Glu Asp Val Asp Leu Thr Leu
325 330 335

Asn Trp Gly Arg Leu Ser Ser Val Leu Pro Asp Tyr His Gly Gln Asp
340 345 350

Ser Val Arg Val Gly Arg Ile Ser Phe Gly Ser Ile Asn Ala Ile Leu
355 360 365

Gly Ser Val Ala Leu Ile Leu Asn Cys His His His Ala Ser Ala Val
370 375 380

Ala Arg Lys Asp Glu Leu
385 390

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Lys Asp Glu Leu
1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

His Asp Glu Phe
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

His Asp Glu Leu
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Arg Asp Glu Phe
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Arg Asp Glu Leu
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Trp Asp Glu Leu
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Tyr Asp Glu Leu
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

His Glu Glu Phe
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

His Glu Glu Leu
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Lys Glu Glu Leu
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Arg Glu Glu Leu
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Lys Ala Glu Leu
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Lys Cys Glu Leu
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Lys Phe Glu Leu
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Lys Gly Glu Leu
1

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Lys His Glu Leu
1

-continued

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Lys Leu Glu Leu
1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Lys Asn Glu Leu
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Lys Gln Glu Leu
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Lys Arg Glu Leu
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Lys Ser Glu Leu
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Lys Val Glu Leu
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Lys Trp Glu Leu
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Lys Tyr Glu Leu
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Lys Glu Asp Leu
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Lys Ile Glu Leu
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Asp Lys Glu Leu
1

<210> SEQ ID NO 87
<211> LENGTH: 4
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 87

Phe Asp Glu Leu
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Lys Asp Glu Phe
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Lys Lys Glu Leu
1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

His Ala Asp Leu
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

His Ala Glu Leu
1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

His Ile Glu Leu
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

His Asn Glu Leu
1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

His Thr Glu Leu
1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Lys Thr Glu Leu
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

His Val Glu Leu
1

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Asn Asp Glu Leu
1

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
peptide -continued

<400> SEQUENCE: 98

Gln Asp Glu Leu
1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Arg Glu Asp Leu
1

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Arg Asn Glu Leu
1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Arg Thr Asp Leu
1

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Arg Thr Glu Leu
1

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Ser Asp Glu Leu
1

<210> SEQ ID NO 104
<211> LENGTH: 4

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Thr Asp Glu Leu
1

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Ser Lys Glu Leu
1

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Ala Leu Glu Asp Glu Leu
1 5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

His Ala Glu Asp Glu Leu
1 5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

His Leu Glu Asp Glu Leu
1 5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Lys Leu Glu Asp Glu Leu 1 5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Ile Arg Ser Asp Glu Leu
1 5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Glu Arg Ser Thr Glu Leu
1 5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Arg Pro Ser Thr Glu Leu
1 5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Ala Ser Gly Gly Pro Glu
1 5

<210> SEQ ID NO 114
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (5)..(6)
<223> OTHER INFORMATION: May or may not be present
<220> FEATURE:
<221> NAME/KEY: MISC_FEATURE
<222> LOCATION: (10)..(11)
<223> OTHER INFORMATION: May or may not be present
<220> FEATURE:
<221> NAME/KEY: MISC_FEATURE
<222> LOCATION: (15)..(16)
<223> OTHER INFORMATION: May or may not be present
<220> FEATURE:

<221> NAME/KEY: MISC_FEATURE
<222> LOCATION: (20)..(21)
<223> OTHER INFORMATION: May or may not be present
<220> FEATURE:
<221> NAME/KEY: MISC_FEATURE
<222> LOCATION: (25)..(26)
<223> OTHER INFORMATION: May or may not be present
<220> FEATURE:
<221> NAME/KEY: MISC_FEATURE
<222> LOCATION: (30)..(31)
<223> OTHER INFORMATION: May or may not be present
<220> FEATURE:
<221> NAME/KEY: MISC_FEATURE
<222> LOCATION: (35)..(36)
<223> OTHER INFORMATION: May or may not be present
<220> FEATURE:
<221> NAME/KEY: MISC_FEATURE
<222> LOCATION: (40)..(41)
<223> OTHER INFORMATION: May or may not be present
<220> FEATURE:
<221> NAME/KEY: MISC_FEATURE
<222> LOCATION: (45)..(46)
<223> OTHER INFORMATION: May or may not be present
<220> FEATURE:
<221> NAME/KEY: MISC_FEATURE
<222> LOCATION: (50)..(51)
<223> OTHER INFORMATION: May or may not be present
<220> FEATURE:
<221> NAME/KEY: MISC_FEATURE
<222> LOCATION: (3)..(52)
<223> OTHER INFORMATION: This region may encompass 1-10 'Gly(2-4)Ser' repeating units wherein some positions may be absent

<400> SEQUENCE: 114

```
Ala Met Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Ala Met
    50
```

<210> SEQ ID NO 115
<211> LENGTH: 210
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (2)..(6)
<223> OTHER INFORMATION: May or may not be present
<220> FEATURE:
<221> NAME/KEY: MISC_FEATURE
<222> LOCATION: (9)..(13)
<223> OTHER INFORMATION: May or may not be present
<220> FEATURE:
<221> NAME/KEY: MISC_FEATURE
<222> LOCATION: (16)..(20)
<223> OTHER INFORMATION: May or may not be present
<220> FEATURE:
<221> NAME/KEY: MISC_FEATURE
<222> LOCATION: (23)..(27)
<223> OTHER INFORMATION: May or may not be present
<220> FEATURE:
<221> NAME/KEY: MISC_FEATURE
<222> LOCATION: (30)..(34)
<223> OTHER INFORMATION: May or may not be present
<220> FEATURE:
<221> NAME/KEY: MISC_FEATURE
<222> LOCATION: (37)..(41)

-continued

<223> OTHER INFORMATION: May or may not be present
<220> FEATURE:
<221> NAME/KEY: MISC_FEATURE
<222> LOCATION: (44)..(48)
<223> OTHER INFORMATION: May or may not be present
<220> FEATURE:
<221> NAME/KEY: MISC_FEATURE
<222> LOCATION: (51)..(55)
<223> OTHER INFORMATION: May or may not be present
<220> FEATURE:
<221> NAME/KEY: MISC_FEATURE
<222> LOCATION: (58)..(62)
<223> OTHER INFORMATION: May or may not be present
<220> FEATURE:
<221> NAME/KEY: MISC_FEATURE
<222> LOCATION: (65)..(69)
<223> OTHER INFORMATION: May or may not be present
<220> FEATURE:
<221> NAME/KEY: MISC_FEATURE
<222> LOCATION: (72)..(76)
<223> OTHER INFORMATION: May or may not be present
<220> FEATURE:
<221> NAME/KEY: MISC_FEATURE
<222> LOCATION: (79)..(83)
<223> OTHER INFORMATION: May or may not be present
<220> FEATURE:
<221> NAME/KEY: MISC_FEATURE
<222> LOCATION: (86)..(90)
<223> OTHER INFORMATION: May or may not be present
<220> FEATURE:
<221> NAME/KEY: MISC_FEATURE
<222> LOCATION: (93)..(97)
<223> OTHER INFORMATION: May or may not be present
<220> FEATURE:
<221> NAME/KEY: MISC_FEATURE
<222> LOCATION: (100)..(104)
<223> OTHER INFORMATION: May or may not be present
<220> FEATURE:
<221> NAME/KEY: MISC_FEATURE
<222> LOCATION: (107)..(111)
<223> OTHER INFORMATION: May or may not be present
<220> FEATURE:
<221> NAME/KEY: MISC_FEATURE
<222> LOCATION: (114)..(118)
<223> OTHER INFORMATION: May or may not be present
<220> FEATURE:
<221> NAME/KEY: MISC_FEATURE
<222> LOCATION: (121)..(125)
<223> OTHER INFORMATION: May or may not be present
<220> FEATURE:
<221> NAME/KEY: MISC_FEATURE
<222> LOCATION: (128)..(132)
<223> OTHER INFORMATION: May or may not be present
<220> FEATURE:
<221> NAME/KEY: MISC_FEATURE
<222> LOCATION: (135)..(139)
<223> OTHER INFORMATION: May or may not be present
<220> FEATURE:
<221> NAME/KEY: MISC_FEATURE
<222> LOCATION: (142)..(146)
<223> OTHER INFORMATION: May or may not be present
<220> FEATURE:
<221> NAME/KEY: MISC_FEATURE
<222> LOCATION: (149)..(153)
<223> OTHER INFORMATION: May or may not be present
<220> FEATURE:
<221> NAME/KEY: MISC_FEATURE
<222> LOCATION: (156)..(160)
<223> OTHER INFORMATION: May or may not be present
<220> FEATURE:
<221> NAME/KEY: MISC_FEATURE
<222> LOCATION: (163)..(167)
<223> OTHER INFORMATION: May or may not be present
<220> FEATURE:
<221> NAME/KEY: MISC_FEATURE
<222> LOCATION: (170)..(174)
<223> OTHER INFORMATION: May or may not be present
<220> FEATURE:
<221> NAME/KEY: MISC_FEATURE -continued
<222> LOCATION: (177)..(181)
<223> OTHER INFORMATION: May or may not be present
<220> FEATURE:
<221> NAME/KEY: MISC_FEATURE
<222> LOCATION: (184)..(188)
<223> OTHER INFORMATION: May or may not be present
<220> FEATURE:
<221> NAME/KEY: MISC_FEATURE
<222> LOCATION: (191)..(195)
<223> OTHER INFORMATION: May or may not be present
<220> FEATURE:
<221> NAME/KEY: MISC_FEATURE
<222> LOCATION: (198)..(202)
<223> OTHER INFORMATION: May or may not be present
<220> FEATURE:
<221> NAME/KEY: MISC_FEATURE
<222> LOCATION: (205)..(209)
<223> OTHER INFORMATION: May or may not be present
<220> FEATURE:
<221> NAME/KEY: MISC_FEATURE
<222> LOCATION: (1)..(210)
<223> OTHER INFORMATION: This sequence may encompass 1-30 '(Gly)X-Ser' repeating units, wherein X represents 1-6 and wherein some positions may be absent

<400> SEQUENCE: 115

Gly Gly Gly Gly Gly Gly Ser Gly Gly Gly Gly Gly Gly Ser Gly Gly
1 5 10 15

Gly Gly Gly Gly Ser Gly Gly Gly Gly Gly Gly Ser Gly Gly Gly Gly
20 25 30

Gly Gly Ser Gly Gly Gly Gly Gly Gly Ser Gly Gly Gly Gly Gly Gly
35 40 45

Ser Gly Gly Gly Gly Gly Gly Ser Gly Gly Gly Gly Gly Gly Ser Gly
50 55 60

Gly Gly Gly Gly Gly Ser Gly Gly Gly Gly Gly Gly Ser Gly Gly Gly
65 70 75 80

Gly Gly Gly Ser Gly Gly Gly Gly Gly Gly Ser Gly Gly Gly Gly Gly
85 90 95

Gly Ser Gly Gly Gly Gly Gly Gly Ser Gly Gly Gly Gly Gly Gly Ser
100 105 110

Gly Gly Gly Gly Gly Gly Ser Gly Gly Gly Gly Gly Gly Ser Gly Gly
115 120 125

Gly Gly Gly Gly Ser Gly Gly Gly Gly Gly Gly Ser Gly Gly Gly Gly
130 135 140

Gly Gly Ser Gly Gly Gly Gly Gly Gly Ser Gly Gly Gly Gly Gly Gly
145 150 155 160

Ser Gly Gly Gly Gly Gly Gly Ser Gly Gly Gly Gly Gly Gly Ser Gly
165 170 175

Gly Gly Gly Gly Gly Ser Gly Gly Gly Gly Gly Gly Ser Gly Gly Gly
180 185 190

Gly Gly Gly Ser Gly Gly Gly Gly Gly Gly Ser Gly Gly Gly Gly Gly
195 200 205

Gly Ser
210

<210> SEQ ID NO 116
<211> LENGTH: 210
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (2)..(6)
<223> OTHER INFORMATION: May or may not be present
<220> FEATURE:
<221> NAME/KEY: MISC_FEATURE
<222> LOCATION: (9)..(13)
<223> OTHER INFORMATION: May or may not be present
<220> FEATURE:
<221> NAME/KEY: MISC_FEATURE
<222> LOCATION: (16)..(20)
<223> OTHER INFORMATION: May or may not be present
<220> FEATURE:
<221> NAME/KEY: MISC_FEATURE
<222> LOCATION: (23)..(27)
<223> OTHER INFORMATION: May or may not be present
<220> FEATURE:
<221> NAME/KEY: MISC_FEATURE
<222> LOCATION: (30)..(34)
<223> OTHER INFORMATION: May or may not be present
<220> FEATURE:
<221> NAME/KEY: MISC_FEATURE
<222> LOCATION: (37)..(41)
<223> OTHER INFORMATION: May or may not be present
<220> FEATURE:
<221> NAME/KEY: MISC_FEATURE
<222> LOCATION: (44)..(48)
<223> OTHER INFORMATION: May or may not be present
<220> FEATURE:
<221> NAME/KEY: MISC_FEATURE
<222> LOCATION: (51)..(55)
<223> OTHER INFORMATION: May or may not be present
<220> FEATURE:
<221> NAME/KEY: MISC_FEATURE
<222> LOCATION: (58)..(62)
<223> OTHER INFORMATION: May or may not be present
<220> FEATURE:
<221> NAME/KEY: MISC_FEATURE
<222> LOCATION: (65)..(69)
<223> OTHER INFORMATION: May or may not be present
<220> FEATURE:
<221> NAME/KEY: MISC_FEATURE
<222> LOCATION: (72)..(76)
<223> OTHER INFORMATION: May or may not be present
<220> FEATURE:
<221> NAME/KEY: MISC_FEATURE
<222> LOCATION: (79)..(83)
<223> OTHER INFORMATION: May or may not be present
<220> FEATURE:
<221> NAME/KEY: MISC_FEATURE
<222> LOCATION: (86)..(90)
<223> OTHER INFORMATION: May or may not be present
<220> FEATURE:
<221> NAME/KEY: MISC_FEATURE
<222> LOCATION: (93)..(97)
<223> OTHER INFORMATION: May or may not be present
<220> FEATURE:
<221> NAME/KEY: MISC_FEATURE
<222> LOCATION: (100)..(104)
<223> OTHER INFORMATION: May or may not be present
<220> FEATURE:
<221> NAME/KEY: MISC_FEATURE
<222> LOCATION: (107)..(111)
<223> OTHER INFORMATION: May or may not be present
<220> FEATURE:
<221> NAME/KEY: MISC_FEATURE
<222> LOCATION: (114)..(118)
<223> OTHER INFORMATION: May or may not be present
<220> FEATURE:
<221> NAME/KEY: MISC_FEATURE
<222> LOCATION: (121)..(125)
<223> OTHER INFORMATION: May or may not be present
<220> FEATURE:
<221> NAME/KEY: MISC_FEATURE
<222> LOCATION: (128)..(132)
<223> OTHER INFORMATION: May or may not be present
<220> FEATURE:
<221> NAME/KEY: MISC_FEATURE
<222> LOCATION: (135)..(139)
<223> OTHER INFORMATION: May or may not be present
<220> FEATURE:

<221> NAME/KEY: MISC_FEATURE
<222> LOCATION: (142)..(146)
<223> OTHER INFORMATION: May or may not be present
<220> FEATURE:
<221> NAME/KEY: MISC_FEATURE
<222> LOCATION: (149)..(153)
<223> OTHER INFORMATION: May or may not be present
<220> FEATURE:
<221> NAME/KEY: MISC_FEATURE
<222> LOCATION: (156)..(160)
<223> OTHER INFORMATION: May or may not be present
<220> FEATURE:
<221> NAME/KEY: MISC_FEATURE
<222> LOCATION: (163)..(167)
<223> OTHER INFORMATION: May or may not be present
<220> FEATURE:
<221> NAME/KEY: MISC_FEATURE
<222> LOCATION: (170)..(174)
<223> OTHER INFORMATION: May or may not be present
<220> FEATURE:
<221> NAME/KEY: MISC_FEATURE
<222> LOCATION: (177)..(181)
<223> OTHER INFORMATION: May or may not be present
<220> FEATURE:
<221> NAME/KEY: MISC_FEATURE
<222> LOCATION: (184)..(188)
<223> OTHER INFORMATION: May or may not be present
<220> FEATURE:
<221> NAME/KEY: MISC_FEATURE
<222> LOCATION: (191)..(195)
<223> OTHER INFORMATION: May or may not be present
<220> FEATURE:
<221> NAME/KEY: MISC_FEATURE
<222> LOCATION: (198)..(202)
<223> OTHER INFORMATION: May or may not be present
<220> FEATURE:
<221> NAME/KEY: MISC_FEATURE
<222> LOCATION: (205)..(209)
<223> OTHER INFORMATION: May or may not be present
<220> FEATURE:
<221> NAME/KEY: MISC_FEATURE
<222> LOCATION: (1)..(210)
<223> OTHER INFORMATION: This sequence may encompass 1-30 '(Ser)X-Gly' repeating units, wherein X represents 1-6 and wherein some positions may be absent

<400> SEQUENCE: 116

```
Ser Ser Ser Ser Ser Ser Gly Ser Ser Ser Ser Ser Ser Gly Ser Ser
1               5                   10                  15

Ser Ser Ser Ser Gly Ser Ser Ser Ser Ser Ser Gly Ser Ser Ser Ser
            20                  25                  30

Ser Ser Gly Ser Ser Ser Ser Ser Ser Gly Ser Ser Ser Ser Ser Ser
        35                  40                  45

Gly Ser Ser Ser Ser Ser Ser Gly Ser Ser Ser Ser Ser Ser Gly Ser
    50                  55                  60

Ser Ser Ser Ser Ser Gly Ser Ser Ser Ser Ser Ser Gly Ser Ser Ser
65                  70                  75                  80

Ser Ser Ser Gly Ser Ser Ser Ser Ser Ser Gly Ser Ser Ser Ser Ser
                85                  90                  95

Ser Gly Ser Ser Ser Ser Ser Ser Gly Ser Ser Ser Ser Ser Ser Gly
            100                 105                 110

Ser Ser Ser Ser Ser Ser Gly Ser Ser Ser Ser Ser Ser Gly Ser Ser
        115                 120                 125

Ser Ser Ser Ser Gly Ser Ser Ser Ser Ser Ser Gly Ser Ser Ser Ser
    130                 135                 140

Ser Ser Gly Ser Ser Ser Ser Ser Ser Gly Ser Ser Ser Ser Ser Ser
145                 150                 155                 160

Gly Ser Ser Ser Ser Ser Ser Gly Ser Ser Ser Ser Ser Ser Gly Ser
```

165 170 175

Ser Ser Ser Ser Ser Gly Ser Ser Ser Ser Ser Ser Gly Ser Ser Ser
180 185 190

Ser Ser Ser Gly Ser Ser Ser Ser Ser Ser Gly Ser Ser Ser Ser Ser
195 200 205

Ser Gly
210

<210> SEQ ID NO 117
<211> LENGTH: 150
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(150)
<223> OTHER INFORMATION: This sequence may encompass 1-30 'Gly-Gly-Gly-Gly-Ser' repeating units wherein some positions may be absent

<400> SEQUENCE: 117

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser Gly Gly Gly Gly Ser Gly Gly Gly Gly Ser Gly Gly Gly Gly
50 55 60

Ser Gly Gly Gly Gly Ser Gly Gly Gly Gly Ser Gly Gly Gly Gly Ser
65 70 75 80

Gly Gly Gly Gly Ser Gly Gly Gly Gly Ser Gly Gly Gly Gly Ser Gly
85 90 95

Gly Gly Gly Ser Gly Gly Gly Gly Ser Gly Gly Gly Gly Ser Gly Gly
100 105 110

Gly Gly Ser Gly Gly Gly Gly Ser Gly Gly Gly Gly Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser
145 150

<210> SEQ ID NO 118
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (2)..(30)
<223> OTHER INFORMATION: May or may not be present wherein some positions may be absent

<400> SEQUENCE: 118

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly Gly Gly Gly
20 25 30

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

```
Gly Lys Ser Ser Gly Ser Gly Ser Glu Ser Lys Ser
1               5                   10
```

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

```
Gly Ser Thr Ser Gly Ser Gly Lys Ser Ser Glu Gly Lys Gly
1               5                   10
```

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

```
Gly Ser Thr Ser Gly Ser Gly Lys Ser Ser Glu Gly Ser Gly Ser Thr
1               5                   10                  15

Lys Gly
```

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

```
Gly Ser Thr Ser Gly Ser Gly Lys Pro Gly Ser Gly Glu Gly Ser Thr
1               5                   10                  15

Lys Gly
```

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

```
Glu Gly Lys Ser Ser Gly Ser Gly Ser Glu Ser Lys Glu Phe
1               5                   10
```

<210> SEQ ID NO 124
<211> LENGTH: 5
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 124

Ser Arg Ser Ser Gly
1 5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Ser Gly Ser Ser Cys
1 5

<210> SEQ ID NO 126
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Ala Met Gly Arg Ser Gly Gly Gly Cys Ala Gly Asn Arg Val Gly Ser
1 5 10 15

Ser Leu Ser Cys Gly Gly Leu Asn Leu Gln Ala Met
20 25

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Gly Gly Gly Gly Ser Gly Gly Gly Gly Ser Gly Gly Gly Gly Ser
1 5 10 15

<210> SEQ ID NO 128
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Gly Gly Gly Ser
1

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Gly Gly Gly Gly Ser
1 5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Gly Gly Gly Gly Ser Gly Gly Gly
1 5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Gly Gly Ser Gly Gly Gly Gly
1 5

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Gly Ser Thr Ser Gly Gly Gly Ser Gly Gly Gly Ser Gly Gly Gly Gly
1 5 10 15

Ser Ser

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Gly Ser Thr Ser Gly Ser Gly Lys Pro Gly Ser Ser Glu Gly Ser Thr
1 5 10 15

Lys Gly

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Asn Trp Ser His Pro Gln Phe Glu Lys
1 5

-continued

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Gly Ile Asp Pro Glu Glu Gly Arg Phe Asn Asn
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

His Gly Gln Asp Ser Val Arg Val Gly Arg
1               5                   10

DE-IMMUNIZED SHIGA TOXIN A SUBUNIT EFFECTOR POLYPEPTIDES FOR APPLICATIONS IN MAMMALS

CROSS-REFERENCE TO RELATED APPLICATIONS

This application is a continuation of U.S. application Ser. No. 15/114,487, filed Jul. 27, 2016, now abandoned, which is a national stage application of International Application No. PCT/US2015/012970, filed Jan. 26, 2015, which claims the benefit of U.S. Provisional Application No. 62/049,325, filed Sep. 11, 2014 and U.S. Provisional Application No. 61/932,000, filed Jan. 27, 2014, the contents of all of which are herein incorporated by reference in their entireties.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Jun. 11, 2021, is named MTEM_024_03US_SeqList_ST25.txt and is about 175 kilobytes in size.

FIELD OF THE INVENTION

The present invention relates to de-immunized Shiga toxin effector polypeptides derived from A Subunits of naturally occurring Shiga toxins. Polypeptides of the invention are beneficial alone or as components of molecules, e.g. therapeutics, for administration to mammals where reducing associated immune responses is desirable. For example, the polypeptides of this invention may be used as components of specifically targeted molecules, e.g. immunotoxins and ligand-toxin fusions, for the targeted killing of specific cell types. Proteins of the invention have uses as, e.g., components of therapeutics and diagnostics for the diagnosis, prognosis, and treatment of a variety of diseases, disorders and conditions, including cancers, tumors, immune disorders, and microbial infections.

BACKGROUND

Shiga toxins have been synthetically engineered for medical applications by rational alterations to the toxin's structure, characteristics, and biological activities (see, e.g. U.S. Pat. No. 7,713,915, EP1051482, EP1727827, EP1945660; applications: US2009/0156417 A1, EP2228383 B1, EP2402367 A1, US2013/0196928 A1, WO2014164680, WO201464693, U.S. 61/951,110; U.S. 61/951,121, each of which is incorporated by reference herein in its entirety). Shiga toxin A Subunits are stable, enzymatically active, and cytotoxic even if truncated or fused to other protein domains (Haddad J et al., *J Bacteriol* 175: 4970-8 (1993); Al-Jaufy A et al., *Infect Immun* 62: 956-60 (1994); Al-Jaufy A et al., *Infect Immun* 63: 3073-8 (1995); LaPointe P. et al., *J Biol Chem* 280: 23310-18 (2005); Di R et al., *Toxicon* 57: 525-39 (2011)). These Shiga toxin A Subunit-derived polypeptides may be linked or fused to immunoglobulin domains or receptor ligands through chemical conjugation or recombinant protein engineering in order to create cell-targeted therapeutic molecules. One aim of such molecular engineering is to design chimeric molecules with the dual functionality of: 1) delivering toxins to specific cell types or places within an organism after systemic administration; and 2) effectuating a targeted cytotoxicity to specific cells using potent cytotoxic mechanisms effective in eukaryotic cells.

One of the main limitations of therapeutic applications involving synthetically engineered proteins from non-human sources is immunogenicity. Antigenicity and/or immunogenicity results from the ability of an antigenic epitope of a molecule to induce an antibody and/or immune response when that molecule is administered in vivo. Most therapeutic proteins are believed to induce an immune response of some sort, which ranges from production of low-level, low-affinity and transient antibodies like IgM to high-level, high-affinity IgG antibodies (Schellekens H, *Clin Ther* 24: 1720-30 (2002); Schellekens H, *Nat Rev Drug Discov* 1: 457-62 (2002)). Unwanted immunogenicity of a therapeutic product could result in unfavorable consequences, such as a reduced efficacy, altered pharmacokinetics, general immune and hypersensitivity reactions, anaphylaxis, and anaphylactoid reactions (Buttel I et al., *Biologicals* 39: 100-9 (2011)). For example, the production of neutralizing antibodies or anti-drug antibodies in a patient can limit the long-term effectiveness of repeated doses or chronic administration of a therapeutic.

Because unwanted immune responses can pose significant safety and/or efficacy issue(s) for a therapeutic, minimizing antigenicity and/or immunogenicity is often desirable when developing therapeutic proteins. Unfortunately, at present and, despite extensive laboratory and clinical research, it is not possible to predict before administration to a patient the extent to which a novel therapeutic protein will be immunogenic (Descotes J, Gouraud A, *Expert Opin Drug Metab Toxicol* 4: 1537-49 (2008)). This is due in large part to both a lack of current understanding about and the heterogeneity of mechanisms of antibody generation by the adaptive immune systems of vertebrates. For example, analyses of antigen-antibody complexes have revealed no determinative structural feature(s) of a generic epitope, except perhaps for a higher likelihood of exposed hydrophilic and bulky amino acids with high solvent accessible surface areas.

Despite these difficulties, various strategies are presently utilized to reduce the immunogenic potential of a protein (see e.g. Onda M et al., *Proc. Natl Acad Sci USA* 105: 11311-6 (2008); Vallera D et al., *Mol Cancer Ther* 9: 1872-83 (2010)). The immunogenic potential of a protein can be reduced by removing or disrupting epitopes likely to be recognized by the adaptive immune system. Epitope disruption or removal can be accomplished by mutation, e.g. truncation, deletion, or amino acid substitution, or humanization (Nagata S, Pastan I, *Adv Drug Deliv Rev* 61: 977-85 (2009); Baker M et al., *Self Nonself* 1: 314-22 (2010)).

For de-immunization of a therapeutic molecule, priority is often given to identifying and disrupting B-lymphocyte (B-cell) antigenic epitopes likely to produce high affinity antibodies due to affinity maturation. After antigen activation, B-cells can differentiate into either plasma cells or memory cells. Activated B-cells can undergo class-switching to change from expressing low-affinity IgM and IgD antibodies to expressing a single Ig isotype, IgG, IgE, IgA, or IgD, which recognizes a discrete antigenic epitope (Klein U et al., *Nat Rev Immunol* 8: 22-33 (2008)). Activated B-cells expressing single Ig isotypes can undergo selection for those B-cells which produce antibodies with high-affinity to specific antigenic epitopes. Thus, the disruption of an epitope in a therapeutic may prevent, upon administration to a subject of the therapeutic, the production of high affinity antibodies that specifically bind that epitope as well as the formation of long-lived memory B-cells targeting that epitope.

Currently there are no standard techniques for accurate and comprehensive B-cell epitope prediction in a polypeptide (Sathish J et al., *Nat Rev Drug Discov* 12: 306-24 (2013)). B-cell epitopes can be identified by various empirical methods using a combination of mutagenesis and antibodies, immunization, or phage display screening of immunoglobulin libraries. Putative B-cell epitopes can be predicted using computational tools which scan for predicted linear and discontinuous epitopes in a given polypeptide sequence which may then be disrupted in attempts to silence them (Larsen et al., *Immunome Res* 2: 2 (2006); El-Manzalawy et al., *J Mol Recognit* 21: 243-55 (2008); Sollner J et al., *Immunome Res* 4: 1 (2008); Bryson C et al., *BioDrugs* 24: 1-8 (2010); Yao B et al., *PLoS One* 8: e62249 (2013)). These computational B-cell epitope predictions are not highly accurate and thus must be verified experimentally (see Nagata, *Adv Drug Deliv Rev* 61: 977-85 (2009)). Epitope disruption is often attempted by mutating charged and/or aromatic residues within putative B-cell epitopes to alanine residues (Onda M et al., *J Immunol* 177: 8822-34 (2006); Lui W et al., *Proc Natl Acad Sci USA* 109: 11782-7 (2012); Yumura K et al., *Protein Sci* 22: 213-21 (2012)). Furthermore, the accurate mapping and disruption of all potential epitopes, while maintaining biotherapeutic activity, may be an elusive goal for larger proteins (Brauer F et al., *Antimicrob Agents Chemother* 57: 678-88 (2013)).

Shiga toxins show promise for being engineered into useful products for therapeutic and diagnostic applications, but their potential immunogenicity may be an obstacle to uses in medical applications. Shiga toxins are bacterial proteins which are highly foreign to the human immune system. However, the antigenic and/or immunogenic sites within the A Subunits of Shiga toxins have not been systematically mapped. It would be desirable to have improved Shiga toxin A Subunit-derived polypeptides with reduced antigenicity and/or immunogenicity which retain sufficient Shiga toxin effector functions for medical applications, e.g., as components of various therapeutics involving targeted delivery of cytotoxicity to specific cell types.

SUMMARY OF THE INVENTION

The present invention provides Shiga toxin effector polypeptides which have reduced antigenic and/or immunogenic potential in mammals (referred to herein as "de-immunized"). In addition, the present invention provides cytotoxic proteins and diagnostic proteins comprising de-immunized Shiga toxin effector polypeptides. De-immunized polypeptides derived from Shiga toxin A Subunits may be linked to one or more polypeptides that mediate cell targeting via specific extracellular binding interactions to enable the engineering of improved therapeutics for cell type specific targeting of cellular internalization and Shiga toxin cytotoxicity. The linking of detection promoting agents with de-immunized Shiga toxin effector region polypeptides enables the engineering of improved diagnostic molecules for detecting the presence of specific cell types. The polypeptides and proteins of the invention have uses for targeted cell killing, delivering exogenous materials into specific cell types, obtaining diagnostic information, and as therapeutics for the treatment of a variety of diseases, disorders, and conditions, including cancers, immune disorders, and microbial infections.

A polypeptide of the invention comprises a Shiga toxin effector region comprising a polypeptide derived from the amino acid sequence of the A Subunit of at least one member of the Shiga toxin family with at least one predicted B-cell epitope removed or disrupted by mutation in such a way that at least one Shiga toxin effector function is retained.

Certain embodiments of the polypeptides of the invention comprise a Shiga toxin effector region comprising a polypeptide derived from the amino acid sequence of the A Subunit of at least one member of the Shiga toxin family with at least one predicted B-cell epitope removed or disrupted by mutation in such a way that at least one Shiga toxin effector function is retained; and wherein an ectopic, MHC class I-restricted, T-cell epitope is not introduced by any B-cell epitope disruption. MHC class I-restricted, T-cell epitopes are known or can be predicted by the skilled worker. The term ectopic refers to MHC class I-restricted, T-cell epitopes which are not natively present in the polypeptide before said polypeptide was de-immunized, i.e. the parental polypeptide before one or more B-cell epitope was removed and/or disrupted.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected from the group of natively positioned amino acid residues consisting of: 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; or 210-218 of SEQ ID NO:3; wherein the Shiga toxin effector region is capable of exhibiting a Shiga toxin effector function.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected from the group of natively positioned amino acid residues consisting of: 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; or 210-218 of SEQ ID NO:3; wherein the Shiga toxin effector region is capable of exhibiting a significant level of a Shiga toxin effector function.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected the group of natively positioned amino acid residues consisting of: 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; or 210-218 of SEQ ID NO:3; wherein the Shiga toxin effector region is capable of a Shiga toxin effector function; and wherein the disruption is not of a single epitope region and does not consist solely of the amino acid residue substitution selected from the group consisting of: S96Y of SEQ ID NO:1 or SEQ ID NO:2; Y114S of SEQ ID NO:1 or SEQ ID NO:2; R179A of SEQ ID NO:1 or SEQ ID NO:2; R179H of SEQ ID NO:1 or SEQ ID NO:2; L185A of SEQ ID NO:1 or SEQ ID NO:2; R188A of SEQ ID NO:1 or SEQ ID NO:2; R205A of SEQ ID NO:1 or SEQ ID NO:2; R179A/R188A of SEQ ID NO:1; or SEQ ID NO:2; or A188V of SEQ ID NO:3.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected from the group of natively positioned amino acid residues consisting of: 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; or 210-218 of SEQ ID NO:3; wherein the Shiga toxin effector region is capable of exhibiting a significant level of a Shiga toxin effector function; and wherein the disruption is not of a single epitope region and does not consist solely of the amino acid residue substitution selected from the group consisting of: S96Y of SEQ ID NO:1 or SEQ ID NO:2; Y114S of SEQ ID NO:1 or SEQ ID NO:2; R179A of SEQ ID NO:1 or SEQ ID NO:2; R179H of SEQ ID NO:1 or SEQ ID NO:2; L185A of SEQ ID NO:1 or SEQ ID NO:2; R188A of SEQ ID NO:1 or SEQ ID NO:2; R205A of SEQ ID NO:1 or SEQ ID NO:2; R179A/R188A of SEQ ID NO:1; or SEQ ID NO:2; or A188V of SEQ ID NO:3.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected from the group of natively positioned amino acid residues consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; wherein the Shiga toxin effector region is capable of exhibiting a Shiga toxin effector function; and wherein the Shiga toxin effector region comprises no amino terminus truncation overlapping with a disrupted epitope region of the Shiga toxin A Subunit from which derived which overlaps with a disrupted epitope region.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected from the group of natively positioned amino acid residues consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; wherein the Shiga toxin effector region is capable of exhibiting a significant level of a Shiga toxin effector function; and wherein the Shiga toxin effector region comprises no amino terminus truncation overlapping with a disrupted epitope region of the Shiga toxin A Subunit from which derived which overlaps with a disrupted epitope region.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected from the group of natively positioned amino acid residues consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; wherein the Shiga toxin effector region is capable of exhibiting a Shiga toxin effector function; wherein the disruption is not of a single epitope region and does not consist solely of the amino acid residue substitution R63W of SEQ ID NO:1 or SEQ ID NO:2; and wherein the Shiga toxin effector region comprises no amino terminus truncation overlapping with a disrupted epitope region of the Shiga toxin A Subunit from which derived which overlaps with a disrupted epitope region.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected from the group of natively positioned amino acid residues consisting of: 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; wherein the Shiga toxin effector region is capable of exhibiting a Shiga toxin effector function; and wherein the Shiga toxin effector region comprises no carboxy terminus truncation overlapping with a disrupted epitope region of the of the Shiga toxin A Subunit from which derived which overlaps with a disrupted epitope region.

Certain embodiments of the invention provide polypeptides comprising a de-immunized Shiga toxin effector region comprising an amino acid sequence derived from an A Subunit of a member of the Shiga toxin Family, the Shiga toxin effector region comprising a disruption of at least one epitope region of the Shiga toxin A Subunit amino acid sequence selected from the group of natively positioned amino acid residues consisting of: 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; wherein the Shiga toxin effector region is capable of exhibiting a Shiga toxin effector function; wherein the disruption is not of a single epitope region and does not solely consist of the amino acid residue substitution selected from the group consisting of: R248H of SEQ ID NO:1 or SEQ ID NO:2; A250V of SEQ ID NO:1 or SEQ ID NO:2; R251H of SEQ ID NO:1 or SEQ ID NO:2; A253G of SEQ ID NO:1 or SEQ ID NO:2; S254T of SEQ ID NO:1 or SEQ ID NO:2; C261A of SEQ ID NO:1 or SEQ ID NO:2; R289K of SEQ ID NO:1 or SEQ ID NO:2; R248H and R251H of SEQ ID NO:1 or SEQ ID NO:2; A253G and S254T of SEQ ID NO:1 or SEQ ID NO:2; the deletion of S247-M252 of SEQ ID NO:1; S246F of SEQ ID NO:3; A282V of SEQ ID NO:3; I291V of SEQ ID NO:3; S246F/I291V of SEQ ID NO:3; and wherein the Shiga toxin effector region comprises no carboxy terminus truncation overlapping with a disrupted epitope region of the of the Shiga toxin A Subunit from which derived which overlaps with a disrupted epitope region.

In certain further embodiments, the de-immunized Shiga toxin effector region polypeptide of the invention comprises an epitope disruption which comprises a deletion of at least one amino acid within an epitope region provided herein. In certain further embodiments, a polypeptide of the invention comprises an epitope disruption which comprises an insertion of at least one amino acid within an epitope region provided. In certain further embodiments, the polypeptides comprise a disruption which comprises an inversion or other rearrangement of amino acids, wherein at least one inverted amino acid is within the epitope region provided. In certain further embodiments, the polypeptides comprise an epitope disruption which comprises an amino acid residue mutation, such as a single amino acid substitution to a non-standard amino acid or an amino acid with a chemically modified side chain.

In certain embodiments, the de-immunized Shiga toxin effector regions comprise an epitope disruption which comprises an amino acid residue substitution within an epitope region provided herein. In certain further embodiments, the polypeptides comprise at least one substitution to an amino acid selected from the group consisting of: A, G, V, L, I, P, C, M, F, S, D, N, Q, H, and K. In certain further embodiments, the polypeptide comprise a substitution selected from the group consisting of: D to A, D to G, D to V, D to L, D to I, D to F, D to S, D to Q, E to A, E to G, E to V, E to L, E to I, E to F, E to S, E to Q, E to N, E to D, E to M, E to R, G to A, H to A, H to G, H to V, H to L, H to I, H to F, H to M, K to A, K to G, K to V, K to L, K to I, K to M, K to H, L to A, L to G, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, Y to A, Y to G, Y to V, Y to L, Y to I, Y to F, and Y to M.

In certain embodiments, the de-immunized Shiga toxin effector regions comprise a disruption which comprises an amino acid residue substitution within an epitope region, wherein the substitution occurs at the natively positioned amino acid selected from the group of natively positioned amino acid residues consisting of: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 45 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 53 of SEQ ID NO:1 or SEQ ID NO:2; 55 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 109 of SEQ ID NO:1, SEQ ID NO:2, or SEQ ID NO:3; 110 of SEQ ID NO:1 or SEQ ID NO:2; 112 of SEQ ID NO:1, SEQ ID NO:2, or SEQ ID NO:3; SE 147 of SEQ ID NO:1, SEQ ID NO:2, or SEQ ID NO:3; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 204 of SEQ ID NO:3; 205 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2. In certain further embodiments, the polypeptides comprise an epitope disruption which comprises an amino acid residue substitution within an epitope region, wherein the substitution is to any non-conservative amino acid and the substitution occurs at the amino acid residue selected from the group of natively positioned amino acid residues consisting of: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 45 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 53 of SEQ ID NO:1 or SEQ ID NO:2; 55 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 109 of SEQ ID NO:1, SEQ ID NO:2, or SEQ ID NO:3; 110 of SEQ ID NO:1 or SEQ ID NO:2; 112 of SEQ ID NO:1, SEQ ID NO:2, or SEQ ID NO:3; SE 147 of SEQ ID NO:1, SEQ ID NO:2, or SEQ ID NO:3; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 204 of SEQ ID NO:3; 205 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2. A non-conservative amino acid substitution is a substitution of one amino acid with another amino acid which has one or more markedly different biochemical properties, such as, e.g., charged to uncharged, polar to hydrophobic, and bulky to small. In certain further embodiments, the polypeptides comprise an epitope disruption which comprises an amino acid residue substitution within an epitope region, wherein the substitution occurs at the natively positioned amino acid residue and the substitution is to an amino acid selected from the group consisting of: K1 to A, G, V, L, I, F, M and H; T4 to A, G, V, L, I, F, M, and S; S8 to A, G, V, I, L, F, and M; T9 to A, G, V, I, L, F, M, and S; S9 to A, G, V, L, I, F, and M; K11 to A, G, V, L, I, F, M and H; S33 to A, G, V, L, I, F, and M; S45 to A, G, V, L, I, F, and M; T45 to A, G, V, L, I, F, and M; D47 to A, G, V, L, I, F, S, and Q; N48 to A, G, V, L, and M; L49 to A or G; D53 to A, G, V, L, I, F, S, and Q; R55 to A, G, V, L, I, F, M, Q, S, K, and H; D58 to A, G, V, L, I, F, S, and Q; P59 to A, G, and F; E60 to A, G, V, L, I, F, S, Q, N, D, M, and R; E61 to A, G, V, L, I, F, S, Q, N, D, M, and R; G62 to A; D94 to A, G, V, L, I, F, S, and Q; S96 to A, G, V, I, L, F, and M; S109 to A, G, V, I, L, F, and M; T109 to A, G, V, I, L, F, M, and S; G110 to A; S112 to A, G, V, L, I, F, and M; G147 to A; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; S186 to A, G, V, I, L, F, and M; G187 to A; R188 to A, G, V, L, I, F, M, Q, S, K, and H; 5189 to A, G, V, I, L, F, and M; R204 to A, G, V, L, I, F, M, Q, S, K, and H; R205 to A, G, V, L, I, F, M, Q, S, K and H; 5247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, M, and S.

For certain embodiments, the polypeptides of the invention comprise the de-immunized Shiga toxin effector region derived from amino acids 75 to 251 of SEQ ID NO:1, SEQ ID NO:2, or SEQ ID NO:3. In certain further embodiments, the polypeptides of the invention comprise a de-immunized Shiga toxin effector region derived from amino acids 1 to 251 of SEQ ID NO:1, SEQ ID NO:2, or SEQ ID NO:3; and/or amino acids 1 to 261 of SEQ ID NO:1, SEQ ID NO:2, or SEQ ID NO:3. In certain embodiments, the polypeptides of the invention comprise the de-immunized Shiga toxin effector region derived from amino acids 1 to 241 SEQ ID NO:1, SEQ ID NO:2, or SEQ ID NO:3.

For certain embodiments, the polypeptides of the invention comprise the de-immunized Shiga toxin effector region comprising or consisting essentially of any one of SEQ ID NOs: 4-52.

Certain embodiments of the invention provide a protein comprising a binding region for cell targeting linked to a de-immunized Shiga-toxin-Subunit-A derived region which exhibits one or more Shiga toxin effector function(s), e.g. cytotoxic activity. The proteins of the invention comprise a de-immunized Shiga toxin effector region comprising a polypeptide of the invention and a binding region comprising one or more polypeptides which are capable of specifically binding at least one extracellular target biomolecule.

In certain embodiments of the proteins of the present invention, the binding region comprises a polypeptide selected from the group consisting of: a complementary determining region 3 (CDR3) fragment constrained FR3-CDR3-FR4 (FR3-CDR3-FR4) polypeptide, single-domain antibody fragment (sdAb), nanobody, heavy-chain antibody domain derived from a camelid (VHH fragment), heavy-chain antibody domain derived from a cartilaginous fish, immunoglobulin new antigen receptors (IgNARs), $V_{NAR}$ fragment, single-chain variable fragment (scFv), antibody variable fragment (Fv), antigen-binding fragment (Fab), Fd fragment, small modular immunopharmaceutical (SMIP) domain, fibronectin-derived $10^{th}$ fibronectin type III domain (10Fn3) (e.g. monobody), tenacsin type III domain (e.g. TNfn3), ankyrin repeat motif domain (ARD), low-density-lipoprotein-receptor-derived A-domain (A domain of LDLR or LDLR-A), lipocalin (anticalin), Kunitz domain, Protein-A-derived Z domain, gamma-B crystalline-derived domain (Affilin), ubiquitin-derived domain, Sac7d-derived polypeptide, Fyn-derived SH2 domain (affitin), miniprotein, C-type lectin-like domain scaffold, engineered antibody mimic, and any genetically manipulated counterparts of any of the foregoing that retain binding functionality.

In certain embodiments of the present invention, upon administration of the de-immunized cytotoxic protein of the present invention to a cell physically coupled with an extracellular target biomolecule of the binding region of the cytotoxic protein, the cytotoxic protein is capable of causing death of the cell.

In certain embodiments of the present invention, upon administration of the de-immunized cytotoxic protein of the present invention to two different populations of cell types with respect to the presence of an extracellular target biomolecule, the cytotoxic protein is capable of causing cell death to the cell-types physically coupled with an extracellular target biomolecule of the cytotoxic protein's binding region at a $CD_{50}$ at least three times or less than the $CD_{50}$ to cell types which are not physically coupled with an extracellular target biomolecule of the cytotoxic protein's binding region.

In certain embodiments of the proteins of the present invention, the binding region is designed or selected by its ability to bind an extracellular target biomolecule selected from the group consisting of: CD20, CD22, CD40, CD79, CD25, CD30, HER2/neu/ErbB2, EGFR, EpCAM, EphB2, prostate-specific membrane antigen, Cripto, CDCP1, endoglin, fibroblast activated protein, Lewis-Y, CD19, CD21, CS1/SLAMF7, CD33, CD52, EpCAM, CEA, gpA33, Mucins, TAG-72, carbonic anhydrase IX, folate binding protein, ganglioside GD2, ganglioside GD3, ganglioside GM2, ganglioside Lewis-Y2, VEGFR, Alpha Vbeta3, Alpha5beta1, ErbB1/EGFR, Erb3, c-MET, IGF1R, EphA3, TRAIL-R1, TRAIL-R2, RANKL, FAP, Tenascin, CD64, mesothelin, BRCA1, MART-1/MelanA, gp100, tyrosinase, TRP-1, TRP-2, MAGE-1, MAGE-3, GAGE-1/2, BAGE, RAGE, NY-ESO-1, CDK-4, beta-catenin, MUM-1, caspase-8, KIAA0205, HPVE6, SART-1, PRAME, carcinoembryonic antigen, prostate specific antigen, prostate stem cell antigen, human aspartyl (asparaginyl) beta-hydroxylase, EphA2, HER3/ErbB-3, MUC1, MART-1/MelanA, gp100, tyrosinase associated antigen, HPV-E7, Epstein Barr Virus antigens, Bcr-Abl, alpha-fetoprotein antigen, 17-A1, bladder tumor antigen, CD38, CD15, CD23, CD52, CD53, CD88, CD129, CD183, CD191, CD193, CD244, CD294, CD305, C3AR, FceRla, galectin-9, mrp-14, siglec-8, siglec-10, CD49d, CD13, CD44, CD54, CD63, CD69, CD123, CD193, TLR4, FceRla, IgE, CD107a, CD203c, CD14, CD15, CD33, CD64, CD68, CD80, CD86, CD105, CD115, F4/80, ILT-3, Galectin-3, CD11a-c, GITRL, MHC Class II, CD284-TLR4, CD107-Mac3, CD195-CCR5, HLA-DR, CD16/32, CD282-TLR2, CD11c, CD123, and any immunogenic fragment of any of the foregoing.

In certain embodiments, the proteins of the invention comprise a carboxy-terminal endoplasmic reticulum retention/retrieval signal motif of a member of the KDEL family. In certain further embodiments, the proteins of the present invention comprise a carboxy-terminal endoplasmic reticulum retention/retrieval signal motif is selected from the group consisting of: KDEL (SEQ ID NO: 60), HDEF (SEQ ID NO: 61), HDEL (SEQ ID NO: 62), RDEF (SEQ ID NO: 63), RDEL (SEQ ID NO: 64), WDEL (SEQ ID NO: 65), YDEL (SEQ ID NO: 66), HEEF (SEQ ID NO: 67), HEEL (SEQ ID NO: 68), KEEL (SEQ ID NO: 69), REEL (SEQ ID NO: 70), KAEL (SEQ ID NO: 71), KCEL (SEQ ID NO: 72), KFEL (SEQ ID NO: 73), KGEL (SEQ ID NO: 74), KHEL (SEQ ID NO: 75), KLEL (SEQ ID NO: 76), KNEL (SEQ ID NO: 77), KQEL (SEQ ID NO: 78), KREL (SEQ ID NO: 79), KSEL (SEQ ID NO: 80), KVEL (SEQ ID NO: 81), KWEL (SEQ ID NO: 82), KYEL (SEQ ID NO: 83), KEDL (SEQ ID NO: 84), KIEL (SEQ ID NO: 85), DKEL (SEQ ID NO: 86), FDEL (SEQ ID NO: 87), KDEF (SEQ ID NO: 88), KKEL (SEQ ID NO: 89), HADL (SEQ ID NO: 90), HAEL (SEQ ID NO: 91), HIEL (SEQ ID NO: 92), HNEL (SEQ ID NO:

93), HTEL (SEQ ID NO: 94), KTEL (SEQ ID NO: 95), HVEL (SEQ ID NO: 96), NDEL (SEQ ID NO: 97), QDEL (SEQ ID NO: 98), REDL (SEQ ID NO: 99), RNEL (SEQ ID NO: 100), RTDL (SEQ ID NO: 101), RTEL (SEQ ID NO: 102), SDEL (SEQ ID NO: 103), TDEL (SEQ ID NO: 104), and SKEL (SEQ ID NO: 105).

For certain embodiments, the protein of the present invention comprises a binding region and a de-immunized Shiga toxin effector region which are physically oriented within the protein such that said binding region is not located adjacent to the amino-terminus of the Shiga toxin effector region.

For certain embodiments, the proteins of the present invention comprise a Shiga toxin effector region derived from amino acids 75 to 251 of SEQ ID NO:1, SEQ ID NO:2, or SEQ ID NO:3. Certain further embodiments provide proteins in which the Shiga toxin effector region is derived from amino acids 1 to 251 of SEQ ID NO:1, SEQ ID NO:2, or SEQ ID NO:3; and/or amino acids 1 to 261 of SEQ ID NO:1, SEQ ID NO:2, or SEQ ID NO:3. In certain embodiments, the proteins of the present invention comprise a Shiga toxin effector region is derived from amino acids 1 to 241 SEQ ID NO:1, SEQ ID NO:2, or SEQ ID NO:3.

For certain embodiments, the proteins of the invention comprise the de-immunized Shiga toxin effector region comprising or consisting essentially of any one of SEQ ID NOs: 4-52.

For certain embodiments, the protein of the present invention comprises or consists essentially of SEQ ID NO:53, SEQ ID NO:54, SEQ ID NO:55, SEQ ID NO:56, SEQ ID NO:57, SEQ ID NO:58, or SEQ ID NO:59.

In certain embodiments, the proteins of the invention comprise a de-immunized Shiga toxin effector region which further comprises a mutation relative to a naturally occurring A Subunit of a member of the Shiga toxin family that changes the enzymatic activity of the Shiga toxin effector region, the mutation selected from at least one amino acid residue deletion or substitution, such as, e.g., A231E, R75A, Y77S, Y114S, E167D, R170A, R176K and/or W203A in SEQ ID NO:1, SEQ ID NO:2, or SEQ ID NO:3. In certain further embodiments, the proteins of the present invention comprise a mutation which reduces or eliminates catalytic activity but retains at least one other Shiga toxin effector function(s).

The present invention also provides pharmaceutical compositions comprising a polypeptide and/or protein of the invention and at least one pharmaceutically acceptable excipient or carrier; and the use of such a protein or a composition comprising it in methods of the invention as further described herein.

Beyond the polypeptides, proteins, and compositions of the present invention, polynucleotides capable of encoding a polypeptide comprising a de-immunized Shiga toxin effector region or protein of the present invention comprising a de-immunized Shiga toxin effector region of the invention are within the scope of the present invention, as well as expression vectors which comprise a polynucleotide of the invention and host cells comprising an expression vector of the invention. Host cells comprising an expression vector may be used, e.g., in methods for producing a polypeptide and/or protein of the invention, or a polypeptide component or fragment thereof, by recombinant expression.

Additionally, the present invention provides methods of selectively killing cell(s) comprising the step of contacting a cell(s) with a protein of the invention or a pharmaceutical composition comprising such a protein of the invention. In certain embodiments, the step of contacting the cell(s) occurs in vitro. In certain other embodiments, the step of contacting the cell(s) occurs in vivo.

The present invention further provides methods of treating diseases, disorders, and/or conditions in patients in need thereof comprising the step of administering to a patient in need thereof a therapeutically effective amount of a composition comprising a de-immunized Shiga toxin effector region polypeptide of the invention, a polypeptide and/or protein comprising it, or a composition comprising any of the foregoing (e.g., a pharmaceutical composition). In certain embodiments, the disease, disorder, or condition to be treated using this method of the invention is selected from: a cancer, tumor, immune disorder, or microbial infection. In certain embodiments of this method, the cancer to be treated is selected from the group consisting of: bone cancer, breast cancer, central/peripheral nervous system cancer, gastrointestinal cancer, germ cell cancer, glandular cancer, head-neck cancer, hematological cancer, kidney-urinary tract cancer, liver cancer, lung/pleura cancer, prostate cancer, sarcoma, skin cancer, and uterine cancer. In certain embodiments of this method, the immune disorder to be treated is an immune disorder associated with a disease selected from the group consisting of: amyloidosis, ankylosing spondylitis, asthma, Crohn's disease, diabetes, graft rejection, graft-versus-host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjogren's syndrome, ulcerative colitis, and vasculitis.

Among certain embodiments of the present invention is a composition comprising a de-immunized Shiga toxin effector region polypeptide of the invention, a polypeptide and/or protein comprising it, or a composition comprising any of the foregoing, for the treatment or prevention of a cancer, tumor, immune disorder, or microbial infection. Among certain embodiments of the present invention is the use of a composition of matter of the invention in the manufacture of a medicament for the treatment or prevention of a cancer, tumor, immune disorder, or microbial infection.

Certain embodiments of the proteins of the present invention may be used to deliver one or more additional exogenous materials into a cell physically coupled with an extracellular target biomolecule of the protein of the present invention. Additionally, the present invention provides a method for delivering exogenous material to the inside of a cell(s) comprising contacting the cell(s), either in vitro or in vivo, with a protein, pharmaceutical composition, and/or diagnostic composition of the present invention. The present invention further provides a method for delivering exogenous material to the inside of a cell(s) in a patient in need thereof, the method comprising the step of administering to the patient a protein of the present invention, wherein the target cell(s) is physically coupled with an extracellular target biomolecule of the protein of the present invention.

Among certain embodiments of the present invention is the use of a compound (e.g. a polypeptide or protein) of the invention and/or composition (e.g. a pharmaceutical composition or diagnostic composition) of the invention in the diagnosis, prognosis, or characterization of a disease, disorder, or condition.

Among certain embodiments of the present invention is a diagnostic composition comprising a de-immunized Shiga toxin effector region polypeptide of the invention, a polypeptide and/or protein comprising it, or a composition comprising any of the foregoing, and a detection promoting agent for the collection of information, such as diagnostically useful information about a cell type, tissue, organ, disease, disorder, condition, or patient.

Among certain embodiments of the present invention is the method of detecting a cell using a protein and/or diagnostic composition of the invention comprising the steps of contacting a cell with said protein and/or diagnostic composition and detecting the presence of said protein and/or diagnostic composition. In certain embodiments, the step of contacting the cell(s) occurs in vitro. In certain embodiments, the step of contacting the cell(s) occurs in vivo. In certain embodiments, the step of detecting the cell(s) occurs in vitro. In certain embodiments, the step of detecting the cell(s) occurs in vivo.

For example, a diagnostic composition of the invention may be used to detect a cell in vivo by administering to a mammalian subject a composition comprising protein of the present invention which comprises a detection promoting agent and then detecting the presence of the protein of the present invention either in vitro or in vivo. The information collected may regard the presence of a cell physically coupled with an extracellular target of the binding region of the protein of the present invention and may be useful in the diagnosis, prognosis, characterization, and/or treatment of a disease, disorder, or condition. Certain compounds (e.g. polypeptides and proteins) of the invention, compositions (e.g. pharmaceutical compositions and diagnostic compositions) of the invention, and methods of the invention may be used to determine if a patient belongs to a group that responds to a pharmaceutical composition of the invention.

Certain embodiments of the polypeptides of the present invention may be utilized as an immunogen or as a component of an immunogen for the immunization and/or vaccination of a mammal.

Among certain embodiments of the present invention are kits comprising a composition of matter of the present invention, and optionally, instructions for use, additional reagent(s), and/or pharmaceutical delivery device(s).

These and other features, aspects and advantages of the present invention will become better understood with regard to the following description, appended claims, and accompanying figures. The aforementioned elements of the invention may be individually combined or removed freely in order to make other embodiments of the invention, without any statement to object to such combination or removal hereinafter.

BRIEF DESCRIPTION OF THE FIGURES

FIG. 1 shows the general arrangement of exemplary de-immunized polypeptides and cytotoxic proteins.

FIG. 2 shows that the D58A substitution in a de-immunized Shiga toxin effector region effectively disrupted the epitope recognized by pAb2 under denaturing conditions and reduced the antigenicity of the polypeptide comprising a Shiga toxin effector region.

FIG. 3 shows that the D58A substitution in the context of multiple epitope region disruption variants of de-immunized Shiga toxin effector regions effectively disrupted the epitope recognized by pAb2 under denaturing conditions and reduced the antigenicity of the polypeptide a Shiga toxin effector region.

FIG. 4 shows that multiple-epitope-region-disruption variants of de-immunized Shiga toxin effector regions disrupted the epitopes recognized by pAb2 and mAb1 under denaturing conditions. These multiple-epitope-region-disruption variants have reduced antigenicity as compared to a polypeptide comprising the parental, wild-type, Shiga toxin effector region.

FIG. 5 shows that multiple-epitope-region-disruption variants of de-immunized Shiga toxin effector regions effectively disrupted the epitopes recognized by pAb2 and/or mAb1 under denaturing conditions. These multiple-epitope-region-disruption variants have reduced antigenicity as compared to a polypeptide comprising the parental, wild-type, Shiga toxin effector region.

FIG. 6 shows that a de-immunized Shiga toxin effector region comprising multiple epitope-region disruptions resulted in a very effective disruption of the epitope recognized by mAb1 under native protein folding conditions. This multiple-epitope-region-disruption variant had reduced antigenicity as compared to a polypeptide comprising the parental, wild-type, Shiga toxin effector region.

FIG. 7 shows that a de-immunized Shiga toxin effector region comprising multiple epitope-region disruptions resulted in reduced, in vivo, antibody response(s) by a mammalian immune system. This multiple-epitope-region-disruption variant had reduced immunogenicity as compared to a polypeptide comprising the parental, wild-type, Shiga toxin effector region.

DETAILED DESCRIPTION

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope of the invention to those skilled in the art.

In order that the present invention may be more readily understood, certain terms are defined below. Additional definitions may be found within the detailed description of the invention.

As used in the specification and the appended claims, the terms "a," "an" and "the" include both singular and the plural referents unless the context clearly dictates otherwise.

As used in the specification and the appended claims, the term "and/or" when referring to two species, A and B, means at least one of A and B. As used in the specification and the appended claims, the term "and/or" when referring to greater than two species, such as A, B, and C, means at least one of A, B, or C, or at least one of any combination of A, B, or C (with each species in singular or multiple possibility).

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout this specification, the term "including" is used to mean "including but not limited to." "Including" and "including but not limited to" are used interchangeably.

The term "amino acid residue" or "amino acid" includes reference to an amino acid that is incorporated into a protein, polypeptide, or peptide. The term "polypeptide" includes any polymer of amino acids or amino acid residues. The term "polypeptide sequence" refers to a series of amino acids or amino acid residues which physically comprise a polypeptide. A "protein" is a macromolecule comprising one or more polypeptides chains. A "peptide" is a small polypeptide of sizes less than a total of 15-20 amino acid residues. The term "amino acid sequence" refers to a series of amino acids or amino acid residues which physically comprise a peptide or polypeptide depending on the length. Unless otherwise indicated, polypeptide and protein sequences disclosed herein are written from left to right representing their order from an amino terminus to a carboxy terminus.

The terms "amino acid," "amino acid residue," "amino acid sequence," or "polypeptide sequence" includes naturally occurring amino acids and, unless otherwise limited, also include known analogs of natural amino acids that can function in a similar manner as naturally occurring amino acids, such as selenocysteine, pyrrolysine, N-formylmethionine, gamma-carboxyglutamate, hydroxyprolinehypusine, pyroglutamic acid, and selenomethionine. The amino acids referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid or Aspartate | Asp | D |
| Cysteine | Cys | C |
| Glutamic Acid or Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The phrase "conservative substitution" with regard to a polypeptide, refers to a change in the amino acid composition of the polypeptide that does not substantially alter the function and structure of the overall polypeptide (see Creighton, *Proteins: Structures and Molecular Properties* (W. H. Freeman and Company, New York (2nd ed., 1992)).

As used herein, the terms "expressed," "expressing," or "expresses" and grammatical variants thereof refer to translation of a polynucleotide or nucleic acid into a polypeptide or protein. The expressed polypeptide or proteins may remain intracellular, become a component of the cell surface membrane or be secreted into an extracellular space.

As used herein, the symbol "α" is shorthand for an immunoglobulin-type binding region capable of binding to the biomolecule following the symbol. The symbol "α" is used to refer to the functional characteristic of an immunoglobulin-type binding region based on its capability of binding to the biomolecule following the symbol.

The symbol "::" means the polypeptide regions before and after it are physically linked together to form a continuous polypeptide.

As used in the specification, the symbol "/" when located between two amino acid residue substitutions means the amino acid residue substitutions on either side of the "/" or comprised within the same molecule.

For purposes of the present invention, the phrase "derived from" means the polypeptide region comprises amino acid sequences originally found in a protein and may now comprise additions, deletions, truncations, or other alterations from the original sequence such that overall function and structure are substantially conserved.

For purposes of the present invention, the term "effector" means providing a biological activity, such as cytotoxicity, biological signaling, enzymatic catalysis, subcellular routing, and/or intermolecular binding resulting in the recruit of a factor(s) and/or an allosteric effect(s).

For purposes of the present invention, a Shiga toxin effector function is a biological activity conferred by a polypeptide region derived from a Shiga toxin A Subunit. Non-limiting examples of Shiga toxin effector functions include cellular internalization, subcellular routing, catalytic activity, and cytotoxicity. Non-limiting examples of Shiga toxin catalytic activities include ribosome inactivation, protein synthesis inhibition, N-glycosidase activity, polynucleotide:adenosine glycosidase activity, RNAase activity, and DNAase activity. RIPS can depurinate nucleic acids, polynucleosides, polynucleotides, rRNA, ssDNA, dsDNA, mRNA (and polyA), and viral nucleic acids (Barbieri L et al., *Biochem J* 286: 1-4 (1992); Barbieri L et al., *Nature* 372: 624 (1994); Ling J et al., *FEBS Lett* 345: 143-6 (1994); Barbieri L et al., *Biochem J* 319: 507-13 (1996); Roncuzzi L, Gasperi-Campani A, *FEBS Lett* 392: 16-20 (1996); Stirpe F et al., *FEBS Lett* 382: 309-12 (1996); Barbieri L et al., *Nucleic Acids Res* 25: 518-22 (1997); Wang P, Turner N, *Nucleic Acids Res* 27: 1900-5 (1999); Barbieri L et al., *Biochim Biophys Acta* 1480: 258-66 (2000); Barbieri L et al., *J Biochem* 128: 883-9 (2000); Bagga S et al., *J Biol Chem* 278: 4813-20 (2003); Picard D et al., *J Biol Chem* 280: 20069-75 (2005)). Some RIPs show antiviral activity and superoxide dismutase activity (Erice A et al., *Antimicrob Agents Chemother* 37: 835-8 (1993); Au T et al., *FEBS Lett* 471: 169-72 (2000); Parikh B, Turner N, *Mini Rev Med Chem* 4: 523-43 (2004); Sharma N et al., *Plant Physiol* 134: 171-81 (2004)). Shiga toxin catalytic activities have been observed both in vitro and in vivo. Assays for Shiga toxin effector activity can measure various activities, such as, e.g., protein synthesis inhibitory activity, depurination activity, inhibition of cell growth, cytotoxicity, supercoiled DNA relaxation activity, and/or nuclease activity.

The term "selective cytotoxicity" with regard to the cytotoxic activity of a cytotoxic protein refers to the relative levels of cytotoxicity between a targeted cell population and a non-targeted bystander cell population, which can be expressed as a ratio of the half-maximal cytotoxic concentration ($CD_{50}$) for a targeted cell type over the $CD_{50}$ for an untargeted cell type to show preferentiality of cell killing of the targeted cell type.

As used herein, the retention of Shiga toxin effector function refers to a level of Shiga toxin functional activity, as measured by an appropriate quantitative assay with reproducibility, comparable to a wild-type Shiga toxin effector polypeptide control. For ribosome inhibition, retained Shiga toxin effector function is exhibiting an $IC_{50}$ of 10,000 pM or less. For cytotoxicity in a target positive cell kill assay, retained Shiga toxin effector function is exhibiting a $CD_{50}$ of 1,000 nM or less, depending on the cell type and its expression of the appropriate extracellular target biomolecule.

As used herein, "de-immunized" means reduced antigenic and/or immunogenic potential after administration to a mammal. This includes a reduced antigenic and/or immunogenic potential overall despite the introduction of one or more new epitopes.

Introduction

The present invention provides improved polypeptides derived from A Subunits of members of the Shiga toxin family with reduced immunogenic potential. These improved Shiga toxin effector polypeptides may be utilized in various compositions, e.g. cytotoxic therapeutics, therapeutic delivery agents, diagnostic molecules, and immunization materials.

Despite the attractiveness of using Shiga toxins as components of therapeutics, bacterial toxins tend to be immunogenic to mammals. Unwanted immunogenicity in protein therapeutics has resulted in reduced efficacy, unpredictable pharmacokinetics, and undesirable immune responses that limit dosages and repeat administrations. Although there is a need for molecules comprising de-immunized Shiga-toxin-derived polypeptides that have reduced immunogenic potential to help avoid unwanted immune responses, there exists no predictable method to successfully identify and remove internal B-cell epitopes while maintaining Shiga toxin effector function(s).

Although some antigenic and/or immunogenic epitopes might be removed by truncation, the main challenge is silencing epitopes within the Shiga toxin polypeptide's effector domains, e.g. its enzymatic domain, while retaining the desired Shiga toxin effector functions, e.g., potent ribosome inhibition and directing subcellular routing. While these internal epitopes may be diminished or abolished by mutation and/or chemical modification, the challenge is to do so while preserving Shiga toxin effector functions. It is a significant challenge to disrupt antigenic sites by amino acid substitution in a protein while preserving protein function because functionally constrained residues and structures must be maintained and certain positions do not tolerate certain amino acid substitutions without impacting protein structure, stability, and/or function (see Cantor J et al., *Methods in Enzymology* 502: Ch. 12 pp. 291-301 (2012)).

Extensive empirical experimentation on Shiga toxin derived polypeptide regions was performed to arrive at the present invention. As described in more detail in the Examples, amino acid substitutions were created in predicted B-cell epitopes, and the resulting polypeptides were tested for retention of desired Shiga toxin effector functions. The antigenicity and/or immunogenicity of each epitope is predicted to be reduced or eliminated by the amino acid substitutions provided, which in turn reduces the overall antigenicity and/or immunogenicity of any compositions of matter comprising at least one provided epitope disruption. The de-immunized Shiga toxin effector polypeptides which were identified as having reduced immunogenic potential while maintaining Shiga toxin function(s), were not predictable a priori, despite attempts at de-immunization of distantly related bacterial protein toxins, such as *Pseudomonas* exotoxin A.

Polypeptides comprising de-immunized Shiga toxin effector regions of the invention may be used as components of recombinant immunotoxins and ligand-toxin fusions for the targeted killing of specific cell types and the treatment of a variety of diseases, including cancers, immune disorders, and microbial infections. Additionally, the polypeptides of the invention may be used as components of cell-type specific internalizing molecules for the precise delivery of exogenous materials, such as detection promoting agents for diagnostic information gathering. Further, the polypeptides of the invention, independently or as components of Shiga holotoxins, may be used in immunization materials designed to avoid antibody creation to specific epitopes while eliciting immune responses to Shiga toxins.

I. The General Structure of Shiga Toxin Effector Polypeptides and Proteins of the Present Invention The present invention provides various polypeptides comprising Shiga toxin effector regions with reduced immunogenic potential but which retain Shiga toxin effector functionality(s), such as cellular internalization, subcellular routing, catalytic activity, and cytotoxicity. A polypeptide of the invention comprises a Shiga toxin effector region comprising a disruption of at least one epitope region described herein. A protein of the invention comprises a de-immunized Shiga toxin effector region and a binding region comprising one or more polypeptides capable of specifically binding at least one extracellular target biomolecule.

The Shiga toxin family of protein toxins is composed of various naturally occurring toxins that are structurally and functionally related, e.g., Shiga toxin, Shiga-like toxin 1, and Shiga-like toxin 2 (Johannes L, Römer W, *Nat Rev Microbiol* 8: 105-16 (2010)). Members of the Shiga toxin family share the same overall structure and mechanism of action (Engedal, N et al., *Microbial Biotech* 4: 32-46 (2011)). For example, Stx, SLT-1 and SLT-2 display indistinguishable enzymatic activity in cell free systems (Head S et al., *J Biol Chem* 266: 3617-21 (1991); Tesh V et al., *Infect Immun* 61: 3392-402 (1993); Brigotti M et al., *Toxicon* 35:1431-1437 (1997)).

A. De-Immunized Shiga Toxin Effector Region Polypeptides

For purposes of the present invention, the phrase "Shiga toxin effector region" refers to a polypeptide region derived from a Shiga toxin A Subunit of a member of the Shiga toxin family that is capable of exhibiting at least one Shiga toxin function. Shiga toxin functions include, e.g., cell entry, lipid membrane deformation, directing subcellular routing, avoiding degradation, catalytically inactivating ribosomes, effectuating cytotoxicity, and effectuating cytostatic effects.

As used herein, the retention of "significant" Shiga toxin effector function refers to a level of Shiga toxin functional activity, as measured by an appropriate quantitative assay with reproducibility comparable to a wild-type Shiga toxin effector polypeptide control. For in vitro ribosome inhibition, significant Shiga toxin effector function is exhibiting an $IC_{50}$ of 300 pM or less depending on the source of the ribosomes (e.g. bacteria, archaea, or eukaryote (algae, fungi, plants, or animals)). This is significantly greater inhibition as compared to the approximate $IC_{50}$ of 100,000 pM for the catalytically inactive SLT-1A 1-251 double mutant (Y77S, E167D). For cytotoxicity in a target positive cell kill assay in laboratory cell culture, significant Shiga toxin effector function is exhibiting a $CD_{50}$ of 100, 50, or 30 nM or less, depending on the cell line and its expression of the appropriate extracellular target biomolecule. This is significantly greater cytotoxicity to the appropriate target cell line as compared to SLT-1A alone, without a cell targeting binding region, which has a $CD_{50}$ of 100-10,000 nM, depending on the cell line.

For some samples, accurate values for either $IC_{50}$ or $CD_{50}$ might be unobtainable due to the inability to collect the required data points for an accurate curve fit. Inaccurate $IC_{50}$ and/or $CD_{50}$ values should not be considered when determining significant Shiga toxin effector function activity. Data insufficient to accurately fit a curve as described in the analysis of the data from exemplary Shiga toxin effector function assays, such as, e.g., assays described in the Examples, should not be considered as representative of actual Shiga toxin effector function. For example, theoretically neither an $IC_{50}$ nor $CD_{50}$ can be determined if greater than 50% ribosome inhibition or cell death, respectively, does not occur in a concentration series for a given sample.

The failure to detect activity in Shiga toxin effector function may be due to improper expression, polypeptide folding, and/or polypeptide stability rather than a lack of cell entry, subcellular routing, and/or enzymatic activity. Assays for Shiga toxin effector functions may not require much polypeptide of the invention to measure significant amounts of Shiga toxin effector function activity. To the extent that an underlying cause of low or no effector function is determined empirically to relate to protein expression or stability, one of skill in the art may be able to compensate for such factors using protein chemistry and molecular engineering techniques known in the art, such that a Shiga toxin functional effector activity may be restored and measured. As examples, improper cell based expression may be compensated for by using different expression control sequences; improper polypeptide folding and/or stability may benefit from stabilizing terminal sequences, or compensatory mutations in non-effector regions which stabilize the three dimensional structure of the protein, etc. When new assays for individual Shiga toxin functions become available, de-immunized Shiga toxin effector polypeptides may be analyzed for any level of those Shiga toxin effector functions, such as a being within 1000-fold or 100-fold or less the activity of a wild-type Shiga toxin effector polypeptide or exhibiting 3-fold to 30-fold or greater activity as compared to a functional knockout Shiga toxin effector polypeptide.

Certain Shiga toxin effector functions are not easily measurable, e.g. subcellular routing functions. Currently there is no routine, quantitative assay to distinguish whether the failure of a de-immunized Shiga toxin effector polypeptide to be cytotoxic is due to improper subcellular routing, but at a time when tests are available, de-immunized Shiga toxin effector polypeptides may be analyzed for any significant level of subcellular routing as compared to the appropriate wild-type Shiga toxin effector region.

It should be noted that even if the cytotoxicity of a Shiga toxin effector polypeptide is reduced relative to wild-type, in practice, applications using attenuated de-immunized Shiga toxin effector polypeptides may be equally or more effective than those using wild-type Shiga toxin effector polypeptides because the reduced antigenicity and/or immunogenicity might offset the reduced cytotoxicity, such as, e.g., by allowing higher dosages or more repeated administrations. Wild-type Shiga toxin effector polypeptides are very potent, being able to kill with only one molecule reaching the cytosol or perhaps 40 molecules being internalized. De-immunized Shiga toxin effector polypeptides with even considerably reduced Shiga toxin effector functions, such as, e.g., subcellular routing or cytotoxicity, as compared to wild-type Shiga toxin effector polypeptides may still be potent enough for practical applications involving targeted cell killing and/or specific cell detection.

The Shiga toxin family encompasses true Shiga toxin (Stx) isolated from *S. dysenteriae* serotype 1, Shiga-like toxin 1 variants (SLT1 or Stx1 or SLT-1 or Slt-I) isolated from serotypes of enterohemorrhagic *E. coli*, and Shiga-like toxin 2 variants (SLT2 or Stx2 or SLT-2) isolated from serotypes of enterohemorrhagic *E. coli*. SLT1 differs by only one residue from Stx, and both have been referred to as Verocytotoxins or Verotoxins (VTs) (O'Brien, *Curr Top Microbiol Immunol* 180: 65-94 (1992)). Although SLT1 and SLT2 variants are only about 53-60% similar to each other at the amino acid sequence level, they share mechanisms of enzymatic activity and cytotoxicity common to the members of the Shiga toxin family (Johannes, *Nat Rev Microbiol* 8: 105-16 (2010)). Over 39 different Shiga toxins have been described, such as the defined subtypes Stx1a, Stx1c, Stx1d, and Stx2a-g (Scheutz F et al., *J Clin Microbiol* 50: 2951-63 (2012)). Members of the Shiga toxin family are not naturally restricted to any bacterial species because Shiga-toxin-encoding genes can spread among bacterial species via horizontal gene transfer (Strauch E et al., *Infect Immun* 69: 7588-95 (2001); Zhaxybayeva O, Doolittle W, *Curr Biol* 21: R242-6 (2011)). As an example of interspecies transfer, a Shiga toxin was discovered in a strain of *A. haemolyticus* isolated from a patient (Grotiuz G et al., *J Clin Microbiol* 44: 3838-41 (2006)). Once a Shiga toxin encoding polynucleotide enters a new subspecies or species, the Shiga toxin amino acid sequence is presumed to be capable of developing slight sequence variations due to genetic drift and/or selective pressure while still maintaining a mechanism of cytotoxicity common to members of the Shiga toxin family (see Scheutz, *J Clin Microbiol* 50: 2951-63 (2012)).

The polypeptides of the invention comprise Shiga toxin effector regions derived from an A Subunit of a member of the Shiga toxin family with at least one putative epitope region disrupted in order to reduce the antigenic and/or immunogenic potential of the polypeptides after administration to a mammal. The term "disrupted" or "disruption" as used herein with regard to an epitope region refers to the deletion of at least one amino acid in an epitope region, inversion of two or more amino acids where at least one of the inverted amino acids is in an epitope region, insertion of at least one amino acid in an epitope region, and mutation of at least one amino acid in an epitope region. An epitope region disruption by mutation includes amino acid substitutions with non-standard amino acids and/or non-natural amino acids. Epitope regions may alternatively be disrupted by mutations comprising the modification of an amino acid by the addition of a covalently-linked chemical structure which masks at least one amino acid in an epitope region, see, e.g. PEGylation (see Zhang C et al., *BioDrugs* 26: 209-15 (2012) and small molecule adjuvants (Flower D, *Expert Opin Drug Discov* 7: 807-17 (2012)).

Certain epitope regions and disruptions are indicated herein by reference to specific amino acid positions of native Shiga toxin A Subunits provided in the Sequence Listing, noting that naturally occurring Shiga toxin A Subunits may comprise precursor forms containing signal sequences of about 22 amino acids at their amino-terminals which are removed to produce mature Shiga toxin A Subunits and are recognizable to the skilled worker. Further, certain epitope region disruptions are indicated herein by reference to specific amino acids (e.g. S for a serine residue) natively present at specific positions within native Shiga toxin A Subunits (e.g. S33 for the serine residue at position 33 from the amino terminus) followed by the amino acid with which that residue has been substituted in the particular mutation under discussion (e.g. S33I represents the amino acid substitution of isoleucine for serine at amino acid residue 33 from the amino terminus).

Certain embodiments of the invention provide polypeptides comprising a Shiga toxin effector region comprising an amino acid sequence derived from an A Subunit of a member of the Shiga toxin Family, the Shiga toxin effector region comprising a disruption of at least one epitope region provided herein (see e.g. Tables 1, 2, and 3). In certain embodiments, a de-immunized Shiga toxin effector region polypeptide of the invention may comprise or consist essentially of full-length Shiga toxin A Subunit (e.g. SLT-1A (SEQ ID NO:1), StxA (SEQ ID NO:2), or SLT-2A (SEQ ID NO:3)) comprising at least one disruption of the amino acid sequence selected from the group of natively positioned amino acids consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; 210-218 of SEQ ID NO:3; 240-258 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, or the equivalent position in a conserved Shiga toxin effector polypeptide and/or non-native Shiga toxin effector polypeptide sequence.

In certain embodiments, a Shiga toxin effector region polypeptide of the invention may comprise or consist essentially of a truncated Shiga toxin A Subunit. Truncations of Shiga toxin A Subunits might result in the deletion of entire epitope regions without affecting toxin effector catalytic activity and cytotoxicity. The smallest Shiga toxin A Subunit fragment exhibiting significant enzymatic activity is a polypeptide composed of residues 75-247 of StxA (Al-Jaufy, *Infect Immun* 62: 956-60 (1994)). Truncating the carboxy-terminus of SLT-1A, StxA, or SLT-2A to amino acids 1-251 removes two predicted B-cell epitope regions, two predicted CD4 positive (CD4+) T-cell epitopes, and a predicted discontinuous B-cell epitope. Truncating the amino-terminus of SLT-1A, StxA, or SLT-2A to 75-293 removes at least three predicted B-cell epitope regions and three predicted CD4+ T-cell epitopes. Truncating both amino- and carboxy-terminals of SLT-1A, StxA, or SLT-2A to 75-251 deletes at least five predicted B-cell epitope regions, four putative CD4+ T-cell epitopes, and one predicted discontinuous B-cell epitope.

In certain embodiments, a Shiga toxin effector region polypeptide of the invention may comprise or consist essentially of a full-length or truncated Shiga toxin A Subunit with at least one mutation, e.g. deletion, insertion, inversion, or substitution, in a provided epitope region. In certain further embodiments, the polypeptides comprise a disruption which comprises a deletion of at least one amino acid within the epitope region. In certain further embodiments, the polypeptides comprise a disruption which comprises an insertion of at least one amino acid within the epitope region. In certain further embodiments, the polypeptides comprise a disruption which comprises an inversion of amino acids, wherein at least one inverted amino acid is within the epitope region. In certain further embodiments, the polypeptides comprise a disruption which comprises a mutation, such as an amino acid substitution to a non-standard amino acid or an amino acid with a chemically modified side chain. Numerous examples of single amino acid substitutions are provided in the Examples.

In certain embodiments, the Shiga toxin effector region polypeptides of the invention may comprise or consist essentially of a full-length or truncated Shiga toxin A Subunit with one or more mutations as compared to the native sequence which comprises at least one amino acid substitution selected from the group consisting of: A, G, V, L, I, P, C, M, F, S, D, N, Q, H, and K. In certain further embodiments, the polypeptide may comprise or consist essentially of a full-length or truncated Shiga toxin A Subunit with a single mutation as compared to the native sequence wherein the substitution is selected from the group consisting of: D to A, D to G, D to V, D to L, D to I, D to F, D to S, D to Q, E to A, E to G, E to V, E to L, E to I, E to F, E to S, E to Q, E to N, E to D, E to M, E to R, G to A, H to A, H to G, H to V, H to L, H to I, H to F, H to M, K to A, K to G, K to V, K to L, K to I, K to M, K to H, L to A, L to G, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, Y to A, Y to G, Y to V, Y to L, Y to I, Y to F, and Y to M.

In certain embodiments, the Shiga toxin effector region polypeptides of the invention comprise or consist essentially of a full-length or truncated Shiga toxin A Subunit with one or more mutations as compared to the native amino acid residue sequence which comprises at least one amino acid substitution within an epitope region, wherein at least one substitution occurs at the natively positioned group of amino acids selected from the group consisting of: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 45 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 53 of SEQ ID NO:1 or SEQ ID NO:2; 55 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 109 of SEQ ID NO:1, SEQ ID NO:2, or SEQ ID NO:3; 110 of SEQ ID NO:1 or SEQ ID NO:2; 112 of SEQ ID NO:1, SEQ ID NO:2, or SEQ ID NO:3; SE 147 of SEQ ID NO:1, SEQ ID NO:2, or SEQ ID NO:3; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 204 of SEQ ID NO:3; 205 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

In certain further embodiments, the Shiga toxin effector region polypeptides of the invention comprise or consist essentially of a full-length or truncated Shiga toxin A Subunit with at least one substitution within an epitope region, wherein at least one amino acid substitution is to a non-conservative amino acid (see, e.g., Table B, infra) relative to a natively occurring amino acid positioned at one of the following native positions: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3;

9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 45 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 53 of SEQ ID NO:1 or SEQ ID NO:2; 55 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 109 of SEQ ID NO:1, SEQ ID NO:2, or SEQ ID NO:3; 110 of SEQ ID NO:1 or SEQ ID NO:2; 112 of SEQ ID NO:1, SEQ ID NO:2, or SEQ ID NO:3; SE 147 of SEQ ID NO:1, SEQ ID NO:2, or SEQ ID NO:3; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 204 of SEQ ID NO:3; 205 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

In certain further embodiments, the Shiga toxin effector region polypeptides of the invention comprise or consist essentially of a full-length or truncated Shiga toxin A Subunit with at least one amino acid substitution selected from the group consisting of: K1 to A, G, V, L, I, F, M and H; T4 to A, G, V, L, I, F, M, and S; S8 to A, G, V, I, L, F, and M; T9 to A, G, V, I, L, F, M, and S; S9 to A, G, V, L, I, F, and M; K11 to A, G, V, L, I, F, M and H; S33 to A, G, V, L, I, F, and M; S45 to A, G, V, L, I, F, and M; T45 to A, G, V, L, I, F, and M; D47 to A, G, V, L, I, F, S, and Q; N48 to A, G, V, L, and M; L49 to A or G; D53 to A, G, V, L, I, F, S, and Q; R55 to A, G, V, L, I, F, M, Q, S, K, and H; D58 to A, G, V, L, I, F, S, and Q; P59 to A, G, and F; E60 to A, G, V, L, I, F, S, Q, N, D, M, and R; E61 to A, G, V, L, I, F, S, Q, N, D, M, and R; G62 to A; D94 to A, G, V, L, I, F, S, and Q; S96 to A, G, V, I, L, F, and M; S109 to A, G, V, I, L, F, and M; T109 to A, G, V, I, L, F, M, and S; G110 to A; S112 to A, G, V, L, I, F, and M; G147 to A; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; S186 to A, G, V, I, L, F, and M; G187 to A; R188 to A, G, V, L, I, F, M, Q, S, K, and H; S189 to A, G, V, I, L, F, and M; R204 to A, G, V, L, I, F, M, Q, S, K, and H; R205 to A, G, V, L, I, F, M, Q, S, K and H; S247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, M, and S. In certain further embodiments, the Shiga toxin effector region polypeptides of the invention comprise or consist essentially of a full-length or truncated Shiga toxin A Subunit with at least one of the following amino acid substitutions KM, T4I, S8I, T8V, T9I, S9I, K11A, K11H, S33I, S45I, T45I, D47G, N48V, N48F, L49A, D53A, D53G, D53N, R55A, R55V, R55L, D58A, D58F, P59A, P59F, E60I, E60T, E60R, E61A, E61V, E61L, G62A, D94A, S96I, S109V, T109V, G110A, S112V, G147A, R179A, T180G, T181I, D183A, D183G, D184A, D184F, L185V, S186A, S186F, G187A, R188A, R188L, S189A, R204A, R205A, S247I, Y247A, R248A, R250A, R251A, D264A, G264A, T286A and/or T286I. These epitope disrupting substitutions may be combined to form a de-immunized Shiga toxin effector polypeptide with multiple substitutions per epitope region and/or multiple epitope regions disrupted while still retaining Shiga toxin effector function. For example, substitutions at the natively positioned residues K1, T4, S8, T8, T9, S9, K11, K11, S33, S45, T45, D47, N48, L49, D53, R55, D58, P59, E60, E61, G62, D94, S96I, S109, T109, G110, S112, G147, R179, T180, T181I, D183, D184, L185, S186, S186, G187, R188, S189, R204A, R205, S247, Y247, R248, R250, R251, D264, G264, T286 and/or T286 may be combined, where possible, with substitutions at the natively positioned residues K1, T4, S8, T8, T9, S9, K11, K11, S33, S45, T45, D47, N48, L49, D53, R55, D58, P59, E60, E61, G62, D94, S96I, S109, T109, G110, S112, G147, R179, T180, T181I, D183, D184, L185, S186, S186, G187, R188, S189, R204A, R205, S247, Y247, R248, R250, R251, D264, G264, T286 and/or T286 to create de-immunized Shiga toxin effector region polypeptides of the invention.

In other embodiments, the Shiga toxin effector region polypeptides of the invention comprises or consists essentially of a truncated Shiga toxin A Subunit which is shorter than a full-length Shiga toxin A Subunit wherein at least one amino acid is disrupted in a natively positioned epitope region provided in the Examples (Tables 1, 2, 3, 4, and/or 5). Shiga-like toxin 1 A Subunit truncations are catalytically active, capable of enzymatically inactivating ribosomes in vitro, and cytotoxic when expressed within a cell (LaPointe, *J Biol Chem* 280: 23310-18 (2005)). The smallest Shiga toxin A Subunit fragment exhibiting full enzymatic activity is a polypeptide composed of residues 1-239 of Slt1A (LaPointe, *J Biol Chem* 280: 23310-18 (2005)). Although the smallest fragment of the Shiga toxin A Subunit reported to retain substantial catalytic activity was residues 75-247 of StxA (Al-Jaufy, *Infect Immun* 62: 956-60 (1994)), a StxA truncation expressed de novo within a eukaryotic cell requires only up to residue 240 to reach the cytosol and exert catalytic inactivation of ribosomes (LaPointe, *J Biol Chem* 280: 23310-18 (2005)).

Although de-immunized Shiga toxin effector region polypeptides of the invention may commonly be smaller than the full length A subunit, it is preferred that the de-immunized Shiga toxin effector region maintain the polypeptide region from amino acid position 77 to 239 (SLT-1A (SEQ ID NO:1) or StxA (SEQ ID NO:2)) or the equivalent in other A Subunits of members of the Shiga toxin family (e.g. 77 to 238 of (SEQ ID NO:3)). For example, in certain embodiments of the invention, the Shiga toxin effector region polypeptides derived from SLT-1A may comprise or consist essentially of amino acids 75 to 251 of SEQ ID NO:1, 1 to 241 of SEQ ID NO:1, 1 to 251 of SEQ ID NO:1, or amino acids 1 to 261 of SEQ ID NO:1 wherein at least one amino acid is disrupted in the natively positioned epitope regions provided in the Examples (Tables 1, 2, 3, 4, and/or 5). Similarly, de-immunized Shiga toxin effector regions derived from StxA may comprise or consist essentially of amino acids 75 to 251 of SEQ ID NO:2, 1 to 241 of SEQ ID NO:2, 1 to 251 of SEQ ID NO:2, or amino acids 1 to 261 of SEQ ID NO:2 wherein at least one amino acid is disrupted in at least one natively positioned epitope region provided in the Examples (Tables 1, 2, 3, 4, and/or 5). Additionally, the Shiga toxin effector regions derived from SLT-2 may comprise or consist essentially of amino acids 75 to 251 of SEQ ID NO:3, 1 to 241 of SEQ ID NO:3, 1 to 251 of SEQ ID NO:3, or amino acids 1 to 261 of SEQ ID NO:3 wherein at least one amino acid is disrupted in at least one natively positioned epitope region provided in the Examples (Tables 1, 2, 3, 4, and/or 5).

The invention further provides variants of the polypeptides of the invention, wherein the Shiga toxin effector region differs from a naturally occurring Shiga toxin A Subunit by only or up to 1, 2, 3, 4, 5, 6, 7, 8, 9, 10, 15, 20, 25, 30, 35, 40 or more amino acid residues (but by no more than that which retains at least 85%, 90%, 95%, 99% or more amino acid sequence identity). Thus, a Shiga toxin effector region polypeptide of the invention derived from an A Subunit of a member of the Shiga toxin family may comprise additions, deletions, truncations, or other alterations from the original sequence so long as at least 85%, 90%, 95%, 99% or more amino acid sequence identity is maintained to a naturally occurring Shiga toxin A Subunit and at least one amino acid is disrupted in at least one natively positioned epitope region provided in the Examples (Tables 1, 2, 3, 4, and/or 5).

Accordingly, in certain embodiments, the Shiga toxin effector region polypeptides comprises or consists essentially of amino acid sequences having at least 55%, 60%, 65%, 70%, 75%, 80%, 85%, 90%, 95%, 97%, 98%, 99%, 99.5% or 99.7% overall sequence identity to a naturally occurring Shiga toxin A Subunit, such as SLT-1A (SEQ ID NO:1), StxA (SEQ ID NO:2), and/or SLT-2A (SEQ ID NO:3) wherein at least one amino acid is disrupted in at least one natively positioned epitope region provided in the Examples (Tables 1, 2, 3, 4, and/or 5).

Optionally, either a full length or a truncated version of the Shiga toxin A Subunit may comprise one or more mutations (e.g. substitutions, deletions, insertions or inversions) so long as at least one amino acid is disrupted in at least one natively positioned epitope region provided in the Examples (Tables 1, 2, 3, 4, and/or 5). It is preferred in certain embodiments of the invention that the de-immunized Shiga toxin effector region polypeptides have sufficient sequence identity to a naturally occurring Shiga toxin A Subunit to retain cytotoxicity after entry into a cell, either by well-known methods of host cell transformation, transfection, infection or induction, or by internalization mediated by a cell-targeting binding region linked with the Shiga toxin effector region polypeptide. The most critical residues for enzymatic activity and/or cytotoxicity in the Shiga toxin A Subunits have been mapped to the following residue-positions: asparagine-75, tyrosine-77, glutamate-167, arginine-170, and arginine-176 among others (Di, *Toxicon* 57: 525-39 (2011)). In any one of the embodiments of the invention, the de-immunized Shiga toxin effector region polypeptides may preferably but not necessarily maintain one or more conserved amino acids at positions, such as those found at positions 77, 167, 170, and 176 in StxA, SLT-1A, or the equivalent conserved position in other members of the Shiga toxin family which are typically required for cytotoxic activity. The capacity of a cytotoxic protein of the invention to cause cell death, e.g. its cytotoxicity, may be measured using any one or more of a number of assays well known in the art.

B. Proteins Comprising De-Immunized Shiga Toxin Effector Regions

Proteins of the invention comprise a de-immunized Shiga toxin effector region comprising a polypeptide of the invention linked to an extracellular target biomolecule specific binding region. Binding regions of the proteins of the invention comprise one or more polypeptides capable of selectively and specifically binding an extracellular target biomolecule. Binding regions may comprise one or more various polypeptide moieties, such as ligands whether synthetic or naturally occurring ligands and derivatives thereof, immunoglobulin derived domains, synthetically engineered scaffolds as alternatives to immunoglobulin domains, and the like.

There are numerous binding regions known in the art that are useful for targeting polypeptides to specific cell-types via their binding characteristics, such as ligands, monoclonal antibodies, engineered antibody derivatives, and engineered alternatives to antibodies.

According to one specific, but non-limiting aspect, the binding region of the protein of the invention comprises a naturally occurring ligand or derivative thereof that retains binding functionality to an extracellular target biomolecule, commonly a cell surface receptor. For example, various cytokines, growth factors, and hormones known in the art may be used to target the cytotoxic protein to the cell-surface of specific cell types expressing a cognate cytokine receptor, growth factor receptor, or hormone receptor. Certain non-limiting examples of ligands include (alternative names are indicated in parentheses) B-cell activating factors (BAFF5, APRIL), colony stimulating factors (CSFs), epidermal growth factors (EGFs), fibroblast growth factors (FGFs), vascular endothelial growth factors (VEGFs), insulin-like growth factors (IGFs), interferons, interleukins (such as IL-2, IL-6, and IL-23), nerve growth factors (NGFs), platelet derived growth factors, transforming growth factors (TGFs), and tumor necrosis factors (TNFs).

According to certain other embodiments, the binding region comprises a synthetic ligand capable of binding an extracellular target biomolecule. One non-limiting example is antagonists to cytotoxic T-lymphocyte antigen 4 (CTLA-4).

According to one specific, but non-limiting aspect, the binding region may comprise an immunoglobulin-type binding region. The term "immunoglobulin-type binding region" as used herein refers to a polypeptide region capable of binding one or more target biomolecules, such as an antigen or epitope. Binding regions may be functionally defined by their ability to bind to target molecules. Immunoglobulin-type binding regions are commonly derived from antibody or antibody-like structures; however, alternative scaffolds from other sources are contemplated within the scope of the term.

Immunoglobulin (Ig) proteins have a structural domain known as an Ig domain. Ig domains range in length from about 70-110 amino acid residues and possess a characteristic Ig-fold, in which typically 7 to 9 antiparallel beta strands arrange into two beta sheets which form a sandwich-like structure. The Ig fold is stabilized by hydrophobic amino acid interactions on inner surfaces of the sandwich and highly conserved disulfide bonds between cysteine residues in the strands. Ig domains may be variable (IgV or V-set), constant (IgC or C-set) or intermediate (IgI or I-set). Some Ig domains may be associated with a complementarity determining region (CDR) which is important for the specificity of antibodies binding to their epitopes. Ig-like domains are also found in non-immunoglobulin proteins and are classified on that basis as members of the Ig superfamily of proteins. The HUGO Gene Nomenclature Committee (HGNC) provides a list of members of the Ig-like domain containing family.

An immunoglobulin-type binding region may be a polypeptide sequence of an antibody or antigen-binding fragment thereof wherein the amino acid sequence has been varied from that of a native antibody or an Ig-like domain of a non-immunoglobulin protein, for example by molecular engineering or selection by library screening. Because of the relevance of recombinant DNA techniques and in vitro library screening in the generation of immunoglobulin-type binding regions, antibodies can be redesigned to obtain desired characteristics, such as smaller size, cell entry, or other therapeutic improvements. The possible variations are many and may range from the changing of just one amino acid to the complete redesign of, for example, a variable region. Typically, changes in the variable region will be made in order to improve the antigen-binding characteristics, improve variable region stability, or reduce the potential for immunogenic responses.

There are numerous immunoglobulin-type binding regions contemplated as components of the present invention. In certain embodiments, the immunoglobulin-type binding region is derived from an immunoglobulin binding region, such as an antibody paratope capable of binding an extracellular target biomolecule. In certain other embodiments, the immunoglobulin-type binding region comprises an engineered polypeptide not derived from any immunoglobulin domain but which functions like an immunoglobulin binding region by providing high-affinity binding to an extracellular target biomolecule. This engineered polypeptide may optionally include polypeptide scaffolds comprising or consisting essentially of complementary determining regions from immunoglobulins as described herein.

There are also numerous binding regions in the prior art that are useful for targeting polypeptides to specific cell-types via their high-affinity binding characteristics. In certain embodiments, the binding region of the present proteins is selected from the group which includes single-domain antibody domains (sdAbs), nanobodies, heavy-chain antibody domains derived from camelids ($V_HH$ fragments), bivalent nanobodies, heavy-chain antibody domains derived from cartilaginous fishes, immunoglobulin new antigen receptors (IgNARs), $V_{NAR}$ fragments, single-chain variable (scFv) fragments, multimerizing scFv fragments (diabodies, triabodies, tetrabodies), bispecific tandem scFv fragments, disulfide stabilized antibody variable (Fv) fragments, disulfide stabilized antigen-binding (Fab) fragments consisting of the $V_L$, $V_H$, $C_L$ and $C_H$ 1 domains, divalent F(ab')2 fragments, Fd fragments consisting of the heavy chain and $C_H1$ domains, single chain Fv-$C_H3$ minibodies, bispecific minibodies, dimeric $C_H2$ domain fragments ($C_H2D$), Fc antigen binding domains (Fcabs), isolated complementary determining region 3 (CDR3) fragments, constrained framework region 3, CDR3, framework region 4 (FR3-CDR3-FR4) polypeptides, small modular immunopharmaceutical (SMIP) domains, and any genetically manipulated counterparts of the foregoing that retain its paratope and binding function (see Saerens D et al., *Curr. Opin. Pharmacol* 8: 600-8 (2008); Dimitrov D, MAbs 1: 26-8 (2009); Weiner L, *Cell* 148: 1081-4 (2012); Ahmad Z et al., *Clin Dev Immunol* 2012: 980250 (2012)).

In accordance with certain other embodiments, the binding region includes engineered, alternative scaffolds to immunoglobulin domains that exhibit similar functional characteristics, such as high-affinity and specific binding of target biomolecules, and enables the engineering of improved characteristics, such as greater stability or reduced immunogenicity. For certain embodiments of the proteins of the invention, the binding region is selected from the group which includes engineered, fibronection-derived, $10^{th}$ fibronectin type III (10Fn3) domain (monobodies, AdNectins™, or AdNexins™); engineered, tenacsin-derived, tenacsin type III domain (Centryns™); engineered, ankyrin repeat motif containing polypeptide (DARPins™); engineered, low-density-lipoprotein-receptor-derived, A domain (LDLR-A) (Avimers™); lipocalin (anticalins); engineered, protease inhibitor-derived, Kunitz domain; engineered, Protein-A-derived, Z domain (Affibodies™); engineered, gamma-B crystalline-derived scaffold or engineered, ubiquitin-derived scaffold (Affilins); Sac7d-derived polypeptides (Nanoffitins® or affitins); engineered, Fyn-derived, SH2 domain (Fynomers®); miniproteins; C-type lectin-like domain scaffolds; engineered antibody mimics; and any genetically manipulated counterparts of the foregoing that retains its binding functionality (Worn A, Plückthun A, *J Mol Biol* 305: 989-1010 (2001); Xu L et al., *Chem Biol* 9: 933-42 (2002); Wikman M et al., *Protein Eng Des Sel* 17: 455-62 (2004); Binz H et al., *Nat Biotechnol* 23: 1257-68 (2005); Hey T et al., *Trends Biotechnol* 23:514-522 (2005); Holliger P, Hudson P, *Nat Biotechnol* 23: 1126-36 (2005); Gill D, Damle N, *Curr Opin Biotech* 17: 653-8 (2006); Koide A, Koide S, *Methods Mol Biol* 352: 95-109 (2007); Byla P et al., *J Biol Chem* 285: 12096 (2010); Zoller F et al., *Molecules* 16: 2467-85 (2011)).

Any of the above binding regions may be used as a component of the present invention so long as the binding region component has a dissociation constant of $10^{-5}$ to $10^{-12}$ moles per liter, preferably less than 200 nanomolar (nM), towards an extracellular target biomolecule.

Extracellular Target Biomolecules

The binding region of the protein of the invention comprises a polypeptide region capable of binding specifically to an extracellular target biomolecule, preferably which is physically-coupled to the surface of a cell type of interest, such as a cancer cell, tumor cell, plasma cell, infected cell, or host cell harboring an intracellular pathogen.

The term "target biomolecule" refers to a biological molecule, commonly a protein or a protein modified by post-translational modifications, such as glycosylation, which is capable of being bound by a binding region to target a protein to a specific cell-type or location within an organism. Extracellular target biomolecules may include various epitopes, including unmodified polypeptides, polypeptides modified by the addition of biochemical functional groups, and glycolipids (see e.g. U.S. Pat. No. 5,091,178; EP 2431743). It is desirable that an extracellular target biomolecule be endogenously internalized or be readily forced to internalize upon interaction with a protein of the invention.

For purposes of the present invention, the term "extracellular" with regard to modifying a target biomolecule refers to a biomolecule that has at least a portion of its structure exposed to the extracellular environment. Extracellular target biomolecules include cell membrane components, transmembrane spanning proteins, cell membrane-anchored biomolecules, cell-surface-bound biomolecules, and secreted biomolecules.

With regard to the present invention, the phrase "physically coupled" when used to describe a target biomolecule means both covalent and/or non-covalent intermolecular interactions that couple the target biomolecule, or a portion thereof, to the outside of a cell, such as a plurality of non-covalent interactions between the target biomolecule and the cell where the energy of each single interaction is on the order of about 1-5 kiloCalories (e.g. electrostatic bonds, hydrogen bonds, Van der Walls interactions, hydrophobic forces, etc.). All integral membrane proteins can be found physically coupled to a cell membrane, as well as peripheral membrane proteins. For example, an extracellular target biomolecule might comprise a transmembrane spanning region, a lipid anchor, a glycolipid anchor, and/or be non-covalently associated (e.g. via non-specific hydrophobic interactions and/or lipid binding interactions) with a factor comprising any one of the foregoing.

The binding regions of the proteins of the invention may be designed or selected based on numerous criteria, such as the cell-type specific expression of their target biomolecules and/or the physical localization of their target biomolecules with regard to specific cell types. For example, certain proteins of the present invention comprise binding domains capable of binding cell-surface targets which are expressed exclusively by only one cell-type to the cell surface. This permits the targeted cell-killing of specific cell types with a high preferentiality (at least a 3-fold cytotoxic effect) over "bystander" cell types that do not express the extracellular target biomolecule. Alternatively, the expression of the target biomolecule of the binding region may be non-exclusive to one cell type if the extracellular target biomolecule is expressed in low enough amounts and/or physically coupled in low amounts with cell types that are not to be targeted. This also permits the targeted cell-killing of specific cell types with a high preferentiality (at least a 3-fold cytotoxic effect) over "bystander" cell types that do not express significant amounts of the extracellular target biomolecule or are not physically coupled to significant amounts of the extracellular target biomolecule. A targeted cell may be killed using the cytotoxic proteins of the invention under varied conditions of the cell, such as ex vivo, in vitro cultured, or in vivo—including cells in situ in their native locations within a multicellular organism.

Extracellular target biomolecules of the binding region of the proteins of the invention may include biomarkers over-proportionately or exclusively present on cancer cells, immune cells, and cells infected with intracellular pathogens, such as viruses, bacteria, fungi, prions, or protozoans.

De-Immunized Shiga Toxin Effector Regions

In certain embodiments of the proteins of the invention, one or more amino acid residues may be mutated, inserted, or deleted in order to increase the enzymatic activity of the de-immunized Shiga toxin effector region. For example, mutating residue-position alanine-231 in Stx1A to glutamate increased its enzymatic activity in vitro (Suhan M, Hovde C, *Infect Immun* 66: 5252-9 (1998)).

In certain embodiments of the proteins of the invention, one or more amino acid residues may be mutated or deleted in order to reduce or eliminate catalytic and/or cytotoxic activity of the de-immunized Shiga toxin effector region. The catalytic and/or cytotoxic activity of the A Subunits of members of the Shiga toxin family may be diminished or eliminated by mutation or truncation as long as at least one amino acid is disrupted in at least one natively positioned epitope region provided in the Examples (Tables 1, 2, 3, 4, and/or 5). The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan, *Infect Immun* 66: 5252-9 (1998)). Mutating both glutamate-167 and arginine-170 eliminated the enzymatic activity of Slt-I A1 in a cell-free ribosome inactivation assay (LaPointe, *J Biol Chem* 280: 23310-18 (2005)). In another approach using de novo expression of Slt-I A1 in the endoplasmic reticulum, mutating both glutamate-167 and arginine-170 or truncating SLt-I A1 to residues 1-239 eliminated Slt-I A1 fragment cytotoxicity at that expression level (LaPointe, *J Biol Chem* 280: 23310-18 (2005)).

The proteins of the invention each comprise a de-immunized Shiga toxin effector region polypeptide which retains at least one Shiga toxin effector function but which may be engineered from a cytotoxic parental molecule to a protein with diminished or abolished cytotoxicity for non-cytotoxic functions, e.g., effectuating cytostasis, delivery of exogenous materials, and/or detection of cell types, by mutating one or more key residues for enzymatic activity. This general structure is modular in that the polypeptides of the invention may be linked to any number of diverse compositions of matter, such as binding regions and/or detection promoting agents for various applications as described herein.

The immunogenicity of a molecule (the ability to induce an antibody and/or cell-mediated immune response) can be assessed by observing any immune response (antibody and/or immune cell-mediated) to the molecule after administration to a living organism, such as a chordate. Certain immune responses can be measured, such as the amount and formation of antibodies specifically targeting the administered molecule over time. The presence of antibodies which specifically bind the administered molecule indicate 1) the pre-existence of one or more antibodies which recognized the administered molecule and/or 2) the induction of the de novo formation of one or more antibodies which recognize the administered molecule.

The existence of pre-formed anti-molecule antibodies can be determined by investigating pre-administration serum for the presence of anti-molecule antibodies. The induction of de novo anti-"administered molecule" antibody formation can be determined by monitoring post-administration serum for the amount of anti-molecule antibodies generated over time.

The amount of antibodies induced in chordates after the administration of a molecule (e.g. Shiga toxin effector region polypeptide) can be measured by comparing the amount of pre-administration, anti-molecule antibodies to the amount of post-administration, anti-molecule antibodies. The amount of anti-"administered molecule" antibodies induced in a chordate after administration is indicative of the general immunogenicity of the molecule and the molecule's ability to induce various immune responses in various chordates, such as inducing increased and diversified anti-molecule antibody production after administration, immune cell-mediated immune responses, molecule neutralizing activities, hypersensitivity reactions, anaphylaxis, anaphylactoid reactions, and other immune responses.

It may be difficult to gauge the immunogenicity of a weakly immunogenic molecule without a reference point, such as another more immunogenic molecule. The relative immunogenicity of two molecules (e.g. a wild-type Shiga toxin effector region polypeptide and a de-immunized Shiga toxin effector polypeptide) can be assessed by observing the relative differences in anti-molecule antibodies produced for each molecule respectively after administration of each molecule individually to different organisms. The relative induction of de novo anti-"administered molecule" antibody formation can be determined by measuring the relative differences in post-administration sera for the amount of anti-molecule antibodies generated over time, for each molecule respectively.

The amount of antibodies induced in a chordate, such as a mouse, treated with different molecules (e.g. a wild-type Shiga toxin effector region polypeptide and a de-immunized Shiga toxin effector polypeptide) can be measured with standard ELISA-based assays and used to compare the relative immunogenicity of the different molecules.

Endoplasmic Reticulum Retention/Retrieval Signal Motif of a Member of the KDEL Family For purposes of the present invention, the phrase "endoplasmic reticulum retention/retrieval signal motif," KDEL-type signal motif ("KDEL" disclosed as SEQ ID NO: 60), or signal motif refers to any member of the KDEL family capable of functioning within a eukaryotic cell to promote subcellular localization of a protein to the endoplasmic reticulum via KDEL receptors.

The carboxy-terminal lysine-asparagine-glutamate-leucine (KDEL (SEQ ID NO: 60)) sequence is a canonical, endoplasmic reticulum retention and retrieval signal motif for soluble proteins in eukaryotic cells and is recognized by the KDEL receptors (see, Capitani M, Sallese M, *FEBS Lett* 583: 3863-71 (2009), for review). The KDEL family of signal motifs includes many KDEL-like motifs, such as HDEL (SEQ ID NO: 62), RDEL (SEQ ID NO: 64), WDEL (SEQ ID NO: 65), YDEL (SEQ ID NO: 66), HEEL (SEQ ID NO: 68), KEEL (SEQ ID NO: 69), REEL (SEQ ID NO: 70), KFEL (SEQ ID NO: 73), KIEL (SEQ ID NO: 85), DKEL (SEQ ID NO: 86), KKEL (SEQ ID NO: 89), HNEL (SEQ ID NO: 93), HTEL (SEQ ID NO: 94), KTEL (SEQ ID NO: 95), and HVEL (SEQ ID NO: 96), all of which are found at the carboxy-terminals of proteins which are known to be residents of the lumen of the endoplasmic reticulum of throughout multiple phylogenetic kingdoms (Munro S, Pelham H, *Cell* 48: 899-907 (1987); Raykhel I et al., *J Cell Biol* 179: 1193-204 (2007)). The KDEL signal motif family includes at least 46 polypeptide variants shown using synthetic constructs (Raykhel, *J Cell Biol* 179: 1193-204 (2007)). Additional KDEL signal motifs include ALEDEL (SEQ ID NO: 106), HAEDEL (SEQ ID NO: 107), HLEDEL (SEQ ID NO: 108), KLEDEL (SEQ ID NO: 109), IRSDEL (SEQ ID NO: 110), ERSTEL (SEQ ID NO: 111), and RPSTEL (SEQ ID NO: 112) (Alanen H et al., *J Mol Biol* 409: 291-7 (2011)). A generalized consensus motif representing the majority of KDEL signal motifs has been described as [KRHQSA]-[DENQ]-E-L (Hulo N et al., *Nucleic Acids Res* 34: D227-30 (2006)).

Proteins containing KDEL family signal motifs are bound by KDEL receptors distributed throughout the Golgi complex and transported to the endoplasmic reticulum by a microtubule-dependent mechanism for release into the lumen of the endoplasmic reticulum (Griffiths G et al., *J Cell Biol* 127: 1557-74 (1994); Miesenböck G, Rothman J, *J Cell Biol* 129: 309-19 (1995)). KDEL receptors dynamically cycle between the Golgi complex and endoplasmic reticulum (Jackson M et al., *EMBO J.* 9: 3153-62 (1990); Schutze M et al., *EMBO J.* 13: 1696-1705 (1994)).

For purposes of the present invention, the members of the KDEL family include synthetic signal motifs able to function within a eukaryotic cell to promote subcellular localization of a protein to the endoplasmic reticulum via KDEL receptors. In other words, some members of the KDEL family might not occur in nature or have yet to be observed in nature but have or may be constructed and empirically verified using methods known in the art; see e.g., Raykhel I et al., *J Cell Biol* 179: 1193-204 (2007).

As a component of certain embodiments of the proteins of the invention, the KDEL-type signal motif is physically located, oriented, or arranged within the protein such that it is on a carboxy-terminal.

For the purposes of the present invention, the specific order or orientation is not fixed for the Shiga toxin effector region and the binding region in relation to each other or the entire protein's N-terminal(s) and C-terminal(s) (see e.g. FIG. 1). In the proteins of the invention, the binding regions and Shiga toxin effector regions may be directly linked to each other and/or suitably linked to each other via one or more intervening polypeptide sequences, such as with one or more linkers well known in the art. Optionally, a protein of the invention may further comprise a carboxy-terminal endoplasmic retention/retrieval signal motif, such as KDEL (SEQ ID NO: 60).

The general structure of the proteins of the present invention is modular, in that various, diverse binding regions may be used with the same de-immunized Shiga toxin effector region to provide for diverse targeting of various extracellular target biomolecules and thus targeting of cytotoxicity, cytostasis, and/or exogenous material delivery to various diverse cell types. De-immunized Shiga toxin effector regions which are not cytotoxic due to improper subcellular routing may still be useful for delivering exogenous materials into cells.

II. Linkages Connecting Polypeptide Components of the Invention and/or their Subcomponents Individual polypeptide and/or protein components of the invention, e.g., the binding regions and Shiga toxin effector regions (which may be cytotoxic and/or harbor one or more mutations altering, reducing or eliminating catalytic activity and/or cytotoxicity), may be suitably linked to each other via one or more linkers well known in the art and/or described herein. Individual polypeptide subcomponents of the binding regions, e.g. heavy chain variable regions ($V_H$), light chain variable regions ($V_L$), CDR, and/or ABR regions, may be suitably linked to each other via one or more linkers well known in the art and/or described herein (see e.g. Weisser N, Hall J, *Biotechnol Adv* 27: 502-20 (2009); Chen X et al., *Adv Drug Deliv Rev* 65: 1357-69 (2013)). Protein components of the invention, e.g., multi-chain binding regions, may be suitably linked to each other or other polypeptide components of the invention via one or more linkers well known in the art. Peptide components of the invention, e.g., KDEL family endoplasmic reticulum retention/retrieval signal motifs, may be suitably linked to another component of the invention via one or more linkers, such as a proteinaceous linker, which are well known in the art.

Suitable linkers are generally those which allow each polypeptide component of the invention to fold with a three-dimensional structure very similar to the polypeptide components produced individually without any linker or other component. Suitable linkers include single amino acids, peptides, polypeptides, and linkers lacking any of the aforementioned such as various non-proteinaceous carbon chains, whether branched or cyclic (see e.g. Chen X et al., *Adv Drug Deliv Rev* 65: 1357-69 (2013)).

Suitable linkers may be proteinaceous and comprise one or more amino acids, peptides, and/or polypeptides. Proteinaceous linkers are suitable for both recombinant fusion proteins and chemically linked conjugates. A proteinaceous linker typically has from about 2 to about 50 amino acid residues, such as, e.g., from about 5 to about 30 or from about 6 to about 25 amino acid residues. The length of the linker selected will depend upon a variety of factors, such as, e.g., the desired property or properties for which the linker is being selected (see e.g. Chen X et al., *Adv Drug Deliv Rev* 65: 1357-69 (2013)).

Suitable linkers may be non-proteinaceous, such as, e.g. chemical linkers (see e.g. Dosio F et al., *Toxins* 3: 848-83

(2011); Feld J et al., *Oncotarget* 4: 397-412 (2013)). Various non-proteinaceous linkers known in the art may be used to link binding regions to the Shiga toxin effector regions, such as linkers commonly used to conjugate immunoglobulin-derived polypeptides to heterologous polypeptides. For example, polypeptide regions may be linked using the functional side chains of their amino acid residues and carbohydrate moieties such as, e.g., a carboxy, amine, sulfhydryl, carboxylic acid, carbonyl, hydroxyl, and/or cyclic ring group. For example, disulfide bonds and thioether bonds may be used to link two or more polypeptides (see e.g. Fitzgerald D et al., *Bioconjugate Chem* 1: 264-8 (1990); Pasqualucci L et al., *Haematologica* 80: 546-56 (1995)). In addition, non-natural amino acid residues may be used with other functional side chains, such as ketone groups (see e.g. Sun S et al., *Chembiochem* July 18 (2014); Tian F et al., *Proc Natl Acad Sci USA* 111: 1766-71 (2014)). Examples of non-proteinaceous chemical linkers include but are not limited to N-succinimidyl (4-iodoacetyl)-aminobenzoate, S—(N-succinimidyl) thioacetate (SATA), N-succinimidyl-oxycarbonyl-cu-methyl-a-(2-pyridyldithio) toluene (SMPT), N-succinimidyl 4-(2-pyridyldithio)-pentanoate (SPP), succinimidyl 4-(N-maleimidomethyl) cyclohexane carboxylate (SMCC or MCC), sulfosuccinimidyl (4-iodo-acetyl)-aminobenzoate, 4-succinimidyl-oxycarbonyl-α-(2-pyridyldithio) toluene, sulfosuccinimidyl-6-(α-methyl-α-(pyridyldithiol)-toluamido) hexanoate, N-succinimidyl-3-(-2-pyridyldithio)-proprionate (SPDP), succinimidyl 6(3(-(-2-pyridyldithio)-proprionamido) hexanoate, sulfosuccinimidyl 6(3(-(-2-pyridyldithio)-propionamido) hexanoate, maleimidocaproyl (MC), maleimidocaproyl-valine-citrulline-p-aminobenzyloxycarbonyl (MC-vc-PAB), 3-maleimidobenzoic acid N-hydroxysuccinimide ester (MBS), alpha-alkyl derivatives, sulfoNHS-ATMBA (sulfo-succinimidyl N-[3-(acetylthio)-3-methylbutyryl-beta-alanine]), sulfodicholorphenol, 2-iminothiolane, 3-(2-pyridyl-dithio)-propionyl hydrazide, Ellman's reagent, dichlorotriazinic acid, and S-(2-thiopyridyl)-L-cysteine (see e.g. Thorpe P et al., *Eur J Biochem* 147: 197-206 (1985); Thorpe P et al., *Cancer Res* 47: 5924-31 (1987); Thorpe P et al., *Cancer Res* 48: 6396-403 (1988); Grossbard M et al., *Blood* 79: 576-85 (1992); Lui C et al., *Proc Natl Acad Sci USA* 93: 8618-23 (1996); Doronina S et al., *Nat Biotechnol* 21: 778-84 (2003); Feld J et al., *Oncotarget* 4: 397-412 (2013)).

Suitable linkers, whether proteinaceous or non-proteinaceous, may include, e.g., protease sensitive, environmental redox potential sensitive, pH sensitive, acid cleavable, photocleavable, and/or heat sensitive linkers (see e.g. Dosio F et al., *Toxins* 3: 848-83 (2011); Chen X et al., *Adv Drug Deliv Rev* 65: 1357-69 (2013); Feld J et al., *Oncotarget* 4: 397-412 (2013)).

Proteinaceous linkers may be chosen for incorporation into recombinant fusion proteins of the invention. For recombinant fusion proteins of the invention, linkers typically comprise about 2 to 50 amino acid residues, preferably about 5 to 30 amino acid residues (Argos P, *J Mol Biol* 211: 943-58 (1990); Williamson M, *Biochem J* 297: 240-60 (1994); George R, Heringa J, *Protein Eng* 15: 871-9 (2002); Kreitman R, *AAPS J* 8: E532-51 (2006)). Commonly, proteinaceous linkers comprise a majority of amino acid residues with polar, uncharged, and/or charged residues, such as, e.g., threonine, proline, glutamine, glycine, and alanine (see e.g. Huston J et al. *Proc Natl Acad Sci U.S.A.* 85: 5879-83 (1988); Pastan I et al., *Annu Rev Med* 58: 221-37 (2007); Li J et al., Cell Immunol 118: 85-99 (1989); Cumber A et al. *Bioconj Chem* 3: 397-401 (1992); Friedman P et al., *Cancer Res* 53: 334-9 (1993); Whitlow M et al., *Protein Engineering* 6: 989-95 (1993); Siegall C et al., *J Immunol* 152: 2377-84 (1994); Newton et al. *Biochemistry* 35: 545-53 (1996); Ladurner et al. J Mol Biol 273: 330-7 (1997); Kreitman R et al., *Leuk Lymphoma* 52: 82-6 (2011); U.S. Pat. No. 4,894,443). Non-limiting examples of proteinaceous linkers include alanine-serine-glycine-glycine-proline-glutamate (ASGGPE (SEQ ID NO: 113)), valine-methionine (VM), alanine-methionine (AM), AM$(G_{2\ to\ 4}S)_x$AM where G is glycine, S is serine, and x is an integer from 1 to 10 (SEQ ID NO: 114).

Proteinaceous linkers may be selected based upon the properties desired. Proteinaceous linkers may be chosen by the skilled worker with specific features in mind, such as to optimize one or more of the fusion molecule's folding, stability, expression, solubility, pharmacokinetic properties, pharmacodynamic properties, and/or the activity of the fused domains in the context of a fusion construct as compared to the activity of the same domain by itself. For example, proteinaceous linkers may be selected based on flexibility, rigidity, and/or cleavability (see e.g. Chen X et al., *Adv Drug Deliv Rev* 65: 1357-69 (2013)). The skilled worker may use databases and linker design software tools when choosing linkers. Certain linkers may be chosen to optimize expression (see e.g. Turner D et al., *J Immunol Methods* 205: 43-54 (1997)). Certain linkers may be chosen to promote intermolecular interactions between identical polypeptides or proteins to form homomultimers or different polypeptides or proteins to form heteromultimers. For example, proteinaceous linkers may be selected which allow for desired non-covalent interactions between polypeptide components of the proteins of the invention, such as, e.g., interactions related to the formation dimers and other higher order multimers (see e.g. U.S. Pat. No. 4,946,778).

Flexible proteinaceous linkers are often greater than 12 amino acid residues long and rich in small, non-polar amino acid residues, polar amino acid residues, and/or hydrophilic amino acid residues, such as, e.g., glycines, serines, and threonines (see e.g. Bird R et al., *Science* 242: 423-6 (1988); Friedman P et al., *Cancer Res* 53: 334-9 (1993); Siegall C et al., *J Immunol* 152: 2377-84 (1994)). Flexible proteinaceous linkers may be chosen to increase the spatial separation between components and/or to allow for intramolecular interactions between components. For example, various "GS" linkers are known to the skilled worker and are composed of multiple glycines and/or one or more serines, sometimes in repeating units, such as, e.g., $(G_xS)_n$ (SEQ ID NO: 115), $(S_xG)_n$ (SEQ ID NO: 116), $(GGGGS)_n$ (SEQ ID NO: 117), and $(G)_n$ (SEQ ID NO: 118). in which x is 1 to 6 and n is 1 to 30 (see e.g. WO 96/06641). Non-limiting examples of flexible proteinaceous linkers include GKSSGSGSESKS (SEQ ID NO: 119), GSTSGSGKSSEGKG (SEQ ID NO: 119), GSTSGSGKSSEGSGSTKG (SEQ ID NO: 120), GSTSGSGKSSEGKG (SEQ ID NO: 121), GSTSGSGKPGSGEGSTKG (SEQ ID NO: 122), EGKSSGSGSESKEF (SEQ ID NO: 123), SRSSG (SEQ ID NO: 124), and SGSSC (SEQ ID NO: 125).

Rigid proteinaceous linkers are often stiff alpha-helical structures and rich in proline residues and/or one or more strategically placed prolines (see Chen X et al., *Adv Drug Deliv Rev* 65: 1357-69 (2013)). Rigid linkers may be chosen to prevent intramolecular interactions between linked components.

Suitable linkers may be chosen to allow for in vivo separation of components, such as, e.g., due to cleavage and/or environment-specific instability (see Dosio F et al.,

*Toxins* 3: 848-83 (2011); Chen X et al., *Adv Drug Deliv Rev* 65: 1357-69 (2013)). In vivo cleavable proteinaceous linkers are capable of unlinking by proteolytic processing and/or reducing environments often at a specific site within an organism or inside a certain cell type (see e.g. Doronina S et al., *Bioconjug Chem* 17: 144-24 (2006); Erickson H et al., *Cancer Res* 66: 4426-33 (2006)). In vivo cleavable proteinaceous linkers often comprise protease sensitive motifs and/or disulfide bonds formed by one or more cysteine pairs (see e.g. Pietersz G et al., *Cancer Res* 48: 4469-76 (1998); The J et al., *J Immunol Methods* 110: 101-9 (1998); see Chen X et al., *Adv Drug Deliv Rev* 65: 1357-69 (2013)). In vivo cleavable proteinaceous linkers can be designed to be sensitive to proteases that exist only at certain locations in an organism, compartments within a cell, and/or become active only under certain physiological or pathological conditions (such as, e.g., proteases with abnormally high levels, proteases overexpressed at certain disease sites, and proteases specifically expressed by a pathogenic microorganism). For example, there are proteinaceous linkers known in the art which are cleaved by proteases present only intracellularly, proteases present only within specific cell types, and proteases present only under pathological conditions like cancer or inflammation, such as, e.g., R-x-x-R motif and AMGRSGGGCAGNRVGSSLSCGGLNLQAM (SEQ ID NO: 126).

In certain embodiments of the proteins of the invention, a linker may be used which comprises one or more protease sensitive sites to provide for cleavage by a protease present within a target cell. In certain embodiments of the proteins of the invention, a linker may be used which is not cleavable to reduce unwanted toxicity after administration to a vertebrate organism.

Suitable linkers may include, e.g., protease sensitive, environmental redox potential sensitive, pH sensitive, acid cleavable, photocleavable, and/or heat sensitive linkers, whether proteinaceous or non-proteinaceous (see Chen X et al., *Adv Drug Deliv Rev* 65: 1357-69 (2013)).

Suitable cleavable linkers may include linkers comprising cleavable groups which are known in the art such as, e.g., Zarling D et al., *J Immunol* 124: 913-20 (1980); Jung S, Moroi M, *Biochem Biophys Acta* 761: 152-62 (1983); Bouizar Z et al., *Eur J Biochem* 155: 141-7 (1986); Park L et al., *J Biol Chem* 261: 205-10 (1986); Browning J, Ribolini A, *J Immunol* 143: 1859-67 (1989); Joshi S, Burrows R, *J Biol Chem* 265: 14518-25 (1990)).

Suitable linkers may include pH sensitive linkers. For example, certain suitable linkers may be chosen for their instability in lower pH environments to provide for dissociation inside a subcellular compartment of a target cell. For example, linkers that comprise one or more trityl groups, derivatized trityl groups, bismaleimideothoxy propane groups, adipic acid dihydrazide groups, and/or acid labile transferrin groups, may provide for release of components of the proteins of the invention, e.g. a polypeptide component, in environments with specific pH ranges (see e.g. Welhöner H et al., *J Biol Chem* 266: 4309-14 (1991); Fattom A et al., *Infect Immun* 60: 584-9 (1992)). Certain linkers may be chosen which are cleaved in pH ranges corresponding to physiological pH differences between tissues, such as, e.g., the pH of tumor tissue is lower than in healthy tissues (see e.g. U.S. Pat. No. 5,612,474).

Photocleavable linkers are linkers that are cleaved upon exposure to electromagnetic radiation of certain wavelength ranges, such as light in the visible range (see e.g. Goldmacher V et al., *Bioconj Chem* 3: 104-7 (1992)). Photocleavable linkers may be used to release a component of a protein of the invention, e.g. a polypeptide component, upon exposure to light of certain wavelengths. Non-limiting examples of photocleavable linkers include a nitrobenzyl group as a photocleavable protective group for cysteine, nitrobenzyloxycarbonyl chloride cross-linkers, hydroxypropylmethacrylamide copolymer, glycine copolymer, fluorescein copolymer, and methylrhodamine copolymer (Hazum E et al., *Pept Proc Eur Pept Symp,* 16th, Brunfeldt K, ed., 105-110 (1981); Senter et al., *Photochem Photobiol* 42: 231-7 (1985); Yen et al., *Makromol Chem* 190: 69-82 (1989); Goldmacher V et al., *Bioconj Chem* 3: 104-7 (1992)). Photocleavable linkers may have particular uses in linking components to form proteins of the invention designed for treating diseases, disorders, and conditions that can be exposed to light using fiber optics.

In certain embodiments of the proteins of the invention, a binding region is linked to a Shiga toxin effector region using any number of means known to the skilled worker, including both covalent and noncovalent linkages (see e.g. Chen X et al., *Adv Drug Deliv Rev* 65: 1357-69 (2013); Behrens C, Liu B, *MAbs* 6: 46-53 (2014).

In certain embodiments of the proteins of the invention, the protein comprises a binding region which is a scFv with a linker connecting a heavy chain variable ($V_H$) domain and a light chain variable ($V_L$) domain. There are numerous linkers known in the art suitable for this purpose, such as, e.g., the 15-residue $(Gly4Ser)_3$ peptide (SEQ ID NO: 127). Suitable scFv linkers which may be used in forming non-covalent multivalent structures include GGS, GGGS (SEQ ID NO: 128), GGGGS (SEQ ID NO: 129), GGGGSGGG (SEQ ID NO: 130), GGSGGGG (SEQ ID NO: 131), GSTSGGGSGGGSGGGGSS (SEQ ID NO: 132), and GSTSGSGKPGSSEGSTKG (SEQ ID NO: 133) (Plückthun A, Pack P, *Immunotechnology* 3: 83-105 (1997); Atwell J et al., *Protein Eng* 12: 597-604 (1999); Wu A et al., *Protein Eng* 14: 1025-33 (2001); Yazaki P et al., *J Immunol Methods* 253: 195-208 (2001); Carmichael J et al., *J Mol Biol* 326: 341-51 (2003); Arndt M et al., *FEBS Lett* 578: 257-61 (2004); Bie C et al., *World J Hepatol* 2: 185-91 (2010)).

Suitable methods for linkage of the components of the proteins of the invention may be by any method presently known in the art for accomplishing such, so long as the attachment does not substantially impede the binding capability of the binding regions, the cellular internalization of the protein, and/or desired toxin effector functions of the Shiga toxin effector region as measured by an appropriate assay, including assays described herein.

For the purposes of the present invention, the specific order or orientation is not fixed for the Shiga toxin effector region and the cell-targeting binding region in relation to each other or the entire protein (see e.g. FIG. 1). The components of the polypeptides and proteins of the invention may be arranged in any order provided that the desired activities of the binding region and the Shiga toxin effector region are not eliminated. In the above embodiments of polypeptides and proteins of the invention, the binding regions, Shiga toxin effector regions (which may be cytotoxic and/or harbor one or more mutations reducing or eliminating catalytic activity and/or cytotoxicity), and endoplasmic reticulum retention/retrieval signal motif may be directly linked to each other and/or suitably linked to each other via one or more intervening polypeptide sequences, such as with one or more linkers well known in the art and/or described herein.

III. Examples of Specific Structural Variations of the De-Immunized Shiga Toxin Effector Region Polypeptides and Proteins To create a de-immunized Shiga toxin effector polypeptide, in principle any amino acid in the provided epitope regions may be disrupted by various means, such as, e.g., deletion, insertion, inversion, rearrangement, substitution, and chemical modification of side chains. However, disrupting certain amino acids and polypeptide regions using certain disruptions are more likely to successfully reduce antigenicity and/or immunogenicity while retaining a Shiga toxin effector function. For example, terminal truncations and internal amino acid substitutions are preferred because they maintain the overall amino acid spacing of the Shiga toxin effector region and thus are more likely to maintain Shiga toxin effector functions.

Among certain embodiments of the present invention, the polypeptides comprise the de-immunized Shiga toxin effector region comprising or consisting essentially of amino acids 75 to 251 of SLT-1A (SEQ ID NO:1), StxA (SEQ ID NO:2), and/or SLT-2A (SEQ ID NO:3) wherein at least one amino acid is disrupted in the natively positioned epitope regions provided in the Examples (Tables 1, 2, 3, 4, and/or 5). Among certain other embodiments are polypeptides comprising a de-immunized Shiga toxin effector region derived from amino acids 1 to 241 of SLT-1A (SEQ ID NO:1), StxA (SEQ ID NO:2), and/or SLT-2A (SEQ ID NO:3) wherein at least one amino acid is disrupted in the natively positioned epitope regions provided in the Examples (Tables 1, 2, 3, 4, and/or 5). Further embodiments are polypeptides comprising a de-immunized Shiga toxin effector region derived from amino acids 1 to 251 of SLT-1A (SEQ ID NO:1), StxA (SEQ ID NO:2), and/or SLT-2A (SEQ ID NO:3) wherein at least one amino acid is disrupted in the natively positioned epitope regions provided in the Examples (Tables 1, 2, 3, 4, and/or 5). Further embodiments are polypeptides comprising a de-immunized Shiga toxin effector region which is derived from amino acids 1 to 261 of SLT-1A (SEQ ID NO:1), StxA (SEQ ID NO:2), and/or SLT-2A (SEQ ID NO:3) wherein at least one amino acid is disrupted in the natively positioned epitope regions provided in the Examples (Tables 1, 2, 3, 4, and/or 5).

There are numerous, diverse, internal amino acid substitutions that can be used to create de-immunized Shiga toxin effector region polypeptides of the invention.

Of the possible substitute amino acids to use within an epitope region, the following substitute amino acid residues are predicted to be the most likely to reduce the antigenicity and/or immunogenicity of an epitope—G, D, E, S, T, R, K, and H. Except for glycine, these residues all represent polar and/or charged residues.

Of the possible amino acids to substitute with, the following amino acids A, G, V, L, I, P, C, M, F, S, D, N, Q, H, and K are predicted to be the most likely to reduce antigenicity and/or immunogenicity while retaining a significant Shiga toxin effector function depending on the amino acid substituted for. Generally, the substitution should change a polar and/or charged amino acid residue to a non-polar and uncharged residue. In addition, it may be beneficial to epitope disruption to reduce the overall amino acid residue's R-group functional side chain size and/or length. For example, alanine is generally an acceptable substitution for any amino acid residue, and, for glycine residues, alanine is the preferred choice. Serine is generally only an acceptable substitution for glutamate residues. Aspartate is generally only an acceptable substitution for glutamate residues. Lysine is generally only an acceptable substitution for arginine residues. Glutamine is generally only an acceptable substitution for glutamate, lysine, or arginine residues. Histidine is generally only an acceptable substitution for lysine and arginine residues. However, despite these generalities of substitutions most likely to confer epitope disruption, because the aim is to preserve significant Shiga toxin effector function(s), the substitute amino acid might be more likely to preserve Shiga toxin effector function(s) if it resembles the amino acid substituted for, such as, e.g., a nonpolar and/or uncharged residue of similar size substituted for a polar and/or charged residue.

Based on the empirical evidence in the Examples, certain amino acid positions in the A Subunits of Shiga toxins are predicted to tolerate epitope disruptions while still retaining significant Shiga toxin effector functions. For example, the following natively occurring positions tolerated amino acid substitutions, either alone or in combination, while retaining a Shiga toxin effector function(s) such as cytotoxicity—1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 45 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 53 of SEQ ID NO:1 or SEQ ID NO:2; 55 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 109 of SEQ ID NO:1, SEQ ID NO:2, or SEQ ID NO:3; 110 of SEQ ID NO:1 or SEQ ID NO:2; 112 of SEQ ID NO:1, SEQ ID NO:2, or SEQ ID NO:3; SE 147 of SEQ ID NO:1, SEQ ID NO:2, or SEQ ID NO:3; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 204 of SEQ ID NO:3; 205 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

The empirical data in the Examples point towards other epitope disrupting substitutions and combinations of epitope disrupting substitutions that can reduce antigenicity and/or immunogenicity while retaining a significant Shiga toxin effector function such as, e.g., new combinations of the aforementioned truncations and positions tolerating substitutions as well as new substitutions at identical positions or conserved positions in related Shiga toxins.

It is predictable that other amino acid substitutions to amino acid residues of a conservative functional group may reduce antigenicity and/or immunogenicity while retaining a significant Shiga toxin effector function. For example, other substitutions known to the skilled worker to be similar to any of T4I, S8I, T8V, T9I, S9I, K11A, K11H, S33I, S45I, T45I, D47G, N48V, N48F, L49A, D53A, D53G, D53N, R55A, R55V, R55L, D58A, D58F, P59A, P59F, E60I, E60T, E60R, E61A, E61V, E61L, G62A, D94A, S96I, S109V, T109V, G110A, S112V, G147A, R179A, T180G, T181I, D183A, D183G, D184A, D184F, L185V, S186A, S186F, G187A, R188A, R188L, S189A, R204A, R205A, S247I, Y247A, R248A, R250A, R251A, D264A, G264A, T286A and/or T286I may disrupt an epitope while maintaining at least one Shiga toxin effector function. In particular, amino acid substitutions to conservative amino acid residues similar to KM, T4I, S8I, T8V, T9I, S9I, K11A, K11H, S33I, S45I, T45I, D47G, N48V, N48F, L49A, D53A, D53G, D53N, R55A, R55V, R55L, D58A, D58F, P59A, P59F, E60I, E60T, E60R, E61A, E61V, E61L, G62A, D94A, S96I, S109V, T109V, G110A, S112V, G147A, R179A, T180G, T181I, D183A, D183G, D184A, D184F, L185V, S186A, S186F, G187A, R188A, R188L, S189A, R204A, R205A, S247I, Y247A, R248A, R250A, R251A, D264A, G264A, T286A and/or T286I may have the same or similar effects. In certain embodiments, a Shiga toxin effector region polypeptide of the invention may comprise similar conservative amino acid substitutions such as, e.g., K1 to A, G, V, L, I, F, M and H; T4 to A, G, V, L, F, M, and S; S8 to A, G, V, I, L, F, and M; T9 to A, G, V, I, L, F, M, and S; S9 to A, G, V, L, I, F, and M; K11 to A, G, V, L, I, F, M and H; S33 to A, G, V, L, I, F, and M; S45 to A, G, V, L, I, F, and M; T45 to A, G, V, L, I, F, and M; D47 to A, G, V, L, I, F, S, and Q; N48 to A, G, V, L, and M; L49 to A or G; D53 to A, G, V, L, I, F, S, and Q; R55 to A, G, V, L, I, F, M, Q, S, K, and H; D58 to A, G, V, L, I, F, S, and Q; P59 to A, G, and F; E60 to A, G, V, L, I, F, S, Q, N, D, M, and R; E61 to A, G, V, L, I, F, S, Q, N, D, M, and R; G62 to A; D94 to A, G, V, L, I, F, S, and Q; S96 to A, G, V, I, L, F, and M; S109 to A, G, V, I, L, F, and M; T109 to A, G, V, I, L, F, M, and S; G110 to A; S112 to A, G, V, L, I, F, and M; G147 to A; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; S186 to A, G, V, I, L, F, and M; G187 to A; R188 to A, G, V, L, I, F, M, Q, S, K, and H; S189 to A, G, V, I, L, F, and M; R204 to A, G, V, L, I, F, M, Q, S, K, and H; R205 to A, G, V, L, I, F, M, Q, S, K and H; S247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, M, and S.

Similarly, amino acid substitutions which remove charge, polarity, and/or reduce side chain length can disrupt an epitope while maintaining at least one Shiga toxin effector function. In certain embodiments, a Shiga toxin effector region polypeptide of the invention may comprise one or more epitopes disrupted by substitutions such that side chain charge is removed, polarity is removed, and/or side chain length is reduced such as, e.g., substituting the appropriate amino acid selected from the following group A, G, V, L, I, P, C, M, F, S, D, N, Q, H, or K for the amino acid residue at position 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 45 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 53 of SEQ ID NO:1 or SEQ ID NO:2; 55 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 109 of SEQ ID NO:1, SEQ ID NO:2, or SEQ ID NO:3; 110 of SEQ ID NO:1 or SEQ ID NO:2; 112 of SEQ ID NO:1, SEQ ID NO:2, or SEQ ID NO:3; SE 147 of SEQ ID NO:1, SEQ ID NO:2, or SEQ ID NO:3; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 204 of SEQ ID NO:3; 205 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2. In certain embodiments, a Shiga toxin effector region polypeptide of the invention may comprise one or more of the following amino acid substitutions: K1 to A, G, V, L, I, F, M and H; T4 to A, G, V, L, I, F, M, and S; S8 to A, G, V, I, L, F, and M; T9 to A, G, V, I, L, F, M, and S; S9 to A, G, V, L, I, F, and M; K11 to A, G, V, L, I, F, M and H; S33 to A, G, V, L, I, F, and M; S45 to A, G, V, L, I, F, and M; T45 to A, G, V, L, I, F, and M; D47 to A, G, V, L, I, F, S, and Q; N48 to A, G, V, L, and M; L49 to A or G; D53 to A, G, V, L, I, F, S, and Q; R55 to A, G, V, L, I, F, M, Q, S, K, and H; D58 to A, G, V, L, I, F, S, and Q; P59 to A, G, and F; E60 to A, G, V, L, I, F, S, Q, N, D, M, and R; E61 to A, G, V, L, I, F, S, Q, N, D, M, and R; G62 to A; D94 to A, G, V, L, I, F, S, and Q; S96 to A, G, V, I, L, F, and M; S109 to A, G, V, I, L, F, and M; T109 to A, G, V, I, L, F, M, and S; G110 to A; S112 to A, G, V, L, I, F, and M; G147 to A; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; S186 to A, G, V, I, L, F, and M; G187 to A; R188 to A, G, V, L, I, F, M, Q, S, K, and H; 5189 to A, G, V, I, L, F, and M; R204 to A, G, V, L, I, F, M, Q, S, K, and H; R205 to A, G, V, L, I, F, M, Q, S, K and H; 5247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, M, and S.

In addition, any amino acid substitution in one epitope region of a Shiga toxin effector polypeptide which disrupts an epitope while retaining significant Shiga toxin effector function is combinable with any other amino acid substitution in the same or a different epitope region which disrupts an epitope while retaining significant Shiga toxin effector function to form a de-immunized Shiga toxin effector polypeptide with multiple epitope regions disrupted while still retaining a significant level of Shiga toxin effector function. In certain embodiments, a Shiga toxin effector region polypeptide of the invention may comprise one or more of the following combinations: KIM may be combined with S8I, T9I, K11A, S33I, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; S8I may be combined with KM, T9I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; T9I may be combined with KM, S8I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; S9I may be combined with KM, S8I, T9I, K11A, S33I, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; K11A may be combined with KM, S8I, T9I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; S33I may be combined with KM, S8I, T9I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; S45V or S45I may be combined with KM, S8I, T9I, K11A, S33I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; T45I may be combined with KIM, S8I, T9I, K11A, S33I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; D53A may be combined with KM, S8I, T9I, K11A, S33I, S45I, T45I, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; R55A KM, S8I, T9I, K11A, S33I, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; D58A or D58F may be combined with KM, S8I, T9I, K11A, S33I, S45I, T45I, D53A, R55A, P59A, E60I, E60R, E61A, G62A, G110A, D94A, S96I, G147A, T180G, T181I, D183A, D184A, D184F, S186A, G187A, R188A, S189A, R204A, R205A, S247I, D264A, G264A, G265A, and/or T286I; R55A may be combined with KM, S8I, T9I, K11A, S33I, S45I, T45I, D53A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; P59A may be combined with KM, S8I, T9I, K11A, S33I, S45I, T45I, D53A, R55A, D58A, D58F, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; E60R may be combined with KM, S8I, T9I, K11A, S33I, S45I, T45I, D53A, R55A, D58A, D58F, P59A, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; E60I or E60A may be combined with KM, S8I, T9I, K11A, S45I, T45I, D53A, R55A, D58A, D58F, P59A, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; E61A may be combined with KM, S8I, T9I, K11A, S45I, T45I, D53A, R55A, D58A, D58F, P59A, E60I, E60R, G62A, D94A, S96I, G110A, G147A, T180G, T181I, D183A, D184A, D184F, S186A, G187A, R188A, S189A, R204A, R205A, S247I, D264A, G264A, G265A, and/or T286I; G62A may be combined with KM, S8I, T9I, K11A, S45I, T45I, D53A, R55A, D58A, D58F, P59A, E60I, E60R, E61A, D94A, S96I, G110A, G147A, T180G, T181I, D183A, D184A, D184F, S186A, G187A, R188A, S189A, R204A, R205A, S247I, D264A, G264A, G265A, and/or T286I; D94A may be combined with KM, T9I, K11A, S33I, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; S96I may be combined with KM, T9I, K11A, S33I, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, G265A, and/or T286I; G110A may be combined with T9I, K11A, S33I, S45I, T45I, D53A, R55A, D58A, D58F, P59A, E60I, E60R, E61A, G62A, D94A, S96I, G147A, T180G, T181I, D183A, D184A, D184F, S186A, G187A, R188A, S189A, R204A, R205A, S247I, D264A, G264A, G265A, and/or T286I; G147A may be combined with KM, T9I, K11A, S33I, S45I, T45I, D53A, R55A, D58A, D58F, P59A, E60I, E60R, E61A, G62A, D94A, S96I, G110A, T180G, T181I, D183A, D184A, D184F, S186A, G187A, R188A, S189A, R204A, R205A, S247I, D264A, G264A, G265A, and/or T286I; T180G may be combined with KM, S8I, T9I, K11A, S33I, S45I, T45I, D53A, R55A, D58A, D58F, P59A, E60I, E60R, E61A, G62A, D94A, S96I, G110A, G147A, T181I, D183A, D184A, D184F, S186A, G187A, R188A, S189A, R204A, R205A, S247I, D264A, G264A, G265A, and/or T286I; T181I may be combined with KM, S8I, T9I, K11A, S45I, T45I, D53A, R55A, D58A, D58F, P59A, E60I, E60R, E61A, G62A, D94A, S96I, G110A, G147A, T180G, D183A, D184A, D184F, S186A, G187A, R188A, S189A, R204A, R205A, S247I, D264A, G264A, G265A, and/or T286I; D183A may be combined with S8I, T9I, K11A, S33I, S45I, T45I, D53A, R55A, D58A, D58F, P59A, E60I, E60R, E61A, G62A, D94A, S96I, G110A, G147A, T180G, T181I, D184A, D184F, S186A, G187A, R188A, S189A, R204A, R205A, S247I, D264A, G264A, G265A, and/or T286I; D184A or D184F may be combined with KM, S8I, T9I, K11A, S33I, S45I, T45I, D53A, R55A, D58A, D58F, P59A, E60I, E60R, E61A, G62A, D94A, S96I, G110A, G147A, T180G, T181I, D183A, S186A, G187A, R188A, S189A, R204A, R205A, S247I, D264A, G264A, G265A, and/or T286I; R204A may be combined with KM, S8I, T9I, K11A, S33I, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R205A, S247I, D264A, G264A, G265A, and/or T286I; R205A may be combined with KM, S8I, T9I, K11A, S33I, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, S247I, D264A, G264A, G265A, and/or T286I; S247I may be combined with KM, S8I, T9I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, D264A, G264A, G265A, and/or T286I; D264A may be combined with KM, S8I, T9I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, G264A, G265A, and/or T286I; G264A may be combined with K1M, S8I, T9I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G265A, and/or T286I; G265A may be combined with KM, S8I, T9I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, and/or T286I; and/or T286I may be combined with KM, S8I, T9I, K11A, S45I, T45I, D53A, R55A, D58A, D58F, P59A, E60I, E60R, E61A, G62A, D94A, S96I, G110A, G147A, T180G, T181I, D183A, D184A, D184F, S186A, G187A, R188A, S189A, R204A, R205A, S247I, D264A, G264A, and/or G265A.

Based on the empirical evidence in the Examples, certain amino acid regions in the A Subunits of Shiga toxins are predicted to tolerate epitope disruptions while still retaining significant Shiga toxin effector functions. For example, the epitope regions natively positioned at 1-15, 53-66, 55-66, 94-115 and 180-190 tolerated multiple amino acid substitution combinations simultaneously without losing Shiga toxin enzymatic activity and often without losing cytotoxicity (see Examples).

The linking of cell targeting binding regions with de-immunized Shiga toxin effector region polypeptides enables the engineering of cell-type specific targeting of the potent Shiga toxin cytotoxicity with fewer potential adverse effects resulting from antigenicity and/or immunogenicity when administered to a mammal, e.g., a human subject. Proteins of the invention comprise de-immunized Shiga toxin effector regions derived from the A Subunits of members of the Shiga toxin family linked to binding regions which can bind specifically to at least one extracellular target biomolecule in physical association with a cell, such as a target biomolecule expressed on the surface of a cell. This general structure is modular in that any number of diverse cell-targeting binding regions may be linked to the de-immunized Shiga toxin effector region polypeptides of the invention.

Among certain embodiments of the present invention, the proteins comprise a binding region derived from an immunoglobulin-type polypeptide selected for specific and high-affinity binding to a surface antigen on the cell surface of a cancer cell, where the antigen is restricted in expression to cancer cells (see Glokler J et al., *Molecules* 15: 2478-90 (2010); Liu Y et al., *Lab Chip* 9: 1033-6 (2009). In accordance with other embodiments, the binding region is selected for specific and high-affinity binding to a surface antigen on the cell surface of a cancer cell, where the antigen is over-expressed or preferentially expressed by cancer cells as compared to non-cancer cells. Some representative target biomolecules include, but are not limited to, the following enumerated targets associated with cancers and/or specific immune cell types.

Many immunoglobulin-type binding regions that recognize epitopes associated with cancer cells exist in the prior art, such as binding regions that target annexin AI, B3 melanoma antigen, B4 melanoma antigen, CD2, CD3, CD4, CD20 (B-lymphocyte antigen protein CD20), CD22, CD25 (interleukin-2 receptor IL2R), CD30 (TNFRSF8), CD38 (cyclic ADP ribose hydrolase), CD40, CD44 (hyaluronan receptor), ITGAV (CD51), CD66, CD71 (transferrin receptor), CD73, CD74 (HLA-DR antigens-associated invariant chain), CD79, CD98, endoglin (END, CD105), CD106 (VCAM-1), chemokine receptor type 4 (CDCR-4, fusin, CD184), CD200, insulin-like growth factor 1 receptor (CD221), mucin1 (MUC1, CD227), basal cell adhesion molecule (B-CAM, CD239), CD248 (endosialin, TEM1), tumor necrosis factor receptor 10b (TNFRSF10B, CD262), tumor necrosis factor receptor 13B (TNFRSF13B, TACI, CD276), vascular endothelial growth factor receptor 2 (KDR, CD309), epithelial cell adhesion molecule (EpCAM, CD326), human epidermal growth factor receptor 2 (HER2, Neu, ErbB2, CD340), cancer antigen 15-3 (CA15-3), cancer antigen 19-9 (CA 19-9), cancer antigen 125 (CA125, MUC16), CA242, carcinoembryonic antigen-related cell adhesion molecules (e.g. CEACAM3 (CD66d) and CEACAM5), carcinoembryonic antigen protein (CEA), chondroitin sulfate proteoglycan 4 (CSP4, MCSP, NG2), CTLA4, DLL4, epidermal growth factor receptor (EGFR, ErbB1), folate receptor (FOLR), G-28, ganglioside GD2, ganglioside GD3, HLA-Dr10, HLA-DRB, human epidermal growth factor receptor 1 (HER1), Ephrin type-B receptor 2 (EphB2), epithelial cell adhesion molecule (EpCAM), fibroblast activation protein (FAP/seprase), insulin-like growth factor 1 receptor (IGF1R), interleukin 2 receptor (IL-2R), interleukin 6 receptor (IL-6R), integrins alpha-V beta-3 ($\alpha_V\beta_3$), integrins alpha-V beta-5 ($\alpha v\beta 5$), integrins alpha-5 beta-1 ($\alpha_5\beta_1$), L6, MPG, melanoma-associated antigen 1 protein (MAGE-1), melanoma-associated antigen 3 (MAGE-3), mesothelin (MSLN), MPG, MS4A, p21, p97, polio virus receptor-like 4 (PVRL4), protease-activated-receptors (such as PAR1), prostate-specific membrane antigen protein (PSMA), trophoblast glycoprotein (TPGB), and tumor-associated calcium signal transducers (TACSTDs) (see e.g. Lui B et al., *Cancer Res* 64: 704-10 (2004); Novellino L et al., *Cancer Immunol Immunother* 54: 187-207 (2005); Bagley R et al., *Int J Oncol* 34: 619-27 (2009); Gerber H et al., *mAbs* 1: 247-53 (2009); Beck A et al., *Nat Rev Immunol* 10: 345-52 (2010); Andersen J et al., *J Biol Chem* 287: 22927-37 (2012); Nolan-Stevaux O et al., *PLoS One* 7: e50920 (2012); Rust S et al., *Mol Cancer* 12: 11 (2013)). This list of target biomolecules is intended to be non-limiting. It will be appreciated by the skilled worker that any desired target biomolecule associated with a cancer cell or other desired cell type may be used to design or select a binding region to be coupled with the Shiga toxin effector region to produce a protein of the invention.

Examples of other target biomolecules which are strongly associated with cancer cells and immunoglobulin-type binding regions known to bind them include BAGE proteins (B melanoma antigens), basal cell adhesion molecules (BCAMs or Lutheran blood group glycoproteins), bladder tumor antigen (BTA), cancer-testis antigen NY-ESO-1, cancer-testis antigen LAGE proteins, CD19 (B-lymphocyte antigen protein CD19), CD21 (complement receptor-2 or complement 3d receptor), CD26 (dipeptidyl peptidase-4, DPP4, or adenosine deaminase complexing protein 2), CD33 (sialic acid-binding immunoglobulin-type lectin-3), CD52 (CAMPATH-1 antigen), CD56, CS1 (SLAM family number 7 or SLAMF7), cell surface A33 antigen protein (gpA33), Epstein Barr Virus antigen proteins, GAGE/PAGE proteins (melanoma associated cancer/testis antigens), hepatocyte growth factor receptor (HGFR or c-Met), MAGE proteins, melanoma antigen recognized by T-cells 1 protein (MART-1/MelanA, MARTI), mucins, Preferentially Expressed Antigen of Melanoma (PRAME) proteins, prostate specific antigen protein (PSA), prostate stem cell antigen protein (PSCA), Receptor for Advanced Glycation Endroducts (RAGE), tumor-associated glycoprotein 72 (TAG-72), vascular endothelial growth factor receptors (VEGFRs), and Wilms' tumor antigen.

Examples of other target biomolecules which are strongly associated with cancer cells are carbonic anhydrase IX (CA9/CAIX), Claudin proteins (CLDN3, CLDN4), ephrin type-A receptor 3 (EphA3), folate binding proteins (FBP), ganglioside GM2, insulin-like growth factor receptors, integrins (such as CD11a-c), receptor activator of nuclear factor kappa B (RANK), receptor tyrosine-protein kinase erB-3, tumor necrosis factor receptor 10A (TRAIL-R1/DR4), tumor necrosis factor receptor 10B (TRAIL-R2), Tenascin C, and CD64 (FcγRI) (see Hough C et al., *Cancer Res* 60: 6281-7 (2000); Thepen T et al., *Nat Biotechnol* 18: 48-51 (2000); Pastan I et al., *Nat Rev Cancer* 6: 559-65 (2006); Pastan, *Annu Rev Med* 58: 221-37 (2007); Fitzgerald D et al., *Cancer Res* 71: 6300-9 (2011); Scott A et al., *Cancer Immun* 12: 14-22 (2012)). This list of target biomolecules is intended to be non-limiting.

In addition, there are numerous other examples of contemplated, target biomolecules such as ADAM metalloproteinases (e.g. ADAM-9, ADAM-10, ADAM-12, ADAM-15, ADAM-17), ADP-ribosyltransferases (ART1, ART4), antigen F4/80, bone marrow stroma antigens (BST1, BST2), break point cluster region-c-abl oncogene (BCR-ABL) proteins, C3aR (complement component 3a receptors), CD7, CD13, CD14, CD15 (Lewis X or stage-specific embryonic antigen 1), CD23 (FC epsilon RII), CD49d, CD53, CD54 (intercellular adhesion molecule 1), CD63 (tetraspanin), CD69, CD80, CD86, CD88 (complement component 5a receptor 1), CD115 (colony stimulating factor 1 receptor), CD123 (interleukin-3 receptor), CD129 (interleukin 9 receptor), CD183 (chemokine receptor CXCR3), CD191 (CCR1), CD193 (CCR3), CD195 (chemokine receptor CCR5), CD203c, CD225 (interferon-induced transmembrane protein 1), CD244 (Natural Killer Cell Receptor 2B4), CD282 (toll-like receptor 2), CD284 (Toll-like receptor 4), CD294 (GPR44), CD305 (leukocyte-associated immunoglobulin-like receptor 1), ephrin type-A receptor 2 (EphA2), FceRla, galectin-9, alpha-fetoprotein antigen 17-A1 protein, human aspartyl (asparaginyl) beta-hydroxylase (HAAH), immunoglobulin-like transcript ILT-3, lysophosphatidlglycerol acyltransferase 1 (LPGAT1/IAA0205), lysosome-associated membrane proteins (LAMPs, such as CD107), melanocyte protein PMEL (gp100), myeloid-related protein-14 (mrp-14), receptor tyrosine-protein kinase erbB-3, SART proteins, scavenger receptors (such as CD64 and CD68), Siglecs (sialic acid-binding immunoglobulin-type lectins), syndecans (such as SDC1 or CD138), tyrosinase, tyrosinease-related protein 1 (TRP-1), tyrosinease-related protein 2 (TRP-2), tyrosinase associated antigen (TAA), APO-3, BCMA, CD2, CD3, CD4, CD8, CD18, CD27, CD28, CD29, CD41, CD49, CD90, CD95 (Fas), CD103, CD104, CD134 (OX40), CD137 (4-1BB), CD152 (CTLA-4), chemokine receptors, complement proteins, cytokine receptors, histocompatibility proteins, ICOS, interferon-alpha, interferon-beta, c-myc, osteoprotegerin, PD-1, RANK, TACI, TNF receptor superfamily member (TNF-R1, TNFR-2), Apo2/TRAIL-R1, TRAIL-R2, TRAIL-R3, and TRAIL-R4 (see Scott A et al., *Cancer Immunity* 12: 14 (2012); Cheever M et al., *Clin Cancer Res* 15: 5323-37 (2009)), for target biomolecules and note the target molecules described therein are non-limiting examples). It will be appreciated by the skilled worker that any desired target biomolecule may be used to design or select a binding region to be coupled with a de-immunized Shiga toxin effector region to produce a protein of the invention.

In certain embodiments, the binding region comprises or consists essentially of an immunoglobulin-type polypeptide selected for specific and high-affinity binding to the cellular surface of a cell type of the immune system. For example, immunoglobulin-type binding domains are known that bind to CD1, CD2, CD3, CD4, CD5, CD6, CD7, CD8, CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD33, CD34, CD35, CD36, CD37, CD38, CD40, CD41, CD56, CD61, CD62, CD66, CD95, CD117, CD123, CD235, CD146, CD326, interleukin-2 receptor (IL-2R), receptor activator of nuclear factor kappa B (RANKL), SLAM-associated protein (SAP), and TNFSF18 (tumor necrosis factor ligand 18 or GITRL).

For certain embodiments, the de-immunized cytotoxic protein comprises or consists essentially of amino acids of SEQ ID NO:53, SEQ ID NO:54, SEQ ID NO:55, or SEQ ID NO:56. These de-immunized CD20-binding cytotoxic protein embodiments may be used to treat and/or diagnosis bone cancer, leukemia, lymphoma, melanoma, myeloma, amyloidosis, ankylosing spondylitis, asthma, Crohn's disease, diabetes, graft rejection, graft-versus-host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjogren's syndrome, ulcerative colitis, and/or vasculitis.

For certain embodiments, the de-immunized cytotoxic protein comprises or consists essentially of amino acids of SEQ ID NO:57, SEQ ID NO:58, or SEQ ID NO:59. These de-immunized HER-2-binding cytotoxic protein embodiments may be used to treat and/or diagnosis of breast cancer, cervical cancer, head-neck cancer (e.g. oropharynx), gastro-intestinal cancer (e.g. esophageal and colorectal), kidney-urinary tract cancer (e.g. bladder), lung/pleura cancer, and ovarian cancer.

In certain embodiments, the binding region comprises or consists essentially of a ligand selected for targeting an extracellular receptor. Some representative ligands include, but are not limited to, the following bone morphogenetic proteins and activin membrane-bound inhibitor BAMBI (also known as TGFBR), CD137L (also known as 4-1BB), decoy receptor 3 DcR3 (also known as TR6 and TNFRSF6B), and the tumor necrosis factor TWEAK (also known as TNFSF12 and APO3L). For more non-limiting exemplary ligands, see Table 12 in the Examples.

De-immunized Shiga toxin effector regions which become non-toxic after epitope disruption, e.g. Shiga toxin effector regions comprising R179A, may still be useful for delivering exogenous materials into cells. De-immunized Shiga toxin effector regions which retain only a significant level of the Shiga toxin function of catalytic activity are still useful as enzymatically active, de-immunized components of molecules.

It is within the scope of the invention to use fragments, variants, and/or derivatives of the polypeptides and proteins of the invention which contain a functional extracellular target biomolecule binding site, and even more preferably capable of binding the target biomolecule with high affinity (e.g. as shown by $K_D$). For example, any binding region comprising a polypeptide that binds to a target biomolecule, preferably expressed on a cell surface, with a dissociation constant of $10^{-5}$ to $10^{-12}$ moles per liter, preferably less than 200 nM, may be substituted for use in making molecules of the invention (e.g. de-immunized Shiga toxin effector polypeptides and cytotoxic proteins) and methods of the invention.

IV. General Functions of the De-Immunized Shiga Toxin Effector Region Polypeptides and Proteins The polypeptides and proteins of the invention have improved usefulness for administration to mammalian species as either a therapeutic and/or diagnostic agent because of the reduced likelihood of producing undesired immune responses in mammals. Importantly, in polypeptides of the invention, the desired biological functions of the original Shiga toxin effector regions were preserved after the B-cell epitope(s) was disrupted. In addition, B-cell epitopes often coincide or overlap with epitopes of mature CD4+ T-cells, thus the disruption of a B-cell epitope often simultaneously disrupts a CD4+ T-cell epitope.

The various de-immunized Shiga toxin effector polypeptides of the invention might differ in their antigenicity profiles when administered to various mammals, but are expected to have reduced antigenicity and/or immunogenicity. It is not necessary to completely eliminate all immunogenicity from a Shiga toxin derived polypeptide in order to improve its use in medical applications involving administration to a mammal (see Nagata, *Adv Drug Deliv Rev* 61: 977-85 (2009)). The modification of only a few dominant amino acids in a therapeutic protein can greatly reduce its antigenicity and/or immunogenicity without perturbing the protein's overall stability, structure, and function. However, Shiga toxin effector polypeptide regions with disruptions in more immunogenic B-cell epitopes are expected to be more advantageous for administration to mammals when it is desirable to avoid unwanted B-cell and/or CD4+ T-cell immune responses.

The present invention provides various de-immunized Shiga toxin effector polypeptides which may be used as components of various compositions of matter, such as cell-targeted cytotoxic proteins and diagnostic compositions. In particular, the de-immunized Shiga toxin effector polypeptides have uses as components of various protein therapeutics, such as, e.g. immunotoxins and ligand-toxin fusions, for the targeted killing of specific cell types for the treatment of a variety of diseases, including cancers, immune disorders, and microbial infections.

The present invention also provides various cytotoxic proteins comprising de-immunized Shiga toxin effector regions functionally associated with binding regions to effectuate cell targeting such that the cytotoxic proteins selectively kill, inhibit the growth of, deliver exogenous material to and/or detect specific cell types. The binding regions of the proteins of the invention are capable of binding specifically to at least one extracellular target biomolecule in physical association with a cell, such as a target biomolecule expressed on the surface of a cell. The linking of cell targeting binding regions with de-immunized Shiga toxin effector region polypeptides enables the engineering of cell-type specific targeting of the potent Shiga toxin cytotoxicity and/or cytostasis.

In certain embodiments, the proteins of the invention are capable of binding extracellular target biomolecules associated with the cell surface of particular cell types and entering those cells. Once internalized within a targeted cell type, certain embodiments of the proteins of the invention are capable of routing an enzymatically active, cytotoxic, Shiga toxin effector polypeptide fragment into the cytosol of the target cell. Once in the cytosol of a targeted cell type, certain embodiments of the cytotoxic proteins of the invention are capable of enzymatically inactivating ribosomes and eventually killing the cell. Alternatively, nontoxic variants of the proteins of the invention may be used to deliver additional exogenous materials into target cells, such as peptides, polypeptides, proteins, polynucleotides, and detection promoting agents. This system is modular, in that any number of diverse binding regions can be used to target this potent cytotoxicity to various, diverse cell types.

A. Cell Kill Via Targeted Shiga Toxin Cytotoxicity

Because members of the Shiga toxin family are adapted to killing eukaryotic cells, cytotoxic proteins designed using de-immunized Shiga toxin effector regions can show potent cell-kill activity. The A Subunits of members of the Shiga toxin family comprise enzymatic domains capable of killing a eukaryotic cell once in the cell's cytosol. The disruption of B-cell epitopes did not significantly alter the cytotoxic mechanism of certain Shiga toxin effector regions of the invention. Thus, the de-immunized cytotoxic proteins of the invention maintain potent cytotoxicity while reducing the likelihood of certain immune responses when administered to a mammal.

In certain embodiments of the de-immunized cytotoxic proteins of the invention, upon contacting a cell physically coupled with an extracellular target biomolecule of the binding region of a cytotoxic protein of the invention (target+ cell), the cytotoxic protein is capable of causing death of the cell. Cell kill may be accomplished using a cytotoxic protein of the invention under varied conditions of target cells, such as an ex vivo manipulated target cell, a target cell cultured in vitro, a target cell within a tissue sample cultured in vitro, or a target cell in vivo.

B. Selective Cytotoxicity Among Cell Types

By targeting the delivery of enzymatically active, de-immunized, Shiga toxin regions using high-affinity binding regions to specific cell types, this potent cell-kill activity can be restricted to preferentially killing selected cell types.

In certain embodiments, upon administration of the protein of the invention to a mixture of cell types, the protein is capable of selectively killing those cells which are physically coupled with an extracellular target biomolecule compared to cell types not physically coupled with an extracellular target biomolecule. Because members of the Shiga toxin family are adapted for killing eukaryotic cells, cytotoxic proteins designed using Shiga toxin effector regions can show potent cytotoxic activity. By targeting the delivery of enzymatically active Shiga toxin regions to specific cell types using high-affinity binding regions, this potent cell kill activity can be restricted to killing only those cell types desired to be targeted by their physical association with a target biomolecule of the chosen binding regions.

In certain embodiments, the cytotoxic protein of the invention is capable of selectively or preferentially causing the death of a specific cell type within a mixture of two or more different cell types. This enables the targeted cytotoxic activity to specific cell types with a high preferentiality, such as a 3-fold cytotoxic effect, over "bystander" cell types that do not express the target biomolecule. Alternatively, the expression of the target biomolecule of the binding region may be non-exclusive to one cell type if the target biomolecule is expressed in low enough amounts and/or physically coupled in low amounts with cell types that are not to be targeted. This enables the targeted cell-killing of specific cell types with a high preferentiality, such as a 3-fold cytotoxic effect, over "bystander" cell types that do not express significant amounts of the target biomolecule or are not physically coupled to significant amounts of the target biomolecule.

In certain further embodiments, upon administration of the cytotoxic protein to two different populations of cell types, the cytotoxic protein is capable of causing cell death as defined by the half-maximal cytotoxic concentration ($CD_{50}$) on a population of target cells, whose members express an extracellular target biomolecule of the binding region of the cytotoxic protein, at a dose at least three-times lower than the $CD_{50}$ dose of the same cytotoxic protein to a population of cells whose members do not express an extracellular target biomolecule of the binding region of the cytotoxic protein.

In certain embodiments, the cytotoxic activity toward populations of cell types physically coupled with an extracellular target biomolecule is at least 3-fold higher than the cytotoxic activity toward populations of cell types not physically coupled with any extracellular target biomolecule of the binding region. According to the present invention, selective cytotoxicity may be quantified in terms of the ratio (a/b) of (a) cytotoxicity towards a population of cells of a specific cell type physically coupled with a target biomolecule of the binding region to (b) cytotoxicity towards a population of cells of a cell type not physically coupled with a target biomolecule of the binding region. In certain embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of cells or cell types physically coupled with a target biomolecule of the binding region compared to populations of cells or cell types not physically coupled with a target biomolecule of the binding region.

This preferential cell-killing function allows a targeted cell to be killed by certain cytotoxic proteins of the invention under varied conditions and in the presence of non-targeted bystander cells, such as ex vivo manipulated mixtures of cell types, in vitro cultured tissues with mixtures of cell types, or in vivo in the presence of multiple cell types (e.g. in situ or in its native location within a multicellular organism).

C. Delivery of Additional Exogenous Material into the Interior of Targeted Cells In addition to cytotoxic and cytostatic applications, proteins of the invention optionally may be used for information gathering and diagnostic functions. Further, non-toxic variants of the cytotoxic proteins of the invention, or optionally toxic variants, may be used to deliver additional exogenous materials to and/or label the interiors of cells physically coupled with an extracellular target biomolecule of the cytotoxic protein. Various types of cells and/or cell populations which express target biomolecules to at least one cellular surface may be targeted by the proteins of the invention for receiving exogenous materials. The functional components of the present invention are modular, in that various Shiga toxin effector regions and additional exogenous materials may be linked to various binding regions to provide diverse applications, such as non-invasive in vivo imaging of tumor cells.

Because the proteins of the invention, including nontoxic forms thereof, are capable of entering cells physically coupled with an extracellular target biomolecule recognized by its binding region, certain embodiments of the proteins of the invention may be used to deliver additional exogenous materials into the interior of targeted cell types. In one sense, the entire protein of the invention is an exogenous material which will enter the cell; thus, the "additional" exogenous materials are heterologous materials linked to but other than the core cytotoxic protein itself. De-immunized Shiga toxin effector regions which become non-toxic after epitope disruption may still be useful for delivering exogenous materials into cells (e.g. R179A).

"Additional exogenous material" as used herein refers to one or more molecules, often not generally present within a native target cell, where the proteins of the present invention can be used to specifically transport such material to the interior of a cell. Non-limiting examples of additional exogenous materials are peptides, polypeptides, proteins, polynucleotides, small molecule chemotherapeutic agents, and detection promoting agents.

In certain embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA). In certain embodiments, the additional exogenous material is an antigen, such as antigens derived from bacterial proteins, viral proteins, proteins mutated in cancer, proteins aberrantly expressed in cancer, or T-cell complementary determining regions. For example, exogenous materials include antigens, such as those characteristic of antigen-presenting cells infected by bacteria, and T-cell complementary determining regions capable of functioning as exogenous antigens. Additional examples of exogenous materials include polypeptides and proteins larger than an antigenic peptide, such as enzymes. Exogenous materials comprising polypeptides or proteins may optionally comprise one or more antigens whether known or unknown to the skilled worker.

D. Information Gathering for Diagnostic Functions

Certain proteins of the invention have uses in the in vitro and/or in vivo detection of specific cells, cell types, and/or cell populations. In certain embodiments, the proteins described herein are used for both diagnosis and treatment, or for diagnosis alone. When the same cytotoxic protein is used for both diagnosis and treatment, the cytotoxic protein variant which incorporates a detection promoting agent for diagnosis may be rendered nontoxic by catalytic inactivation of a Shiga toxin effector region via one or more amino acid substitutions, including exemplary substitutions described herein. Nontoxic forms of the cytotoxic proteins of the invention that are conjugated to detection promoting agents optionally may be used for diagnostic functions, such as for companion diagnostics used in conjunction with a therapeutic regimen comprising the same or a related binding region.

The ability to conjugate detection promoting agents known in the art to various proteins of the invention provides useful compositions for the detection of cancer, tumor, immune, and infected cells. These diagnostic embodiments of the proteins of the invention may be used for information gathering via various imaging techniques and assays known in the art. For example, diagnostic embodiments of the proteins of the invention may be used for information gathering via imaging of intracellular organelles (e.g. endocytotic, Golgi, endoplasmic reticulum, and cytosolic compartments) of individual cancer cells, immune cells, or infected cells in a patient or biopsy sample.

Various types of information may be gathered using the diagnostic embodiments of the proteins of the invention whether for diagnostic uses or other uses. This information may be useful, for example, in diagnosing neoplastic cell types, determining therapeutic susceptibilities of a patient's disease, assaying the progression of antineoplastic therapies over time, assaying the progression of immunomodulatory therapies over time, assaying the progression of antimicrobial therapies over time, evaluating the presence of infected cells in transplantation materials, evaluating the presence of unwanted cell types in transplantation materials, and/or evaluating the presence of residual tumor cells after surgical excision of a tumor mass.

For example, subpopulations of patients might be ascertained using information gathered using the diagnostic variants of the proteins of the invention, and then individual patients could be categorized into subpopulations based on their unique characteristic(s) revealed using those diagnostic embodiments. For example, the effectiveness of specific pharmaceuticals or therapies might be one type of criterion used to define a patient subpopulation. For example, a nontoxic diagnostic variant of a particular cytotoxic protein of the invention may be used to differentiate which patients are in a class or subpopulation of patients predicted to respond positively to a cytotoxic variant of the same protein of the invention. Accordingly, associated methods for patient identification, patient stratification, and diagnosis using de-immunized proteins of the invention, including non-toxic variants of cytotoxic proteins of the invention, are considered to be within the scope of the present invention.

E. Immunization/Vaccination Materials and Anti-Toxins

The polypeptides of the invention have uses as biased immunization and/or vaccination materials for driving the elicitation of immune responses to specific epitopes in the presence of a de-immunized Shiga toxin effector region polypeptide of the invention. Infections by Shiga toxin producing microorganisms are responsible for morbidity and mortality (Johannes, *Nat Rev Microbiol* 8: 105-16 (2010)). Shiga toxin producing bacteria are the leading cause of hemolytic uremic syndrome (HUS) and Shigellosis, as well as the associated conditions such as hemorrhagic colitis and diarrhea (see Karmali M, *Mol Biotechnol* 26: 117-22 (2004)). In addition, Shiga toxins are classified by the U.S. Centers for Disease Control and Prevention (CDC) as category B biothreat agents for their potential to be used as a bioweapon.

Mammalian antibodies elicited during immune responses to a Shiga holotoxin or Shiga toxin subunit may be either neutralizing or non-neutralizing depending on the epitope. Furthermore, antibodies recognizing Shiga toxins may have different neutralizing effects depending on which Shiga toxin subunit comprises the epitope of the antibody (Krautz-Peterson G et al., *Infect Immun* 76: 1931-9 (2008)). Certain polypeptides of the invention are thus useful in methods to artificially drive mammalian immune responses away from certain epitope regions, such as, e.g., which elicit undesirable non-neutralizing antibodies and towards other epitopes, such as, e.g., which elicit desirable neutralizing and/or protective antibodies.

Certain polypeptides of the invention have uses as biased immunization and/or vaccination materials in methods for reducing and/or eliminating the antigenicity and/or immunogenicity of specific epitopes while permitting the elicitation of immune responses to undisrupted, native epitopes. Immunization techniques for mammals may be used to generate anti-Shiga toxin antibodies which are biased away from a selected epitope region(s) of a Shiga toxin A Subunit.

In addition, certain polypeptides of the invention may be used in various screening methods, such as, e.g., protein display screening and in vitro selections, for generation, identification, and affinity maturation of various binding domains, such as, e.g., immunoglobulin-type domains, which bind Shiga toxins such that screen selections are biased away from a selected epitope region(s) of a Shiga toxin A Subunit (see Glöckler J et al., *Molecules* 15: 2478-90 (2010); Bradbury A et al., *Nat Biotechnol* 29: 245-54 (2011); Chen T, Keating A, *Protein Sci* 21: 949-63 (2012); Geyer C et al., *Methods Mol Biol* 901: 11-32 (2012)). These methods are particularly useful for targeting discontinuous epitopes which cannot be targeted in the absence of other untargeted epitopes. These methods are used to generate novel neutralizing antibodies and non-immunoglobulin type domains which inhibit Shiga toxin toxicity (see Perera L et al., *J Clin Microbiol* 26: 2127-31 (1988); Mukherjee J et al., *Infect Immun* 70: 5896-9 (2002); Smith M et al., *Infect Immun* 77: 2730-40 (2009); Rocha L et al., *Toxins* 4: 729-47 (2012); Tremblay J et al., *Infect Immun* 81: 4592-603 (2013); Skinner C et al., *PLoS One* 9: e99854 (2014)).

Certain polypeptides of the invention may be used as immunization materials in methods for the creation and/or production of biased anti-Shiga toxin antibodies or anti-toxins. Immunization techniques for mammals may be used to generate anti-Shiga toxin antibodies which are biased away from a selected epitope region(s) of a Shiga toxin A Subunit. For example, certain polypeptides of the invention may be used as an immunization material to generate anti-Shiga toxin A Subunit antibodies which are biased away from a selected epitope region(s) of a Shiga toxin A Subunit. In addition, by combining a de-immunized Shiga toxin A Subunit of the invention with Shiga toxin B Subunits, immunization techniques may be used to generate anti-Shiga toxin antibodies biased toward epitopes present on native Shiga toxin B Subunits and/or interfaces between the Shiga toxin subunits present in the holotoxin. These anti-Shiga toxin antibodies have uses in methods involving immunodetection assays and for the creation of Shiga toxin neutralizing antibodies or anti-toxins (see Mukherjee J et al., *Infect Immun* 70: 5896-9 (2002); Sheoran A et al., *Infect Immun* 71: 3125-30 (2003); Cheng L et al., *Toxins* 5: 1845-58 (2013); He X et al., *J Immunol Methods* 389: 18-28 (2013); Tremblay J et al., *Infect Immun* 81: 4592-603 (2013)). Therefore, certain polypeptides of the invention may be used to better generate Shiga toxin neutralizing antibodies which then may be administered as a protective agent, therapeutic agent, or engineered into a protective and/or therapeutic for the treatment of infections by Shiga toxin producing microorganisms or other exposures to Shiga toxins (see Fujii J et al., *Microb Pathog* 25: 139-46 (1998); Mukherjee J et al., *Infect Immun* 70: 5896-9 (2002); Sheoran A et al., *Infect Immun* 71: 3125-30 (2003); Gao X et al., *Vaccine* 29: 6656-63 (2011); Cheng L et al., *Toxins* 5: 1845-58 (2013); He X et al., *J Immunol Methods* 389: 18-28 (2013); Tremblay J et al., *Infect Immun* 81: 4592-603 (2013); Vance D et al., *J Biol Chem* 288: 36538-47 (2013)).

Certain polypeptides of the invention may be used as vaccination materials in methods for the creation and/or production of biased anti-Shiga toxin antibodies. Vaccination techniques may be used with compositions comprising certain polypeptides of the invention to confer a mammal with active immunity to a future infection by a Shiga toxin producing microorganism or other exposure to a Shiga toxin (see Bosworth B et al., *Infect Immun* 64: 55-60 (1996); Rabinovitz B et al., *J Dairy Sci* 95: 3318-26 (2012)). Vaccine design may take into account the differences between epitopes that elicit neutralizing antibodies versus non-neutralizing antibodies with the possibility of non-neutralizing antibodies interfering with protective, neutralizing antibodies in a subject.

For example, in a study of five antibodies to a Shiga holotoxin, only one showed neutralizing activity and this one bound both the A and B Subunits (He X et al., *J Immunol*

*Methods* 389: 18-28 (2013)). Similarly for the AB toxin ricin, a neutralizing antibody recognizes an interface between the A and B Subunits and prevents the liberation of an A Subunit fragment (O'Hara J, Mantis N, *J Immunol Methods* 395: 71-8 (2013)).

For vaccination purposes, it might be more favorable to bias vaccine materials to elicit antibody responses primarily to external epitopes and/or epitopes which span interfaces of the A Subunit with the B Subunit in a holotoxin structure (O'Hara J, Mantis N, *J Immunol Methods* 395: 71-8 (2013); O'Hara J et al., *Curr Top Microbiol Immunol* 357: 209-41 (2012)). For example, vaccinations to ricin may have benefited from the elimination of a native immunogenic region that elicits only non-protective, non-neutralizing antibodies (Olsnes S, *Toxicon* 44: 361-70 (2004)). Similarly, the removal of an immunodominant region of ricin might have biased antibody responses away from producing non-neutralizing antibodies to certain epitopes (O'Hara J et al., *Vaccine* 28: 7035-46 (2010)) or even away from producing toxin-enhancing antibodies (Maddaloni M et al., *J Immunol* 172: 6221-8 (2004)). To that end, the elimination of certain epitopes within isolated regions of Shiga toxin A could remove undesired epitopes and drive antibody creation of more desirable epitopes, such as epitopes spanning Shiga toxin subunit interfaces.

The polypeptides of the invention useful as biased immunization and/or vaccination materials may benefit from reductions and/or eliminations of Shiga toxin effector functions, such as enzymatic activity and/or cytotoxicity (He X et al., *J Immunol Methods* 389: 18-28 (2013); Skinner C et al., *PLoS One* 9: e99854 (2014)). Reduction or elimination of a Shiga toxin effector function may be accomplished by using one or more truncations and/or amino acid substitutions known to the skilled worker or discovered by the skilled worker using well-known methods. In addition, reduction or elimination of a Shiga toxin effector function may be accomplished by using the substitutions described in the Examples which exhibited attenuated, severely reduced, and/or loss of activity in a Shiga toxin effector assay, such as, e.g., ribosome inhibition and targeted cytotoxicity.

V. Variations in the Polypeptide Sequence of the De-Immunized Shiga Toxin Effector Region Polypeptides and Proteins The skilled worker will recognize that variations may be made to de-immunized Shiga toxin effector region polypeptides and proteins of the invention, and polynucleotides encoding any of the former, without diminishing their biological activities, e.g., by maintaining the overall structure and function of the toxin effector region in conjunction with one or more epitope disruptions which reduce antigenic and/or immunogenic potential. For example, some modifications may facilitate expression, purification, and/or pharmacokinetic properties, and/or immunogenicity. Such modifications are well known to the skilled worker and include, for example, a methionine added at the amino terminus to provide an initiation site, additional amino acids placed on either terminus to create conveniently located restriction sites or termination codons, and biochemical affinity tags fused to either terminus to provide for convenient detection and/or purification.

Also contemplated herein is the inclusion of additional amino acid residues at the amino and/or carboxy termini, such as sequences for epitope tags or other moieties. The additional amino acid residues may be used for various purposes including, e.g., facilitating cloning, facilitating expression, post-translational modification, facilitating synthesis, purification, facilitating detection, and administration. Non-limiting examples of epitope tags and moieties are chitin binding protein domains, enteropeptidase cleavage sites, Factor Xa cleavage sites, FIAsH tags, FLAG tags, green fluorescent proteins (GFP), glutathione-S-transferase moieties, HA tags, maltose binding protein domains, myc tags, polyhistidine tags, ReAsH tags, STREP-TAG, Strep-Tag® II, TEV protease sites, thioredoxin domans, thrombin cleavage site, and V5 epitope tags.

In certain of the above embodiments, the polypeptide sequence of the de-immunized Shiga toxin effector region polypeptides and/or proteins of the invention are varied by one or more conservative amino acid substitutions introduced into the polypeptide region(s) as long as at least one amino acid is disrupted in at least one natively positioned epitope region provided herein. As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids (see, for example, Table B, infra). An example of a conservative substitution with a residue normally not found in endogenous, mammalian peptides and proteins is the conservative substitution of an arginine or lysine residue with, for example, ornithine, canavanine, aminoethylcysteine, or another basic amino acid. For further information concerning phenotypically silent substitutions in peptides and proteins see, e.g., Bowie J et al., *Science* 247: 1306-10 (1990).

TABLE B

Examples of Conservative Amino Acid Substitutions

| I | II | III | IV | V | VI | VII | VIII | IX | X | XI | XII | XIII | XIV |
|---|---|---|---|---|---|---|---|---|---|---|---|---|---|
| A | D | H | C | F | N | A | C | F | A | C | A | A | D |
| G | E | K | I | W | Q | G | M | H | C | D | C | C | E |
| P | Q | R | L | Y | S | I | P | W | F | E | D | D | G |
| S | N | | M | | T | L | | Y | G | H | G | E | K |
| T | | | V | | | V | | | H | K | N | G | P |
| | | | | | | | | | I | N | P | H | Q |
| | | | | | | | | | L | Q | S | K | R |
| | | | | | | | | | M | R | T | N | S |
| | | | | | | | | | R | S | V | Q | T |
| | | | | | | | | | T | T | | R | |
| | | | | | | | | | V | | | S | |
| | | | | | | | | | W | | | P | |
| | | | | | | | | | Y | | | T | |

In the conservative substitution scheme in Table B, exemplary conservative substitutions of amino acids are grouped by physicochemical properties—I: neutral, hydrophilic; II: acids and amides; III: basic; IV: hydrophobic; V: aromatic, bulky amino acids, VI hydrophilic uncharged, VII aliphatic uncharged, VIII non-polar uncharged, IX cycloalkenyl-associated, X hydrophobic, XI polar, XII small, XIII turn-permitting, and XIV flexible. For example, conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

Additional conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

In certain embodiments, the de-immunized Shiga toxin effector region polypeptides and/or proteins of the invention may comprise functional fragments or variants of a polypeptide region of the invention that have, at most, 20, 15, 10, 9, 8, 7, 6, 5, 4, 3, 2, or 1 amino acid substitutions compared to a polypeptide sequence recited herein, as long as it retains a disruption of at least one amino acid in a natively positioned epitope region provided in the Examples (Tables 1, 2, 3, 4, and/or 5) and as long as it exhibits a significant level of a Shiga toxin effector function alone and/or as a component of a therapeutic and/or diagnostic composition. Variants of the de-immunized Shiga toxin effector region polypeptides and/or proteins of the invention are within the scope of the invention as a result of changing a polypeptide of the protein of the invention by altering one or more amino acids or deleting or inserting one or more amino acids, such as within the binding region or the Shiga toxin effector region, in order to achieve desired properties, such as changed cytotoxicity, changed cytostatic effects, changed immunogenicity, and/or changed serum half-life. A de-immunized Shiga toxin effector region polypeptide and/or a polypeptide of a protein of the invention may further be with or without a signal sequence.

In certain embodiments, the de-immunized Shiga toxin effector region polypeptides and/or proteins of the invention shares at least 85%, 90%, 95%, 96%, 97%, 98%, 99% or more amino acid sequence identity to any one of the amino acid sequences of a protein recited herein, as long as it retains a disruption of at least one amino acid in a natively positioned epitope region provided in the Examples (Tables 1, 2, 3, 4, and/or 5) and measurable biological activity, such as cytotoxicity, extracellular target biomolecule binding, enzymatic catalysis, subcellular routing, or catalytically inactivating ribosomes.

In certain embodiments, the de-immunized Shiga toxin effector region polypeptides and/or proteins of the invention may be altered to change the enzymatic activity and/or cytotoxicity of the Shiga toxin effector region as long as at least one amino acid is disrupted in a natively positioned epitope region provided in the Examples (Tables 1, 2, 3, 4, and/or 5). This change may or may not result in a change in the cytotoxicity of the Shiga toxin effector region polypeptide or cytotoxic protein of which the altered Shiga toxin effector region is a component. Possible alterations include mutations to the Shiga toxin effector region polypeptide selected from the group consisting of: a truncation, deletion, inversion, insertion and substitution as long as at least one amino acid is disrupted in a natively positioned epitope region provided in the Examples (Tables 1, 2, 3, 4, and/or 5).

The cytotoxicity of the A Subunits of members of the Shiga toxin family may be reduced or eliminated by mutation or truncation. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Slt-I A1 in a cell-free ribosome inactivation assay (LaPointe, *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe, *J Biol Chem* 280: 23310-18 (2005)). A truncation analysis demonstrated that a fragment of StxA from residues 75 to 268 still retains significant enzymatic activity in vitro (Haddad, *J Bacteriol* 175: 4970-8 (1993)). A truncated fragment of Slt-I A1 containing residues 1-239 displayed significant enzymatic activity in vitro and cytotoxicity by de novo expression in the cytosol (LaPointe, *J Biol Chem* 280: 23310-18 (2005)). Expression of a Slt-I A1 fragment truncated to residues 1-239 in the endoplasmic reticulum was not cytotoxic because it could not retrotranslocate to the cytosol (LaPointe, *J Biol Chem* 280: 23310-18 (2005)).

The most critical residues for enzymatic activity and/or cytotoxicity in the Shiga toxin A Subunits were mapped to the following residue-positions: asparagine-75, tyrosine-77, tyrosine-114, glutamate-167, arginine-170, arginine-176, and tryptophan-203 among others (Di, *Toxicon* 57: 525-39 (2011)). In particular, a double-mutant construct of Stx2A containing glutamate-E167-to-lysine and arginine-176-to-lysine mutations was completely inactivated; whereas, many single mutations in Stx1 and Stx2 showed a 10-fold reduction in cytotoxicity. Further, truncation of Stx1A to 1-239 or 1-240 reduced its cytotoxicity, and similarly, truncation of Stx2A to a conserved hydrophobic residue reduced its cytotoxicity. The most critical residues for binding eukaryotic ribosomes and/or eukaryotic ribosome inhibition in the Shiga toxin A Subunit have been mapped to the following residue-positions: arginine-172, arginine-176, arginine-179, arginine-188, tyrosine-189, valine-191, and leucine-233 among others (McCluskey A et al., *PLoS One* 7: e31191 (2012).

Shiga-like toxin 1 A Subunit truncations are catalytically active, capable of enzymatically inactivating ribosomes in vitro, and cytotoxic when expressed within a cell (LaPointe, *J Biol Chem* 280: 23310-18 (2005)). The smallest Shiga toxin A Subunit fragment exhibiting full enzymatic activity is a polypeptide composed of residues 1-239 of Slt1A (LaPointe, *J Biol Chem* 280: 23310-18 (2005)). Although the smallest fragment of the Shiga toxin A Subunit reported to retain substantial catalytic activity was residues 75-247 of StxA (Al-Jaufy, *Infect Immun* 62: 956-60 (1994)), a StxA truncation expressed de novo within a eukaryotic cell requires only up to residue 240 to reach the cytosol and exert catalytic inactivation of ribosomes (LaPointe, *J Biol Chem* 280: 23310-18 (2005)).

In certain embodiments of the de-immunized Shiga toxin effector region polypeptides and/or proteins of the invention derived from SLT-1A (SEQ ID NO:1) or StxA (SEQ ID NO:2), these changes include substitution of the asparagine at position 75, tyrosine at position 77, tyrosine at position 114, glutamate at position 167, arginine at position 170, arginine at position 176, and/or substitution of the tryptophan at position 203. Examples of such substitutions will be known to the skilled worker based on the prior art, such as asparagine at position 75 to alanine, tyrosine at position 77 to serine, substitution of the tyrosine at position 114 to serine, substitution of the glutamate at position 167 to glutamate, substitution of the arginine at position 170 to alanine, substitution of the arginine at position 176 to lysine, and/or substitution of the tryptophan at position 203 to alanine. Other mutations which either enhance or reduce Shiga toxin enzymatic activity and/or cytotoxicity are within the scope of the invention and may be determined using well known techniques and assays disclosed herein.

The de-immunized Shiga toxin effector region polypeptides and/or proteins of the invention may optionally be conjugated to one or more additional agents which may include therapeutic and/or diagnostic agents known in the art, including such agents as described herein.

VI. Production, Manufacture, and Purification of a De-Immunized Shiga Toxin Effector Region Polypeptide or Protein The de-immunized Shiga toxin effector region polypeptides and proteins of the invention may be produced using biochemical engineering techniques well known to those of skill in the art. For example, Shiga toxin effector region polypeptides and proteins of the invention may be manufactured by standard synthetic methods, by use of recombinant expression systems, or by any other suitable method. Thus, Shiga toxin effector region polypeptides and proteins of the invention may be synthesized in a number of ways, including, e.g. methods comprising: (1) synthesizing a polypeptide or polypeptide component of a protein using standard solid-phase or liquid-phase methodology, either stepwise or by fragment assembly, and isolating and purifying the final peptide compound product; (2) expressing a polynucleotide that encodes a polypeptide or polypeptide component of a protein of the invention in a host cell and recovering the expression product from the host cell or host cell culture; or (3) cell-free in vitro expression of a polynucleotide encoding a polypeptide or polypeptide component of a protein of the invention, and recovering the expression product; or by any combination of the methods of (1), (2) or (3) to obtain fragments of the peptide component, subsequently joining (e.g. ligating) the fragments to obtain the peptide component, and recovering the peptide component.

It may be preferable to synthesize a de-immunized Shiga toxin effector region polypeptide or a polypeptide or polypeptide component of a protein of the invention by means of solid-phase or liquid-phase peptide synthesis. Shiga toxin effector region polypeptides and proteins of the invention may suitably be manufactured by standard synthetic methods. Thus, peptides may be synthesized by, e.g. methods comprising synthesizing the peptide by standard solid-phase or liquid-phase methodology, either stepwise or by fragment assembly, and isolating and purifying the final peptide product. In this context, reference may be made to WO 1998/11125 or, inter alia, Fields G et al., *Principles and Practice of Solid-Phase Peptide Synthesis* (Synthetic Peptides, Grant G, ed., Oxford University Press, U.K., 2nd ed., 2002) and the synthesis examples therein.

De-immunized Shiga toxin effector region polypeptides and proteins of the invention may be prepared (produced and purified) using recombinant techniques well known in the art. In general, methods for preparing polypeptides by culturing host cells transformed or transfected with a vector comprising the encoding polynucleotide and recovering the polypeptide from cell culture are described in, e.g. Sambrook J et al., *Molecular Cloning: A Laboratory Manual* (Cold Spring Harbor Laboratory Press, NY, U.S., 1989); Dieffenbach C et al., *PCR Primer: A Laboratory Manual* (Cold Spring Harbor Laboratory Press, N.Y., U.S., 1995). Any suitable host cell may be used to produce a Shiga toxin effector region polypeptide and/or protein of the invention. Host cells may be cells stably or transiently transfected, transformed, transduced or infected with one or more expression vectors which drive expression of a polypeptide of the invention. In addition, a Shiga toxin effector region polypeptide and/or protein of the invention may be produced by modifying the polynucleotide encoding a polypeptide or protein of the invention that result in altering one or more amino acids or deleting or inserting one or more amino acids in order to achieve desired properties, such as changed cytotoxicity, changed cytostatic effects, changed immunogenicity, and/or changed serum half-life.

There are a wide variety of expression systems which may be chosen to produce a protein of the invention. For example, host organisms for expression of proteins of the invention include prokaryotes, such as *E. coli* and *B. subtilis*, eukaryotic cells, such as yeast and filamentous fungi (like *S. cerevisiae, P. pastoris, A. awamori*, and *K. lactis*), algae (like *C. reinhardtii*), insect cell lines, mammalian cells (like CHO cells), plant cell lines, and eukaryotic organisms such as transgenic plants (like *A. thaliana* and *N. benthamiana*).

Accordingly, the present invention also provides methods for producing de-immunized Shiga toxin effector region polypeptides and/or proteins of the invention according to above recited methods and using a polynucleotide encoding part or all of a polypeptide of the invention or a polypeptide component of a protein of the invention, an expression vector comprising at least one polynucleotide of the invention capable of encoding part or all of a polypeptide of the invention when introduced into a host cell, and/or a host cell comprising a polynucleotide or expression vector of the invention.

When a polypeptide or protein is expressed using recombinant techniques in a host cell or cell-free system, it is advantageous to separate (or purify) the desired polypeptide or protein away from other components, such as host cell factors, in order to obtain preparations that are of high purity or are substantially homogeneous. Purification can be accomplished by methods well known in the art, such as centrifugation techniques, extraction techniques, chromatographic and fractionation techniques (e.g. size separation by gel filtration, charge separation by ion-exchange column, hydrophobic interaction chromatography, reverse phase chromatography, chromatography on silica or cation-exchange resins such as DEAE and the like, chromatofocusing, and Protein A SEPHAROSE chromatography to remove contaminants), and precipitation techniques (e.g. ethanol precipitation or ammonium sulfate precipitation). Any number of biochemical purification techniques may be used to increase the purity of a Shiga toxin effector region polypeptide and/or protein of the invention. In certain embodiments, the polypeptides and proteins of the invention may optionally be purified in homo-multimeric forms (i.e. a protein complex of two or more identical polypeptides or proteins of the invention).

In the Examples below are descriptions of non-limiting examples of methods for producing a protein of the invention, as well as specific but non-limiting aspects of production for exemplary proteins of the invention.

VII. Pharmaceutical and Diagnostic Compositions Comprising a De-Immunized Shiga Toxin Effector Region Polypeptide or Protein The present invention provides polypeptides and proteins for use, alone or in combination with one or more additional therapeutic agents, in a pharmaceutical composition, for treatment or prophylaxis of conditions, diseases, disorders, or symptoms described in further detail below (e.g. cancers, malignant tumors, non-malignant tumors, growth abnormalities, immune disorders, and microbial infections). The present invention further provides pharmaceutical compositions comprising a polypeptide or protein of the invention, or a pharmaceutically acceptable salt or solvate thereof, according to the invention, together with at least one pharmaceutically acceptable carrier, excipient, or vehicle. In certain embodiments, the pharmaceutical composition of the invention may comprise homo-multimeric and/or hetero-multimeric forms of the polypeptides or proteins of the invention. The pharmaceutical compositions will be useful in methods of treating, ameliorating, or preventing a disease, condition, disorder, or symptom described in further detail below. Each such disease, condition, disorder, or symptom is envisioned to be a separate embodiment with respect to uses of a pharmaceutical composition according to the invention. The invention further provides pharmaceutical compositions for use in at least one method of treatment according to the invention, as described in more detail below.

As used herein, the terms "patient" and "subject" are used interchangeably to refer to any organism, commonly vertebrates such as humans and animals, which presents symptoms, signs, and/or indications of at least one disease, disorder, or condition. These terms include mammals such as the non-limiting examples of primates, livestock animals (e.g. cattle, horses, pigs, sheep, goats, etc.), companion animals (e.g. cats, dogs, etc.) and laboratory animals (e.g. mice, rabbits, rats, etc.).

As used herein, "treat," "treating," or "treatment" and grammatical variants thereof refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease, disorder, or condition. With regard to tumors and/or cancers, treatment includes reduction in overall tumor burden and/or individual tumor size.

As used herein, the terms "prevent," "preventing," "prevention" and grammatical variants thereof refer to an approach for preventing the development of, or altering the pathology of, a condition, disease, or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount" or "therapeutically effective amount" is an amount or dose of a composition (e.g. a therapeutic composition or agent) that produces at least one desired therapeutic effect in a subject, such as preventing or treating a target condition or beneficially alleviating a symptom associated with the condition. The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly (see e.g. *Remington: The Science and Practice of Pharmacy* (Gennaro A, ed., Mack Publishing Co., Easton, PA, U.S., 19th ed., 1995)).

Diagnostic compositions comprise a polypeptide or protein of the invention and one or more detection promoting agents. Various detection promoting agents are known in the art, such as isotopes, dyes, colorimetric agents, contrast enhancing agents, fluorescent agents, bioluminescent agents, and magnetic agents. These agents may be incorporated into the polypeptide or protein of the invention at any position. The incorporation of the agent may be via an amino acid residue(s) of the cytotoxic protein or via some type of linkage known in the art, including via linkers and/or chelators. The incorporation of the agent is in such a way to enable the detection of the presence of the diagnostic composition in a screen, assay, diagnostic procedure, and/or imaging technique.

When producing or manufacturing a diagnostic composition of the invention, a protein of the invention may be directly or indirectly linked to one or more detection promoting agents. There are numerous detection promoting agents known to the skilled worker which can be operably linked to the polypeptides or proteins of the invention for information gathering methods, such as for diagnostic and/or prognostic applications to diseases, disorders, or conditions of an organism (see e.g. Cai W et al., J Nucl Med 48: 304-10 (2007); Nayak T, Brechbiel M, Bioconjug Chem 20: 825-41 (2009); Paudyal P et al., Oncol Rep 22: 115-9 (2009); Qiao J et al., PLOS ONE 6: e18103 (2011); Sano K et al., Breast Cancer Res 14: R61 (2012)). For example, detection promoting agents include image enhancing contrast agents, such as fluorescent dyes (e.g. ALEXA680, indocyanine green, and Cy5.5), isotopes and radionuclides, such as 11C, 13N, 15O, 18F, 32P, 51Mn, 52mMn, 52Fe, 55Co, 62Cu, 64Cu,67Cu, 67Ga, 68Ga, 72As, 73Se, 75Br, 76Br, 82mRb, 83Sr, 86Y, 90Y, 89Zr, 94mTc, 94Tc, 99mTc, 110In, 111In, 120I, 123I, 124I, 125I, 131I, 154Gd, 155Gd, 156Gd, 157Gd, 158Gd, 177Lu, 186Re, 188Re, and 223R; paramagnetic ions, such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III); metals, such as lanthanum (III), gold (III), lead (II), and bismuth (III); ultrasound-contrast enhancing agents, such as liposomes; radiopaque agents, such as barium, gallium, and thallium compounds. Detection promoting agents may be incorporated directly or indirectly by using an intermediary functional group, such as chelators like 2-benzyl DTPA, PAMAM, NOTA, DOTA, TETA, analogs thereof, and functional equivalents of any of the foregoing (see Leyton J et al., Clin Cancer Res 14: 7488-96 (2008)).

There are numerous standard techniques known to the skilled worker for incorporating, affixing, and/or conjugating various detection promoting agents to proteins, especially to immunoglobulins and immunoglobulin-derived domains (Wu A, Methods 65: 139-47 (2014)). Similarly, there are numerous imaging approaches known to the skilled worker, such as non-invasive in vivo imaging techniques commonly used in the medical arena, for example: computed tomography imaging (CT scanning), optical imaging (including direct, fluorescent, and bioluminescent imaging), magnetic resonance imaging (MRI), positron emission tomography (PET), single-photon emission computed tomography (SPECT), ultrasound, and x-ray computed tomography imaging (see Kaur S et al., *Cancer Lett* 315: 97-111 (2012), for review).

Production or Manufacture of a Pharmaceutical and/or Diagnostic Composition Comprising a De-Immunized Shiga Toxin Effector Region Polypeptide or Protein Pharmaceutically acceptable salts or solvates of any of the polypeptides and proteins of the invention are likewise within the scope of the present invention.

The term "solvate" in the context of the present invention refers to a complex of defined stoichiometry formed between a solute (in casu, a polypeptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

Polypeptides and proteins of the present invention, or salts thereof, may be formulated as pharmaceutical compositions prepared for storage or administration, which typically comprise a therapeutically effective amount of a compound of the invention, or a salt thereof, in a pharmaceutically acceptable carrier. The term "pharmaceutically acceptable carrier" includes any of the standard pharmaceutical carriers. Pharmaceutically acceptable carriers for therapeutic use are well known in the pharmaceutical art, and are described, for example, in *Remington's Pharmaceutical Sciences* (Mack Publishing Co. (A. Gennaro, ed., 1985). As used herein, "pharmaceutically acceptable carrier" includes any and all physiologically acceptable, i.e. compatible, solvents, dispersion media, coatings, antimicrobial agents, isotonic, and absorption delaying agents, and the like. Pharmaceutically acceptable carriers or diluents include those used in formulations suitable for oral, rectal, nasal or parenteral (including subcutaneous, intramuscular, intravenous, intradermal, and transdermal) administration. Exemplary pharmaceutically acceptable carriers include sterile aqueous solutions or dispersions and sterile powders for the extemporaneous preparation of sterile injectable solutions or dispersions. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants. In certain embodiments, the carrier is suitable for intravenous, intramuscular, subcutaneous, parenteral, spinal or epidermal administration (e.g. by injection or infusion). Depending on selected route of administration, the cytotoxic protein or other pharmaceutical component may be coated in a material intended to protect the compound from the action of low pH and other natural inactivating conditions to which the active cytotoxic protein may encounter when administered to a patient by a particular route of administration.

The formulations of the pharmaceutical compositions of the invention may conveniently be presented in unit dosage form and may be prepared by any of the methods well known in the art of pharmacy. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration. Subcutaneous or transdermal modes of administration may be particularly suitable for therapeutic proteins described herein.

The pharmaceutical compositions of the invention may also contain adjuvants such as preservatives, wetting agents, emulsifying agents and dispersing agents. Preventing the presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

In another aspect, the present invention provides pharmaceutical compositions comprising one or a combination of different polypeptides and/or proteins of the invention, or an ester, salt or amide of any of the foregoing, and at least one pharmaceutically acceptable carrier.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g. glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g. sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a polypeptide or protein of the invention in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a polypeptide or protein of the invention is designed to be administered by, e.g. intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

As described elsewhere herein, a polypeptide or protein of the invention may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see e.g. *Sustained and Controlled Release Drug Delivery Systems* (Robinson J, ed., Marcel Dekker, Inc., NY, U.S., 1978)).

In certain embodiments, the pharmaceutical composition of the invention may be formulated to ensure a desired distribution in vivo. For example, the blood-brain barrier excludes many large and/or hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 catenin and the like.

Pharmaceutical compositions include parenteral formulations designed to be used as implants or particulate systems. Examples of implants are depot formulations composed of polymeric or hydrophobic components such as emulsions, ion exchange resins, and soluble salt solutions. Examples of particulate systems are microspheres, microparticles, nanocapsules, nanospheres, and nanoparticles (see e.g. Honda M et al., *Int J Nanomedicine* 8: 495-503 (2013); Sharma A et al., *Biomed Res Int* 2013: 960821 (2013); Ramishetti S, Huang L, *Ther Deliv* 3: 1429-45 (2012)). Controlled release formulations may be prepared using polymers sensitive to ions, such as, e.g. liposomes, polaxamer 407, and hydroxyapatite.

VIII. Polynucleotides, Expression Vectors, and Host Cells

Beyond the polypeptides and proteins of the present invention, the polynucleotides which encode the polypeptides and proteins of the invention, or functional portions thereof, are within the scope of the present invention. The term "polynucleotide" is equivalent to the term "nucleic acids" both of which include polymers of deoxyribonucleic acids (DNAs), polymers of ribonucleic acids (RNAs), analogs of these DNAs or RNAs generated using nucleotide analogs, and derivatives, fragments and homologs thereof. The polynucleotide of the invention may be single-, double-, or triple-stranded. Disclosed polynucleotides are specifically disclosed to include all polynucleotides capable of encoding an exemplary cytotoxic protein, for example, taking into account the wobble known to be tolerated in the third position of RNA codons, yet encoding for the same amino acid as a different RNA codon (see Stothard P, *Biotechniques* 28: 1102-4 (2000)).

In one aspect, the invention provides polynucleotides which encode a de-immunized Shiga toxin effector region polypeptide and/or a protein of the invention, or a fragment or derivative thereof. The polynucleotides may include, e.g., nucleic acid sequence encoding a polypeptide at least 50%, 55%, 60%, 65%, 70%, 75%, 80%, 85%, 90%, 95%, 99% or more, identical to a polypeptide comprising one of the amino acid sequences of the protein. The invention also includes polynucleotides comprising nucleotide sequences that hybridize under stringent conditions to a polynucleotide which encodes de-immunized Shiga toxin effector region polypeptide and/or a protein of the invention, or a fragment or derivative thereof, or the antisense or complement of any such sequence.

Derivatives or analogs of the polynucleotides (or de-immunized Shiga toxin effector region polypeptides and/or proteins) of the invention include, inter alia, polynucleotide (or polypeptide) molecules having regions that are substantially homologous to the polynucleotides, de-immunized Shiga toxin effector region polypeptides, or proteins of the invention, e.g. by at least about 45%, 50%, 70%, 80%, 95%, 98%, or even 99% identity (with a preferred identity of 80-99%) over a polynucleotide or polypeptide sequence of the same size or when compared to an aligned sequence in which the alignment is done by a computer homology program known in the art. An exemplary program is the GAP program (Wisconsin Sequence Analysis Package, Version 8 for UNIX, Genetics Computer Group, University Research Park, Madison, WI, U.S.) using the default settings, which uses the algorithm of Smith T, Waterman M, *Adv. Appl. Math.* 2: 482-9 (1981). Also included are polynucleotides capable of hybridizing to the complement of a sequence encoding the proteins of the invention under stringent conditions (see e.g. Ausubel F et al., *Current Protocols in Molecular Biology* (John Wiley & Sons, New York, NY, U.S., 1993)), and below. Stringent conditions are known to those skilled in the art and may be found in *Current Protocols in Molecular Biology* (John Wiley & Sons, NY, U.S., Ch. Sec. 6.3.1-6.3.6 (1989)).

The present invention further provides expression vectors that comprise the polynucleotides within the scope of the invention. The polynucleotides capable of encoding the de-immunized Shiga toxin effector region polypeptides and/or proteins of the invention may be inserted into known vectors, including bacterial plasmids, viral vectors and phage vectors, using material and methods well known in the art to produce expression vectors. Such expression vectors will include the polynucleotides necessary to support production of contemplated Shiga toxin effector region polypeptides and/or proteins of the invention within any host cell of choice or cell-free expression systems (e.g. pTxb1 and pIVEX2.3 described in the Examples below). The specific polynucleotides comprising expression vectors for use with specific types of host cells or cell-free expression systems are well known to one of ordinary skill in the art, can be determined using routine experimentation, or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in the context of the present invention, an expression vector encoding a Shiga toxin effector region polypeptide and/or a protein comprising a single polypeptide chain (e.g. a scFv genetically recombined with a Shiga toxin effector region) includes at least an expression unit for the single polypeptide chain, whereas a protein comprising, e.g. two or more polypeptide chains (e.g. one chain comprising a $V_L$ domain and a second chain comprising a $V_H$ domain linked to a toxin effector region) includes at least two expression units, one for each of the two polypeptide chains of the protein. For expression of multi-chain proteins of the invention, an expression unit for each polypeptide chain may also be separately contained on different expression vectors (e.g. expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Creation and isolation of host cell lines comprising a polynucleotide of the invention or capable of producing a polypeptide and/or protein of the invention can be accomplished using standard techniques known in the art.

De-immunized Shiga toxin effector region polypeptides and/or proteins within the scope of the present invention may be variants or derivatives of the polypeptides and proteins described herein that are produced by modifying the polynucleotide encoding a polypeptide and/or protein by altering one or more amino acids or deleting or inserting one or more amino acids that may render it more suitable to achieve desired properties, such as more optimal expression by a host cell.

IX. Delivery Devices and Kits

In certain embodiments, the invention relates to a device comprising one or more compositions of matter of the invention, such as a pharmaceutical composition, for delivery to a subject. Thus, a delivery device comprising one or more compounds of the invention can be used to administer to a patient a composition of matter of the invention by various delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

Also within the scope of the invention are kits comprising at least one composition of matter of the invention, and optionally, packaging and instructions for use. Kits may be useful for drug administration and/or diagnostic information gathering. A kit of the invention may optionally comprise at least one additional reagent (e.g., standards, markers and the like). Kits typically include a label indicating the intended use of the contents of the kit. The kit may further comprise reagents and other tools for detecting a cell type (e.g. tumor cell) in a sample or in a subject, or for diagnosing whether a patient belongs to a group that responds to a therapeutic strategy which makes use of a compound, composition or related method of the invention as described herein.

X. Methods for Using a De-Immunized Shiga Toxin Effector Region Polypeptide or Protein or a Pharmaceutical and/or Diagnostic Composition Thereof Generally, it is an object of the invention to provide pharmacologically active agents, as well as compositions comprising the same, that can be used in the prevention and/or treatment of diseases, disorders, and conditions, such as certain cancers, tumors, growth abnormalities, immune disorders, or further pathological conditions mentioned herein. Accordingly, the present invention provides methods of using the polypeptides, proteins, and pharmaceutical compositions of the invention for the targeted killing of cells, for delivering additional exogenous materials into targeted cells, for labeling of the interiors of targeted cells, for collecting diagnostic information, and for treating diseases, disorders, and conditions as described herein.

In particular, it is an object of the invention to provide such pharmacologically active agents, compositions, and/or methods that have certain advantages compared to the agents, compositions, and/or methods that are currently known in the art. Accordingly, the present invention provides methods of using polypeptides and proteins with specified polypeptide sequences and pharmaceutical compositions thereof. For example, any of the polypeptide sequences in SEQ ID NOs: 4-59 may be specifically utilized as a component of the protein used in the following methods.

The present invention provides methods of killing a cell comprising the step of contacting the cell, either in vitro or in vivo, with a polypeptide, protein, or pharmaceutical composition of the present invention. The polypeptides, proteins, and pharmaceutical compositions of the invention can be used to kill a specific cell type upon contacting a cell or cells with one of the claimed compositions of matter. In certain embodiments, a cytotoxic polypeptide, protein, or pharmaceutical composition of the present invention can be used to kill specific cell types in a mixture of different cell types, such as mixtures comprising cancer cells, infected cells, and/or hematological cells. In certain embodiments, a cytotoxic polypeptide, protein, or pharmaceutical composition of the present invention can be used to kill cancer cells in a mixture of different cell types. In certain embodiments, a cytotoxic polypeptide, protein, or pharmaceutical composition of the present invention can be used to kill specific cell types in a mixture of different cell types, such as pre-transplantation tissues. In certain embodiments, a polypeptide, protein, or pharmaceutical composition of the present invention can be used to kill specific cell types in a mixture of cell types, such as pre-administration tissue material for therapeutic purposes. In certain embodiments, a polypeptide, protein, or pharmaceutical composition of the present invention can be used to selectively kill cells infected by viruses or microorganisms, or otherwise selectively kill cells expressing a particular extracellular target biomolecule, such as a cell surface biomolecule. The polypeptides, proteins, and pharmaceutical compositions of the invention have varied applications, including, e.g., uses in depleting unwanted cell types from tissues either in vitro or in vivo, uses in modulating immune responses to treat graft versus host disease, uses as antiviral agents, uses as anti-parasitic agents, and uses in purging transplantation tissues of unwanted cell types.

In certain embodiments, a cytotoxic polypeptide, protein, or pharmaceutical composition of the present invention, alone or in combination with other compounds or pharmaceutical compositions, can show potent cell-kill activity when administered to a population of cells, in vitro or in vivo in a subject such as in a patient in need of treatment. By targeting the delivery of enzymatically active Shiga toxin regions using high-affinity binding regions to specific cell types, this potent cell-kill activity can be restricted to specifically and selectively kill certain cell types within an organism, such as certain cancer cells, neoplastic cells, malignant cells, non-malignant tumor cells, or infected cells.

The present invention provides a method of killing a cell in a patient in need thereof, the method comprising the step of administering to the patient at least one cytotoxic polypeptide or protein of the present invention, or a pharmaceutical composition thereof.

Certain embodiments of the cytotoxic polypeptide, protein, or pharmaceutical compositions thereof can be used to kill a cancer cell in a patient by targeting an extracellular biomolecule found physically coupled with a cancer or tumor cell. The terms "cancer cell" or "cancerous cell" refers to various neoplastic cells which grow and divide in an abnormally accelerated fashion and will be clear to the skilled person. The term "tumor cell" includes both malignant and non-malignant cells. Generally, cancers and/or tumors can be defined as diseases, disorders, or conditions that are amenable to treatment and/or prevention. The cancers and tumors (either malignant or non-malignant) which are comprised by cancer cells and/or tumor cells will be clear to the skilled person. Neoplastic cells are often associated with one or more of the following: unregulated growth, lack of differentiation, local tissue invasion, angiogenesis, and metastasis.

Certain embodiments of the cytotoxic polypeptide or protein of the invention, or pharmaceutical compositions thereof, can be used to kill an immune cell (whether healthy or malignant) in a patient by targeting an extracellular biomolecule found physically coupled with an immune cell.

Certain embodiments of the cytotoxic polypeptide or protein of the invention, or pharmaceutical compositions thereof, can be used to kill an infected cell in a patient by targeting an extracellular biomolecule found physically coupled with an infected cell.

It is within the scope of the present invention to utilize the protein of the invention or pharmaceutical composition thereof for the purposes of purging patient cell populations (e.g. bone marrow) of malignant, neoplastic, or otherwise unwanted T-cells and/or B-cells and then reinfusing the T-cell and/or B-cells depleted material into the patient (see e.g. van Heeckeren W et al., *Br J Haematol* 132: 42-55 (2006); (see e.g. Alpdogan O, van den Brink M, *Semin Oncol* 39: 629-42 (2012)).

It is within the scope of the present invention to utilize the protein of the invention or pharmaceutical composition thereof for the purposes of ex vivo depletion of T cells and/or B-cells from isolated cell populations removed from a patient. In one non-limiting example, the protein of the invention can be used in a method for prophylaxis of organ and/or tissue transplant rejection wherein the donor organ or tissue is perfused prior to transplant with a cytotoxic protein of the invention or a pharmaceutical composition thereof in order to purge the organ of donor T-cells and/or B-cells (see e.g. Alpdogan O, van den Brink M, *Semin Oncol* 39: 629-42 (2012)).

It is also within the scope of the present invention to utilize the protein of the invention or pharmaceutical composition thereof for the purposes of depleting T-cells and/or B-cells from a donor cell population as a prophylaxis against graft-versus-host disease, and induction of tolerance, in a patient to undergo a bone marrow and or stem cell transplant (see e.g. van Heeckeren W et al., *Br J Haematol* 132: 42-55 (2006); (see e.g. Alpdogan O, van den Brink M, *Semin Oncol* 39: 629-42 (2012)).

Certain embodiments of the cytotoxic polypeptide or protein of the invention, or pharmaceutical compositions thereof, can be used to kill an infected cell in a patient by targeting an extracellular biomolecule found physically coupled with an infected cell.

Additionally, the present invention provides a method of treating a disease, disorder, or condition in a patient comprising the step of administering to a patient in need thereof a therapeutically effective amount of at least one of the cytotoxic polypeptide or protein of the invention, or a pharmaceutical composition thereof. Contemplated diseases, disorders, and conditions that can be treated using this method include cancers, malignant tumors, non-malignant tumors, growth abnormalities, immune disorders, and microbial infections. Administration of a "therapeutically effective dosage" of a compound of the invention can result in a decrease in severity of disease symptoms, an increase in frequency and duration of disease symptom-free periods, or a prevention of impairment or disability due to the disease affliction.

The therapeutically effective amount of a compound of the present invention will depend on the route of administration, the type of mammal being treated, and the physical characteristics of the specific patient under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

An acceptable route of administration may refer to any administration pathway known in the art, including but not limited to aerosol, enteral, nasal, ophthalmic, oral, parenteral, rectal, vaginal, or transdermal (e.g. topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

For administration of a pharmaceutical composition of the invention, the dosage range will generally be from about 0.0001 to 100 milligrams per kilogram (mg/kg), and more, usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular patient.

Pharmaceutical compositions of the invention will typically be administered to the same patient on multiple occasions. Intervals between single dosages can be, for example, 2-5 days, weekly, monthly, every two or three months, every six months, or yearly. Intervals between administrations can also be irregular, based on regulating blood levels or other markers in the subject or patient. Dosage regimens for a compound of the invention include intravenous administration of 1 mg/kg body weight or 3 mg/kg body weight with the compound administered every two to four weeks for six dosages, then every three months at 3 mg/kg body weight or 1 mg/kg body weight.

A pharmaceutical composition of the present invention may be administered via one or more routes of administration, using one or more of a variety of methods known in the art. As will be appreciated by the skilled worker, the route and/or mode of administration will vary depending upon the desired results. Routes of administration for polypeptides, proteins, and pharmaceutical compositions of the invention include, e.g. intravenous, intramuscular, intradermal, intraperitoneal, subcutaneous, spinal, or other parenteral routes of administration, for example by injection or infusion. In other embodiments, a polypeptide, protein, or pharmaceutical composition of the invention may be administered by a non-parenteral route, such as a topical, epidermal or mucosal route of administration, for example, intranasally, orally, vaginally, rectally, sublingually, or topically.

Therapeutic polypeptides, proteins, or pharmaceutical compositions of the invention may be administered with one or more of a variety of medical devices known in the art. For example, in one embodiment, a pharmaceutical composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

A polypeptide, protein, or pharmaceutical composition of the present invention may be administered alone or in combination with one or more other therapeutic or diagnostic agents. A combination therapy may include a cytotoxic protein of the invention or pharmaceutical composition thereof combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

Treatment of a patient with a polypeptide, protein, or pharmaceutical composition of the invention preferably leads to cell death of targeted cells and/or the inhibition of growth of targeted cells. As such, cytotoxic proteins of the invention, and pharmaceutical compositions comprising them, will be useful in methods for treating a variety of pathological disorders in which killing or depleting target cells may be beneficial, such as, inter alia, cancer, tumors, other growth abnormalities, immune disorders, and infected cells. The present invention provides methods for suppressing cell proliferation, and treating cell disorders, including neoplasia, overactive B-cells, and overactive T-cells.

In certain embodiments, polypeptides, proteins, and pharmaceutical compositions of the invention can be used to treat or prevent cancers, tumors (malignant and non-malignant), growth abnormalities, immune disorders, and microbial infections. In a further aspect, the above ex vivo method can be combined with the above in vivo method to provide methods of treating or preventing rejection in bone marrow transplant recipients, and for achieving immunological tolerance.

In certain embodiments, the present invention provides methods for treating malignancies or neoplasms and other blood cell associated cancers in a mammalian subject, such as a human, the method comprising the step of administering to a subject in need thereof a therapeutically effective amount of a cytotoxic protein or pharmaceutical composition of the invention.

The cytotoxic polypeptides, proteins, and pharmaceutical compositions of the invention have varied applications, including, e.g., uses in removing unwanted T-cells, uses in modulating immune responses to treat graft-versus-host disease, uses as antiviral agents, uses as antimicrobial agents, and uses in purging transplantation tissues of unwanted cell types. The cytotoxic polypeptides, proteins, and pharmaceutical compositions of the present invention are commonly anti-neoplastic agents—meaning they are capable of treating and/or preventing the development, maturation, or spread of neoplastic or malignant cells by inhibiting the growth and/or causing the death of cancer or tumor cells.

In certain embodiments, a polypeptide, protein, or pharmaceutical composition of the present invention is used to treat a B-cell-, plasma cell- or antibody-mediated disease or disorder, such as for example leukemia, lymphoma, myeloma, Human Immunodeficiency Virus-related diseases, amyloidosis, hemolytic uremic syndrome, polyarteritis, septic shock, Crohn's Disease, rheumatoid arthritis, ankylosing spondylitis, psoriatic arthritis, ulcerative colitis, psoriasis, asthma, Sjogren's syndrome, graft-versus-host disease, graft rejection, diabetes, vasculitis, scleroderma, and systemic lupus erythematosus.

In another aspect, certain embodiments of the polypeptides, proteins, and pharmaceutical compositions of the present invention are antimicrobial agents—meaning they are capable of treating and/or preventing the acquisition, development, or consequences of microbiological pathogenic infections, such as caused by viruses, bacteria, fungi, prions, or protozoans.

It is within the scope of the present invention to provide a prophylaxis or treatment for diseases or conditions mediated by T-cells or B-cells by administering the cytotoxic protein or the invention, or a pharmaceutical composition thereof, to a patient for the purpose of killing T-cells or B-cells in the patient. This usage is compatible with preparing or conditioning a patient for bone marrow transplantation, stem cell transplantation, tissue transplantation, or organ transplantation, regardless of the source of the transplanted material, e.g. human or non-human sources.

It is within the scope of the present invention to provide a bone marrow recipient for prophylaxis or treatment of host-versus-graft disease via the targeted cell-killing of host T-cells using a cytotoxic polypeptide, protein, or pharmaceutical composition of the present invention.

The cytotoxic polypeptides, proteins, and pharmaceutical compositions of the present invention can be utilized in a method of treating cancer comprising administering to a patient, in need thereof, a therapeutically effective amount of a cytotoxic polypeptide, protein, or pharmaceutical composition of the present invention. In certain embodiments of the methods of the present invention, the cancer being treated is selected from the group consisting of: bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), and uterine cancer.

The polypeptides, proteins, and pharmaceutical compositions of the present invention can be utilized in a method of treating an immune disorder comprising administering to a patient, in need thereof, a therapeutically effective amount of the cytotoxic protein or a pharmaceutical composition of the present invention. In certain embodiments of the methods of the present invention, the immune disorder is related to an inflammation associated with a disease selected from the group consisting of: amyloidosis, ankylosing spondylitis, asthma, Crohn's disease, diabetes, graft rejection, graft-versus-host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjogren's syndrome, ulcerative colitis, and vasculitis.

Among certain embodiments of the present invention is using the polypeptide or protein of the invention as a component of a pharmaceutical composition or medicament for the treatment or prevention of a cancer, tumor, other growth abnormality, immune disorder, and/or microbial infection. For example, immune disorders presenting on the skin of a patient may be treated with such a medicament in efforts to reduce inflammation. In another example, skin tumors may be treated with such a medicament in efforts to reduce tumor size or eliminate the tumor completely.

Beneficial clinical effects may be obtained by treatment regimens involving the sequential administration of multiple cytotoxic proteins of the invention to the same subject where each cytotoxic protein comprises a Shiga toxin effector region de-immunized in a different region in order to avoid or reduce the development of a prolonged immune response(s) to a single cytotoxic protein from treatment regimens involving serial administration of an identical therapeutic.

Certain cytotoxic polypeptides, proteins, and pharmaceutical compositions of the invention may be used in molecular neurosurgery applications such as immunolesioning and neuronal tracing (see, Wiley R, Lappi D, *Adv Drug Deliv Rev* 55: 1043-54 (2003), for review). For example, the targeting domain may be selected or derived from various ligands, such as neurotransmitters and neuropeptides, which target specific neuronal cell types by binding neuronal surface receptors, such as a neuronal circuit specific G-protein coupled receptor. Similarly, the targeting domain may be selected from or derived from antibodies that bind neuronal surface receptors. Because Shiga toxins robustly direct their own retrograde axonal transport, certain cytotoxic proteins of the invention may be used to kill a neuron(s) which expresses the extracellular target at a site of cytotoxic protein injection distant from the cell body (see Llewellyn-Smith I et al., *J Neurosci Methods* 103: 83-90 (2000)). These neuronal cell-type-specific-targeting cytotoxic polypeptides and proteins have uses in neuroscience research, such as for elucidating mechanisms of sensations (see e.g. Mishra S, Hoon M, *Science* 340: 968-71 (2013)), and creating model systems of neurodegenerative diseases, such as Parkinson's and Alzheimer's (see e.g. Hamlin A et al., *PLoS One* e53472 (2013)).

Among certain embodiments of the present invention is a method of using a polypeptide, protein, pharmaceutical composition, and/or diagnostic composition of the invention to label or detect the interiors of neoplastic cells and/or immune cell types. Based on the ability of certain polypeptides, proteins, and pharmaceutical compositions of the invention to enter specific cell types and route within cells via retrograde intracellular transport, the interior compartments of specific cell types are labeled for detection. This can be performed on cells in situ within a patient or on cells and tissues removed from an organism, e.g. biopsy material.

Among certain embodiment of the present invention is a method of using a polypeptide, protein, pharmaceutical composition, and/or diagnostic composition of the invention to detect the presence of a cell type for the purpose of information gathering regarding diseases, conditions and/or disorders. The method comprises contacting a cell with a diagnostically sufficient amount of a cytotoxic molecule to detect the cytotoxic molecule by an assay or diagnostic technique. The phrase "diagnostically sufficient amount" refers to an amount that provides adequate detection and accurate measurement for information gathering purposes by the particular assay or diagnostic technique utilized. Generally, the diagnostically sufficient amount for whole organism in vivo diagnostic use will be a non-cumulative dose of between 0.1 mg to 100 mg of the detection promoting agent linked protein of the invention per kg of subject per subject. Typically, the amount of polypeptide or protein of the invention used in these information gathering methods will be as low as possible provided that it is still a diagnostically sufficient amount. For example, for in vivo detection in an organism, the amount of polypeptide, protein, or pharmaceutical composition of the invention administered to a subject will be as low as feasibly possible.

The cell-type specific targeting of polypeptides and proteins of the invention combined with detection promoting agents provides a way to detect and image cells physically coupled with an extracellular target biomolecule of a binding region of the molecule of the invention. Imaging of cells using the polypeptides or proteins of the invention may be performed in vitro or in vivo by any suitable technique known in the art. Diagnostic information may be collected using various methods known in the art, including whole body imaging of an organism or using ex vivo samples taken from an organism. The term "sample" used herein refers to any number of things, but not limited to, fluids such as blood, urine, serum, lymph, saliva, anal secretions, vaginal secretions, and semen, and tissues obtained by biopsy procedures. For example, various detection promoting agents may be utilized for non-invasive in vivo tumor imaging by techniques such as magnetic resonance imaging (MM), optical methods (such as direct, fluorescent, and bioluminescent imaging), positron emission tomography (PET), single-photon emission computed tomography (SPECT), ultrasound, x-ray computed tomography, and combinations of the aforementioned (see, Kaur S et al., *Cancer Lett* 315: 97-111 (2012), for review).

Among certain embodiments of the present invention is a method of using a polypeptide, protein, or pharmaceutical composition of the invention as a diagnostic composition to label or detect the interiors of cancer, tumor, and/or immune cell types (see e.g., Koyama Y et al., *Clin Cancer Res* 13: 2936-45 (2007); Ogawa M et al., *Cancer Res* 69: 1268-72 (2009); Yang L et al., *Small* 5: 235-43 (2009)). Based on the ability of certain polypeptides, proteins, and pharmaceutical compositions of the invention to enter specific cell types and route within cells via retrograde intracellular transport, the interior compartments of specific cell types are labeled for detection. This can be performed on cells in situ within a patient or on cells and tissues removed from an organism, e.g. biopsy material.

Diagnostic compositions of the invention may be used to characterize a disease, disorder, or condition as potentially treatable by a related pharmaceutical composition of the invention. Certain compositions of matter of the invention may be used to determine whether a patient belongs to a group that responds to a therapeutic strategy which makes use of a compound, composition or related method of the invention as described herein or is well suited for using a delivery device of the invention.

Diagnostic compositions of the invention may be used after a disease, e.g. a cancer, is detected in order to better characterize it, such as to monitor distant metastases, heterogeneity, and stage of cancer progression. The phenotypic assessment of disease disorder or infection can help prognostication and prediction during therapeutic decision making. In disease reoccurrence, certain methods of the invention may be used to discriminate localized versus systemic problems.

Diagnostic compositions of the invention may be used to assess responses to therapeutic(s) regardless of the type of therapeutic, e.g. small molecule drug, biological drug, or cell-based therapy. For example, certain embodiments of the diagnostics of the invention may be used to measure changes in tumor size, changes in antigen positive cell populations including number and distribution, or monitoring a different marker than the antigen targeted by a therapy already being administered to a patient (see Smith-Jones P et al., *Nat. Biotechnol* 22: 701-6 (2004); Evans M et al., *Proc. Natl. Acad. Sci. U.S.A.* 108: 9578-82 (2011)).

Certain embodiments of the method used to detect the presence of a cell type may be used to gather information regarding diseases, disorders, and conditions, such as, for example bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), uterine cancer, AIDS, amyloidosis, ankylosing spondylitis, asthma, autism, cardiogenesis, Crohn's disease, diabetes, erythematosus, gastritis, graft rejection, graft-versus-host disease, Grave's disease, Hashimoto's thyroiditis, hemolytic uremic syndrome, HIV-related diseases, lupus erythematosus, lymphoproliferative disorders, multiple sclerosis, myasthenia gravis, neuroinflammation, polyarteritis, psoriasis, psoriatic arthritis, rheumatoid arthritis, scleroderma, septic shock, Sjogren's syndrome, systemic lupus erythematosus, ulcerative colitis, vasculitis, cell proliferation, inflammation, leukocyte activation, leukocyte adhesion, leukocyte chemotaxis, leukocyte maturation, leukocyte migration, neuronal differentiation, acute lymphoblastic leukemia (ALL), T acute lymphocytic leukemia/lymphoma (ALL), acute myelogenous leukemia, acute myeloid leukemia (AML), B-cell chronic lymphocytic leukemia (B-CLL), B-cell prolymphocytic lymphoma, Burkitt's lymphoma (BL), chronic lymphocytic leukemia (CLL), chronic myelogenous leukemia (CIVIL-BP), chronic myeloid leukemia (CIVIL), diffuse large B-cell lymphoma, follicular lymphoma, hairy cell leukemia (HCL), Hodgkin's Lymphoma (HL), intravascular large B-cell lymphoma, lymphomatoid granulomatosis, lymphoplasmacytic lymphoma, MALT lymphoma, mantle cell lymphoma, multiple myeloma (MM), natural killer cell leukemia, nodal marginal B-cell lymphoma, Non-Hodgkin's lymphoma (NHL), plasma cell leukemia, plasmacytoma, primary effusion lymphoma, pro-lymphocytic leukemia, promyelocytic leukemia, small lymphocytic lymphoma, splenic marginal zone lymphoma, T-cell lymphoma (TCL), heavy chain disease, monoclonal gammopathy, monoclonal immunoglobulin deposition disease, myelodysplastic syndromes (MDS), smoldering multiple myeloma, and Waldenstrom macroglobulinemia.

In certain embodiments, the polypeptides and proteins of the invention, or pharmaceutical compositions thereof, are used for both diagnosis and treatment, or for diagnosis alone.

The polypeptides of the invention have uses as immunization materials for eliciting immune responses to specific epitopes based on the presence of a disruption(s) in a selected epitope region(s). A polypeptide of the invention may be used as an immunization material for the administration to a mammal and/or used in a display screen to generate an immunoglobulin domain recognizing a Shiga toxin.

The present invention is further illustrated by the following non-limiting examples of selectively cytotoxic proteins comprising de-immunized Shiga toxin effector regions derived from A Subunits of members of the Shiga toxin family and binding regions capable of binding extracellular target biomolecules physically coupled to specific cell types.

EXAMPLES

The following examples demonstrate certain embodiments of the present invention. However, it is to be understood that these examples are for illustration purposes only and do not intend, nor should any be construed, to be wholly definitive as to conditions and scope of this invention. The experiments in the following examples were carried out using standard techniques, which are well known and routine to those of skill in the art, except where otherwise described in detail.

In order to improve Shiga toxin-derived polypeptide regions for therapeutic and diagnostic applications in mammals, predicted B-cell epitopes throughout entire toxin effector regions were systematically disrupted with the goal of dampening mammalian B-cell mediated immune responses. Amino acid sequences representing A Subunits of multiple Shiga toxins were analyzed to identify putative antigenic and/or immunogenic epitopes. Computational tools were used to predict B-cell and T-cell epitopes, including considerations of publicly available protein database structural data. Epitope predictions were validated empirically. Various de-immunized Shiga toxin effector polypeptides were experimentally tested for loss of epitopes present in native Shiga toxin A Subunits and retention of Shiga toxin effector functions. The biological activities of exemplary de-immunized Shiga toxin effector polypeptides as components of various cytotoxic proteins were compared to cytotoxic proteins comprising non-de-immunized Shiga toxin effector polypeptides, referred to herein as "wild-type" or "WT."

The following examples of de-immunized Shiga toxin effector polypeptides demonstrate the retention of Shiga toxin effector functions as components of various cytotoxic proteins. The exemplary cytotoxic proteins bound to target biomolecules expressed by targeted cell types and entered the targeted cells. The internalized cytotoxic proteins effectively routed their de-immunized Shiga toxin effector regions to the cytosol to inactivate ribosomes and subsequently caused the apoptotic death of the targeted cells similar to cytotoxic proteins comprising wild-type Shiga toxin effector regions. Furthermore, the following examples demonstrate that multiple epitope disruptions can be combined in Shiga toxin effector region polypeptides to reduce the overall antigenicity and/or immunogenicity of a cytotoxic protein of the invention while retaining potent cytotoxicity.

Example 1. Predicting Immunogenic and Antigenic Epitopes in Shiga Toxin A Subunits The antigenic and/or immunogenic sites within the A Subunits of Shiga toxins had never been systematically mapped. Computational methods were utilized to predict antigenic and/or immunogenic epitopes in various Shiga toxin A Subunits. Both B-cell epitopes and CD4+ T-cell epitopes with potential to elicit responses in mammalian immune systems were predicted in silico.

Linear B-cell epitopes were predicted for the mature A Subunit of Shiga-like toxin 1 (SLT-1A; SEQ ID NO:1) from the polypeptide sequence and 3D structural data of Shiga-Like Toxin Chain A (PDB ID: 1DM0_A) by ProImmune Inc. (Sarasota, FL, U.S.) using their REVEAL® system.

In parallel, B-cell epitopes were predicted from the amino acid sequences of the A Subunits of Shiga toxin (StxA; SEQ ID NO:2), Shiga-like toxin 1 (SLT-1A; SEQ ID NO:1), and Shiga-like toxin 2 (Stx2A; SEQ ID NO:3) using the BcePred webserver (Saha S, Raghava G, *Lecture Notes in Comput Sci* 3239: 197-204 (2004)), Bepipred Linear Epitope Prediction (Larsen J et al., *Immunome Res* 2: 2 (2006)), and ElliPro Antibody epitope prediction (Haste Andersen P et al., *Protein Sci* 15: 2558-67 (2006); Ponomarenko J, Bourne P, *BMC Struct Biol* 7: 64 (2007)). The various computational methods revealed similar predictions for B-cell epitope regions in the three prototypical Shiga toxin A Subunits (Tables 1-3).

TABLE 1

B-Cell Epitope Predictions for the Mature, Native A Subunit of Shiga-like Toxin 1 (SEQ ID NO:1) natively positioned amino acid positions

| REVEAL | BcePred | Bepipred | ElliPro |
|---|---|---|---|
| | 29-35 | 28-34 | 27-37 |
| 42-48 | 39-46 | 43-47 | |
| 58-66 | 55-61 | 56-64 | 57-66 |
| 96-103 | 105-111 | 100-115 | 96-110 |
| 144-151 | 141-147 | 147-151 | 144-153 |
| 183-189 | 181-187 | 183-185 | 180-190 |
| | | 211-219 | |
| 243-251 | | | 243-257 |
| 257-268 | 261-267 | 254-268 | |
| 289-293 | 285-291 | | 262-293 |

TABLE 2

| B-Cell Epitope Predictions for the Mature, Native A Subunit of Shiga Toxin (SEQ ID NO:2) natively positioned amino acid positions | | | |
|---|---|---|---|
| REVEAL | BcePred | Bepipred | ElliPro |
| | 29-35 | 28-34 | 27-37 |
| 42-48 | 39-46 | 44-47 | |
| 58-66 | 55-61 | 56-64 | 57-66 |
| 96-103 | 105-111 | 100-115 | 96-110 |
| 144-151 | 141-147 | 147-151 | 144-153 |
| 183-189 | 181-187 | 183-185 | 180-190 |
| | | 211-219 | |
| 243-251 | | | 243-257 |
| 257-268 | 261-267 | 254-268 | |
| 289-293 | 285-291 | | 262-293 |

TABLE 3

| B-Cell Epitope Predictions for the Mature, Native A Subunit of Shiga-like Toxin 2 (SEQ ID NO:3) natively positioned amino acid positions | | |
|---|---|---|
| BcePred | Bepipred | ElliPro |
| 3-11 | 8-14 | |
| 29-35 | 28-36 | 26-37 |
| | | 42-48 |
| | 57-62 | 56-66 |
| 108-115 | 109-115 | 96-110 |
| 141-156 | | 140-153 |
| | 179-188 | 180-191 |
| | 210-218 | 210-217 |
| 240-257 | 244-258 | 241-255 |
| | | 262-278 |
| | | 281-297 |

Previous sequence alignment studies predicted immune epitope regions in Shiga toxin A Subunits which might be antigenic and/or immunogenic based on an epitope in ricin bound by a neutralizing antibody (Lebeda F, Olson M, *Int J Biol Macromol* 24: 19-26 (1999); Zemla A, Ecale Zhou C, *Bioinform Biol Insights* 2: 5-13 (2008)). It was predicted that there might be a conserved immunogenic epitope in StxA around residues 90-107 and in Stx2A around residues 112-129 (Zemla A, Ecale Zhou C, *Bioinform Biol Insights* 2: 5-13 (2008)). However, this prediction was admittedly unreliable due to key differences between the plant toxin ricin and the bacterial Shiga toxins, such as, e.g., the large amount of sequence variability between ricin and Shiga toxins, the lack of a N-terminal alpha helix in the A subunits of Shiga toxins, and the predicted region is shorter and less solvent-exposed in Shiga toxins compared to ricin ((Fraser M et al., Nature Struct Biol 1: 59 (1994); Lebeda F, Olson M, *Int J Blot Macromol* 24: 19-26 (1999); Zemla A, Ecale Zhou C, *Bioinform Biol Insights* 2: 5-13 (2008)).

The Immune Epitope Database (IEDB) curated by the National Institutes of Allergy and Infectious Diseases of the U.S. (NIAID) is said to provide all experimentally characterized B- and T-cell epitopes of Shiga toxins. Currently, the IEDB provides only a single epitope for only a single Shiga toxin A Subunit (Stx2dA): IEDB identification number 110493, an experimentally determined, discontinuous B-cell epitope comprising amino acids 42-49, 96-100, and 245-260 (Smith M et al., *Infect Immun* 77: 2730-40 (2009)).

The nine predicted B-cell epitope regions identified by more than one method in SLT-1A (Table 4) were disrupted in the following Examples.

TABLE 4

| Nine Putative B-Cell Epitope Regions Shared by Prototypical Shiga toxin A Subunits | | | |
|---|---|---|---|
| | natively positioned amino acid positions | | |
| Epitope Region | SLT-1A | StxA | SLT-2A |
| | | | 3-14 |
| 1 | 27-37 | 27-37 | 26-37 |
| 2 | 39-48 | 39-48 | 42-49 |
| 3 | 55-66 | 55-66 | 56-66 |
| 4 | 96-115 | 96-115 | 96-115 |
| 5 | 141-153 | 141-153 | 140-156 |
| 6 | 180-190 | 180-190 | 179-191 |
| | | | 210-218 |
| 7 | 243-257 | 243-257 | 240-260 |
| 8 | 254-268 | 254-268 | 262-278 |
| 9 | 285-293 | 285-293 | 281-297 |

In addition, Shiga toxin A Subunits were analyzed using the Epitopia webserver for predicting B-cell epitopes and immunogenic residues (Rubinstein N et al., *BMC Bioinformatics* 10: 287 (2009)). Epitopia was used to identify linear amino acid residue regions predicted to be immunogenic in SLT-1A based on an Epitopia score of 4 or 5 ("high") for the majority of amino acid residues in a linear amino acid residue stretch. The Epitopia analysis predicted an immunogenic region occurs from amino acid residues 1 to 15 in SLT-1A (designated as Epitope Region 0 below, see Table 5, infra). Based on the Epitopia analysis, the immunogenic epitope region 2 in SLT-1A (see Table 4) might include position 49. Based on the Epitopia analysis, the immunogenic epitope region 3 in SLT-1A (see Table 4) might include position 53 and extend to around position 62-66 (designated as Epitope Region 3* below, see Table 5, infra), the Epitope Region 4 in SLT-1A (see Table 4) might include position 94 (designated as Epitope Region 4* below, see Table 5, infra), and the epitope region 6 in SLT-1A (see Table 4) might start at position 179 and extend to around position 188-190 (designated as Epitope Region 6* below, see Table 5, infra). Note the starred B-cell epitope regions all completely encompass their respective overlapping region with the same numerical identifier.

These ten epitope regions (#0-9) were compared for overlap with predicted CD4+ T-cell epitopes. T-cell epitopes were predicted for the mature A Subunit of Shiga-like toxin 1 (SEQ ID NO:1) by the REVEAL™ Immunogenicity System (IS) T-cell assay performed by ProImmune Inc. (Sarasota, FL, U.S.). This assay uses multiple overlapping peptide sequences from the subject protein to test for the elicitation of any immune response by CD4+ T-cells from healthy donor cell samples depleted of CD8+ T-cells. Of the 13 predicted B-cell epitope regions, all of them overlapped with at least one predicted CD4+ T-cell epitope (Table 5). All the predicted B-cell epitope regions in Table 5 were disrupted or deleted individually or in combination in the following Examples.

TABLE 5

| Predicted B-Cell Epitope Regions with Overlapping Predicted CD4+ T-Cell Epitopes | | |
|---|---|---|
| | natively positioned amino acid positions | |
| Epitope Region | B-Cell Epitope Region | T-Cell Epitope (ProImmune) |
| 0 | 1-15 | 4-33 |
| 1 | 27-37 | 4-33; 34-78 |
| 2 | 39-48 | 34-78 |
| 3* | 53-66 | 34-78 |
| 3 | 55-66 | 34-78 |
| 4* | 94-115 | 77-103 |
| 4 | 96-115 | 77-103 |
| 5 | 141-153 | 128-168 |
| 6* | 179-190 | 160-183 |
| 6 | 180-190 | 160-183 |
| 7 | 243-257 | 236-258 |
| 8 | 254-268 | 236-258 |
| 9 | 285-293 | 274-293 |

Example 2. De-Immunization of Shiga Toxin Effector Polypeptides

Deletions and/or amino acid substitutions were made in the putative B-cell and T-cell epitopes of Shiga toxin effector polypeptides derived from the A Subunit of Shiga-like Toxin 1 (SLT-1A). In addition to the described point mutations that disrupted predicted epitopes, some constructs comprised one or more point mutations that had no apparent effect on Shiga toxin effector enzymatic activity or cytotoxicity, such as, e.g., R223A in SLT-1A, C242S in SLT-1A, and/or C261S in SLT-1A.

In this example, a Shiga toxin effector polypeptide region was derived from the A Subunit of Shiga-like Toxin 1 (SLT-1A). A polynucleotide that encoded amino acids 1-251 of SLT-1A was used as a template to create various polynucleotides encoding various Shiga toxin effector polypeptides with one or more disruptions of a predicted B-cell epitope(s). Shiga toxin effector polypeptides comprising one or more epitope disruptions were expressed from these polynucleotides to explore which disruptions might most effectively de-immunize various Shiga toxin effector polypeptides in the context of a cytotoxic protein of the invention.

Truncating the carboxy-terminus of SLT-1A to amino acids 1-251 of SEQ ID NO: 1 removed the last two B-cell epitope regions (Table 5, #8 and #9), the last two CD4+ T-cell epitope regions (Table 5, #8 and #9), and the highest scoring discontinuous B-cell epitope predicted by ElliPro (289-293). In addition, the truncation at position 251 might disrupt the seventh epitope region comprising putative B-cell and T-cell epitopes (Table 5).

Rationally selected amino acid substitutions (see Table 6) were created in the truncated Shiga toxin effector polypeptide comprising amino acids 1-251 of SEQ ID NO:1 using methods known in the art. In epitope region #0 (see Table 5), at least seven different amino acid substitutions were made and tested (see Table 6). In epitope region #0, the lysine natively located at position 1 in the mature A Subunits of Shiga-like toxin 1 (SEQ ID NO:1) and Shiga toxin (SEQ ID NO:2) was mutated to methionine (K1M)). In epitope region #0, the threonine natively located at position 4 in the mature A Subunits of Shiga-like toxin 1 (SEQ ID NO:1) and Shiga toxin (SEQ ID NO:2) was mutated to isoleucine (T4I). In epitope region #0, the serine natively located at position 8 in the mature A Subunits of Shiga-like toxin 1 (SEQ ID NO:1) and Shiga toxin (SEQ ID NO:2) was mutated to isoleucine (S8I). In epitope region #0, the threonine natively located at position 9 in the mature A Subunits of Shiga-like toxin 1 (SEQ ID NO:1) and Shiga toxin (SEQ ID NO:2) was mutated to isoleucine (T9I) and to valine (T9V). In epitope region #0, the lysine natively located at position 11 in the mature A Subunits of Shiga-like toxin 1 (SEQ ID NO:1) and Shiga toxin (SEQ ID NO:2) was mutated to alanine (K11A) and to histidine (K11H). The following five amino acid residues mutated in epitope region #0: K1, T4, S8, T9, and K11, were predicted by the Epitopia webserver to be solvent exposed.

In epitope region #1 (see Table 5), the serine natively located at position 33 in the mature A Subunits of Shiga-like toxin 1 (SEQ ID NO:1) and Shiga toxin (SEQ ID NO:2) was mutated to isoleucine (S33I).

In epitope region #2 (see Table 5), the serine natively located at position 45 in the mature A Subunit of Shiga-like toxin 1 (SEQ ID NO:1) was mutated to valine (S45V) and to isoleucine (S45I). In epitope region #2 (see Table 5), the aspartate natively located at position 47 in the mature A Subunit of Shiga-like toxin 1 (SEQ ID NO:1) was mutated to glycine (D47G). In epitope region #2 (see Table 5), the asparagine natively located at position 48 in the mature A Subunit of Shiga-like toxin 1 (SEQ ID NO:1) was mutated to valine (N48V) and to phenylalanine (N48F).

In epitope region #3* (see Table 5), the aspartate natively located at position 53 in the mature A Subunit of Shiga-like toxin 1 (SEQ ID NO:1) and Shiga toxin (SEQ ID NO:2) was mutated to alanine (D53A), glycine (D53G), and asparagine (D53N). The D53 residue was predicted by the Epitopia webserver to be solvent exposed and have an immunogenicity scale value of 5 or "high." In epitope region #3 and #3* (see Table 5), the arginine natively located at position 55 in the mature A Subunit of Shiga-like toxin 1 (SEQ ID NO:1) and Shiga toxin (SEQ ID NO:2) was mutated to alanine (R55A), to valine (R55V), and to leucine (R55L). In epitope region #3 and #3*, the aspartate natively located at position 58 in the mature A Subunit of Shiga-like toxin 1 (SEQ ID NO:1) and Shiga toxin (SEQ ID NO:2) was mutated to alanine (D58A), to valine (D58V), and to phenylalanine (D58F). In epitope region #3 and #3*, the proline natively located at position 59 in the mature A Subunit of Shiga-like toxin 1 (SEQ ID NO:1) and Shiga toxin (SEQ ID NO:2) was mutated to alanine (P59A). In epitope region #3 and #3*, the glutamate natively located at position 60 in the mature A Subunit of Shiga-like toxin 1 (SEQ ID NO:1) and Shiga toxin (SEQ ID NO:2) was mutated to isoleucine (E60I), to threonine (E60T), and to arginine (E60R). In epitope region #3 and #3*, the glutamate natively located at position 61 in the mature A Subunit of Shiga-like toxin 1 (SEQ ID NO:1) and Shiga toxin (SEQ ID NO:2) was mutated to alanine (E61A), to valine (E61V), and to leucine (E61L). In epitope region #3 and #3*, the glycine natively located at position 62 in the mature A Subunit of Shiga-like toxin 1 (SEQ ID NO:1) and Shiga toxin (SEQ ID NO:2) was mutated to alanine (G62A).

In epitope region #4* (see Table 5), the aspartate natively located at position 94 in the mature A Subunit of Shiga-like toxin 1 (SEQ ID NO:1) and Shiga toxin (SEQ ID NO:2) was mutated to alanine (D94A). This D94 residue was predicted by the Epitopia webserver to be solvent exposed and have an immunogenicity scale value of 5 or "high." In epitope region #4 and #4* (see Table 5), the serine natively located at position 96 in the mature A Subunit of Shiga-like toxin 1

(SEQ ID NO:1) and Shiga toxin (SEQ ID NO:2) was mutated to isoleucine (S96I). In epitope region #4 and #4* (see Table 5), the serine natively located at position 109 in the mature A Subunit of Shiga-like toxin 1 (SEQ ID NO:1) and Shiga toxin (SEQ ID NO:2) was mutated to valine (S109V). In epitope region #4 and #4* (see Table 5), the glycine natively located at position 110 in the mature A Subunit of Shiga-like toxin 1 (SEQ ID NO:1) and Shiga toxin (SEQ ID NO:2) was mutated to alanine (G110A). In epitope region #4 and #4* (see Table 5), the serine natively located at position 112 in the mature A Subunit of Shiga-like toxin 1 (SEQ ID NO:1) and Shiga toxin (SEQ ID NO:2) was mutated to valine (S112V).

In epitope region #5 (see Table 5), the glycine natively located at position 147 in the mature A Subunit of Shiga-like toxin 1 (SEQ ID NO:1) and Shiga toxin (SEQ ID NO:2) was mutated to alanine (G147A).

In epitope region 6* (see Table 5), the arginine natively located at position 179 in the mature A Subunit of Shiga-like toxin 1 (SEQ ID NO:1) and Shiga toxin (SEQ ID NO:2) was mutated to alanine (R179A). This R179 residue was predicted by the Epitopia webserver to be exposed and have an immunogenicity value of 5 or "high." In epitope region #6 and #6* (see Table 5), the threonine natively located at position 180 in the mature A Subunit of Shiga-like toxin 1 (SEQ ID NO:1) and Shiga toxin (SEQ ID NO:2) was mutated to glycine (T180G). In epitope region #6 and #6* (see Table 5), the threonine natively located at position 181 in the mature A Subunit of Shiga-like toxin 1 (SEQ ID NO:1) and Shiga toxin (SEQ ID NO:2) was mutated to isoleucine (T181I). In epitope region #6 and #6* (see Table 5), the aspartate natively located at position 183 in the mature A Subunit of Shiga-like toxin 1 (SEQ ID NO:1) and Shiga toxin (SEQ ID NO:2) was mutated to alanine (D183A) and to glycine (D183G). In epitope region #6 and #6*, the aspartate natively located at position 184 in the mature A Subunit of Shiga-like toxin 1 (SEQ ID NO:1) and Shiga toxin (SEQ ID NO:2) was mutated to alanine (D184A) or phenylalanine (D184F). In epitope region #6 and #6* (see Table 5), the leucine natively located at position 185 in the mature A Subunit of Shiga-like toxin 1 (SEQ ID NO:1) and Shiga toxin (SEQ ID NO:2) was mutated to valine (L185V). In epitope region #6 and #6*, the serine natively located at position 186 in the mature A Subunit of Shiga-like toxin 1 (SEQ ID NO:1) and Shiga toxin (SEQ ID NO:2) was mutated to alanine (S186A) and to phenylalanine (S186F). In epitope region #6 and #6*, the glycine natively located at position 187 in the mature A Subunit of Shiga-like toxin 1 (SEQ ID NO:1) and Shiga toxin (SEQ ID NO:2) was mutated to alanine (G187A). In epitope region #6 and #6*, the arginine natively located at position 188 in the mature A Subunit of Shiga-like toxin 1 (SEQ ID NO:1) and Shiga toxin (SEQ ID NO:2) was mutated to alanine (R188A) and to leucine (R188L). In epitope region #6 and #6*, the serine natively located at position 189 in the mature A Subunit of Shiga-like toxin 1 (SEQ ID NO:1) and Shiga toxin (SEQ ID NO:2) was mutated to alanine (S189A).

In epitope region #7 (see Table 5), the arginine natively located at position 248 in the mature A Subunit of Shiga-like toxin 1 (SEQ ID NO:1) and Shiga toxin (SEQ ID NO:2) was mutated to alanine (R248A). In epitope region #7, the arginine natively located at position 251 in the mature A Subunit of Shiga-like toxin 1 (SEQ ID NO:1) and Shiga toxin (SEQ ID NO:2) was mutated to alanine (R251A).

The leucine natively located at position 49 in the mature A Subunit of Shiga-like toxin 1 (SEQ ID NO:1) and Shiga toxin (SEQ ID NO:2) was mutated to alanine (L49A). This L49 residue was predicted by the Epitopia webserver to be solvent exposed and have an immunogenicity value of 4. The arginine natively located at position 205 in the mature A Subunit of Shiga-like toxin 1 (SEQ ID NO:1) and Shiga toxin (SEQ ID NO:2) was mutated to alanine (R205A). This R205 residue was predicted by the Epitopia webserver to be solvent exposed and have an immunogenicity value of 5 or "high."

TABLE 6

Amino Acid Substitutions in Exemplary Shiga Toxin Effector Polypeptides

| | | natively positioned amino acid positions | |
|---|---|---|---|
| Epitope Region Disrupted | Substitution | B-Cell Epitope Region | T-Cell Epitope Region |
| 0 | K1M | 1-15 | 4-33 |
| 0 | T4I | 1-15 | 4-33 |
| 0 | S8I | 1-15 | 4-33 |
| 0 | T9V | 1-15 | 4-33 |
| 0 | T9I | 1-15 | 4-33 |
| 0 | K11A | 1-15 | 4-33 |
| 0 | K11H | 1-15 | 4-33 |
| 1 | S33I | 27-37 | 4-33, 34-78 |
| 2 | S45V | 39-48 | 34-78 |
| 2 | S45I | 39-48 | 34-78 |
| 2 | D47G | 39-48 | 34-78 |
| 2 | N48V | 39-48 | 34-78 |
| 2 | N48F | 39-48 | 34-78 |
| — | L49A | immunogenic residue | 34-78 |
| 3* | D53A | 53-66 | 34-78 |
| 3* | D53G | 53-66 | 34-78 |
| 3* | D53N | 53-66 | 34-78 |
| 3 & 3* | R55A | 55-66 | 34-78 |
| 3 & 3* | R55V | 55-66 | 34-78 |
| 3 & 3* | R55L | 55-66 | 34-78 |
| 3 & 3* | I57F | 55-66 | 34-78 |
| 3 & 3* | D58A | 55-66 | 34-78 |
| 3 & 3* | D58F | 55-66 | 34-78 |
| 3 & 3* | P59A | 55-66 | 34-78 |
| 3 & 3* | P59F | 55-66 | 34-78 |
| 3 & 3* | E60I | 55-66 | 34-78 |
| 3 & 3* | E60T | 55-66 | 34-78 |
| 3 & 3* | E60R | 55-66 | 34-78 |
| 3 & 3* | E61A | 55-66 | 34-78 |
| 3 & 3* | E61V | 55-66 | 34-78 |
| 3 & 3* | E61L | 55-66 | 34-78 |
| 3 & 3* | G62A | 55-66 | 34-78 |
| 4* | D94A | 94-115 | 77-103 |
| 4 & 4* | S96I | 96-115 | 77-103 |
| 4 & 4* | SI 09 V | 96-115 | |
| 4 & 4* | G110A | 96-115 | |
| 4 & 4* | S112V | 96-115 | |
| 5 | G147A | 141-153 | 128-168 |
| 6* | R179A | 179-190 | 160-183 |
| 6 & 6* | T180G | 180-190 | 160-183 |
| 6 & 6* | T181I | 180-190 | 160-183 |
| 6 & 6* | D183A | 180-190 | 160-183 |
| 6 & 6* | D183G | 180-190 | 160-183 |
| 6 & 6* | DI 84 A | 180-190 | |
| 6 & 6* | D184F | 180-190 | |
| 6 & 6* | L185V | 180-190 | |
| 6 & 6* | S186A | 180-190 | |
| 6 & 6* | S186F | 180-190 | |
| 6 & 6* | G187A | 180-190 | |
| 6 & 6* | R188A | 180-190 | |
| 6 & 6* | R188L | 180-190 | |
| 6 & 6* | S189A | 180-190 | |
| — | R205A | immunogenic residue | |
| 7 | R248A | 243-257 | 236-258 |
| 7 | R251A | 243-257 | 236-258 |

The amino acid substitution comprising Shiga toxin effector polypeptides were tested as components of putative cytotoxic proteins with cell-targeting binding regions. The cytotoxic proteins comprised an immunoglobulin-type binding region and Shiga toxin effector region linked together to form a fusion protein. These putative cytotoxic fusion proteins were produced by expression from polynucleotides encoding them using a bacterial system known in the art.

Example 3. Empirically Testing De-Immunized Shiga Toxin Effector Polypeptides for Retention of One or More Shiga Toxin Effector Functions Various de-immunized Shiga toxin effector region polypeptides were empirically tested for retention of enzymatic activity and cytotoxicity.

The retention of enzymatic activity of Shiga toxin effector polypeptides after de-immunization was tested using a ribosome inhibition assay in the context of the Shiga toxin effector polypeptide as a component of a cytotoxic protein. In certain experiments, the full-length coding sequence of the cytotoxic protein of this example began or ended with a polynucleotide encoding a Strep-Tag® II to facilitate detection and purification.

The ribosome inactivation capabilities of de-immunized cytotoxic proteins were determined using a cell-free, in vitro protein translation assay using the TNT® Quick Coupled Transcription/Translation kit (L1170 Promega Madison, WI, U.S.). The kit includes Luciferase T7 Control DNA (L4821 Promega Madison, WI, U.S.) and TNT® Quick Master Mix. The ribosome activity reaction was prepared according to manufacturer's instructions. A series of 10-fold dilutions of the protein comprising a mutated Shiga toxin effector polypeptide region to be tested was prepared in an appropriate buffer and a series of identical TNT reaction mixture components were created for each dilution. Each sample in the dilution series was combined with each of the TNT reaction mixtures along with the Luciferase T7 Control DNA. The test samples were incubated for 1.5 hours at 30 degrees Celsius (° C.). After the incubation, Luciferase Assay Reagent (E1483 Promega, Madison, WI, U.S.) was added to all test samples and the amount of luciferase protein translation was measured by luminescence according to manufacturer's instructions. The level of translational inhibition was determined by non-linear regression analysis of log-transformed concentrations of total protein versus relative luminescence units. Using statistical software (GraphPad Prism, San Diego, CA, U.S.), the half maximal inhibitory concentration ($IC_{50}$) value was calculated for each sample using the Prism software function of log(inhibitor) vs. response (three parameters) [Y=Bottom+((Top−Bottom)/(1+10^(X−Log IC50)))] under the heading dose-response-inhibition. The $IC_{50}$ for each protein comprising a de-immunized Shiga toxin effector polypeptide region and a control protein comprising a wild-type Shiga toxin effector region with no internal epitope disruptions were calculated.

Exemplary Shiga toxin effector polypeptide regions which exhibited ribosome inhibition are indicated in Table 7. As reported in Table 7, a substitution-comprising construct exhibiting an $IC_{50}$ within 10-fold of a wild-type SLT-1A control construct is considered to exhibit ribosome inhibition activity comparable to wild-type; a construct exhibiting an $IC_{50}$ between 10-fold to 100-fold of a wild-type SLT-1A control is considered to exhibit attenuated activity as compared to wild-type; and a construct exhibiting an $IC_{50}$ greater than 100-fold of a wild-type SLT-1A control is considered severely impaired or inactive (severely impaired/inactive).

TABLE 7

Ribosome Inhibition Activities of Exemplary Shiga Toxin Effector Polypeptides

| Epitope Region | Substitution(s) | In Vitro Ribosome Inhibition ($IC_{50}$) |
|---|---|---|
| 0 | K1M, K11A | comparable to wild-type |
| 0 | S8I | comparable to wild-type |
| 0 | T9I | comparable to wild-type |
| 1 | S33I | comparable to wild-type |
| 2 | S45I | comparable to wild-type |
| 3* | D53A | comparable to wild-type |
| 3 & 3* | R55A | comparable to wild-type |
| 3 & 3* | D58A | comparable to wild-type |
| 3 & 3* | D58F | comparable to wild-type |
| 3 & 3* | P59A | comparable to wild-type |
| 3 & 3* | E60I | comparable to wild-type |
| 3 & 3* | E60R | comparable to wild-type |
| 3 & 3* | E61A | comparable to wild-type |
| 3 & 3* | G62A | comparable to wild-type |
| 4 & 4* | D94A, S96I | comparable to wild-type |
| 6* | R179A | severely impaired or inactive |
| 6 & 6* | D183A | comparable to wild-type |
| 6 & 6* | D184A | comparable to wild-type |
| 6 & 6* | D184F | comparable to wild-type |
| 6 & 6* | R188A | comparable to wild-type |
| 6 & 6* | D183A, D184A, R188A | comparable to wild-type |
| — | R205A | comparable to wild-type |

The retention of cytotoxic activity of various exemplary Shiga toxin effector polypeptides after de-immunization was tested using a target-cell-kill assay in the context of the Shiga toxin effector polypeptide as a component of a cytotoxic protein with a binding region capable of specific and high-affinity binding to an extracellular target biomolecule expressed and physically-coupled to the cellular surface of target cells (i.e. "target-expressing cells" or "target biomolecule positive cells"). The cytotoxicity levels of de-immunized cytotoxic proteins were determined using target-expressing cells as compared to cells that do not express a target biomolecule of the cytotoxic protein's binding region.

Target-expressing cells were plated ($2\times10^3$ cells per well for adherent cells, plated the day prior to protein addition or $7.5\times10^3$ cells per well for suspension cells, plated the same day as protein addition) in 20 μL cell culture medium in 384 well plates. A series of 10-fold dilutions of each protein comprising a mutated Shiga toxin effector polypeptide region to be tested was prepared in an appropriate buffer, and 5 μL of the dilutions or buffer control were added to the cells. Control wells containing only media were used for baseline correction. The cell samples were incubated with the proteins or just buffer for 3 days at 37° C. and in an atmosphere of 5% carbon dioxide ($CO_2$). The total cell survival or percent viability was determined using a luminescent readout using the CellTiter-Glo® Luminescent Cell Viability Assay (G7573 Promega Madison, WI, U.S.) according to the manufacturer's instructions.

The Percent Viability of experimental wells was calculated using the following equation: (Test RLU−Average Media RLU)/(Average Cells RLU−Average Media RLU)*100. Log polypeptide concentration versus Percent Viability was plotted in Prism (GraphPad Prism, San Diego, CA, U.S.) and log (inhibitor) versus response (3 parameter) analysis was used to determine the half-maximal cytotoxic concentration (CD50) value for the tested proteins. The $CD_{50}$ for each protein comprising a de-immunized Shiga toxin effector polypeptide and wild-type control protein with no internal epitope disruptions were calculated.

The cytotoxicity of exemplary Shiga toxin effector polypeptide regions is indicated in Table 8. As reported in Table 8, a substitution-comprising construct exhibiting a $CD_{50}$ within 10-fold of a wild-type SLT-1A control construct is considered to exhibit cytotoxicity comparable to a wild-type; a construct exhibiting a $CD_{50}$ between 10-fold to 100-fold of a wild-type SLT-1A control is considered to exhibit attenuated cytotoxicity as compared to wild-type; and a construct exhibiting a $CD_{50}$ greater than 100-fold of a wild-type SLT-1A control is considered severely impaired/inactive.

TABLE 8

Cytotoxic Activities of Exemplary Shiga Toxin Effector Polypeptides

| Epitope Region | Substitution(s) | Cytotoxicity ($CD_{50}$) |
|---|---|---|
| 0 | K1M, K11A | comparable to wild-type |
| 0 | S8I | comparable to wild-type |
| 0 | T9I | attenuated |
| 1 | S33I | comparable to wild-type |
| 2 | S45I | comparable to wild-type |
| 3* | D53A | comparable to wild-type |
| 3 & 3* | R55A | comparable to wild-type |
| 3 & 3* | D58A | comparable to wild-type |
| 3 & 3* | D58F | comparable to wild-type |
| 3 & 3* | P59A | comparable to wild-type |
| 3 & 3* | E60I | comparable to wild-type |
| 3 & 3* | E60R | comparable to wild-type |
| 3 & 3* | E61A | comparable to wild-type |
| 3 & 3* | G62A | comparable to wild-type |
| 4 & 4* | D94A, S96I | attenuated |
| 6* | R179A | severely impaired or inactive |
| 6 & 6* | D183A | comparable to wild-type |
| 6 & 6* | D184A | comparable to wild-type |
| 6 & 6* | D184F | attenuated |
| 6 & 6* | R188A | comparable to wild-type |
| 6 & 6* | D183A, D184A, R188A | comparable to wild-type |
| — | R205A | comparable to wild-type |

The term "successful" is used to mean one or more amino acid residue substitutions in a predicted epitope region resulted in a Shiga toxin effector region polypeptide which retained one or more Shiga toxin effector functions. Three substitutions (D183A, D184A, and R188A) which were successful individually in the same epitope region (#6 & 6*) were combined to generate a de-immunized Shiga toxin effector polypeptide (D183A/D184A/R188A) retaining Shiga toxin effector function comparable to wild-type (Tables 7 and 8). These results suggest that some successful amino acid substitutions in the same epitope region of a Shiga toxin effector polypeptide may be combined to create epitope disruptions with greater overall epitope disruption while still retaining significant levels of one or more Shiga toxin effector function. Similarly, both epitope regions #0 and #4 & 4* successfully tolerated multiple amino acid substitutions within their respective regions (Tables 7 and 8: K1M/K11A and D94A/S96I). Reinforcing the idea that various exemplary substitutions in the same epitope region may be combined to create epitope disruptions with greater overall epitope disruption while still retaining significant levels of one or more Shiga toxin effector function.

In addition, other Shiga toxin effector region polypeptides were tested for Shiga toxin effector functions and epitope disruption using the methods as described in the Examples herein, where the Shiga toxin effector region polypeptides comprised multiple amino acids substitutions within a single predicted B-cell epitope region. The regions tested were the following natively positioned regions present in the mature A Subunit of Shiga-like toxin 1 (SEQ ID NO:1) and Shiga toxin (SEQ ID NO:2): 4-12, 43-52, 53-61, 104-112, and 180-188. These single-region, multi-substitution constructs were created in various combinations in the context of a cytotoxic protein comprising a Shiga toxin effector region comprising residues 1-251 of SLT-1A (SEQ ID NO:1). These constructs retained ribosome inhibition comparable to a wild-type SLT-1A effector construct and were selectively cytotoxic to target cells. These constructs comprised one or more of the following amino acid substitutions in various combinations with other amino acid substitutions in a single region: region 4-12: T4I, T9V, and K11H; region 43-52: S45V, D47G, N48V, N48F, and L49A; region 53-61: D53G, D53N, R55V, R55L, D58V, E60T, E61V and E61L; region 104-112: S109V, G110A, and S112V; region 180-188: T180G, T181I, D183G, L185V, S186F, and R188L. In addition, Western analysis of these constructs showed reduced or abolished recognition of each construct by one or more antibodies that can recognize wild-type SLT-1A (mAb1, pAb1, and pAb2 described in Example 4).

In addition, epitope region #7 is disrupted by the substitution R248A or R251 without any significant effect on either ribosome inhibition activity or cytotoxicity. R248A or R251A may be successfully introduced into the exemplary Shiga toxin effector region polypeptides described above without altering either ribosome inhibition or cytotoxicity.

Individual epitope disruptions mentioned above as well as new disruptions were combined to create various combinations of Shiga toxin effector polypeptides (Table 9) comprising disruptions of two or more epitope regions, and then empirically examined for retention of Shiga toxin effector functions as described in this Example. Table 9 lists the activities exhibited by constructs with combinations of amino acid substitutions, within a single epitope region or in as many as five different epitope regions, using the terms described previously.

TABLE 9

Multi-Epitope-Region Amino-Acid-Substitution Combinations in De-Immunized Shiga Toxin Effector Polypeptides and Cytotoxic Proteins

| Epitope Regions Disrupted | Substitutions | Ribosome Inhibition | Cytotoxicity |
|---|---|---|---|
| 3/3*, 4/4* | E60I, G110A | comparable to wild-type | comparable to wild-type |
| 3/3*, 5 | E60I, G147A | comparable to wild-type | comparable to wild-type |
| 2, 6/6* | S45I, R188A | comparable to wild-type | comparable to wild-type |
| 1, 4/4*, 5 | S33I, G110A, G147A | comparable to wild-type | comparable to wild-type |

TABLE 9-continued

Multi-Epitope-Region Amino-Acid-Substitution Combinations in De-Immunized Shiga Toxin Effector Polypeptides and Cytotoxic Proteins

| Epitope Regions Disrupted | Substitutions | Ribosome Inhibition | Cytotoxicity |
|---|---|---|---|
| 2, 4/4*, 5 | S45I, G110A,G147A | comparable to wild-type | comparable to wild-type |
| 3/3*, 4/*4, 5 | D58A, G110A, G147A | comparable to wild-type | comparable to wild-type |
| 3/3*, 4/*4, 5 | E60I, G110A, G147A | comparable to wild-type | comparable to wild-type |
| 2, 3/3*, 4/*4, 5 | S45I, D58A, E60I, G110A, G147A | comparable to wild-type | comparable to wild-type |
| 2, 3/3*, 4/*4, 5 | S45I, D58A, E60I, G62A, G110A, G147A | comparable to wild-type | attenuated |
| 2, 4/4*, 5, 6/6* | S45I, G110A, G147A, D183A, D184A, R188A | comparable to wild-type | comparable to wild-type |
| 3/3*, 4/*4, 5, 6/6* | D58A, G110A, G147A, S186A | comparable to wild-type | comparable to wild-type |
| 3/3*, 4/*4, 5, 6/6* | D58A, G110A, G147A, G187A | comparable to wild-type | comparable to wild-type |
| 3/3*, 4/*4, 5, 6/6* | D58A, G110A, G147A, R188A | comparable to wild-type | comparable to wild-type |
| 3/3*, 4/*4, 5, 6/6* | D58A, G110A, G147A, S189A | comparable to wild-type | comparable to wild-type |
| 3/3*, 4/*4, 5, 6/6* | D58A, G110A, G147A, S186A, R188A | comparable to wild-type | attenuated |
| 3/3*, 4/*4, 5, 6/6* | D58A, G110A, G147A, G187A, R188A | comparable to wild-type | attenuated |
| 1, 2, 3/3*, 4/*4, 5 | S33I, S45I, D58A, G110A, G147A | comparable to wild-type | comparable to wild-type |
| 2, 3/3*, 4/*4, 5, 6/6* | S45I, D58A, E60I, G110A, G147A, D183A, D184A, R188A | comparable to wild-type | attenuated |
| 2, 3/3*, 4/*4, 5, 6/6* | S45I, D58A, E60I, G62A, G110A, G147A, D183A, D184A, R188A | comparable to wild-type | attenuated |

These results suggest generally that most if not all successful amino acid substitutions in one epitope region of a Shiga toxin effector polypeptide, meaning any substitution empirically shown to retain a Shiga toxin effector function and predicted to disrupt an epitope, may be combined with most if not all other successful amino acid substitutions in a different epitope region to form a de-immunized Shiga toxin effector polypeptide with multiple epitope regions disrupted while still retaining at least one Shiga toxin effector function.

Example 4. Empirically Testing De-Immunized Shiga Toxin Effector Polypeptides for Disruption of Antigenic and/or Immunogenic Epitope(s)

Experimental testing was performed to confirm disruption of B-cell epitopes based on empirically verifiable epitopes recognized by known antibodies. Western analyses were performed to determine epitope disruptions under denaturing conditions. Enzyme-linked immunosorbent assay (ELISA) analyses were performed to determine epitope disruptions under more native protein folding conditions (i.e. non-denaturing conditions).

Cytotoxic proteins comprising Streptag® II and wildtype Shiga toxin effector polypeptide regions or de-immunized Shiga toxin effector polypeptide regions were loaded in equal amounts to replicate 4-20% sodium dodecyl sulfate (SDS) polyacrylamide gels (Lonza, Basel, CH) and electrophoresed under denaturing conditions. The resulting gels were either analyzed by COOMASSIE™ staining or transferred to polyvinyl difluoride (PVDF) membranes using the iBlot® (Life Technologies, Carlsbad, CA, U.S.) system according to manufacturer's instructions. The resulting membranes were probed under standard conditions using the following antibodies: rabbit polyclonal α-NWSHPQFEK (SEQ ID NO: 134) (A00626, Genscript, Piscataway, NJ, U.S.) which recognizes the polypeptide NWSHPQFEK also known as Streptag® II, mouse monoclonal α-StxA (anti-SLT-1A mAb1 or mAb1) (BEI NR-867 BEI Resources, Manassas, VA, U.S.), rabbit polyclonal antibody α-SLT-1A (anti-SLT-1A pAb1 or pAb1) (Harlan Laboratories, Inc. Indianapolis, IN, U.S., custom antibody production, raised against SLT-1A amino acids 1-251), and rabbit polyclonal antibody α-SLT-1A (anti-SLT-1A pAb2 or pAb2) (Genscript, Piscataway, NJ, U.S., custom antibody production), which was raised against the peptides RGIDPEEGRFNN (SEQ ID NO: 135) and HGQDSVRVGR (SEQ ID NO: 136). The peptide sequence RGIDPEEGRFNN (SEQ ID NO: 135) spans the putative B-cell epitope region #3 (Table 5), and the peptide sequence HGQDSVRVGR (SEQ ID NO: 136) is located at 214-223 in SLT-1A and StxA. Membrane bound antibodies were detected using standard conditions and, when appropriate, using horseradish peroxidase (HRP) conjugated secondary antibodies (goat anti-rabbit-HRP or goat anti-mouse-HRP, Thermo Scientific, Rockford, IL, U.S.). FIGS. 2-5 show Western blots with the lanes of the gels and/or membranes numbered and the figure legends indicate by the same respective numbering which Shiga toxin effector regions were comprised within the protein loaded into each lane.

The D58A substitution successfully disrupted one of the epitopes recognized by the polyclonal α-SLT-1A pAb2

(FIG. 2). Similarly, the D58A/G110A/G147A triple substitution and S33I/S45I/D58A/G110A/G147A quintuple substitution mutants showed strong disruption of at least one of the epitopes recognized by α-SLT-1A pAb2 (FIG. 3; FIG. 4) and partial disruption of at least one of the epitopes recognized by α-SLT-1A pAb1 (FIG. 3).

The 5451/G110A/G147A and 5331/G110A/G147A triple substitution mutants showed partial disruption of at least one of the epitopes recognized by α-SLT-1A pAb1 (FIG. 3). The S45I/G110A/G147A triple mutant strongly disrupted the epitope recognized by the monoclonal antibody mAb1 and partially disrupted the epitope recognized by the polyclonal α-SLT-1A pAb2 (FIG. 3; FIG. 4). The D58A/G110A/G147A triple mutant very effectively disrupted the epitope recognized by the monoclonal antibody mAb1 and at least one of the epitopes recognized by the polyclonal α-SLT-1A pAb2 (FIG. 3; FIG. 4).

The D183A/D184A/R188A triple mutant showed very effective disruption of the epitope recognized by the monoclonal antibody mAb1 (FIG. 5). The D58A/G110/G147A/R188A quadruple mutant very effectively disrupted the epitope recognized by the monoclonal antibody mAb1 and at least one of the epitopes recognized by the polyclonal α-SLT-1A pAb2 and partially disrupted at least one of the epitopes recognized by α-SLT-1A pAb1 (FIG. 5).

It is likely that the epitopes disrupted in the D58A/G110A/G147A triple, 5451/G110A/G147A triple, and D58A/G110A/G147A/R188A quadruple mutants (one recognized by mAb1 and others recognized by pAb2) most likely reside in two non-continuous regions. Thus, the D58A/G110A/G147A triple, 5451/G110A/G147A triple, and D58A/G110A/G147A/R188A quadruple substitution mutants each comprised a de-immunized Shiga toxin effector region polypeptide verified empirically to have at least two different epitopes disrupted simultaneously.

Similarly, it is likely that certain dominant epitopes disrupted in the D58A/G110A/G147A triple, S45I/G110A/G147A triple, 5331/G110A/G147A triple, D58A/G110A/G147A/R188A quadruple, and S33I/S45I/D58A/G110A/G147A quintuple mutants (epitopes recognized by pAb1 and pAb2) most likely reside in at least two non-continuous regions. Thus, D58A/G110A/G147A triple, 5451/G110A/G147A triple, S33I/G110A/G147A triple, D58A/G110A/G147A/R188A quadruple, and S33I/S45I/D58A/G110A/G147A quintuple mutants probably comprised a de-immunized Shiga toxin effector region polypeptide verified empirically to have at least two different epitopes disrupted simultaneously.

A standard ELISA was used to measure the ability of mAb1 to recognize a de-immunized Shiga toxin effector region with multiple epitope regions disrupted in the context of a cytotoxic protein. The cytotoxic protein bound the target biomolecule of its scFv binding region. The wells of Nunc MaxiSorp® plates in phosphate buffered saline (1×PBS) (Hyclone™ Brand, Fisher Scientific, Waltham, MA, U.S.) were coated with recombinant human target protein of the binding region of the cytotoxic protein. The plates were incubated overnight at 4° C. The wells were washed with 1×PBS 0.05% TWEEN®-20 (PBS-T), and non-specific binding was blocked by incubating the wells with 3% milk in PBS-T for one hour at room temperature. A cytotoxic protein comprising a Streptag® II and a de-immunized Shiga toxin effector region (D58A/G110A/G147A/R188A) was added to the wells at a concentration determined to be above the binding dissociation constant ($K_D$). As a positive control and reference for wild-type activity, a cytotoxic protein comprising a wild-type Shiga toxin effector region and a Streptag® II was added to the wells at the same concentrations.

The plates were incubated at room temperature for one hour to allow for cytotoxic protein binding under non-denaturing conditions. The wells were washed with PBS-T and then incubated with either PBS-T or the mouse monoclonal antibody anti-SLT-1A mAb1 for one hour at room temperature. The wells were washed in PBS-T and then incubated with the detection antibodies: HRP-conjugated antibody directed to Streptag® II or an anti-mouse-HRP-conjugated antibody. The wells were washed in PBS-T and then incubated with Pierce TMB Ultra (Thermo Scientific Inc., Rockford, IL, U.S.). The reactions were stopped with 250 mM hydrochloric acid (HCl). Products of HRP activity were detected by a plate reading device measuring absorbance (Abs) of light set to the wavelength of 450 nanometers (nm). The measured absorbance values were corrected for background by subtracting the absorbance values for coated, blocked wells incubated with PBS instead of any Shiga toxin construct.

Both cytotoxic proteins bound to the human, recombinant protein, target biomolecule of the scFv as measured by high absorbance values for the Streptag® II antibody (FIG. 6). The cytotoxic protein comprising the de-immunized Shiga toxin effector region (D58A/G110A/G147A/R188A) was not recognized by the monoclonal antibody anti-SLT-1A mAb1 (FIG. 6). The positive control cytotoxic protein, which comprised the wild-type Shiga toxin effector polypeptide, was bound by the antibody anti-SLT-1A mAb1 (FIG. 6). These results indicated that the epitope recognized by anti-SLT-1A mAb1 was present in the natively folded, wild-type Shiga toxin effector region, but that epitope was disrupted by the combination of mutations D58A/G110A/G147A/R188A in the natively folded, de-immunized Shiga toxin effector region.

Example 5. Predicting the Disruption of Antigenic and/or Immunogenic Epitopes in Shiga Toxin Effector Polypeptides Each substitution made in Example 4 with an aim to de-immunize a Shiga toxin effector polypeptide while retaining Shiga toxin effector functions was checked for abolishment of the predicted B-cell epitope in the epitope region comprising the substitution using the BcePred web-server with the following: flexibility readout with the default settings of hydrophilicity 2, accessibility 2, exposed surface 2.4, antigenic propensity 1.8, flexibility 1.9, turns 1.9, polarity 2.3, and combined 1.9 (Saha S, Raghava G, *Lecture Notes in Comput Sci* 3239: 197-204 (2004)). Table 10 shows the substitution present in the analysis and the result of the B-cell epitope prediction in the last column. Of note, epitope regions #0 (1-15) and #7 (243-257) were not predicted in wild-type SLT-1A by the BcePred flexibility approach with the default settings. The substitutions tested (see Table 6) did not create de novo any predicted B-cell epitopes by the BcePred flexibility approach (see e.g. Table 10), including KM, S8I, T9I, K11A in epitope region #0; D94A in epitope region #4*; and S96I in epitope regions #4 and 4*. Additionally, the results for other substitutions analyzed using the BcePred computational approach are listed in Table 10 that were not yet empirically tested.

TABLE 10

| B-Cell Epitope Predictions after Amino Acid Substitution | | | |
|---|---|---|---|
| | natively positioned amino acid positions | | |
| Epitope Region # | B-Cell Epitope Region | Substitution | B-Cell Epitope by BcePred |
| 0 | 1-15 | K1M | no change |
| 0 | 1-15 | T4I | no change |
| 0 | 1-15 | S8I | no change |
| 0 | 1-15 | T9V | no change |
| 0 | 1-15 | T9I | no change |
| 0 | 1-15 | K11A | no change |
| 0 | 1-15 | K11H | no change |
| 1 | 27-37 | S33I | eliminated |
| 1 | 27-37 | S45V | eliminated |
| 2 | 39-48 | S45I | eliminated |
| 2 | 39-48 (StxA) | T45I | eliminated |
| 2 | 39-48 | D47G | no change |
| 2 | 39-48 | N48V | no change |
| 2 | 39-48 | N48F | no change |
| 3* | 53-66 | D53A | no change |
| 3* | 53-66 | D53G | no change |
| 3* | 53-66 | D53N | no change |
| 3 & 3* | 55-66 | R55A | no change |
| 3 & 3* | 55-66 | R55V | no change |
| 3 & 3* | 55-66 | R55L | no change |
| 3 & 3* | 55-66 | D58A | eliminated |
| 3 & 3* | 55-66 | D58F | eliminated |
| 3 & 3* | 55-66 | P59A | eliminated |
| 3 & 3* | 55-66 | P59F | eliminated |
| 3 & 3* | 55-66 | E60I | eliminated |
| 3 & 3* | 55-66 | E60T | eliminated |
| 3 & 3* | 55-66 | E60R | no change |
| 3 & 3* | 55-66 | E61A | eliminated |
| 3 & 3* | 55-66 | E61V | eliminated |
| 3 & 3* | 55-66 | E61L | eliminated |
| 3 & 3* | 55-66 | G62A | eliminated |
| 4* | 94-115 | D94A | no change |
| 4 & 4* | 96-115 | S96I | no change |
| 4 & 4* | 96-115 | S109V | eliminated |
| 4 & 4* | 96-115 | G110A | eliminated |
| 4 & 4* | 96-115 | S112V | eliminated |
| 5 | 141-153 | G147A | eliminated |
| 6* | 179-190 | R179A | no change |
| 6 & 6* | 180-190 | T180G | no change |
| 6 & 6* | 180-190 | T181I | no change |
| 6 & 6* | 180-190 | D183A | no change |
| 6 & 6* | 180-190 | D183G | no change |
| 6 & 6* | 180-190 | D184A | eliminated |
| 6 & 6* | 180-190 | D184F | eliminated |
| 6 & 6* | 180-190 | L185V | eliminated |
| 6 & 6* | 180-190 | S186A | eliminated |
| 6 & 6* | 180-190 | S186F | eliminated |
| 6 & 6* | 180-190 | G187A | eliminated |
| 6 & 6* | 180-190 | R188A | eliminated |
| 6 & 6* | 180-190 | R188L | eliminated |
| 6 & 6* | 180-190 | S189A | eliminated |
| 7 | 243-257 | S247I | eliminated |
| 7 | 243-257 | R248A | eliminated |
| 7 | 243-257 | R251A | eliminated |
| 8 | 254-268 | D264A | eliminated |
| 8 | 254-268 | G265A | eliminated |
| 8 | 262-278 (SLT-2A) | G264A | eliminated |
| 9 | 285-293 | T286A | eliminated |
| 9 | 285-293 | T286I | eliminated |

The Western analysis of SLT-1A wildtype compared to SLT-1A D58A (FIG. 2) showed that the BcePred computational flexibility approach accurately predicted the presence of a B-cell epitope at position 55-66 of SLT-1A (Table 1), and the disruption of that epitope region by the D58A substitution was also accurately predicted (Table 10).

Example 6. Empirically Testing the Relative Immunogenicity of a De-Immunized Shiga Toxin Effector Polypeptide Compared to a Wild-Type Shiga Toxin Effector Polypeptide Using a Mammalian Model In this example, the relative immunogenicity of a de-immunized cytotoxic protein of the invention compared to a non-de-immunized cytotoxic protein was determined using a mammalian model of the human immune system. A murine model of mammalian immune systems was used to compare the relative immunogenicity of an exemplary cytotoxic protein comprising an exemplary de-immunized Shiga toxin effector polypeptide to the parental cytotoxic protein comprising a Shiga toxin effector region with only wild-type sequences. Because bacterium-derived Shiga toxin effector region polypeptides are foreign (or non-self) molecular structures to mammals, it was expected that the wild-type Shiga toxin effector polypeptide would exhibit some level of immunogenicity. The relative immunogenicity of a non-mammalian protein determined using mice are generally indicative of its relative immunogenicity for all mammals.

An in-solution ELISA assay was used to determine the relative amount of serum murine antibodies that were specific to different cytotoxic protein samples: cytotoxic proteins comprising either a wild-type Shiga toxin effector polypeptide (amino acids 1-251 of SLT-1A) or an exemplary de-immunized Shiga toxin effector region polypeptide (amino acids 1-251 of SLT-1A with certain amino acid substitutions). Female BALB/c mice were randomly assigned to groups to form groups with six mice each. First, serum samples were collected from each mouse prior to exposure to a cytotoxic protein. Next, each mouse in a group was administered 0.25 mg/kg per dose of the cytotoxic protein comprising either a wild-type (amino acids 1-251 of SLT-1A) or an exemplary de-immunized Shiga toxin effector region (amino acids 1-251 of SLT-1A comprising D58A/G110A/G147A/R188A) by intra-peritoneal injection three times a week over a duration of two weeks for a total of six injections over twelve days. During and after the course of cytotoxic protein administration, murine sera were collected from mice from all the groups to observe anti-"administered protein" levels using an in-solution ELISA assay.

The in-solution anti-"cytotoxic protein" ELISA assay was performed as follows. The same cytotoxic protein used for injections in a mouse group was incubated overnight at 4° C. in solution with the serum of mice from that group, and then the immune complex (consisting of the cytotoxic protein bound to any induced antibodies in the serum) was captured using ELISA plate wells coated with the appropriate target protein. Captured immune complexes comprising murine IgGs were detected using a horseradish-peroxidase-conjugated, anti-mouse IgG, secondary antibody. ELISA plates were developed to detect horseradish peroxidase activity, and the horseradish peroxidase activity or "ELISA signal" was measured at 450 nm using a plate reader. The "ELISA signal" or "ELISA values" were calculated as the absorbance values after subtracting the background signal as measured with a "no serum" negative control. For this in-solution ELISA assay and setup, greater ELISA values indicate stronger immune responses (antibody induction).

None of the mice in any group were measured by this in-solution ELISA assay to have pre-formed serum antibodies recognizing either cytotoxic protein prior to exposure to a cytotoxic protein via injection. Thus, any post-administration detection of anti-"cytotoxic protein" antibodies in these mice using the in-solution ELISA assay represents induced de novo antibody formation which occurred after administration.

For the relative immunogenicity study of this Example, the same cytotoxic protein injected into a group of mice was used in the ELISA assay to capture serum antibodies from the mice of that group. In other words, the antibodies present in the sera from mice in the "wild-type Shiga toxin effector region" group were captured in the ELISA assay with the cytotoxic protein comprising a wild-type Shiga toxin effector region, and the antibodies present in sera from the mice in the "de-immunized Shiga toxin effector region polypeptide" group were captured in the ELISA assay with the exemplary cytotoxic protein comprising the exemplary de-immunized Shiga toxin effector region polypeptide (D58A/G110A/G147A/R188A).

At Day 15 (3 days after the administration of the sixth dose) and Day 22 (10 days after the administration of the sixth dose), an anti-"cytotoxic protein" IgG response was measured by the in-solution ELISA assay described above (FIG. 7). In FIG. 7, the symbols represent individual mice: the filled symbols represent mice administered a cytotoxic protein comprising wild-type Shiga toxin effector region and the open symbols represent mice administered an exemplary cytotoxic protein comprising a de-immunized Shiga toxin effector region polypeptide. In FIG. 7, the vertical lines indicate the mean IgG response signal for each group respectively.

Mice in the group administered the cytotoxic protein comprising a wild-type Shiga toxin effector region had a higher magnitude of antibody response as shown by the ELISA signal than the mice in the group administered the cytotoxic protein comprising the de-immunized Shiga toxin effector region (D58A/G110A/G147A/R188A) at both Day 15 and 22 (FIG. 7). The mean ELISA signal (quantitating antibody response) for the "de-immunized Shiga toxin effector region polypeptide" group was 25% (Day 15) and 39% (Day 22) of the "wild-type Shiga toxin effector region" group. The ELISA signal differences between the "de-immunized Shiga toxin effector region polypeptide" and the "wild-type Shiga toxin effector region" groups were statistically significant based on t-tests (p value was less than 0.005). Using a nominal absorbance value cutoff of 0.9 Abs units to represent a "strong" antibody response, 6/6 (100%) mice in the "wild-type Shiga toxin effector region" group had a strong antibody response at Days 15 or 22, whereas only 3/6 (50%) mice in the "de-immunized Shiga toxin effector region polypeptide" group had a strong antibody response.

The exemplary cytotoxic protein comprising the de-immunized Shiga toxin effector region polypeptide (D58A/G110A/G147A/R188A) showed reduced immunogenicity in a mammalian model (FIG. 7). The decrease in the overall magnitude of antibody induction in mice in the "de-immunized Shiga toxin effector region polypeptide" group, as well as the reduction in the number of mice in this group which induced a potent antibody response, as compared to the "wild-type Shiga toxin effector region" group shows that the de-immunized Shiga toxin effector region polypeptide (D58A/G110A/G147A/R188A) was successfully de-immunized (i.e. has reduced immunogenic potential in mammals), and the exemplary cytotoxic protein comprising it is a de-immunized cytotoxic protein (i.e. has reduced immunogenic potential in mammals).

This exemplary de-immunized cytotoxic protein comprised a Shiga toxin effector region polypeptide comprising four different B-cell epitope region disruptions while retaining three or more Shiga toxin effector functions: catalytic ribosome inhibition, intracellular routing, and cytotoxicity (Table 9). Additionally, the de-immunized Shiga toxin effector region polypeptide of this cytotoxic protein was shown to have disrupted epitopes recognized by mAb1, pAb2, and pAb1 by western blot (FIG. 5) and mAb1 by an ELISA assay (FIG. 6). Therefore, this exemplary cytotoxic protein is a de-immunized cytotoxic protein comprising a de-immunized Shiga toxin effector region polypeptide which has both reduced antigenicity and immunogenicity to mammalian immune systems. The antigenicity and/or immunogenicity of this exemplary cytotoxic protein may be further reduced by introducing additional mutations in the same or additional predicted B-cell epitope regions. Additionally, alternative substitutions at the same or different positions in the already disrupted B-cell epitope regions will result reduced relative immunogenicity.

The relative immunogenicities of various exemplary de-immunized Shiga toxin effector region polypeptides or exemplary cytotoxic protein comprising various de-immunized Shiga toxin effector polypeptide regions are tested in a similar manner. Certain exemplary de-immunized Shiga toxin effector region polypeptides, including 1. (1-251: K1M/K11A/S33I/S45I/D58A/G110A/G147A/R188A), 2. (1-251: KM/K11A/S33I/S45I/D58A/G110A/G147A/D183A/D184A/R188A), 3. (1-251: KIM/K11A/S33I/S45I/D58A/E60I/G110A/G147A/D183A/D184/R188A), 4. (1-251: KIM/K11A/S33I/S45I/R55A/D58A/P59A/E60I/E61A/G62A/G110A/G147A/D183A/D184A/R188A), 5. (1-251: K1M/K11A/S33I/S45I/D58A/G110A/G147A/D183A/D184A/S189A), and 6. (1-251: K1M/K11A/S33I/S45I/R55A/D58A/P59A/E60I/E61A/G62A/G110A/G147A/D183A/D184/R188A/R205A), and SEQ ID NOs:4-52 are compared to Shiga toxin effector polypeptides comprising only wild-type amino acid sequences and/or parental cytotoxic proteins comprising wildtype Shiga toxin effector polypeptide regions using animal models and assays described herein or known to the skilled worker.

In this example, mice are intravenously administered either the de-immunized or wildtype forms 4 times at 7 day intervals. Blood samples are taken from the injected mice and tested by ELISA assays for reactivity to the cytotoxic proteins and/or the Shiga toxin effector polypeptide. Relatively reduced immunogenic responses will be measured in mice injected with certain exemplary de-immunized Shiga toxin effector polypeptides or cytotoxic protein comprising the same as compared to molecules comprising Shiga toxin effector region polypeptides comprising only wild-type amino acid sequences.

Certain exemplary de-immunized cytotoxic protein comprising exemplary de-immunized Shiga toxin effector region polypeptides comprising multiple B-cell epitope region disruptions will retain at a significant level of one or more Shiga toxin effector function: catalytic ribosome inhibition, intracellular routing, and cytotoxicity and have reduced recognition by pre-formed antibodies recognizing anti-Shiga-like Toxin A Subunit antibodies both western blot and/or an ELISA assay. These exemplary cytotoxic protein comprising de-immunized Shiga toxin effector region polypeptides with multiple B-cell epitope region disruptions are de-immunized Shiga toxin effector region polypeptides with reduced antigenicity and/or immunogenicity.

Summary

The previous examples demonstrated that B-cell epitope regions within Shiga toxin effector region polypeptides can be disrupted by amino acid substitutions and result in reductions in both antigenicity and immunogenicity. The amino acid residue substitutions within predicted epitope regions of Shiga toxin effector region polypeptides in the context of a cytotoxic protein which retained at least one Shiga toxin function are summarized in Table 11. All of the exemplary substitutions resulted in Shiga toxin effector regions that functionally retained high cytotoxicity with the concomitant disruption of one or more B-cell epitopes except the substitution R179A interfered with two or more Shiga toxin effector functions.

TABLE 11

Summary of Substitutions in B-Cell Epitope Regions Which Retain Shiga Toxin Effector Functions natively positioned amino acid positions

| B-Cell Epitope Region | Substitution(s) | Epitope Prediction | Ribosome Inhibition | Cytotoxicity |
|---|---|---|---|---|
| 0: 1-15 | K1M/K11A | no change | YES | YES |
| 0: 1-15 | S8I | no change | YES | YES |
| 0: 1-15 | T9I | no change | YES | YES |
| 1: 27-37 | S33I | eliminated | YES | YES |
| 2: 39-48 | S45I | eliminated | YES | YES |
| 3*: 53-66 | D53A | no change | YES | YES |
| 3/3*: 55-66 | R55A | no change | YES | YES |
| 3/3*: 55-66 | D58A | eliminated | YES | YES |
| 3/3*: 55-66 | D58F | eliminated | YES | YES |
| 3/3*: 55-66 | P59A | eliminated | YES | YES |
| 3/3*: 55-66 | E60I | eliminated | YES | YES |
| 3/3*: 55-66 | E60R | no change | YES | YES |
| 3/3*: 55-66 | E61A | eliminated | YES | YES |
| 3/3*: 55-66 | G62A | eliminated | YES | YES |
| 4*: 94-115 | D94A/S96I | no change | YES | YES |
| 6: 180-190 | D183A | no change | YES | YES |
| 6: 180-190 | D184A | eliminated | YES | YES |
| 6: 180-190 | D184F | eliminated | YES | YES |
| 6: 180-190 | R188A | eliminated | YES | YES |
| 6: 180-190 | D183A/D184A/R188A | eliminated | YES | YES |
| immunogenic residue | R205A | eliminated | YES | YES |
| 3/3*, 4/4* | E60I/G110A | eliminated | YES | YES |
| 3/3*, 5 | E60I/G147A | eliminated | YES | YES |
| 2, 6/6* | S45I/R188A | eliminated | YES | YES |
| 1, 4/4*, 5 | S33VG110A/G147A | eliminated | YES | YES |
| 2, 4/4*, 5 | S45I/G110A/G147A | eliminated | YES | YES |
| 3/3*, 4/4*, 5 | D58A/G110A/G147A | eliminated | YES | YES |
| 3/3*, 4/4*, 5 | E60I/G110A/G147A | eliminated | YES | YES |
| 2, 3/3*, 4/4*, 5 | S45I/D58A/E60V G110A/G147A | eliminated | YES | YES |
| 2, 3/3*, 4/4*, 5 | S45I/D58A/E60V G62A/G110A/G147A | eliminated | YES | YES |
| 2, 4/4*, 5, 6/6* | S45I/G110A/G147A/D183A/D184A/R188A | eliminated | YES | YES |
| 3/3*, 4/4*, 5, 6 | D58A/G110A/G147A/S186A | eliminated | YES | YES |
| 3/3*, 4/4*, 5, 6/6* | D58A/G110A/G147A/G187A | eliminated | YES | YES |
| 3/3*, 4/4*, 5, 6/6* | D58A/G110A/G147A/R188A | eliminated | YES | YES |
| 3/3*, 4/4*, 5, 6/6* | D58A/G110A/G147A/S189A | eliminated | YES | YES |
| 3/3*, 4/4*, 5, 6/6* | D58A/G110A/G147A/S186A/R188A | eliminated | YES | YES |
| 3/3*, 4/4*, 5, 6/6* | D58A/G110A/G147A/G187A/R188A | eliminated | YES | YES |
| 1, 2, 3/3*, 4/4*, 5 | S33I/S45I/D58A/G110A/G147A | eliminated | YES | YES |
| 2, 3/3*, 4/4*, 5, 6/6* | S45I/D58A/E60I/G110A/G147A/D183A/D184A/R188A | eliminated | YES | YES |
| 2, 3/3*, 4/4*, 5, 6/6* | S45I/D58A/E60I/G62A/G110A/G147A/D183A/D184A/R188A | eliminated | YES | YES |

Despite the challenges predicting successful substitutions a priori, the data provided in the Examples herein give reasons to believe that certain amino acid substitutions are likely to successfully reduce antigenicity and/or immunogenicity while maintaining significant Shiga toxin effector function(s). For example, substitutions at specific amino acid positions shown herein as successfully tolerating substitutions (Table 11) are most likely to be successful for retaining at least one Shiga toxin effector function when substituted with certain other amino acids. The demonstration that cytotoxic proteins comprising Shiga toxin effector regions retained cytotoxicity when multiple single amino acid substitutions (predicted to disrupt an epitope region and that retained cytotoxicity) were combined (Table 9; Table 11) suggests that successful single amino acid substitution may generally be combined with other successful amino acid substitutions in a different epitope region to generate de-immunized Shiga toxin effector polypeptides which retain significant Shiga toxin effector function(s). Similarly, the demonstration that cytotoxic proteins comprising Shiga toxin effector regions with multiple single amino acid substitutions within the same epitope region retained enzymatic activity (Table 9; Table 11) suggests that successful single amino acid substitution in the same epitope region may generally be combined with other single amino acid substitutions in the same epitope region to generate de-immunized Shiga toxin effector polypeptides which retain significant Shiga toxin effector function(s). The fact that cytotoxic proteins comprising Shiga toxin effector region polypeptides with multiple single amino acid substitutions within the same epitope region retained cytotoxicity (Table 9; Table 11) suggests that successful single amino acid substitution in an epitope region may be combined with other single amino acid substitutions in the same epitope region to generate de-immunized Shiga toxin effector polypeptides which retain significant Shiga toxin effector function(s).

The empirical data demonstrated that certain substitutions (K1M, S8I, T9I, K11A, S33I, S45I, D53A, R55A, D58A, D58F, P59A, E60I, E60R, E61A, G62A, D94A, S96I, G110A, G147A, D183A, D184A, D184F, R188A, R205A, and/or combinations thereof) and certain positions tolerated substitutions (1, 4, 8, 9, 11, 33, 45, 48, 53, 55, 57, 58, 59, 60, 61, 62, 94, 96, 109, 110, 147, 180, 181, 183, 184, 185, 186, 187, 188, 189, 205, 248, and 251) while retaining a significant level of activity for at least one Shiga toxin effector function. These empirical data suggest certain other epitope disrupting substitutions and combinations of epitope disrupting substitutions which may be used to generate de-immunized Shiga toxin effector polypeptides which retain significant Shiga toxin effector function(s). It is predictable that other amino acid substitutions to amino acid residues of a conservative functional group will also be tolerated. For example, other substitutions known to the skilled worker to be similar to any of K1M, T4I, S8I, T9V, T9I, K11A, S33I, S45V, S45I, D47G, N48V, N48F, L49A, D53A, D53G, D53N, R55A, R55L, I57F, D58A, D58F, P59A, P59F, E60I, E60T, E60R, E61A, E61V, E61L, G62A, D94A, S96I, S109V, G110A, S112V, G147A, T180G, T181I, D183A, D183G, D184A, D184F, L185V, S186A, S186F, G187A, R188A, R188L, S189A, R205A, R248A, or R251A will also be able to disrupt an epitope while maintaining at least one Shiga toxin effector function. In particular, amino acid substitutions to conservative amino acid residues similar to KM, T4I, S8I, T9V, T9I, K11A, S33I, S45V, S45I, D47G, N48V, N48F, L49A, D53A, D53G, D53N, R55A, R55L, I57F, D58A, D58F, P59A, P59F, E60I, E60T, E60R, E61A, E61V, E61L, G62A, D94A, S96I, S109V, G110A, S112V, G147A, T180G, T181I, D183A, D183G, D184A, D184F, L185V, S186A, S186F, G187A, R188A, R188L, S189A, R205A, R248A, or R251A will have the same effect. Examples of similar conservative amino acid substitutions include K1 to A, G, V, L, I, F, and H; T4I to A, G, V, L, F, M, and S; S8 to A, G, V, L, F, and M; T9 to A, G, L, F, M, and S; K11 to G, V, L, I, F, and M; S33 to A, G, V, L, F, and M; S45 to A, G, L, F, and M; T45 to A, G, V, L, I, F, and M; D47 to A, V, L, I, F, S, and Q; N48 to A, G, L, I, and M; L49 to G; D53 to V, L, I, F, S, and Q; R55 to G, I, F, M, Q, S, K, and H; D58 to G, V, L, I, S, and Q; P59 to G; E60 to A, G, V, F, S, Q, N, D, and M; E61 to G, I, F, S, Q, N, D, M, and R; D94 to G, V, L, I, F, S, and Q; S96 to A, G, V, L, F, and M; S109 to A, G, I, L, F, and M; T109 to A, G, V, I, L, F, and M; S112 to A, G, L, I, F and M; T180 to A, V, L, I, F, M, and S; T181 to A, G, V, L, F, M, and S; D183 to V, L, I, F, S, and Q; D184 to G, V, L, I, S, and Q; L185 to A and G; S186 to G, V, I, L, F, and M; R188 to G, V, L, I, F, M, Q, S, K, and H; S189 to G, V, I, L, F, and M; R204 to A, G, V, L, I, F, M, Q, S, K, and H; R205 to A, G, V, L, I, F, M, Q, S, K, and H; S247 to A, G, V, I, L, F, and M; Y247 to A, G, V, L, I, and F, R248 to G, V, L, and I; R250 to A, G, V, L, I, and F; and R251 to G, V, L, and I.

Amino acid substitutions which remove charge, polarity, and/or reduce side chain length will also be able to disrupt an epitope while maintaining at least one Shiga toxin effector function. For example, substituting A, G, V, L, I, P, C, M, F, S, D, N, Q, H, and K for amino acid residue K1, T4, S8, T9, K11, S33, S45, D47, N48, L49, D53, R55, 157, D58, P59, E60, E61, G62, D94, S96, S109, T109, G110, S112, G147, T180, T181, D183, D184, L185, S186, G187, R188, S189, R205, R248, or R251 such that side chain charge is removed, polarity is removed, and/or side chain length is reduced. In particular, the following amino acid substitutions will be able to disrupt an epitope while maintaining at least one Shiga toxin effector function: D47, D53, D58, D94, D183, D184, D264 to A, G, V, L, I, S, and N; E60 or E61 to A, G, L, V, I, S, N, Q, D, and M; G62, G110, G147, G187, or G265 to A; K1 or K11 to A, G, L, V, I, F, C, M, P, S, T, N, H, and Q; L49 or L185 to A and G; N48 to A, G, V, L, and I; R55, R188, R205, R247, R248, R250, or R251 to A, G, L, V, I, S, Q, K, M, F, and H; S33, S45, S96, S109, S112, S186, or S189 to A, G, V, and L, and T4, T9, T45, T109, T180, T181, T286 to A, G, V, L, I, M and F.

In addition, amino acid substitution in one epitope region of a Shiga toxin effector polypeptide which disrupts an epitope while retaining significant Shiga toxin effector function is generally predicted to be combinable with other amino acid substitutions in the same or a different epitope region which disrupts an epitope while retaining significant Shiga toxin effector function to form a de-immunized Shiga toxin effector polypeptide with multiple epitope regions disrupted while still retaining a significant level of a Shiga toxin effector function. For example, KM, S8I, T9I, S9I, K11A, 5331, 5451, D53A, R55A, D58A, D58F, P59A, E60I, E60R, E61A, G62A, D94A, 5961, G110A, G147A, D183A, D184A, D184F, S186A, G187A, R188A, S189A, and/or R205A may be combined where possible with KM, S8I, T9I, S9I, K11A, S33I, S45I, D53A, R55A, D58A, D58F, P59A, E60I, E60R, E61A, G62A, D94A, 5961, G110A, G147A, D183A, D184A, D184F, S186A, G187A, R188A, S189A, and/or R205A to create de-immunized Shiga toxin effector region polypeptides of the invention.

Example 7. A Cytotoxic Protein Comprising a De-Immunized Shiga Toxin Effector Polypeptide and a Binding Region Specific to CD20 (αCD20 Fused with SLT-1A)

In this example, the Shiga toxin effector region is a de-immunized Shiga toxin effector polypeptide derived from the A subunit of Shiga-like Toxin 1 (SLT-1A) and comprising one or more de-immunizing amino acid substitutions described in the previous examples. An immunoglobulin-type binding region αCD20-antigen is derived from an immunoglobulin-type domain recognizing human CD20 (see e.g. Haisma et al., *Blood* 92: 184-90 (1999);

Geng S et al., *Cell Mol Immunol* 3: 439-43 (2006); Olafesn T et al., *Protein Eng Des Sel* 23: 243-9 (2010)), which comprises an immunoglobulin-type binding region capable of binding an extracellular part of CD20. CD20 is expressed on multiple cancer cell types, such as, e.g., B-cell lymphoma cells, hairy cell leukemia cells, B-cell chronic lymphocytic leukemia cells, and melanoma cells. In addition, CD20 is an attractive target for therapeutics to treat certain autoimmune diseases, disorders, and conditions involving overactive B-cells.

Construction, Production, and Purification of the Cytotoxic Protein SLT-1A::αCD20

The immunoglobulin-type binding region αCD20 and Shiga toxin effector region (such as, e.g., SEQ ID NOs:4-52) are linked together. For example, a fusion protein is produced by expressing a polynucleotide encoding the αCD20-antigen-binding protein SLT-1A::αCD20 (see, e.g., SEQ ID NOs: 53, 54, 55, and 56). Expression of the SLT-1A::αCD20 cytotoxic protein is accomplished using either bacterial and/or cell-free, protein translation systems as described in the previous examples or known to the skilled worker.

Determining the In Vitro Characteristics of the Cytotoxic Protein SLT-1A::αCD20

The binding characteristics, the maximum specific binding ($B_{max}$) and equilibrium binding constants ($K_D$), of the cytotoxic protein of this example for CD20+ cells and CD20− cells is determined by a fluorescence-based, flow-cytometry assay. The $B_{max}$ for SLT-1A::αCD20 to CD20+ cells is measured to be approximately 50,000-200,000 MFI with a $K_D$ within the range of 0.01-100 nM, whereas there is no significant binding to CD20− cells in this assay.

The ribosome inactivation abilities of the SLT-1A::αCD20 cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αCD20 on protein synthesis in this cell-free assay is approximately 0.1-100 pM.

Determining the Cytotoxicity of the Cytotoxic Protein SLT-1A::αCD20 Using a CD20+ Cell-Kill Assay The cytotoxicity characteristics of SLT-1A::αCD20 are determined by the general cell-kill assay as described above in the previous examples using CD20+ cells. In addition, the selective cytotoxicity characteristics of SLT-1A::αCD20 are determined by the same general cell-kill assay using CD20− cells as a comparison to the CD20+ cells. The $CD_{50}$ of the cytotoxic protein of this example is approximately 0.01-100 nM for CD20+ cells depending on the cell line. The $CD_{50}$ of the cytotoxic protein is approximately 10-10,000 fold greater (less cytotoxic) for cells not expressing CD20 on a cellular surface as compared to cells which do express CD20 on a cellular surface.

Determining Reductions in Antigenicity and/or Immunogenicity

The relative de-immunization of SLT-1A::αCD20 is determined in relation to a wild-type Shiga toxin effector region polypeptide using western analyses, ELISA analyses, and murine models as described in Examples 4 and 6.

Determining the In Vivo Effects of the Cytotoxic Protein SLT-1A::αCD20 Using Animal Models Animal models are used to determine the in vivo effects of the cytotoxic protein SLT-1A::αCD20 on neoplastic cells. Various mice strains are used to test the effect of the cytotoxic protein after intravenous administration on xenograft tumors in mice resulting from the injection into those mice of human neoplastic cells which express CD20 on their cell surfaces.

Example 8. A Cytotoxic Protein Comprising a De-Immunized Shiga Toxin Effector Polypeptide and a Binding Region Specific to HER2 ("αHER2-$V_H$H Fused with SLT-1A")

In this example, the Shiga toxin effector region was derived from the A subunit of Shiga-like Toxin 1 (SLT-1A) and comprising one or more de-immunizing amino acid substitutions described in the previous examples. The immunoglobulin-type binding region is αHER2 VHH derived from a single-domain variable region of the camelid antibody (VHH) protein 5F7, as described in U.S. Patent Application Publication 2011/0059090.

Construction, Production, and Purification of the Cytotoxic Protein "αHER2-$V_H$H Fused with SLT-1A"

The immunoglobulin-type binding region and Shiga toxin effector region are linked together to form a fused protein (see, e.g., SEQ ID NOs: 57, 58, and 59). In this example, a polynucleotide encoding the αHER2-$V_H$H variable region derived from protein 5F7 may be cloned in frame with a polynucleotide encoding a linker known in the art and in frame with a polynucleotide encoding the Shiga toxin effector region comprising amino acids of SEQ ID NOs:4-52. Variants of "αHER2-$V_H$H fused with SLT-1A" cytotoxic proteins are created such that the binding region is optionally located adjacent to the amino-terminus of the Shiga toxin effector region and optionally comprises a carboxy-terminal endoplasmic reticulum signal motif of the KDEL family. Expression of the "αHER2-$V_H$H fused with SLT-1A" cytotoxic protein variants is accomplished using either bacterial and/or cell-free, protein translation systems as described in the previous examples.

Determining the In Vitro Characteristics of the Cytotoxic Protein "αHER2-$V_H$H Fused with SLT-1A"

The binding characteristics of the cytotoxic protein of this example for HER2+ cells and HER2− cells is determined by a fluorescence-based, flow-cytometry assay. The $B_{max}$ for "αHER2-$V_H$H fused with SLT-1A" variants to HER2+ cells is measured to be approximately 50,000-200,000 MFI with a $K_D$ within the range of 0.01-100 nM, whereas there is no significant binding to HER2− cells in this assay.

The ribosome inactivation abilities of the "αHER2-$V_H$H fused with SLT-1A" cytotoxic proteins are determined in a cell-free, in vitro protein translation as described above in the previous examples. The inhibitory effect of the cytotoxic protein of this example on cell-free protein synthesis is significant. The $IC_{50}$ of "αHER2-$V_H$H fused with SLT-1A" variants on protein synthesis in this cell-free assay is approximately 0.1-100 pM.

Determining the Cytotoxicity of the Cytotoxic Protein "αHER2-$V_H$H Fused with SLT-1A" Using a HER2+ Cell-Kill Assay The cytotoxicity characteristics of "αHER2-$V_H$H fused with SLT-1A" variants are determined by the general cell-kill assay as described above in the previous examples using HER2+ cells. In addition, the selective cytotoxicity characteristics of "αHER2-$V_H$H fused with SLT-1A" are determined by the same general cell-kill assay using HER2− cells as a comparison to the HER2+ cells. The $CD_{50}$ of the cytotoxic protein of this example is approximately 0.01-100 nM for HER2+ cells depending on the cell line. The $CD_{50}$ of the cytotoxic protein is approximately 10-10,000 fold greater (less cytotoxic) for cells not expressing HER2 on a cellular surface as compared to cells which do express HER2 on a cellular surface.

Determining Reductions in Antigenicity and/or Immunogenicity

The relative de-immunization of αHER2-$V_H$H fused with SLT-1A is determined in relation to a wild-type Shiga toxin effector region polypeptide using western analyses, ELISA analyses, and murine models as described in Examples 4 and 6.

Determining the In Vivo Effects of the Cytotoxic Protein αHER2-$V_H$H Fused with SLT-1A Using Animal Models Animal models are used to determine the in vivo effects of the cytotoxic protein αHER2-$V_H$H fused with SLT-1A on neoplastic cells. Various mice strains are used to test the effect of the cytotoxic protein after intravenous administration on xenograft tumors in mice resulting from the injection into those mice of human neoplastic cells which express HER2 on their cell surfaces.

Example 9. A Cytotoxic Protein Comprising a De-Immunized Shiga Toxin Effector Polypeptide and a Binding Region Derived from the Antibody αEpstein-Barr-Antigen In this example, the Shiga toxin effector region is a de-immunized Shiga toxin effector polypeptide derived from the A subunit of Shiga-like Toxin 1 (SLT-1A) and comprising one or more de-immunizing amino acid substitutions described in the previous examples. An immunoglobulin-type binding region αEpstein-Barr-antigen is derived from a monoclonal antibody against an Epstein Barr antigen (Fang C et al., *J Immunol Methods* 287: 21-30 (2004)), which comprises an immunoglobulin-type binding region capable of binding a human cell infected by the Epstein-Barr virus or a transformed cell expressing an Epstein-Barr antigen. The Epstein-Barr antigen is expressed on multiple cell types, such as cells infected by an Epstein-Barr virus and cancer cells (e.g. lymphoma and nasopharyngeal cancer cells). In addition, Epstein-Barr infection is associated with other diseases, e.g., multiple sclerosis.

Construction, Production, and Purification of the Cytotoxic Protein SLT-1A::αEpstein-Barr:KDEL The immunoglobulin-type binding region αEpstein-Barr-antigen and Shiga toxin effector region are linked together, and a carboxy-terminal KDEL (SEQ ID NO: 60) is added to form a protein. For example, a fusion protein is produced by expressing a polynucleotide encoding the αEpstein-Barr-antigen-binding protein SLT-1A::αEpsteinBarr::KDEL. Expression of the SLT-1A::αEpsteinBarr::KDEL cytotoxic protein is accomplished using either bacterial and/or cell-free, protein translation systems as described in the previous examples.

Determining the In Vitro Characteristics of the Cytotoxic Protein SLT-1A::αEpsteinBarr::KDEL The binding characteristics of the cytotoxic protein of this example for Epstein-Barr antigen positive cells and Epstein-Barr antigen negative cells is determined by a fluorescence-based, flow-cytometry assay. The $B_{max}$ for SLT-1A::αEpsteinBarr::KDEL to Epstein-Barr antigen positive cells is measured to be approximately 50,000-200,000 MFI with a $K_D$ within the range of 0.01-100 nM, whereas there is no significant binding to Epstein-Barr antigen negative cells in this assay.

The ribosome inactivation abilities of the SLT-1A::αEpsteinBarr:KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αEpsteinBarr::KDEL on protein synthesis in this cell-free assay is approximately 0.1-100 pM.

Determining the Cytotoxicity of the Cytotoxic Protein SLT-1A::αEpsteinBarr::KDEL Using a Cell-Kill Assay The cytotoxicity characteristics of SLT-1A::αEpsteinBarr:KDEL are determined by the general cell-kill assay as described above in the previous examples using Epstein-Barr antigen positive cells. In addition, the selective cytotoxicity characteristics of SLT-1A::αEpsteinBarr:KDEL are determined by the same general cell-kill assay using Epstein-Barr antigen negative cells as a comparison to the Epstein-Barr antigen positive cells. The $CD_{50}$ of the cytotoxic protein of this example is approximately 0.01-100 nM for Epstein-Barr antigen positive cells depending on the cell line. The $CD_{50}$ of the cytotoxic protein is approximately 10-10,000 fold greater (less cytotoxic) for cells not expressing the Epstein-Barr antigen on a cellular surface as compared to cells which do express the Epstein-Barr antigen on a cellular surface.

Determining Reductions in Antigenicity and/or Immunogenicity

The relative de-immunization of SLT-1A::αEpsteinBarr::KDEL is determined in relation to a wild-type Shiga toxin effector region polypeptide using western analyses, ELISA analyses, and murine models as described in Examples 4 and 6.

Determining the In Vivo Effects of the Cytotoxic Protein SLT-1A::αEpsteinBarr::KDEL Using Animal Models Animal models are used to determine the in vivo effects of the cytotoxic protein SLT-1A::αEpsteinBarr::KDEL on neoplastic cells. Various mice strains are used to test the effect of the cytotoxic protein after intravenous administration on xenograft tumors in mice resulting from the injection into those mice of human neoplastic cells which express Epstein-Barr antigens on their cell surfaces.

Example 10. A Cytotoxic Protein Comprising a De-Immunized Shiga Toxin Effector Polypeptide and a Binding Region Derived from the Antibody αLeishmania-Antigen In this example, the Shiga toxin effector region is a de-immunized Shiga toxin effector polypeptide derived from the A subunit of Shiga-like Toxin 1 (SLT-1A) and comprising one or more de-immunizing amino acid substitutions described in the previous examples. An immunoglobulin-type binding region αLeishmania-antigen is derived from an antibody generated, using techniques known in the art, to a cell-surface Leishmania antigen present on human cells harboring an intracellular trypanosomatid protozoa (see Silveira T et al., *Int J Parasitol* 31: 1451-8 (2001); Kenner J et al., *J Cutan Pathol* 26: 130-6 (1999); Berman J and Dwyer, *Clin Exp Immunol* 44: 342-348 (1981)).

Construction, Production, and Purification of the Cytotoxic Protein SLT-1A::αLeishmania::KDEL The immunoglobulin-type binding region α-Leishmania-antigen and Shiga toxin effector region are linked together, and a carboxy-terminal KDEL (SEQ ID NO: 60) is added to form a protein. For example, a fusion protein is produced by expressing a polynucleotide encoding the Leishmania-antigen-binding protein SLT-1A::αLeishmania::KDEL. Expression of the SLT-1A::αLeishmania::KDEL cytotoxic protein is accomplished using either bacterial and/or cell-free, protein translation systems as described in the previous examples.

Determining the In Vitro Characteristics of the Cytotoxic Protein SLT-1A::αLeishmania::KDEL The binding characteristics of the cytotoxic protein of this example for Leishmania antigen positive cells and Leishmania antigen negative cells is determined by a fluorescence-based, flow-cytometry. The $B_{max}$ for SLT-1A::αLeishmania::KDEL to Leishmania antigen positive cells is measured to be approximately 50,000-200,000 MFI with a $K_D$ within the range of 0.01-100 nM, whereas there is no significant binding to Leishmania antigen negative cells in this assay.

The ribosome inactivation abilities of the SLT-1A::αLeishmania::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αLeishmania::KDEL on protein synthesis in this cell-free assay is approximately 0.1-100 pM.

Determining the Cytotoxicity of the Cytotoxic Protein SLT-1A::αLeishmania::KDEL Using a Cell-Kill Assay The cytotoxicity characteristics of SLT-1A::αLeishmania::KDEL are determined by the general cell-kill assay as described above in the previous examples using Leishmania antigen positive cells. In addition, the selective cytotoxicity characteristics of SLT-1A::αLeishmania::KDEL are determined by the same general cell-kill assay using Leishmania antigen negative cells as a comparison to the Leishmania antigen positive cells. The $CD_{50}$ of the cytotoxic protein of this example is approximately 0.01-100 nM for Leishmania antigen positive cells depending on the cell line. The $CD_{50}$ of the cytotoxic protein is approximately 10-10,000 fold greater (less cytotoxic) for cells not expressing the Leishmania antigen on a cellular surface as compared to cells which do express the Leishmania antigen on a cellular surface.

Determining Reductions in Antigenicity and/or Immunogenicity

The relative de-immunization of SLT-1A::αLeishmania::KDEL is determined in relation to a wild-type Shiga toxin effector region polypeptide using western analyses, ELISA analyses, and murine models as described in Examples 4 and 6.

Example 11. A Cytotoxic Protein Comprising a De-Immunized Shiga Toxin Effector Polypeptide and a Binding Region Derived from an Immunoglobulin-Type Binding Region αNeurotensin-Receptor In this example, the Shiga toxin effector region is a de-immunized Shiga toxin effector polypeptide derived from the A subunit of Shiga-like Toxin 1 (SLT-1A) and comprising one or more de-immunizing amino acid substitutions described in the previous examples. An immunoglobulin-type binding region αNeurotensin-Receptor is derived from the DARPin™ (GenBank Accession: 2P2C_R) or a monoclonal antibody (Ovigne J et al., *Neuropeptides* 32: 247-56 (1998)) which binds the human neurotensin receptor. The neurotensin receptor is expressed by various cancer cells, such as breast cancer, colon cancer, lung cancer, melanoma, and pancreatic cancer cells.

Construction, Production, and Purification of the Cytotoxic Protein SLT-1A::αNeurotensinR::KDEL The immunoglobulin-type binding region αNeurotensinR and Shiga toxin effector region are linked together, and a carboxy-terminal KDEL (SEQ ID NO: 60) is added to form a protein. For example, a fusion protein is produced by expressing a polynucleotide encoding the neurotensin-receptor-binding protein SLT-1A::αNeurotensinR::KDEL. Expression of the SLT-1A::αNeurotensinR::KDEL cytotoxic protein is accomplished using either bacterial and/or cell-free, protein translation systems as described in the previous examples.

Determining the In Vitro Characteristics of the Cytotoxic Protein SLT-1A::αNeurotensinR::KDEL The binding characteristics of the cytotoxic protein of this example for neurotensin receptor positive cells and neurotensin receptor negative cells is determined by a fluorescence-based, flow-cytometry. The $B_{max}$ for SLT-1A::αNeurotensinR::KDEL to neurotensin receptor positive cells is measured to be approximately 50,000-200,000 MFI with a $K_D$ within the range of 0.01-100 nM, whereas there is no significant binding to neurotensin receptor negative cells in this assay.

The ribosome inactivation abilities of the SLT-1A::αNeurotensinR::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αNeurotensinR::KDEL on protein synthesis in this cell-free assay is approximately 0.1-100 pM.

Determining the Cytotoxicity of the Cytotoxic Protein SLT-1A::αNeurotensinR::KDEL Using a Cell-Kill Assay The cytotoxicity characteristics of SLT-1A::αNeurotensinR::KDEL are determined by the general cell-kill assay as described above in the previous examples using neurotensin receptor positive cells. In addition, the selective cytotoxicity characteristics of SLT-1A::αNeurotensinR::KDEL are determined by the same general cell-kill assay using neurotensin receptor negative cells as a comparison to the neurotensin receptor positive cells. The $CD_{50}$ of the cytotoxic protein of this example is approximately 0.01-100 nM for neurotensin receptor positive cells depending on the cell line. The $CD_{50}$ of the cytotoxic protein is approximately 10-10,000 fold greater (less cytotoxic) for cells not expressing neurotensin receptor on a cellular surface as compared to cells which do express neurotensin receptor on a cellular surface.

Determining Reductions in Antigenicity and/or Immunogenicity

The relative de-immunization of SLT-1A::αNeurotensinR::KDEL is determined in relation to a wild-type Shiga toxin effector region polypeptide using western analyses, ELISA analyses, and murine models as described in Examples 4 and 6.

Determining the In Vivo Effects of the Cytotoxic Protein SLT-1A::αNeurotensinR::KDEL Using Animal Models Animal models are used to determine the in vivo effects of the cytotoxic protein SLT-1A::αNeurotensinR::KDEL on neoplastic cells. Various mice strains are used to test the effect of the cytotoxic protein after intravenous administration on xenograft tumors in mice resulting from the injection into those mice of human neoplastic cells which express neurotensin receptors on their cell surfaces.

Example 12. A Cytotoxic Protein Comprising a De-Immunized Shiga Toxin Effector Polypeptide and a Binding Region Derived from an Immunoglobulin-Type Binding Region αEGFR In this example, the Shiga toxin effector region is a de-immunized Shiga toxin effector polypeptide derived from the A subunit of Shiga-like Toxin 1 (SLT-1A) and comprising one or more de-immunizing amino acid substitutions described in the previous examples. The binding region αEGFR is derived from the AdNectin™ (GenBank Accession: 3QWQ_B), the Affibody™ (GenBank Accession: 2KZI_A; U.S. Pat. No. 8,598,113), or an antibody, all of which bind one or more human epidermal growth factor receptors. The expression of epidermal growth factor receptors are associated with human cancer cells, such as, e.g., lung cancer cells, breast cancer cells, and colon cancer cells.

Construction, Production, and Purification of the Cytotoxic Protein SLT-1A::αEGFR::KDEL The immunoglobulin-type binding region αEGFR and Shiga toxin effector region are linked together, and a carboxy-terminal KDEL (SEQ ID NO: 60) is added to form a protein. For example, a fusion protein is produced by expressing a polynucleotide encoding the EGFR binding protein SLT-1A::αEGFR::KDEL. Expression of the SLT-1A::αEGFR::KDEL cytotoxic protein is accomplished using either bacterial and/or cell-free, protein translation systems as described in the previous examples.

Determining the In Vitro Characteristics of the Cytotoxic Protein SLT-1A::αEGFR::KDEL The binding characteristics of the cytotoxic protein of this example for EGFR+ cells and EGFR− cells is determined by a fluorescence-based, flow-cytometry. The $B_{max}$ for SLT-1A::αEGFR::KDEL to EGFR+ cells is measured to be approximately 50,000-200,000 MFI with a $K_D$ within the range of 0.01-100 nM, whereas there is no significant binding to EGFR− cells in this assay.

The ribosome inactivation abilities of the SLT-1A::αEGFR::KDEL cytotoxic protein is determined in a cell-free, in vitro protein translation as described above in the previous examples. The inhibitory effect of the cytotoxic protein of this example on cell-free protein synthesis is significant. The IC50 of SLT-1A::αEGFR::KDEL on protein synthesis in this cell-free assay is approximately 0.1-100 pM.

Determining the Cytotoxicity of the Cytotoxic Protein SLT-1A::αEGFR::KDEL Using a Cell-Kill Assay The cytotoxicity characteristics of SLT-1A::αEGFR::KDEL are determined by the general cell-kill assay as described above in the previous examples using EGFR+ cells. In addition, the selective cytotoxicity characteristics of SLT-1A::αEGFR::KDEL are determined by the same general cell-kill assay using EGFR− cells as a comparison to the Leishmania antigen positive cells. The $CD_{50}$ of the cytotoxic protein of this example is approximately 0.01-100 nM for EGFR+ cells depending on the cell line. The $CD_{50}$ of the cytotoxic protein is approximately 10-10,000 fold greater (less cytotoxic) for cells not expressing EGFR on a cellular surface as compared to cells which do express EGFR on a cellular surface.

Determining Reductions in Antigenicity and/or Immunogenicity

The relative de-immunization of SLT-1A::αEGFR::KDEL is determined in relation to a wild-type Shiga toxin effector region polypeptide using western analyses, ELISA analyses, and murine models as described in Examples 4 and 6.

Determining the In Vivo Effects of the Cytotoxic Protein SLT-1A::αEGFR::KDEL Using Animal Models Animal models are used to determine the in vivo effects of the cytotoxic protein SLT-1A::αEGFR::KDEL on neoplastic cells. Various mice strains are used to test the effect of the cytotoxic protein after intravenous administration on xenograft tumors in mice resulting from the injection into those mice of human neoplastic cells which express EGFR(s) on their cell surfaces.

Example 13. A Cytotoxic Protein Comprising a De-Immunized Shiga Toxin Effector Polypeptide and a Binding Region Derived from the Antibody αCCR5

In this example, the Shiga toxin effector region is a de-immunized Shiga toxin effector polypeptide derived from the A subunit of Shiga-like Toxin 1 (SLT-1A) and comprising one or more de-immunizing amino acid substitutions described in the previous examples. An immunoglobulin-type binding region αCCR5 is derived from a monoclonal antibody against human CCR5 (CD195) (Bernstone L et al., *Hybridoma* 31: 7-19 (2012)). CCR5 is predominantly expressed on T-cells, macrophages, dendritic cells, and microglia. In addition, CCR5 plays a role in the pathogenesis and spread of the Human Immunodeficiency Virus (HIV).

Construction, Production, and Purification of the Cytotoxic Protein SLT-1A::αCCR5::KDEL The immunoglobulin-type binding region αCCR5 and Shiga toxin effector region are linked together, and a carboxy-terminal KDEL (SEQ ID NO: 60) is added to form a protein. For example, a fusion protein is produced by expressing a polynucleotide encoding the αCCR5-binding protein SLT-1A::αCCR5::KDEL. Expression of the SLT-1A::αCCR5::KDEL cytotoxic protein is accomplished using either bacterial and/or cell-free, protein translation systems as described in the previous examples.

Determining the In Vitro Characteristics of the Cytotoxic Protein SLT-1A::αCCR5

The binding characteristics of the cytotoxic protein of this example for CCR5+ cells and CCR5− cells is determined by a fluorescence-based, flow-cytometry. The $B_{max}$ for SLT-1A::αCCR5::KDEL to CCR5+ positive cells is measured to be approximately 50,000-200,000 MFI with a $K_D$ within the range of 0.01-100 nM, whereas there is no significant binding to CCR5− cells in this assay.

The ribosome inactivation abilities of the SLT-1A::αCCR5::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αCCR5::KDEL on protein synthesis in this cell-free assay is approximately 0.1-100 pM.

Determining the Cytotoxicity of the Cytotoxic Protein SLT-1A::αCCR5::KDEL Using a Cell-Kill Assay The cytotoxicity characteristics of SLT-1A::αCCR5::KDEL are determined by the general cell-kill assay as described above in the previous examples using CCR5+ cells. In addition, the selective cytotoxicity characteristics of SLT-1A::αCCR5::KDEL are determined by the same general cell-kill assay using CCR5− cells as a comparison to the CCR5+ cells. The $CD_{50}$ of the cytotoxic protein of this example is approximately 0.01-100 nM for CCR5+ cells depending on the cell line. The $CD_{50}$ of the cytotoxic protein is approximately 10-10,000 fold greater (less cytotoxic) for cells not expressing CCR5 on a cellular surface as compared to cells which do express CCR5 on a cellular surface.

Determining Reductions in Antigenicity and/or Immunogenicity

The relative de-immunization of SLT-1A::αCCR5::KDEL is determined in relation to a wild-type Shiga toxin effector region polypeptide using western analyses, ELISA analyses, and murine models as described in Examples 4 and 6.

Determining the In Vivo Effects of the Cytotoxic Protein SLT-1A::αCCR5::KDEL using Animal Models Animal models are used to determine the in vivo effects of the cytotoxic protein SLT-1A::αCCR5::KDEL on depleting T-cells from donor materials (see Tsirigotis P et al., *Immunotherapy* 4: 407-24 (2012)). Non-human primates are used to determine in vivo effects of SLT-1A::αCCR5. Graft versus host disease is analyzed in rhesus macaques after kidney transplantation when the donated organs are pretreated with SLT-1A::αCCR5::KDEL (see Weaver T et al., *Nat Med* 15: 746-9 (2009)). In vivo depletion of peripheral blood T lymphocytes in cynomolgus primates is observed after parenteral administration of different doses of SLT-1A::αCCR5::KDEL. The use of SLT-1A::αCCR5::KDEL to block HIV infection is tested by giving an acute dose of SLT-1A::αCCR5::KDEL to non-human primates in order to severely deplete circulating T-cells upon exposure to a simian immunodeficiency virus (SIV) (see Sellier P et al., *PLoS One* 5: e10570 (2010)).

Example 14. A Cytotoxic Protein Comprising a De-Immunized Shiga Toxin Effector Polypeptide and a Binding Region Derived from an Anti-Env Immunoglobulin Domain In this example, the Shiga toxin effector region is a de-immunized Shiga toxin effector polypeptide derived from the A subunit of Shiga toxin (StxA) and comprising one or more de-immunizing amino acid substitutions described in the previous examples. An immunoglobulin-type binding region αEnv is derived from existing antibodies that bind HIV envelope glycoprotein (Env), such as GP41, GP120, GP140, or GP160 (see e.g. Chen W et al., *J Mol Bio* 382: 779-89 (2008); Chen W et al., *Expert Opin Biol Ther* 13: 657-71 (2013); van den Kerkhof T et al., *Retrovirology* 10: 102 (2013)) or from antibodies generated using standard techniques (see Prabakaran et al., *Front Microbiol* 3: 277 (2012)). Envs are HIV surface proteins that are also displayed on the cell surfaces of HIV-infected cells during HIV replication. Although Envs are expressed in infected cells predominantly in endosomal compartments, sufficient amounts of Envs could be present on a cell surface to be targeted by a highly potent cytotoxic protein of the invention. In addition, Env-targeting cytotoxic proteins might bind HIV virions and enter newly infected cells during the fusion of virions with a host cell.

Because HIV displays a high rate of mutation, it is preferable to use an immunoglobulin domain that binds a functional constrained part of an Env, such as shown by broadly neutralizing antibodies that bind Envs from multiple strains of HIV (van den Kerkhof T et al., *Retrovirology* 10: 102 (2013)). Because the Envs present on an infected cell's surface are believed to present sterically restricted epitopes (Chen W et al., *J Virol* 88: 1125-39 (2014)), it is preferable to use smaller than 100 kD and ideally smaller than 25 kD, such as sdAbs or $V_HH$ domains.

Construction, Production, and Purification of the Cytotoxic Protein SLT-1A::αEnv::KDEL The immunoglobulin-type binding region αEnv and Shiga toxin effector region are linked together, and a carboxy-terminal KDEL is added to form a cytotoxic protein. For example, a fusion protein is produced by expressing a polynucleotide encoding the αEnv-binding protein SLT-1A::αEnv::KDEL. Expression of the SLT-1A::αEnv::KDEL cytotoxic protein is accomplished using either bacterial and/or cell-free, protein translation systems as described in the previous examples.

Determining the In Vitro Characteristics of the Cytotoxic Protein SLT-1A::αEnv::KDEL The binding characteristics of the cytotoxic protein of this example for Env+ cells and Env− cells is determined by a fluorescence-based, flow-cytometry. The $B_{max}$ for SLT-1A::αEnv::KDEL to Env+ positive cells is measured to be approximately 50,000-200,000 MFI with a $K_D$ within the range of 0.01-100 nM, whereas there is no significant binding to Env− cells in this assay.

The ribosome inactivation abilities of the SLT-1A::αEnv::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αEnv::KDEL on protein synthesis in this cell-free assay is approximately 0.1-100 pM.

Determining the Cytotoxicity of the Cytotoxic Protein SLT-1A::αEnv::KDEL Using a Cell-Kill Assay The cytotoxicity characteristics of SLT-1A::αEnv::KDEL are determined by the general cell-kill assay as described above in the previous examples using Env+ cells. In addition, the selective cytotoxicity characteristics of SLT-1A::αEnv::KDEL are determined by the same general cell-kill assay using Env-cells as a comparison to the Env+ cells. The $CD_{50}$ of the cytotoxic protein of this example is approximately 0.01-100 nM for Env+ cells depending on the cell line and/or the HIV strain used to infect the cells to make them Env+. The CD50 of the cytotoxic protein is approximately 10-10,000 fold greater (less cytotoxic) for cells not expressing Env on a cellular surface as compared to cells which do express Env on a cellular surface.

Determining Reductions in Antigenicity and/or Immunogenicity

The relative de-immunization of SLT-1A::αEnv::KDEL is determined in relation to a wild-type Shiga toxin effector region polypeptide using western analyses, ELISA analyses, and murine models as described in Examples 4 and 6.

Determining the In Vivo Effects of the Cytotoxic Protein SLT-1A::αEnv::KDEL using Animal Models The use of SLT-1A::αEnv::KDEL to inhibit HIV infection is tested by administering SLT-1A::αEnv::KDEL to simian immunodeficiency virus (SIV) infected non-human primates (see Sellier P et al., *PLoS One* 5: e10570 (2010)).

Example 15. A Cytotoxic Protein Comprising a De-Immunized Shiga Toxin Effector Polypeptide and a Binding Region Derived from the Antibody αUL18

In this example, the Shiga toxin effector region is a de-immunized Shiga toxin effector polypeptide derived from the A subunit of Shiga-like Toxin 1 (SLT-1A) and comprising one or more de-immunizing amino acid substitutions described in the previous examples. An immunoglobulin-type binding region αUL18 is derived from an antibody generated, using techniques known in the art, to the cell-surface cytomegalovirus protein UL18, which is present on human cells infected with cytomegalovirus (Yang Z, Bjorkman P, *Proc Natl Acad Sci USA* 105: 10095-100 (2008)). The human cytomegalovirus infection is associated with various cancers and inflammatory disorders.

Construction, Production, and Purification of the Cytotoxic Protein SLT-1A::αUL18::KDEL The immunoglobulin-type binding region αUL18 and Shiga toxin effector region are linked together, and a carboxy-terminal KDEL is added to form a protein. For example, a fusion protein is produced by expressing a polynucleotide encoding the αUL18-binding protein SLT-1A::αUL18::KDEL. Expression of the SLT-1A::αUL18::KDEL cytotoxic protein is accomplished using either bacterial and/or cell-free, protein translation systems as described in the previous examples.

Determining the In Vitro Characteristics of the Cytotoxic Protein SLT-1A::αUL18::KDEL The binding characteristics of the cytotoxic protein of this example for cytomegalovirus protein UL18 positive cells and cytomegalovirus protein UL18 negative cells is determined by a fluorescence-based, flow-cytometry. The $B_{max}$ for SLT-1A::αUL18::KDEL to cytomegalovirus protein UL18 positive cells is measured to be approximately 50,000-200,000 MFI with a $K_D$ within the range of 0.01-100 nM, whereas there is no significant binding to cytomegalovirus protein UL18 negative cells in this assay.

The ribosome inactivation abilities of the SLT-1A::αUL18::KDEL cytotoxic protein is determined in a cell-free, in vitro protein translation as described above in the previous examples. The inhibitory effect of the cytotoxic protein of this example on cell-free protein synthesis is significant. The IC50 of SLT-1A::αUL18::KDEL on protein synthesis in this cell-free assay is approximately 0.1-100 pM.

Determining the Cytotoxicity of the Cytotoxic Protein SLT-1A::αUL18::KDEL Using a Cell-Kill Assay The cytotoxicity characteristics of SLT-1A::αUL18::KDEL are determined by the general cell-kill assay as described above in the previous examples using cytomegalovirus protein UL18 positive cells. In addition, the selective cytotoxicity characteristics of SLT-1A::αUL18::KDEL are determined by the same general cell-kill assay using cytomegalovirus protein UL18 negative cells as a comparison to the cytomegalovirus protein UL18 positive cells. The $CD_{50}$ of the cytotoxic protein of this example is approximately 0.01-100 nM for cytomegalovirus protein UL18 positive cells depending on the cell line. The $CD_{50}$ of the cytotoxic protein is approximately 10-10,000 fold greater (less cytotoxic) for cells not expressing the cytomegalovirus protein UL18 on a cellular surface as compared to cells which do express the cytomegalovirus protein UL18 on a cellular surface.

Determining Reductions in Antigenicity and/or Immunogenicity

The relative de-immunization of SLT-1A::αUL18::KDEL is determined in relation to a wild-type Shiga toxin effector region polypeptide using western analyses, ELISA analyses, and murine models as described in Examples 4 and 6.

Example 16. De-Immunized Cytotoxic Proteins Targeting Various Cell Types

In this example, the Shiga toxin effector region is a de-immunized Shiga toxin effector polypeptide derived from the A subunit of Shiga-like Toxin 1 (SLT-1A), Shiga toxin (StxA), and/or Shiga-like Toxin 2 (SLT-2A) with any combination of B-cell epitope regions disrupted. A binding region is derived from the immunoglobulin domain from the molecule chosen from column 1 of Table 12 and which binds the extracellular target biomolecule indicated in column 2 of Table 12. The exemplary cytotoxic proteins of this example are optionally created with a carboxy-terminal KDEL-type signal motif and/or detection promoting agent(s) using reagents and techniques known in the art. The exemplary cytotoxic proteins of this example are tested as described in the previous examples using cells expressing the appropriate extracellular target biomolecules. The exemplary proteins of this example may be used, e.g., to diagnose and treat diseases, conditions, and/or disorders indicated in column 3 of Table 12.

TABLE 12

Various Binding Regions for Cell Targeting of Cytotoxic Proteins

| Source of binding region | Extracellular target | Application(s) |
|---|---|---|
| alemtuzumab | CD52 | B-cell cancers, such as lymphoma and leukemia, and B-cell related immune disorders, such as autoimmune disorders |
| basiliximab | CD25 | T-cell disorders, such as prevention of organ transplant rejections, and some B-cell lineage cancers |
| brentuximab | CD30 | hematological cancers, B-cell related immune disorders, and T-cell related immune disorders |
| catumaxomab | EpCAM | various cancers, such as ovarian cancer, malignant ascites, gastric cancer |
| cetuximab | EGFR | various cancers, such as colorectal cancer and head and neck cancer |
| daclizumab | CD25 | B-cell lineage cancers and T-cell disorders, such as rejection of organ transplants |

TABLE 12-continued

Various Binding Regions for Cell Targeting of Cytotoxic Proteins

| Source of binding region | Extracellular target | Application(s) |
| --- | --- | --- |
| daratumumab | CD38 | hematological cancers, B-cell related immune disorders, and T-cell related immune disorders |
| dinutuximab | ganglioside GD2 | Various cancers, such as breast cancer, myeloid cancers, and neuroblastoma |
| efalizumab | LFA-1 (CD11a) | autoimmune disorders, such as psoriasis |
| ertumaxomab | HER2/neu | various cancers and tumors, such as breast cancer and colorectal cancer |
| gemtuzumab | CD33 | myeloid cancer or immune disorder |
| ibritumomab | CD20 | B-cell cancers, such as lymphoma and leukemia, and B-cell related immune disorders, such as autoimmune disorders |
| ipilimumab | CD152 | T-cell related disorders and various cancers, such as leukemia, melanoma |
| muromonab | CD3 | prevention of organ transplant rejections |
| natalizumab | integrin $\alpha 4$ | autoimmune disorders, such as multiple sclerosis and Crohn's disease |
| obinutuzumab | CD20 | B-cell cancers, such as lymphoma and leukemia, and B-cell related immune disorders, such as autoimmune disorders |
| ocaratuzumab | CD20 | B-cell cancers, such as lymphoma and leukemia, and B-cell related immune disorders, such as autoimmune disorders |
| ocrelizumab | CD20 | B-cell cancers, such as lymphoma and leukemia, and B-cell related immune disorders, such as autoimmune disorders |
| ofatumumab | CD20 | B-cell cancers, such as lymphoma and leukemia, and B-cell related immune disorders, such as autoimmune disorders |
| palivizumab | F protein of respiratory syncytial virus | treat respiratory syncytial virus |
| panitumumab | EGFR | various cancers, such as colorectal cancer and head and neck cancer |
| pertuzumab | HER2/neu | various cancers and tumors, such as breast cancer and colorectal cancer |
| pro 140 | CCR5 | HIV infection and T-cell disorders |
| ramucirumab | VEGFR2 | various cancers and cancer related disorders, such as solid tumors |
| rituximab | CD20 | B-cell cancers, such as lymphoma and leukemia, and B-cell related immune |

TABLE 12-continued

Various Binding Regions for Cell Targeting of Cytotoxic Proteins

| Source of binding region | Extracellular target | Application(s) |
|---|---|---|
| | | disorders, such as autoimmune disorders |
| tocilizumab or atlizumab | IL-6 receptor | autoimmune disorders, such as rheumatoid arthritis |
| tositumomab | CD20 | B-cell cancers, such as lymphoma and leukemia, and B-cell related immune disorders, such as autoimmune disorders |
| trastuzumab | HER2/neu | various cancers and tumors, such as breast cancer and colorectal cancer |
| ublituximab | CD20 | B-cell cancers, such as lymphoma and leukemia, and B-cell related immune disorders, such as autoimmune disorders |
| vedolizumab | integrin $\alpha 4\beta 7$ | autoimmune disorders, such as Crohn's disease and ulcerative colitis |
| CD20 binding scFv(s) Geng S et al., *Cell Mol Immunol* 3: 439-43 (2006); Olafesn T et al., *Protein Eng Des Sel* 23: 243-9 (2010) | CD20 | B-cell cancers, such as lymphoma and leukemia, and B-cell related immune disorders, such as autoimmune disorders |
| CD22 binding scFv(s) Kawas S et al., *MAbs* 3: 479-86 (2011) | CD22 | B-cell cancers or B-cell related immune disorders |
| CD25 binding scFv(s) Muramatsu H et al., *Cancer Lett* 225: 225-36 (2005) | CD25 | various cancers of the B-cell lineage and immune disorders related to T-cells |
| CD30 binding monoclonal antibody(s) Klimka A et al., *Br J Cancer* 83: 252-60 (2000) | CD30 | B-cell cancers or B-cell/T-cell related immune disorders |
| CD33 binding monoclonal antibody(s) Benedict C et al., *J Immunol Methods* 201: 223-31 (1997) | CD33 | myeloid cancer or immune disorder |
| CD38 binding immunoglobulin domains U.S. Pat. No. 8,153,765 | CD38 | hematological cancers, B-cell related immune disorders, and T-cell related immune disorders |
| CD40 binding scFv(s) Ellmark P et al., *Immunology* 106: 456-63 (2002) | CD40 | various cancers and immune disorders |
| CD52 binding monoclonal antibody(s) U.S. Pat. No. 7,910,104 B2 | CD52 | B-cell cancers, such as lymphoma and leukemia, and B-cell related immune disorders, such as autoimmune disorders |
| CD56 binding monoclonal antibody(s) Shin J et al., *Hybridoma* 18: 521-7 (1999) | CD56 | immune disorders and various cancers, such as lung cancer, Merkel cell carcinoma, myeloma |
| CD79 binding monoclonal antibody(s) Zhang L et al., *Ther Immunol* 2: 191-202 (1995) | CD79 | B-cell cancers or B-cell related immune disorders |
| CD248 binding scFv(s) Zhao A et al., *J Immunol Methods* 363: 221-32 (2011) | CD248 | various cancers, such as inhibiting angiogenesis |
| EpCAM binding monoclonal antibody(s) Schanzer J et al., *J Immunother* 29: 477-88 (2006) | EpCAM | various cancers, such as ovarian cancer, malignant ascites, gastric cancer |

TABLE 12-continued

| Various Binding Regions for Cell Targeting of Cytotoxic Proteins | | |
|---|---|---|
| Source of binding region | Extracellular target | Application(s) |
| PSMA binding monoclonal antibody(s) Frigerio B et al., *Eur J Cancer* 49: 2223-32 (2013) | PSMA | prostate cancer |
| Eph-B2 binding monoclonal antibody(s) Abéngozar M et al., *Blood* 119: 4565-76 (2012) | Eph-B2 | for various cancers such as colorectal cancer and prostate cancer |
| Endoglin binding monoclonal antibody(s) Völkel T et al., *Biochim Biophys Res Acta* 1663: 158-66 (2004) | Endoglin | various cancers, such as breast cancer and colorectal cancers |
| FAP binding monoclonal antibody(s) Zhang J et al., *FASEB J* 27: 581-9 (2013) | FAP | various cancers, such as sarcomas and bone cancers |
| CEA binding antibody(s) and scFv(s) Neumaier M et al., *Cancer Res* 50: 2128-34 (1990); Pavoni E et al., *BMC Cancer* 6: 4 (2006); Yazaki P et al., *Nucl Med Biol* 35: 151-8 (2008); Zhao J et al., *Oncol Res* 17: 217-22 (2008) | CEA | various cancers, such as gastrointestinal cancer, pancreatic cancer, lung cancer, and breast cancer |
| CD24 binding monoclonal antibody(s) Kristiansen G et al., *Lab Invest* 90: 1102-16 (2010) | CD24 | various cancers, such as bladder cancer |
| LewisY antigen binding scFv(s) Power B et al., *Protein Sci* 12: 734-47 (2003); monoclonal antibody BR96 Feridani A et al., *Cytometry* 71: 361-70 (2007) | LewisY antigens | various cancers, such as cervical cancer and uterine cancer |
| adalimumab | TNF-α | various cancers and immune disorders, such as Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| afelimomab | TNF-α | various cancers and immune disorders |
| ald518 | IL-6 | various cancers and immune disorders, such as rheumatoid arthritis |
| anrukinzumab or ima-638 | IL-13 | various cancers and immune disorders |
| briakinumab | IL-12, IL-23 | various cancers and immune disorders, such as psoriasis, rheumatoid arthritis, inflammatory bowel diseases, multiple sclerosis |
| brodalumab | IL-17 | various cancers and immune disorders, such as inflammatory diseases |
| canakinumab | IL-1 | various cancers and immune disorders, such as rheumatoid arthritis |
| certolizumab | TNF-α | various cancers and immune disorders, such as Crohn's disease |
| fezakinumab | IL-22 | various cancers and immune disorders, such |

TABLE 12-continued

Various Binding Regions for Cell Targeting of Cytotoxic Proteins

| Source of binding region | Extracellular target | Application(s) |
|---|---|---|
| | | as rheumatoid arthritis, psoriasis |
| ganitumab | IGF-I | various cancers |
| golimumab | TNF-α | various cancers and immune disorders, such as rheumatoid arthritis, psoriatic arthritis, ankylosing spondylitis |
| infliximab | TNF-α | various cancers and immune disorders, such as rheumatoid arthritis, ankylosing spondylitis, psoriatic arthritis, psoriasis, Crohn's disease, ulcerative colitis |
| ixekizumab | IL-17A | various cancers and immune disorders, such as autoimmune diseases |
| mepolizumab | IL-5 | various immune disorders and cancers, such as B-cell cancers |
| nerelimomab | TNF-α | various cancers and immune disorders |
| olokizumab | IL6 | various cancers and immune disorders |
| ozoralizumab | TNF-α | inflammation |
| perakizumab | IL17A | various cancers and immune disorders, such as arthritis |
| placulumab | human TNF | various immune disorders and cancers |
| sarilumab | IL6 | various cancers and immune disorders, such as rheumatoid arthritis, ankylosing spondylitis |
| siltuximab | IL-6 | various cancers and immune disorders |
| sirukumab | IL-6 | various cancers and immune disorders, such as rheumatoid arthritis |
| tabalumab | BAFF | B-cell cancers |
| ticilimumab or tremelimumab | CTLA-4 | various cancers |
| tildrakizumab | IL23 | immunologically mediated inflammatory disorders |
| tnx-650 | IL-13 | various cancers and immune disorders, such as B-cell cancers |
| tocilizumab or atlizumab | IL-6 receptor | various cancers and immune disorders, such as rheumatoid arthritis |
| ustekinumab | IL-12, IL-23 | various cancers and immune disorders, such as multiple sclerosis, psoriasis, psoriatic arthritis |
| Various growth factors: VEGF, EGF1, EGF2, FGF | VEGFR, EGFR, FGFR | various cancer, such as breast cancer and colon cancer, and to inhibit vascularization |
| Various cytokines: IL-2, IL-6, IL-23, CCL2, BAFFs, TNFs, RANKL | IL-2R, IL-6R, IL-23R, CD80/CD86, TNFRSF13/ TNFRSF17, TNFR | various immune disorders and cancers |
| Broadly neutralizing antibodies identified from patient samples Prabakaran et al., *Front Microbiol* 3: 277 (2012) | Influenza surface antigens, e.g. hemagglutinins and influenza matrix protein 2 | viral infections |
| Broadly neutralizing antibodies identified from patient samples Prabakaran et al., | Coronavirus surface antigens | viral infections |

TABLE 12-continued

| Various Binding Regions for Cell Targeting of Cytotoxic Proteins | | |
|---|---|---|
| Source of binding region | Extracellular target | Application(s) |
| *Front Microbiol* 3: 277 (2012) | | |
| Broadly neutralizing antibodies identified from patient samples Prabakaran et al., *Front Microbiol* 3: 277 (2012) | Henipaviruses surface antigens | viral infections |

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety. The disclosures of U.S. provisional patent application ser. Nos. 61/777,130, 61/932,000, 61/951,110, 61/951,121, 62/010,918 and 62/049,325 are each incorporated herein by reference in their entirety. The disclosures of international PCT patent application serial numbers PCT/US2014/023198 and PCT/US2014/023231 are each incorporated herein by reference in their entirety. The complete disclosures of all electronically available biological sequence information from GenBank (National Center for Biotechnology Information, U.S.) for amino acid and nucleotide sequences cited herein are each incorporated herein by reference in their entirety.

| Sequence Listing | | |
|---|---|---|
| ID Number | Text Description | Biological Sequence |
| SEQ ID NO: 1 | Shiga-like toxin 1 Subunit A (SLT-1A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA RMASDEFPSMCPADGRVRGITH NKILWDSSTLGAILMRRTISS |
| SEQ ID NO: 2 | Shiga toxin Subunit A (StxA) | KEFTLDFSTAKTYVDSLNVIRSA IGTPLQTISSGGTSLLMIDSGTGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA RMASDEFPSMCPADGRVRGITH NKILWDSSTLGAILMRRTISS |
| SEQ ID NO: 3 | Shiga-like toxin 2 Subunit A (SLT-2A) | DEFTVDFSSQKSYVDSLNSIRSAI STPLGNISQGGVSVSVINHVLGG NYISLNVRGLDPYSERFNHLRLI MERNNLYVAGFINTETNIFYRFS DFSHISVPDVITVSMTTDSSYSSL QRIADLERTGMQIGRHSLVGSY LDLMEFRGRSMTRASSRAMLRF VTVIAEALRFRQIQRGFRPALSE ASPLYTMTAQDVDLTLNWGRIS NVLPEYRGEEGVRIGRISFNSLS AILGSVAVILNCHSTGSYSVRSV SQKQKTECQIVGDRAAIKVNNV LWEANTIAALLNRKPQDLTEPN Q |

-continued

Sequence Listing

| ID Number | Text Description | Biological Sequence |
|---|---|---|
| SEQ ID NO: 4 | De-immunized SLT-1A (K1M) | MEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 5 | De-immunized SLT-1A (S8I) | KEFTLDFITAKTYVDSLNVIRSAI GTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 6 | De-immunized SLT-1A (T9I) | KEFTLDFSIAKTYVDSLNVIRSAI GTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 7 | De-immunized SLT-1A (K11A) | KEFTLDFSTAATYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 8 | De-immunized SLT-1A (S33I) | KEFTLDFSTAKTYVDSLNVIRSA IGTPLQTISIGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 9 | De-immunized SLT-1A (S45I) | KEFTLDFSTAKTYVDSLNVIRSA IGTPLQTISSGGTSLLMIDSGIGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD |

-continued

| Sequence Listing | | |
|---|---|---|
| ID Number | Text Description | Biological Sequence |
| | | DLSGRSYVMTAEDVDLTLNWG<br>RLSSVLPDYHGQDSVRVGRISFG<br>SINAILGSVALILNCHHHASRVA<br>R |
| SEQ ID NO: 10 | De-immunized SLT-1A (D53A) | KEFTLDFSTAKTYVDSLNVIRSA<br>IGTPLQTISSGGTSLLMIDSGSGD<br>NLFAVAVRGIDPEEGRFNNLRLI<br>VERNNLYVTGFVNRTNNVFYRF<br>ADFSHVTFPGTTAVTLSGDSSYT<br>TLQRVAGISRTGMQINRHSLTTS<br>YLDLMSHSGTSLTQSVARAMLR<br>FVTVTAEALRFRQIQRGFRTTLD<br>DLSGRSYVMTAEDVDLTLNWG<br>RLSSVLPDYHGQDSVRVGRISFG<br>SINAILGSVALILNCHHHASRVA<br>R |
| SEQ ID NO: 11 | De-immunized SLT-1A (R55A) | KEFTLDFSTAKTYVDSLNVIRSA<br>IGTPLQTISSGGTSLLMIDSGSGD<br>NLFAVDVAGIDPEEGRFNNLRLI<br>VERNNLYVTGFVNRTNNVFYRF<br>ADFSHVTFPGTTAVTLSGDSSYT<br>TLQRVAGISRTGMQINRHSLTTS<br>YLDLMSHSGTSLTQSVARAMLR<br>FVTVTAEALRFRQIQRGFRTTLD<br>DLSGRSYVMTAEDVDLTLNWG<br>RLSSVLPDYHGQDSVRVGRISFG<br>SINAILGSVALILNCHHHASRVA<br>R |
| SEQ ID NO: 12 | De-immunized SLT-1A (D58A) | KEFTLDFSTAKTYVDSLNVIRSA<br>IGTPLQTISSGGTSLLMIDSGSGD<br>NLFAVDVRGIAPEEGRFNNLRLI<br>VERNNLYVTGFVNRTNNVFYRF<br>ADFSHVTFPGTTAVTLSGDSSYT<br>TLQRVAGISRTGMQINRHSLTTS<br>YLDLMSHSGTSLTQSVARAMLR<br>FVTVTAEALRFRQIQRGFRTTLD<br>DLSGRSYVMTAEDVDLTLNWG<br>RLSSVLPDYHGQDSVRVGRISFG<br>SINAILGSVALILNCHHHASRVA<br>R |
| SEQ ID NO: 13 | De-immunized SLT-1A (D58F) | KEFTLDFSTAKTYVDSLNVIRSA<br>IGTPLQTISSGGTSLLMIDSGSGD<br>NLFAVDVRGIFPEEGRFNNLRLI<br>VERNNLYVTGFVNRTNNVFYRF<br>ADFSHVTFPGTTAVTLSGDSSYT<br>TLQRVAGISRTGMQINRHSLTTS<br>YLDLMSHSGTSLTQSVARAMLR<br>FVTVTAEALRFRQIQRGFRTTLD<br>DLSGRSYVMTAEDVDLTLNWG<br>RLSSVLPDYHGQDSVRVGRISFG<br>SINAILGSVALILNCHHHASRVA<br>R |
| SEQ ID NO: 14 | De-immunized SLT-1A (P59A) | KEFTLDFSTAKTYVDSLNVIRSA<br>IGTPLQTISSGGTSLLMIDSGSGD<br>NLFAVDVRGIDAEEGRFNNLRLI<br>VERNNLYVTGFVNRTNNVFYRF<br>ADFSHVTFPGTTAVTLSGDSSYT<br>TLQRVAGISRTGMQINRHSLTTS<br>YLDLMSHSGTSLTQSVARAMLR<br>FVTVTAEALRFRQIQRGFRTTLD<br>DLSGRSYVMTAEDVDLTLNWG<br>RLSSVLPDYHGQDSVRVGRISFG<br>SINAILGSVALILNCHHHASRVA<br>R |
| SEQ ID NO: 15 | De-immunized SLT-1A (E60I) | KEFTLDFSTAKTYVDSLNVIRSA<br>IGTPLQTISSGGTSLLMIDSGSGD<br>NLFAVDVRGIDPIEGRFNNLRLI<br>VERNNLYVTGFVNRTNNVFYRF<br>ADFSHVTFPGTTAVTLSGDSSYT |

-continued

Sequence Listing

| ID Number | Text Description | Biological Sequence |
|---|---|---|
| | | TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 16 | De-immunized SLT-1A (E60R) | KEFTLDFSTAKTYVDSLNVIRSA IGTPLQTISSGGTSLLMIDSGSGD NLFAVDVRGIDPREGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 17 | De-immunized SLT-1A (E61A) | KEFTLDFSTAKTYVDSLNVIRSA IGTPLQTISSGGTSLLMIDSGSGD NLFAVDVRGIDPEAGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 18 | De-immunized SLT-1A (G62A) | KEFTLDFSTAKTYVDSLNVIRSA IGTPLQTISSGGTSLLMIDSGSGD NLFAVDVRGIDPEEARFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 19 | De-immunized SLT-1A (D94A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF AAFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 20 | De-immunized SLT-1A (S96I) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFIHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 21 | De-immunized SLT-1A (G110A) | KEFTLDFSTAKTYVDSLNVIRSA IGTPLQTISSGGTSLLMIDSGSGD |

-continued

Sequence Listing

| ID Number | Text Description | Biological Sequence |
|---|---|---|
| | | NLFAVDVRGIDPEEGRFNNLRLI VERNNLYVTGFVNRTNNVFYRF ADFSHVTFPGTTAVTLSADSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 22 | De-immunized SLT-1A (G147A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSATSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 23 | De-immunized SLT-1A (R179A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFATTLD DLSGRSYVMTAEDVDLTLNWG RLSSVLPDYHGQDSVRVGRISFG SINAILGSVALILNCHHHASRVA R |
| SEQ ID NO: 24 | De-immunized SLT-1A (D183A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLA DLSGRSYVMTAEDVDLTLNWG RLSSVLPDYHGQDSVRVGRISFG SINAILGSVALILNCHHHASRVA R |
| SEQ ID NO: 25 | De-immunized SLT-1A (D184A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD ALSGRSYVMTAEDVDLTLNWG RLSSVLPDYHGQDSVRVGRISFG SINAILGSVALILNCHHHASRVA R |
| SEQ ID NO: 26 | De-immunized SLT-1A (D184F) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD FLSGRSYVMTAEDVDLTLNWG RLSSVLPDYHGQDSVRVGRISFG SINAILGSVALILNCHHHASRVA R |

-continued

Sequence Listing

| ID Number | Text Description | Biological Sequence |
|---|---|---|
| SEQ ID NO: 27 | De-immunized SLT-1A (S186A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLAGRSYVMTAEDVDLTLNWG RLSSVLPDYHGQDSVRVGRISFG SINAILGSVALILNCHHHASRVA R |
| SEQ ID NO: 28 | De-immunized SLT-1A (G187A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSARSYVMTAEDVDLTLNWG RLSSVLPDYHGQDSVRVGRISFG SINAILGSVALILNCHHHASRVA R |
| SEQ ID NO: 29 | De-immunized SLT-1A (R188A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGASYVMTAEDVDLTLNWG RLSSVLPDYHGQDSVRVGRISFG SINAILGSVALILNCHHHASRVA R |
| SEQ ID NO: 30 | De-immunized SLT-1A (S189A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRAYVMTAEDVDLTLNWG RLSSVLPDYHGQDSVRVGRISFG SINAILGSVALILNCHHHASRVA R |
| SEQ ID NO: 31 | De-immunized SLT-1A (R205A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG ALSSVLPDYHGQDSVRVGRISFG SINAILGSVALILNCHHHASRVA R |
| SEQ ID NO: 32 | De-immunized SLT-1A (K1M, K11A) | MEFTLDFSTAATYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG |

-continued

| Sequence Listing | | |
|---|---|---|
| ID Number | Text Description | Biological Sequence |
| | | RLSSVLPDYHGQDSVRVGRISFG SINAILGSVALILNCHHHASRVA R |
| SEQ ID NO: 33 | De-immunized SLT-1A (S45I, R188A) | KEFTLDFSTAKTYVDSLNVIRSA IGTPLQTISSGGTSLLMIDSGIGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLD DLSGASYVMTAEDVDLTLNWG RLSSVLPDYHGQDSVRVGRISFG SINAILGSVALILNCHHHASRVA R |
| SEQ ID NO: 34 | De-immunized SLT-1A (E60I, G110A) | KEFTLDFSTAKTYVDSLNVIRSA IGTPLQTISSGGTSLLMIDSGSGD NLFAVDVRGIDPIEGRFNNLRLI VERNNLYVTGFVNRTNNVFYRF ADFSHVTFPGTTAVTLSADSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 35 | De-immunized SLT-1A (E60I, G147A) | KEFTLDFSTAKTYVDSLNVIRSA IGTPLQTISSGGTSLLMIDSGSGD NLFAVDVRGIDPIEGRFNNLRLI VERNNLYVTGFVNRTNNVFYRF ADFSHVTFPGTTAVTLSGDSSYT TLQRVAGISRTGMQINRHSLTTS YLDLMSHSATSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 36 | De-immunized SLT-1A (D94A, S96I) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF AAFIHVTFPGTTAVTLSGDSSYT TLQRVAGISRTGMQINRHSLTTS YLDLMSHSGTSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 37 | De-immunized SLT-1A (S33I, G110A, G147A) | KEFTLDFSTAKTYVDSLNVIRSA IGTPLQTISIGGTSLLMIDSGSGD NLFAVDVRGIDPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 38 | De-immunized SLT-1A (S45I, G110A, G147A) | KEFTLDFSTAKTYVDSLNVIRSA IGTPLQTISSGGTSLLMIDSGIGD NLFAVDVRGIDPEEGRFNNLRLI VERNNLYVTGFVNRTNNVFYRF ADFSHVTFPGTTAVTLSADSSYT TLQRVAGISRTGMQINRHSLTTS |

-continued

Sequence Listing

| ID Number | Text Description | Biological Sequence |
| --- | --- | --- |
| | | YLDLMSHSATSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 39 | De-immunized SLT-1A (D58A, G110A, G147A) | KEFTLDFSTAKTYVDSLNVIRSA IGTPLQTISSGGTSLLMIDSGSGD NLFAVDVRGIAPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 40 | De-immunized SLT-1A (E60I, G110A, G147A) | KEFTLDFSTAKTYVDSLNVIRSA IGTPLQTISSGGTSLLMIDSGSGD NLFAVDVRGIDPIEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 41 | De-immunized SLT-1A (D183A, D184A, R188A) | KEFTLDFSTAKTYVDSLNVIRSA IGTPLQTISSGGTSLLMIDSGSGD NLFAVDVRGIDPEEGRFNNLRLI VERNNLYVTGFVNRTNNVFYRF ADFSHVTFPGTTAVTLSGDSSYT TLQRVAGISRTGMQINRHSLTTS YLDLMSHSGTSLTQSVARAMLR FVTVTAEALRFRQIQRGFRTTLA ALSGASYVMTAEDVDLTLNWG RLSSVLPDYHGQDSVRVGRISFG SINAILGSVALILNCHHHASRVA R |
| SEQ ID NO: 42 | De-immunized SLT-1A (D58A, G110A, G147A, S186A) | KEFTLDFSTAKTYVDSLNVIRSA IGTPLQTISSGGTSLLMIDSGSGD NLFAVDVRGIAPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLAGRSYVMTAEDVDLTLNWG RLSSVLPDYHGQDSVRVGRISFG SINAILGSVALILNCHHHASRVA R |
| SEQ ID NO: 43 | De-immunized SLT-1A (D58A, G110A, G147A, G187A) | KEFTLDFSTAKTYVDSLNVIRSA IGTPLQTISSGGTSLLMIDSGSGD NLFAVDVRGIAPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSARSYVMTAEDVDLTLNWG RLSSVLPDYHGQDSVRVGRISFG SINAILGSVALILNCHHHASRVA R |
| SEQ ID NO: 44 | De-immunized SLT-1A (D58A, G110A, G147A, R188A) | KEFTLDFSTAKTYVDSLNVIRSA IGTPLQTISSGGTSLLMIDSGSGD NLFAVDVRGIAPEEGRFNNLRLI |

-continued

| Sequence Listing | | |
|---|---|---|
| ID Number | Text Description | Biological Sequence |
| | | VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSGASYVMTAEDVDLTLNWG RLSSVLPDYHGQDSVRVGRISFG SINAILGSVALILNCHHHASRVA R |
| SEQ ID NO: 45 | De-immunized SLT-1A (D58A, G110A, G147A, S189A) | KEFTLDFSTAKTYVDSLNVIRSA IGTPLQTISSGGTSLLMIDSGSGD NLFAVDVRGIAPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSGRAYVMTAEDVDLTLNWG RLSSVLPDYHGQDSVRVGRISFG SINAILGSVALILNCHHHASRVA R |
| SEQ ID NO: 46 | De-immunized SLT-1A (S45I D58A E60I G110A G147A) | KEFTLDFSTAKTYVDSLNVIRSA IGTPLQTISSGGTSLLMIDSGIGD NLFAVDVRGIAPIEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |
| SEQ ID NO: 47 | De-immunized SLT-1A (D58A, G110A, G147A, S186A, R188A) | KEFTLDFSTAKTYVDSLNVIRSA IGTPLQTISSGGTSLLMIDSGSGD NLFAVDVRGIAPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLAGASYVMTAEDVDLTLNWG RLSSVLPDYHGQDSVRVGRISFG SINAILGSVALILNCHHHASRVA R |
| SEQ ID NO: 48 | De-immunized SLT-1A (D58A, G110A, G147A, G187A, R188A) | KEFTLDFSTAKTYVDSLNVIRSA IGTPLQTISSGGTSLLMIDSGSGD NLFAVDVRGIAPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSAASYVMTAEDVDLTLNWG RLSSVLPDYHGQDSVRVGRISFG SINAILGSVALILNCHHHASRVA R |
| SEQ ID NO: 49 | De-immunized SLT-1A (S33I, S45I, D58A, G110A, G147A) | KEFTLDFSTAKTYVDSLNVIRSA IGTPLQTISIGGTSLLMIDSGIGD NLFAVDVRGIAPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLD DLSGRSYVMTAEDVDLTLNWG RLSSVLPDYHGQDSVRVGRISFG SINAILGSVALILNCHHHASRVA R |

-continued

Sequence Listing

| ID Number | Text Description | Biological Sequence |
|---|---|---|
| SEQ ID NO: 50 | De-immunized SLT-1A (S45I G110A G147A, D183A, D184A, R188A) | KEFTLDFSTAKTYVDSLNVIRSA IGTPLQTISSGGTSLLMIDSGIGD NLFAVDVRGIDPEEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLA ALSGASYVMTAEDVDLTLNWG RLSSVLPDYHGQDSVRVGRISFG SINAILGSVALILNCHHHASRVA R |
| SEQ ID NO: 51 | De-immunized SLT-1A (S45I D58A E60I G110A G147A, D183A, D184A, R188A) | KEFTLDFSTAKTYVDSLNVIRSA IGTPLQTISSGGTSLLMIDSGIGD NLFAVDVRGIAPIEGRFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLA ALSGASYVMTAEDVDLTLNWG RLSSVLPDYHGQDSVRVGRISFG SINAILGSVALILNCHHHASRVA R |
| SEQ ID NO: 52 | De-immunized SLT-1A (S45I D58A E60I G62A G110A G147A, D183A, D184A, R188A) | KEFTLDFSTAKTYVDSLNVIRSA IGTPLQTISSGGTSLLMIDSGIGD NLFAVDVRGIAPIEARFNNLRLI VERNNLYVTGFVNRTNNVFYRF ADFSHVTFPGTTAVTLSADSSYT TLQRVAGISRTGMQINRHSLTTS YLDLMSHSATSLTQSVARAMLR FVTVTAEALRFRQIQRGFRTTLA ALSGASYVMTAEDVDLTLNWG RLSSVLPDYHGQDSVRVGRISFG SINAILGSVALILNCHHHASRVA R |
| SEQ ID NO: 53 | Cytotoxic Protein: αCD20 fused with de-immunized SLT-1A variant #1 | MQVQLQQPGAELVKPGASVKM SCKTSGYTFTSYNVHWVKQTPG QGLEWIGAIYPGNGDTSFNQKF KGKATLTADKSSSTVYMQLSSL TSEDSAVYYCARSNYYGSSYV WFFDVWGAGTTVTVSSGSTSGS GKPGSGEGSQIVLSQSPTILSASP GEKVTMTCRASSSVSYMDWYQ QKPGSSPKPWIYATSNLASGVPA RFSGSGSGTSYSLTISRVEAEDA ATYYCQQWISNPPTFGAGTKLE LKEFPKPSTPPGSSGGAPKEFTL DFSTAKTYVDSLNVIRSAIGTPL QTISIGGTSLLMIDSGIGDNLFAV DVRGIAPEEGRFNNLRLIVERNN LYVTGFVNRTNNVFYRFADFSH VTFPGTTAVTLSADSSYTTLQRV AGISRTGMQINRHSLTTSYLDLM SHSATSLTQSVARAMLRFVTVT AEALRFRQIQRGFRTTLDDLSGR SYVMTAEDVDLTLNWGRLSSV LPDYHGQDSVRVGRISFGSINAI LGSVALILNCHHHASAVAR |
| SEQ ID NO: 54 | Cytotoxic Protein: αCD20 fused with de-immunized SLT-1A variant #2 | MQVQLVQSGAELVKPGASVKM SCKASGYTFTSYNMHWVKQTP GQGLEWIGAIYPGNGDTSYNQK FKGKATLTADKSSSTAYMQLSS LTSEDSAVYYCARAQLRPNYW YFDVWGAGTTVTVSSGGGGSG GGGSGGGGSGGGGSGGGGSDIV LSQSPAILSASPGEKVTMTCRAS SSVSYMIHWYQQKPGSSPKPWIY ATSNLASGVPARFSGSGSGTSYS LTISRVEAEDAATYYCQQWISNP PTFGAGTKLELKGGGGSGGKEF |

-continued

Sequence Listing

| ID Number | Text Description | Biological Sequence |
|---|---|---|
| | | TLDFSTAKTYVDSLNVIRSAIGT PLQTISIGGTSLLMIDSGIGDNLF AVDVRGIAPEEGRFNNLRLIVER NNLYVTGFVNRTNNVFYRFADF SHVTFPGTTAVTLSADSSYTTLQ RVAGISRTGMQINRHSLTTSYLD LMSHSATSLTQSVARAMLRFVT VTAEALRFRQIQRGFRTTLDDLS GRSYVMTAEDVDLTLNWGRLS SVLPDYHGQDSVRVGRISFGSIN AILGSVALILNCHHHASAVAR |
| SEQ ID NO: 55 | Cytotoxic Protein: αCD20 fused with de-immunized SLT-1A variant #3 | MQVQLQQPGAELVKPGASVKM SCKASGYTFTSYNMHWVKQTP GRGLEWIGAIYPGNGDTSYNQK FKGKATLTADKSSSTAYMQLSS LTSEDSAVYYCARSTYYGGDW YFNVWGAGTTVTVSAGSTSGSG KPGSGEGSTKGQIVLSQSPAILS ASPGEKVTMTCRASSSVSYIHW FQQKPGSSPKPWIYATSNLASGV PVRFSGSGSGTSYSLTISRVEAE DAATYYCQQWTSNPPTFGGGT KLEIKEFPKPSTPPGSSGGAPKEF TLDFSTAKTYVDSLNVIRSAIGT PLQTISIGGTSLLMIDSGIGDNLF AVDVRGIAPEEGRFNNLRLIVER NNLYVTGFVNRTNNVFYRFADF SHVTFPGTTAVTLSADSSYTTLQ RVAGISRTGMQINRHSLTTSYLD LMSHSATSLTQSVARAMLRFVT VTAEALRFRQIQRGFRTTLDDLS GRSYVMTAEDVDLTLNWGRLS SVLPDYHGQDSVRVGRISFGSIN AILGSVALILNCHHHASAVAR |
| SEQ ID NO: 56 | Cytotoxic Protein: αCD20 fused with de-immunized SLT-1A variant #4 | MQVQLQQPGAELVKPGASVKM SCKTSGYTFTSYNVHWVKQTPG QGLEWIGAIYPGNGDTSFNQKF KGKATLTADKSSSTVYMQLSSL TSEDSAVYYCARSNYYGSSYV WFFDVWGAGTTVTVSSGSTSGS GKPGSGEGSQIVLSQSPTILSASP GEKVTMTCRASSSVSYMDWYQ QKPGSSPKPWIYATSNLASGVPA RFSGSGSGTSYSLTISRVEAEDA ATYYCQQWISNPPTFGAGTKLE LKEFPKPSTPPGSSGGAPGILGFV FTLKEFTLDFSTAKTYVDSLNVI RSAIGTPLQTISIGGTSLLMIDSGI GDNLFAVDVRGIAPEEGRFNNL RLIVERNNLYVTGFVNRTNNVF YRFADFSHVTFPGTTAVTLSADS SYTTLQRVAGISRTGMQINRHSL TTSYLDLMSHSATSLTQSVARA MLRFVTVTAEALRFRQIQRGFR TTLDDLSGRSYVMTAEDVDLTL NWGRLSSVLPDYHGQDSVRVG RISFGSINAILGSVALILNCHHHA SAVAR |
| SEQ ID NO: 57 | Cytotoxic Protein: anti-HER2-$V_HH$ fused with de-immunized SLT-1A variant #1 | MEVQLVESGGGLVQAGGSLRLS CAASGITFSINTMGWYRQAPGK QRELVALISSIGDTYYADSVKGR FTISRDNAKNTVYLQMNSLKPE DTAVYYCKRFRTAAQGTDYWG QGTQVTVSSAHHSEDPSSKAPK APKEFTLDFSTAKTYVDSLNVIR SAIGTPLQTISIGGTSLLMIDSGIG DNLFAVDVRGIAPEEGRFNNLR LIVERNNLYVTGFVNRTNNVFY RFADFSHVTFPGTTAVTLSADSS YTTLQRVAGISRTGMQINRHSLT TSYLDLMSHSATSLTQSVARAM LRFVTVTAEALRFRQIQRGFRTT |

-continued

| Sequence Listing | | |
|---|---|---|
| ID Number | Text Description | Biological Sequence |
| | | LDDLSGRSYVMTAEDVDLTLN WGRLSSVLPDYHGQDSVRVGRI SFGSINAILGSVALILNCHHHAS AVAR |
| SEQ ID NO: 58 | Cytotoxic Protein: anti-HER2-$V_H$H fused with de-immunized SLT-1A variant #2 | MKEFTLDFSTAKTYVDSLNVIRS AIGTPLQTISIGGTSLLMIDSGIG DNLFAVDVRGIAPEEGRFNNLR LIVERNNLYVTGFVNRTNNVFY RFADFSHVTFPGTTAVTLSADSS YTTLQRVAGISRTGMQINRHSLT TSYLDLMSHSATSLTQSVARAM LRFVTVTAEALRFRQIQRGFRTT LDDLSGRSYVMTAEDVDLTLN WGRLSSVLPDYHGQDSVRVGRI SFGSINAILGSVALILNCHHHAS AVAREFPKPSTPPGSSGGAPMEV QLVESGGGLVQAGGSLRLSCAA SGITFSINTMGWYRQAPGKQRE LVALISSIGDTYYADSVKGRFTIS RDNAKNTVYLQMNSLKPEDTA VYYCKRFRTAAQGTDYWGQGT QVTVSS |
| SEQ ID NO: 59 | Cytotoxic Protein: anti-HER2-$V_H$H fused with de-immunized SLT-1A variant #3 (αHER2-$V_H$H::SLT-1A::KDEL) | MEVQLVESGGGLVQAGGSLRLS CAASGITFSINTMGWYRQAPGK QRELVALISSIGDTYYADSVKGR FTISRDNAKNTVYLQMNSLKPE DTAVYYCKRFRTAAQGTDYWG QGTQVTVSSEFPKPSTPPGSSGG APKEFTLDFSTAKTYVDSLNVIR SAIGTPLQTISIGGTSLLMIDSGIG DNLFAVDVRGIAPEEGRFNNLR LIVERNNLYVTGFVNRTNNVFY RFADFSHVTFPGTTAVTLSADSS YTTLQRVAGISRTGMQINRHSLT TSYLDLMSHSATSLTQSVARAM LRFVTVTAEALRFRQIQRGFRTT LDDLSGRSYVMTAEDVDLTLN WGRLSSVLPDYHGQDSVRVGRI SFGSINAILGSVALILNCHHHAS AVARKDEL |

The invention claimed is:

1. A cell-targeting molecule comprising a protein as a component of the molecule, wherein the protein consists of:

(a) a binding region capable of specifically binding an extracellular target biomolecule physically coupled to the surface of a cell, wherein the extracellular target biomolecule is not CD38; and (b) a Shiga toxin effector polypeptide comprising an amino acid sequence having at least 90% identity to amino acids 1 to 251 of SEQ ID NO: 1, wherein the amino acid sequence comprises at least four endogenous B-cell epitope regions, and further comprises:

i) a plurality of disrupted endogenous B-cell epitope regions, wherein the disrupted endogenous B-cell epitope regions contain the following amino acid substitutions: S45 of SEQ ID NO: 1 to I, R55 of SEQ ID NO: 1 to L, 157 of SEQ ID NO: 1 to F, P59 of SEQ ID NO: 1 to F, E60 of SEQ ID NO: 1 to T, E61 of SEQ ID NO: 1 to L, G110 of SEQ ID NO: 1 to A, R188 of SEQ ID NO: 1 to A, R248 of SEQ ID NO: 1 to A and R251 of SEQ ID NO: 1 to A;

and ii) the amino acid substitution C242 of SEQ ID NO: 1 to S; and wherein the amino acid sequence comprises an asparagine at the amino acid residue corresponding to position 75 of SEQ ID NO: 1, a tyrosine at the amino acid residue corresponding to position 77 of SEQ ID NO: 1, a tyrosine at the amino acid residue corresponding to position 114 of SEQ ID NO: 1, a glutamate at the amino acid residue corresponding to position 167 of SEQ ID NO: 1, an arginine at the amino acid residue corresponding to position 170 of SEQ ID NO: 1, an arginine at the amino acid residue corresponding to position 176 of SEQ ID NO: 1, and a tryptophan at the amino acid residue corresponding to position 203 of SEQ ID NO: 1.

2. The cell-targeting molecule according to claim 1, wherein the amino acid sequence has at least 95% sequence identity to amino acids 1 to 251 of SEQ ID NO: 1.

3. The cell-targeting molecule of claim 1, wherein the binding region is fused to the carboxy terminus of the Shiga toxin effector polypeptide to form a single, continuous polypeptide.

4. The cell-targeting molecule of claim 1, wherein the binding region comprises an immunoglobulin-type binding region.

5. The cell-targeting molecule of claim 4, wherein the immunoglobulin-type binding region comprises a polypeptide selected from: single-domain antibody fragment, single-chain variable fragment, antibody variable fragment, complementary determining region 3 fragment, constrained FR3-CDR3-FR4 polypeptide, Fd fragment, antigen-binding fragment, fibronectin-derived 10th fibronectin type III domain, tenascin type III domain, ankyrin repeat motif domain, low-density-lipoprotein-receptor-derived A-domain, lipocalin, Kunitz domain, Protein-A-derived Z domain, gamma-B crystallin-derived domain, ubiquitin-derived domain, Sac7d-derived polypeptide, Fyn-derived SH2 domain, miniprotein, C-type lectin-like domain scaffold, a heavy-chain antibody domain derived from a camelid $V_HH$ fragment, heavy-chain antibody domain derived from cartilaginous fish, immunoglobulin new antigen receptor (IgNAR), $V_{NAR}$ fragment, diabody, triabody, tetrabody, bivalent minibody, bispecific tandem scFv, bispecific tandem $V_HH$, and bispecific minibody.

6. The cell-targeting molecule of claim 1, wherein the binding region comprises a linker peptide (GxS)n wherein x is 1 to 6 and n is 1 to 30.

7. The cell-targeting molecule of claim 6, wherein x is 4 and n is 1 (SEQ ID NO: 129.

8. A pharmaceutical composition comprising the cell-targeting molecule of claim 1 and a pharmaceutically acceptable excipient or carrier.

9. A cell-targeting molecule comprising a protein as a component of the molecule, wherein the protein consists of:

(a) a binding region capable of specifically binding an extracellular target biomolecule physically coupled to the surface of a cell, wherein the extracellular target biomolecule is not CD38;

(b) a Shiga toxin effector polypeptide comprising an amino acid sequence having at least 90% identity to amino acids 1 to 251 of SEQ ID NO: 1, wherein the amino acid sequence comprises at least four endogenous B-cell epitope regions, and further comprises:

i) a plurality of disrupted endogenous B-cell epitope regions, wherein the disrupted endogenous B-cell epitope regions contain the following amino acid substitutions: S45 of SEQ ID NO: 1 to I, R55 of SEQ ID NO: 1 to L, 157 of SEQ ID NO: 1 to F, P59 of SEQ ID NO: 1 to F, E60 of SEQ ID NO: 1 to T, E61 of SEQ ID NO: 1 to L, G110 of SEQ ID NO: 1 to A, R188 of SEQ ID NO: 1 to A, R248 of SEQ ID NO: 1 to A and R251 of SEQ ID NO: 1 to A;

and ii) the amino acid substitution C242 of SEQ ID NO: 1 to S; and wherein the amino acid sequence comprises an asparagine at the amino acid residue corresponding to position 75 of SEQ ID NO: 1, a tyrosine at the amino acid residue corresponding to position 77 of SEQ ID NO: 1, a tyrosine at the amino acid residue corresponding to position 114 of SEQ ID NO: 1, a glutamate at the amino acid residue corresponding to position 167 of SEQ ID NO: 1, an arginine at the amino acid residue corresponding to position 170 of SEQ ID NO: 1, an arginine at the amino acid residue corresponding to position 176 of SEQ ID NO: 1, and a tryptophan at the amino acid residue corresponding to position 203 of SEQ ID NO: 1; and (c) a linker between the binding region and the Shiga toxin effector polypeptide.

10. The cell-targeting molecule of claim 9, wherein the amino acid sequence has at least 95% sequence identity to amino acids 1 to 251 of SEQ ID NO: 1.

11. The cell-targeting molecule of claim 9, wherein the binding region comprises an immunoglobulin-type binding region.

12. The cell-targeting molecule of claim 11, wherein the immunoglobulin-type binding region comprises a polypeptide selected from: single-domain antibody fragment, single-chain variable fragment, antibody variable fragment, complementary determining region 3 fragment, constrained FR3-CDR3-FR4 polypeptide, Fd fragment, antigen-binding fragment, fibronectin-derived 10th fibronectin type III domain, tenascin type III domain, ankyrin repeat motif domain, low-density-lipoprotein-receptor-derived A-domain, lipocalin, Kunitz domain, Protein-A-derived Z domain, gamma-B crystallin-derived domain, ubiquitin-derived domain, Sac7d-derived polypeptide, Fyn-derived SH2 domain, miniprotein, C-type lectin-like domain scaffold, a heavy-chain antibody domain derived from a camelid $V_HH$ fragment, heavy-chain antibody domain derived from cartilaginous fish, immunoglobulin new antigen receptor (IgNAR), $V_{NAR}$ fragment, diabody, triabody, tetrabody, bivalent minibody, bispecific tandem scFv, bispecific tandem $V_HH$, and bispecific minibody.

13. The cell-targeting molecule of claim 9, wherein the linker is a peptide (GxS)n wherein x is 1 to 6 and n is 1 to 30.

14. A pharmaceutical composition comprising the cell-targeting molecule of claim 9 and a pharmaceutically acceptable excipient or carrier.

* * * * *

UNITED STATES PATENT AND TRADEMARK OFFICE
CERTIFICATE OF CORRECTION

| | |
|---|---|
| PATENT NO. | : 12,065,469 B2 |
| APPLICATION NO. | : 17/345576 |
| DATED | : August 20, 2024 |
| INVENTOR(S) | : Eric Poma et al. |

It is certified that error appears in the above-identified patent and that said Letters Patent is hereby corrected as shown below:

In the Claims

At Column 279, Claim number 1, Line number 44:
"157"
Should read:
--I57--

Signed and Sealed this
Fifth Day of November, 2024

Katherine Kelly Vidal
*Director of the United States Patent and Trademark Office*